US008841073B2

(12) United States Patent
Landthaler et al.

(10) Patent No.: US 8,841,073 B2
(45) Date of Patent: Sep. 23, 2014

(54) METHODS FOR IDENTIFYING RNA SEGMENTS BOUND BY RNA-BINDING PROTEINS OR RIBONUCLEOPROTEIN COMPLEXES

(75) Inventors: Markus Landthaler, Berlin (DE); Manuel Ascano, Jr., New YorK, NY (US); Markus Hafner, New York, NY (US); Thomas Tuschl, Brooklyn, NY (US); Mohsen Khorshid, Basel (CH); Lukas Burger, Basel (CH); Mihaela Zavolan, Binningen (CH)

(73) Assignee: The Rockefeller University, New York, NY (US)

( * ) Notice: Subject to any disclaimer, the term of this patent is extended or adjusted under 35 U.S.C. 154(b) by 619 days.

(21) Appl. No.: 13/055,976

(22) PCT Filed: Jul. 28, 2009

(86) PCT No.: PCT/US2009/051999

§ 371 (c)(1), (2), (4) Date: May 27, 2011

(87) PCT Pub. No.: WO2010/014636

PCT Pub. Date: Feb. 4, 2010

(65) Prior Publication Data

US 2011/0287412 A1 Nov. 24, 2011

Related U.S. Application Data

(60) Provisional application No. 61/137,265, filed on Jul. 28, 2008.

(51) Int. Cl.
*C12Q 1/68* (2006.01)
*C07H 21/02* (2006.01)
*C07H 21/04* (2006.01)

(52) U.S. Cl.
CPC .................................... *C12Q 1/6869* (2013.01)
USPC ......................... 435/6.11; 536/23.1; 536/24.3

(58) Field of Classification Search
None
See application file for complete search history.

(56) References Cited

U.S. PATENT DOCUMENTS 6,004,749 A 12/1999 Giordano et al.
6,107,029 A 8/2000 Giordano (Continued)

FOREIGN PATENT DOCUMENTS

WO WO0148480 A1 7/2001
WO WO02060924 A2 8/2002
WO WO02070746 A2 9/2002

OTHER PUBLICATIONS

Rinke-Appel, J. et al., RNA, vol. 8, pp. 612-625 (2002).*

(Continued)

*Primary Examiner* — Teresa E Strzelecka
(74) *Attorney, Agent, or Firm* — Hoffmann & Baron, LLP

(57) ABSTRACT

The present invention relates to a method for identifying a binding site on an RNA transcript, wherein the binding site binds to one or more binding moieties. The method includes, among other things, introducing a photoreactive nucleoside into living cells wherein the living cells incorporate the photoreactive nucleoside into RNA transcripts during transcription thereby producing modified RNA transcripts; reverse transcribing the RNA of isolated cross-linked segments thereby generating cDNA transcripts with one mutation wherein the photoreactive nucleoside is transcribed to a mismatched deoxynucleoside; amplifying the cDNA transcripts thereby generating amplicons; and analyzing the sequences of the amplicons aligned against the reference sequence so as to identify the binding site, wherein the sequences of each amplicon having a mutation resulting from the introduction of the photoreactive nucleoside is considered to be a valid amplicon comprising at least a portion of a binding site on the RNA transcript.

27 Claims, 93 Drawing Sheets
(44 of 93 Drawing Sheet(s) Filed in Color)

4-thiouridine (4SU)
5-bromouridine (5BrU)
5-iodouridine (5IU)
6-thioguanosine (6SG)

(56) References Cited

U.S. PATENT DOCUMENTS

| | | | |
|---|---|---|---|
| 6,291,637 | B1 | 9/2001 | Das et al. |
| 6,635,422 | B2 | 10/2003 | Keene et al. |
| 6,961,664 | B2 | 11/2005 | Selifonov et al. |
| 7,410,761 | B2 | 8/2008 | Williams |
| 2003/0211466 | A1 | 11/2003 | Keene et al. |
| 2003/0235830 | A1 | 12/2003 | Keene et al. |
| 2004/0096878 | A1 | 5/2004 | Keene et al. |
| 2004/0259135 | A1 | 12/2004 | Cleary et al. |
| 2005/0227251 | A1 | 10/2005 | Darnell et al. |
| 2007/0082349 | A1 | 4/2007 | Franzen et al. |
| 2008/0038720 | A1 | 2/2008 | Harbison et al. |

OTHER PUBLICATIONS

Hafner, M. et al., Methods, vol. 44, pp. 3-12 (2008).*

Dubreuil, Y.L., Nucl. Acids Res., vol. 19, pp. 3653-3660 (1991).*

Ueda, C.T. et al., RNA, vol. 10, pp. 139-147 (2004).*

Friedlander et al., "Discovering MicroRNA from Deep Sequencing Data Using miR Deep", Nature Biotechnology, vol. 26, No. 4, 407-415 (2008).

Lu et al., "Construction of Small RNA cDNA Libraries for Deep Sequencing", Methods, 43, 110-117 (2007).

Favre et al., "Thionucleobases as Intrinsic Photoaffinity Probes of Nucleic Acid Structure and Nucleic Acid-Protein Interactions", Journal of Photochemistry and Photobiology B: Biology, 42, 109-124 (1998).

Ule et al., "CLIP: A Method for Identifying Protein-RNA Interaction Sites in Living Cells", Methods, 37, 376-386 (2005).

Ule et al., "CLIP Identifies Nova-Regulated RNA Networks in the Brain", Science, vol. 302, 1212-1215 (2003).

Jensen et al., "CLIP: Crosslinking and ImmunoPrecipitation of In Vivo RNA Targets of RNA-Binding Proteins", Methods in Molecular Biology, vol. 488, 85-98 (2008).

Granneman et al., "Identification of Protein Binding Sites on U3 snoRNA and pre-rRNA by UV Cross-linking and High-Throughput Analysis of cDNAs", PNAS, vol. 106, No. 24, 9613-9618 (2009).

Siddharthan et al., "PhyloGibbs: A Gibbs Sampler Incorporating Phylogenetic Information", RECOMB 2004 Ws on Regulatory Genomics, LNBI 3318, 30-41 (2005).

R. Siddharthan, "PhyloGibbs-MP: Module Prediction and Discriminative Motif-Finding by Gibbs Sampling", PLoS Computational Biology, vol. 4, Issue 8, 1-15 (2008).

Licatalosi et al., "HITS-CLIP Yields Genome-Wide Insights into Brain Alternative RNA Processing", Nature07488, vol. 456, 464-470 (2008).

Wang et al., "CLIP: Construction of cDNA Libraries for High-Throughput Sequencing from RNAs Cross-Linked to Proteins in Vivo", Methods, 1-7 (2009).

Wang et al., "Using RNase Sequence Specificity to Refine the Identification of RNA-Protein Binding Regions", BMC Genomics, 9(Suppl 1):S17, 1-11 (2008).

Jack D. Keene, "RNA Regulons: Coordination of Post-Transciptional Events", Nature Reviews/Genetics, vol. 8, 553-543 (2007).

Hafner et al., "Transciptome-Wide Identification of RNA-Binding Protein and MicroRNA Target Sites by PAR-CLIP", Cell, 141, 129-141 and Supplement S1-S8 (2010).

Jensen KB, Atkinson BL, Willis MC, Koch TH, Gold L. Using in vitro selection to direct the covalent attachment of human immunodeficiency virus type 1 Rev protein to high-affinity RNA ligands. Proc Natl Acad Sci U S A. Dec. 19, 1995;92(26):12220-4.

Hockensmith JW, Kubasek WL, Vorachek WR, von Hippel PH. Laser cross-linking of nucleic acids to proteins. Methodology and first applications to the phage T4 DNA replication system. J Bioi Chem. Mar. 15, 1986;261(8):3512-8.

Hecht A, Strahl-Bolsinger S, Grunstein M. Mapping DNA interaction sites of chromosomal proteins. Crosslinking studies in yeast. Methods Mol Biol. 1999; 119;469-79.

Strutt H, Paro R. Mapping DNA target sites of chromatin proteins in vivo by formaldehyde crosslinking. Methods Mol Biol. 1999;119:455-67.

Orlando V. Mapping chromosomal proteins in vivo by formaldehyde-crosslinked-chromatin immunoprecipitation. Trends Biochem Sci. Mar. 2000;25(3):99-104.

Levine TD, Gao F, King PH, Andrews LG, Keene JD. "Hel-N1: an autoimmune RNA-binding protein with specificity for 3' uridylate-rich untranslated regions of growth factor mRNAs." Molec Cell Biol 13: 3494-3504, 1993.

Buckanovich RJ, Darnell RB. The neuronal RNA binding protein Nova-1 recognizes specific RNA targets in vitro and in vivo. Mol Cell Biol. Jun. 1997;17(6):3194-201.

Miyashiro I, Takachi K, Doki Y, Ishikawa O, Ohigashi H, Murata K, Sasaki Y, Imaoka S, Nakaizumi A, Takenaka A, Furukawa H, Hiratsuka M. When is curative gastrectomy justified for gastric cancer with positive peritoneal lavage cytology but negative macroscopic peritoneal implant? World J Surg. Sep. 2005;29(9):1131-4.

Gao FB, Carson CC. Levine T, Keene JD. Selection of a subset of mRNAs from combinatorial 3' untranslated region libraries using neuronal RNA-binding protein Hel-N1. Proc Natl Acad Sci U S A. Nov. 8, 1994;91(23):11207-11.

Zalfa F, Giorgi M, Primerano B, Moro A. Di Penta A. Reis S, Oostra B, Bagni C. The fragile X syndrome protein FMRP associates with BC1 RNA and regulates the translation of specific mRNAs at synapses. Cell. Feb. 7, 2003;112(3):317-27.

Tenenbaum SA, Carson CC, Lager PJ, Keene JD. Identifying mRNA subsets in messenger ribonucleoprotein complexes by using cDNA arrays. Proc Natl Acad Sci U S A. Dec. 19, 2000;97(26):14085-90.

Tenebaum SA, Lager PJ. Carson CC, Keene JD. Ribonomlcs: identifying mRNA subsets in mRNP complexes using antibodies to RNA-binding proteins and genomic arrays. Methods. Feb. 2002;26(2): 191-8.

Brown V, Jin P, Ceman S, Darnell JC, O'Donnell WT, Tenenbaum SA, Jin X, Feng Y, Wilkinson KD. Keene JD, Darnell RB, Warren ST. Microarray identification of FMRP-associated brain mRNAs and altered mRNA translational profiles in fragile X syndrome. Cell. Nov. 16, 2001;107(4):477-87.

Roy PJ, Stuart JM, Lund J, Kim SK. Chromosomal clustering of muscle-expressed genes in *Caenorhabditis elegans*. Nature. Aug. 29, 2002;418(6901 ):975-9.

Elbashir SM, Lendeckel W, Tuschl T. RNA interference is mediated by 21- and 22-nucleotide RNAs. Genes Dev. Jan. 15, 2001;15(2):188-200.

Lagos-Quintana M, Rauhut R, Lendeckel W, Tuschl T. Identification of novel genes coding for small expressed RNAs. Science. Oct. 26, 2001;294(5543):853-8.

Bertrand E, Fromont-Racine M, Pictet R, Grange T. Visualization of the interaction of a regulatory protein with RNA in vivo. : Proc Natl Acad Sci U S A. (1993) 90(8): 3496-3500.

Milt S, Steitz J. Evidence for reassociation of RNA-binding proteins after cell lysis: implications for the interpretation of immunoprecipitation analyses. RNA. Nov. 2004; 10(11): 1692-1694.

Pellé R, Murphy NB. In vivo UV-cross-linking hybridization: a powerful technique for isolating RNA binding proteins. Application to trypanosome mini-exon derived RNA. Nucl. Acids Res. 1993 21 (10): 2453-2458.

Niranjanakumari S, Lasda E, Brazas R, Garcia-Blanco MA. Reversible cross-linking combined with immunoprecipitation to study RNA-protein interactions in vivo. Methods (2002) 26: 182-190.

Teigelkamp S, Whittaker E, Beggs JD. Interaction of the yeast splicing factor PRP8 with substrate RNA during both steps of splicing. Nucleic Acids Research (1995) 23(3): 320-326.

Bertolotti A, Ron D. Alterations in an IRE1-RNA complex in the mammalian unfolded protein response. Journal of Cell Science. (2001)114:3207-3212.

Wahls WP. RNA Associated with a Heterodimeric Protein that Activates a Meiotic Homologous Recombination Hot Spot: RL/RT /PCR Strategy for Cloning any Unknown RNA or DNA. PCR Methods and Applications (1994) 3: 272-277.

Glickman JN, Howe JG, Steitz JA. Structural analyses of EBER1 and EBER2 ribonucleoprotein particles present in Epstein-Barr virus-infected cells. Journal of Virology Mar. 1988; 62(3): 902-911.

(56) References Cited

OTHER PUBLICATIONS

Baranov PV, Sergiev PV, Dontsova OA, Bogdanov AA, Brimacombe R. The Database of Ribosomal Cross links (DRC). Nucleic Acids Research, 1998, vol. 26, No. 1 187-189.

Montpetit A, Payant C, Nolan JM, Brakier-Gingras L. Analysis of the conformation of the 3' major domain of *Escherichia coli*16S ribosomal RNA using site-directed photoaffinity crosslinking. RNA. Nov. 1998; 4(11):1455-1466.

Urlaub H, Hartmuth K, Lührmann R. A two-tracked approach to analyze RNA-protein crosslinking sites in native, nonlabeled small nuclear ribonucleoprotein particles. Methods vol. 26, Issue 2, Feb. 2002, pp. 170-181.

Singh N, Atreya CD, Nakhasi HL. Identification of calreticulin as a rubella virus RNA binding protein. Proc Natl Acad Sci U S A. vol. 91(26): 12770-12774 (1994).

Pogue GP, Cao XQ, Singh NK, Nakhasi HL. 5' sequences of rubella virus RNA stimulate translation of chimeric RNAs and specifically interact with two host-encoded proteins. The Journal of Virology (1993) 67 (12): 7106-7117.

* cited by examiner

FIG. 1A
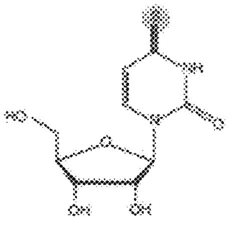
4-thiouridine (4SU)
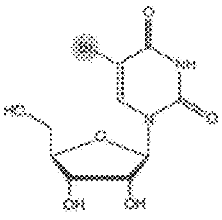
5-bromouridine (5BrU)
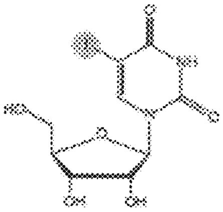
5-iodouridine (5IU)
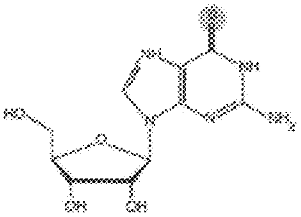
6-thioguanosine (6SG)
FIG. 1B
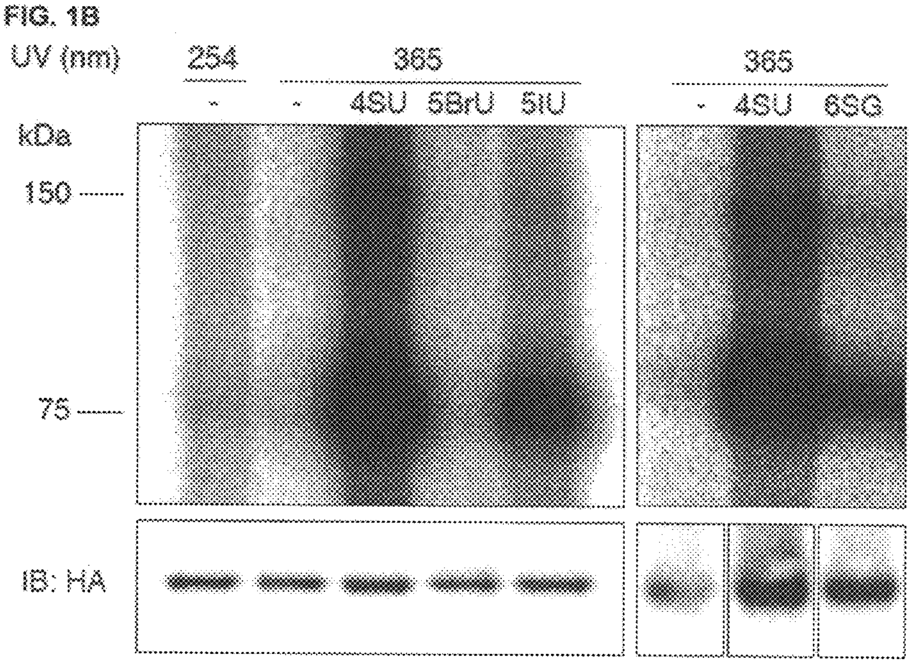

FIG. 2C

3'UTR of ELF1

| | | | |
|---|---|---|---|
| AAATGTTTTTAGATTACTTTTTCAACTGTAAATAATGTACATTTAATGTCACAAGAAAA | clones | error | (SEQ ID NO: 75) |
| ------------ATTACTTTTTCAACTGTAAACAATGTACATTT--------------- | 581 | 1 | (SEQ ID NO: 76) |
| ------------ATTACTTTTTCAACTGTAAATAATGTACACTT--------------- | 239 | 1 | (SEQ ID NO: 77) |
| ------------ATTACTTTTTCAACTGTAAATAATGTACATTT--------------- | 113 | 0 | (SEQ ID NO: 78) |
| --------------ACTTTTTCAACTGTAAACAATGTACATTTAAT------------ | 82 | 1 | (SEQ ID NO: 79) |
| ------------ATTACTTTTTCAACTGTAAATAATGTACATCT--------------- | 67 | 1 | (SEQ ID NO: 80) |

3'UTR of HES1

| | | | |
|---|---|---|---|
| GTGACTGACCATGCACTATATTTGTATATATTTTATATGTTCATATTGGATTGCGCCTT | clones | error | (SEQ ID NO: 81) |
| -------------CACTATATTTGTATACATTTTATATG-------------------- | 527 | 1 | (SEQ ID NO: 82) |
| -------------CACTATATTTGTATACATTTTATATGT------------------- | 130 | 1 | (SEQ ID NO: 83) |
| -------------CACTATATTTGTATACATTTTATA---------------------- | 48 | 1 | (SEQ ID NO: 84) |
| --------------ACTATATTTGTATACATTTTATATG-------------------- | 40 | 1 | (SEQ ID NO: 85) |
| -------------CACTATATTTGTATATATTTTATATGTTCACA-------------- | 22 | 1 | (SEQ ID NO: 86) |

FIG. 3C

3'UTR of CTNNB1

| | reads | errors | |
|---|---|---|---|
| TGTAGAACACTAATTCATAATCACTCTAATTAATTGTAATCT | | | (SEQ ID NO: 87) |
| -----AACACTAATTCATAATCACTCTAATTAACTGT----- | 81 | 1 | (SEQ ID NO: 88) |
| -----AACACTAATTCATAATCACCCTAATTAATTGT----- | 39 | 1 | (SEQ ID NO: 89) |
| -----AACACTAATTCATAATCACTCTAACTAATTGT----- | 29 | 1 | (SEQ ID NO: 90) |
| -----AACACTAATTCATAATCACTCTAATTAATTGT----- | 21 | 0 | (SEQ ID NO: 91) |

3'UTR of HOXD13

| | reads | errors | |
|---|---|---|---|
| CGAGTATGCCATTAACAAATTCATTAACAAGGACAAGCGGCGG | | | (SEQ ID NO: 92) |
| --------CCACTAACAAATTCATTAACAAG------------ | 7 | 1 | (SEQ ID NO: 93) |
| --------CCATTAACAAATTCACTAACAAG------------ | 5 | 1 | (SEQ ID NO: 94) |
| --------CCATTAACAAATCCATTAACAAG------------ | 2 | 1 | (SEQ ID NO: 95) |
| --------CCATTAACAAATTCATTAACAAG------------ | 1 | 0 | (SEQ ID NO: 96) |
| --------CCATTAACAAACTCATTAACAAG------------ | 1 | 1 | (SEQ ID NO: 97) |

C 3'UTR of EEF2

```
GGGGCCCGCTGCGTGCCATCACTCAACCATAACACTTGATGCCGTTTCTTTC clones errors (SEQ ID NO: 105)
---------------CCATCACTCAACCACAACACTTG-------------- 40     1      (SEQ ID NO: 106)
---------------CCATCACTCAACCATAACACTTG-------------- 21     0      (SEQ ID NO: 107)
---------------CCATCACCCAACCATAACACTTG-------------- 14     1      (SEQ ID NO: 108)
---------------CCACCACTCAACCATAACACTTG-------------- 11     1      (SEQ ID NO: 109)
---------------CCATCACTCAACCATAACACCTG-------------- 7      1      (SEQ ID NO: 110)
```

3'UTR of MRPL9

```
TGTCTCCAGTACTTGCCTCATTCTCATCATCCAAACTGAACATTTGTATCCC #Copy errors (SEQ ID NO: 111)
---------------CCTCATTCTCATCACCCAAACTG-------------- 18    1      (SEQ ID NO: 112)
---------------CCTCACTCTCATCATCCAAACTG-------------- 15    1      (SEQ ID NO: 113)
---------------CCTCATTCTCATCATCCAAACTG-------------- 11    0      (SEQ ID NO: 114)
---------------CCTCATTCTCACCATCCAAACTG-------------- 9     1      (SEQ ID NO: 115)
----------------CCCATTCTCATCATCCAAACTG-------------- 9     1      (SEQ ID NO: 116)
```

FIG. 4
D
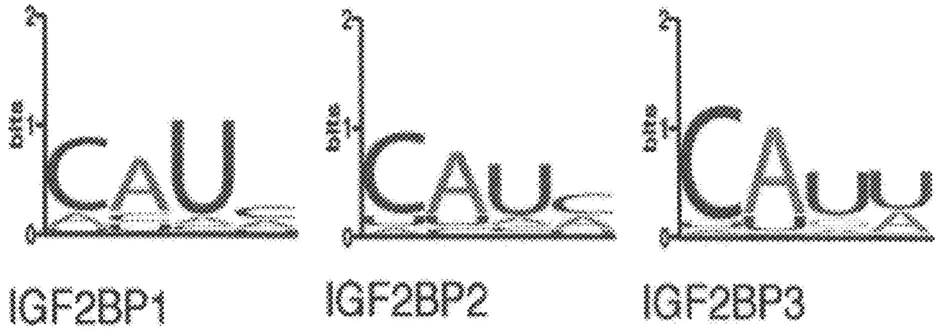
E
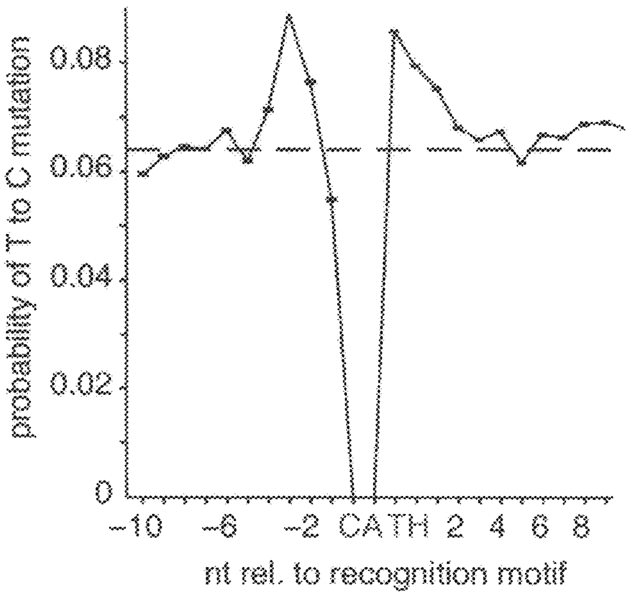

PAG1 3'UTR

```
                                      miR-103
AAGAAGTGACACAAACCTATACTTCATATGCTGCTTTAGTCACCTGAAGA   reads  errors  (SEQ ID NO:119)
--------ACACAAACCTATACTTCACATGCTGCTTT-------------   21     1       (SEQ ID NO: 120)
--------ACACAAACCTATACTTCACATGCTGCT---------------   5      1       (SEQ ID NO: 121)
------------------ATACTTCACATGCTGCTTTA------------   5      1       (SEQ ID NO: 122)
--------ACACAAACCTATACTTCATACGCTGCTTT-------------   4      1       (SEQ ID NO: 123)
--------ACACAAACCTATACTTCACATGCTGCTT--------------   4      1       (SEQ ID NO: 124)
------------------ATACTTCATATGCTGCTTCAG-----------   3      1       (SEQ ID NO: 125)
```

OGT 3'UTR

```
                                    miR-103
TTTACCCTTGACTGCCCCTTCTATGCTGCTTCCAAAAGTGATAGTGTGTG   reads  errors  (SEQ ID NO: 126)
--------------CCCCTTCCATGCTGCTTCCA----------------   7      1       (SEQ ID NO: 127)
--------------CCCCTTCTACGCTGCTTCCA----------------   3      1       (SEQ ID NO: 128)
--------------CCCCTTCTACGCTGCTTCCAA---------------   3      1       (SEQ ID NO: 129)
--------------CCCCTTCTACGCTGCTTCCAAAA-------------   2      1       (SEQ ID NO: 130)
----------ACTGCCCCTTCTACGCTGCTTCC-----------------   2      1       (SEQ ID NO: 131)
```

FIG. 13B
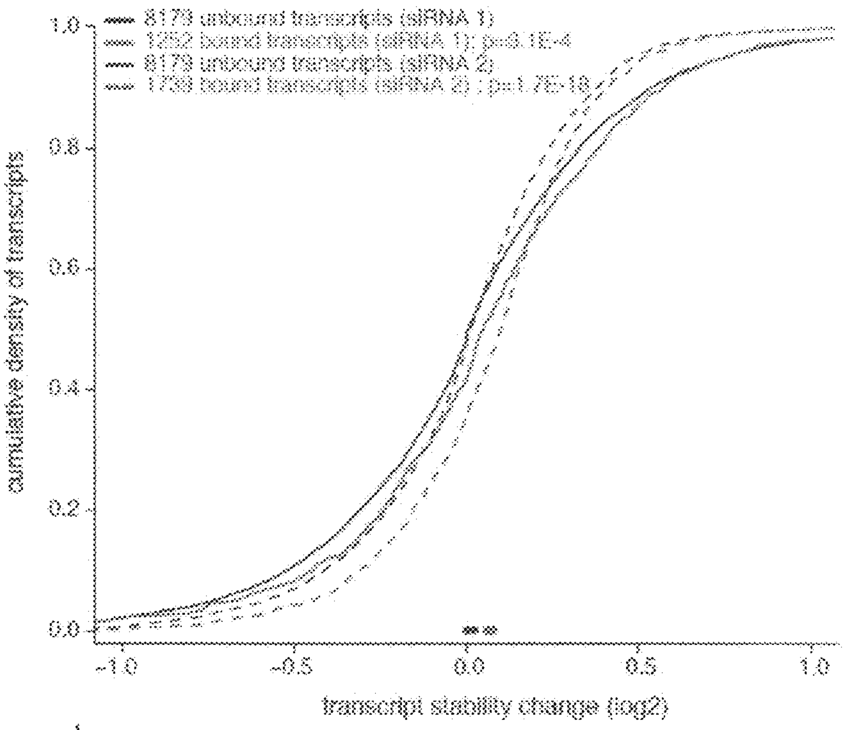
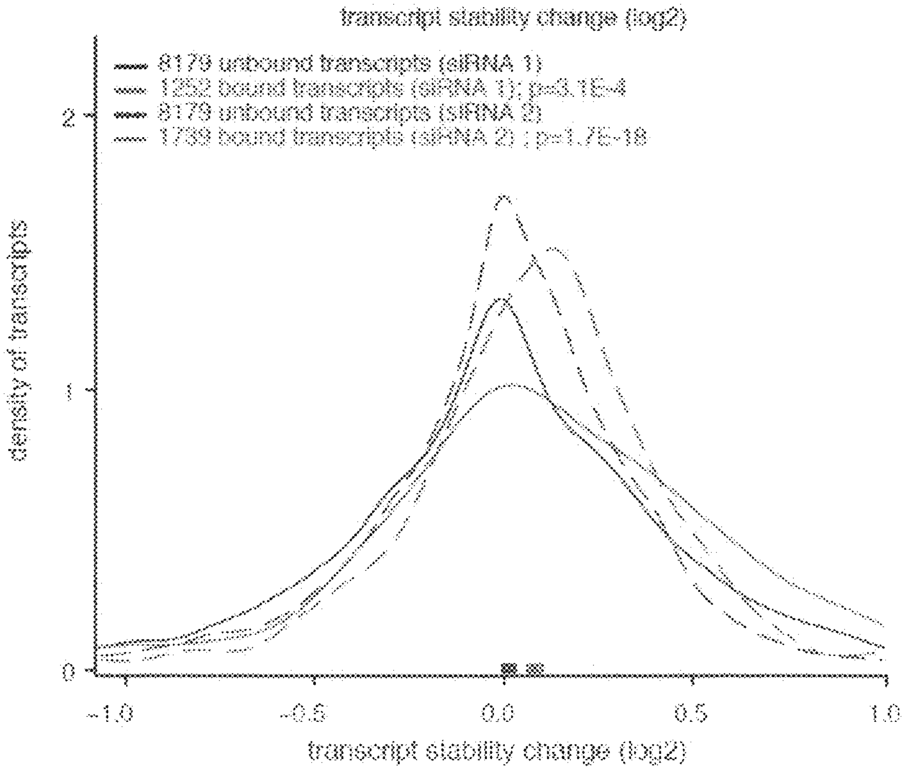

PUM2

FIG. 15C
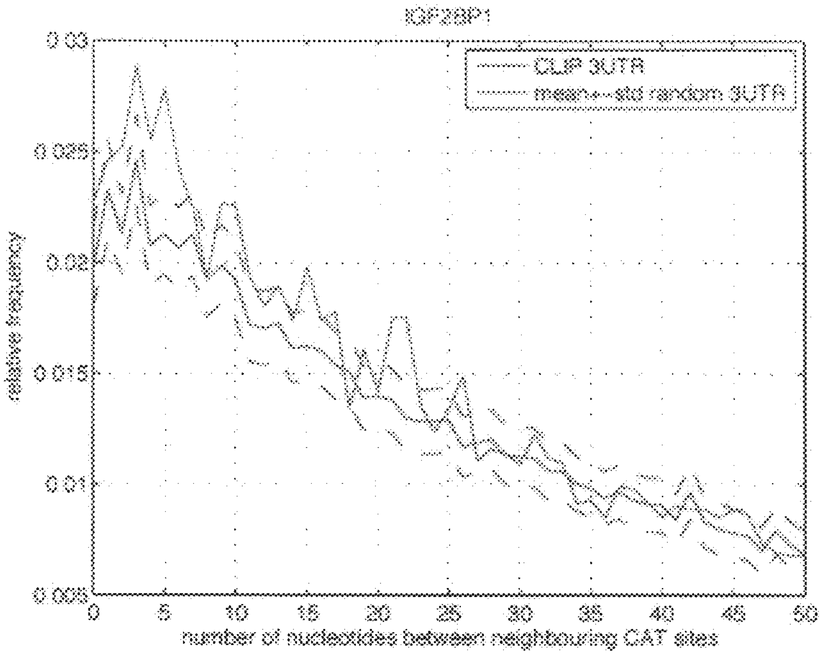
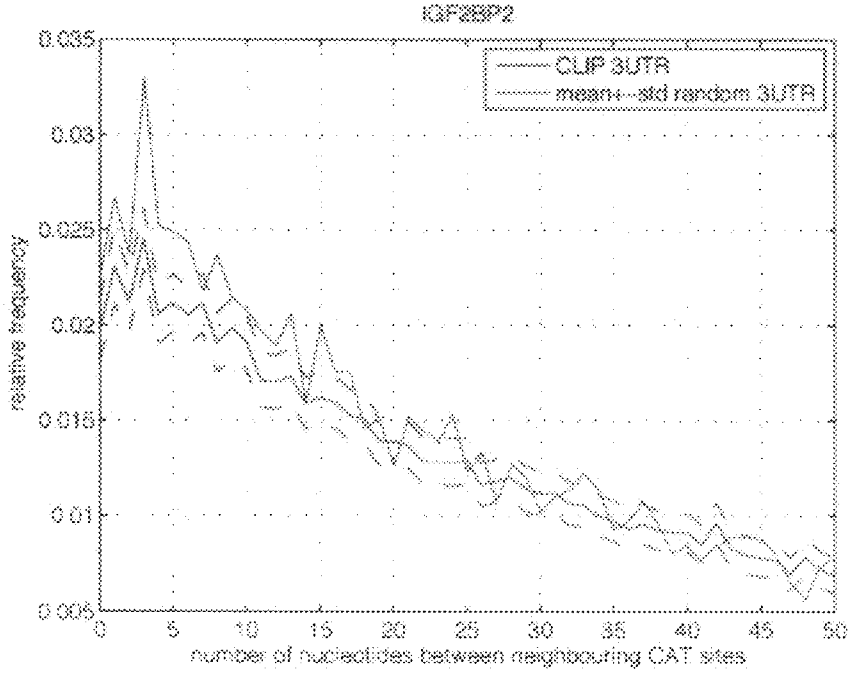

3'UTR MRPL9 (wt) (SEQ ID NO: 144) Kd = 29 ± 2 nM

3'UTR MRPL9 (mutant 1) (SEQ ID NO: 145) Kd = 570 ± 120 nM

3'UTR MRPL9 (mutant 2) (SEQ ID NO: 146) Kd = 76 ± 13 nM

MRPL9 (wt) 23 nt

C2orf43 (wt) 32 nt

QKI 1 seq. 78 nt

3'UTR MRP9 (wt)  CCTCATTTGCATAATCTAACTG  (SEQ ID NO: 147)    Kd = NA
3'UTR C2orf43 (wt) CATACGTTAACTCTCATTTCTACATTGAACT  (SEQ ID NO: 148)  Kd = 2100 ± 500 nM
QKI seq.  TAATTTTTAAGAATTGAGTAATGTGTAGAACAGTAATTCATAATTCATTAATTAATTGTAATCTGGATAAAGTGTA  Kd = 410 ± 50 nM (SEQ ID NO: 149)

FIG. 18A

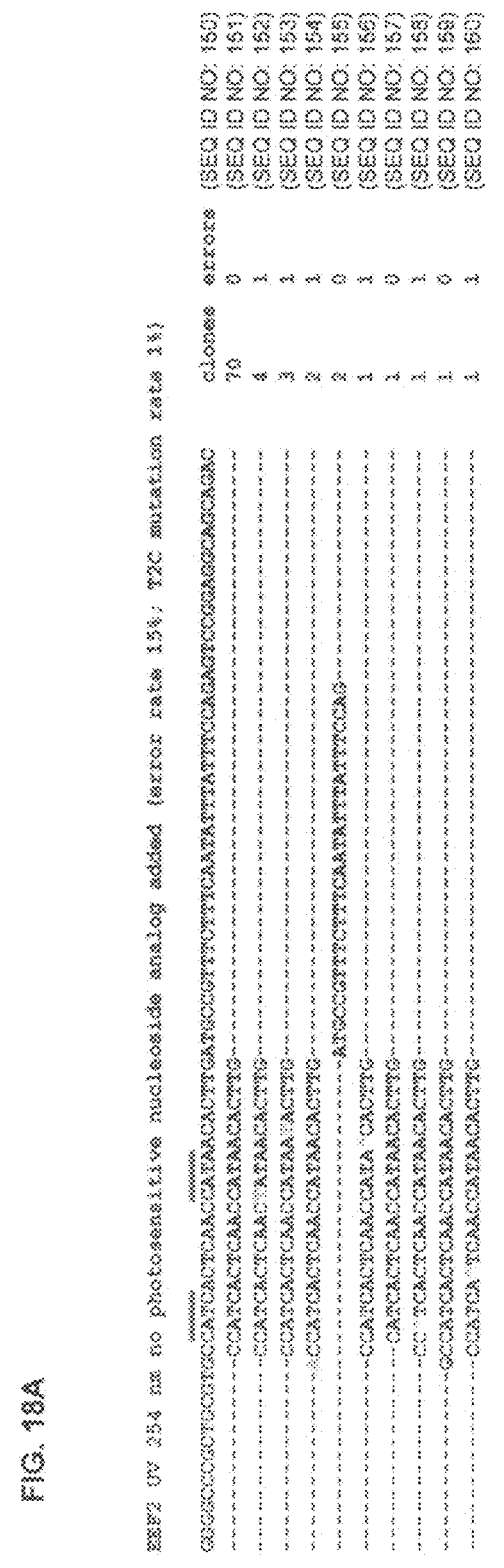

EEF2 UV 254 nm no photosensitive nucleoside analog added (error rate 15%; T2C mutation rate 1%)

| | | | |
|---|---|---|---|
| GGGGCCCGCTGCGTGCCATCACTCAACCATAACACTTGATGCCGTTTCTTTCAATATTTATTTCCAGAGTCCGGAGGCAGCAGAC | clones | errors | (SEQ ID NO: 150) |
| ----------------CCATCACTCAACCATAACACTTG----------------------------------------------- | 70 | 0 | (SEQ ID NO: 151) |
| ----------------CCATCACTCAAC ATAACACTTG----------------------------------------------- | 4 | 1 | (SEQ ID NO: 152) |
| ----------------CCATCACTCAACCATAA ACTTG----------------------------------------------- | 3 | 1 | (SEQ ID NO: 153) |
| ---------------ACCATCACTCAACCATAACACTTG----------------------------------------------- | 2 | 1 | (SEQ ID NO: 154) |
| ---------------------------------------ATGCCGTTTCTTTCAATATTTATTTCCAG------------------ | 2 | 0 | (SEQ ID NO: 155) |
| ----------------CCATCACTCAACCATA CACTTG----------------------------------------------- | 1 | 1 | (SEQ ID NO: 156) |
| -----------------CATCACTCAACCATAACACTTG----------------------------------------------- | 1 | 0 | (SEQ ID NO: 157) |
| ----------------CC TCACTCAACCATAACACTTG----------------------------------------------- | 1 | 1 | (SEQ ID NO: 158) |
| ---------------GCCATCACTCAACCATAACACTTG----------------------------------------------- | 1 | 0 | (SEQ ID NO: 159) |
| ----------------CCATCA TCAACCATAACACTTG----------------------------------------------- | 1 | 1 | (SEQ ID NO: 160) |

FIG. 21A

OGT 3'UTR

```
                                     miR-103
AGO    TTTACCCTTGACTGCCCCTTCTATGCTGCTTCCAAAAGTGATAGTGTGTG    reads errors  (SEQ ID NO: 178)
       --------------CCCCTTCCATGCTGCTTCCA----------------    7     1       (SEQ ID NO: 179)
       --------------CCCCTTCTACGCTGCTTCCA----------------    3     1       (SEQ ID NO: 180)
       --------------CCCCTTCTACGCTGCTTCCAA---------------    3     1       (SEQ ID NO: 181)
       --------------CCCCTTCTACGCTGCTTCCAAAA-------------    2     1       (SEQ ID NO: 182)
       ----------ACTGCCCCTTCTACGCTGCTTCC-----------------    2     1       (SEQ ID NO: 183)

                                     miR-103
TNRC6  TTTACCCTTGACTGCCCCTTCTATGCTGCTTCCAAAAGTGATAGTGTGTG    reads errors  (SEQ ID NO: 184)
       --------------CCCCTTCTATGCTGCTTCCAAAAG------------    3     0       (SEQ ID NO: 185)
       --------------CCCCTTCTACGCTGCTTCCA----------------    2     1       (SEQ ID NO: 186)
       --------------CCCCTTCCATGCTGCTTCCAAA--------------    1     1       (SEQ ID NO: 187)
```

FIG. 21B

RFC3 CDS

```
                                     miR-106b
AGO    TTGGAAGCGTTTGTGGCCAAATTCATGGCACTTTATAAGAAGTTCATGGA    reads errors  (SEQ ID NO: 188)
       ----------------CCAAATTCACGGCACTTTATA-------------    10    1       (SEQ ID NO: 189)
       ----------------CCAAATTCATGGCACTTTACAA------------    10    1       (SEQ ID NO: 190)
       ----------------CCAAATCCATGGCACTTTATA-------------    3     1       (SEQ ID NO: 191)
       ----------------CCAAATCCATGGCACTTTAT--------------    3     1       (SEQ ID NO: 192)
       ----------------CCAAATTCATGGCACTTTATA-------------    2     0       (SEQ ID NO: 193)
       ----------------CCAAATTCATGGCACTTTATAATA----------    2     1       (SEQ ID NO: 194)

                                     miR-106b
TNRC6  TTGGAAGCGTTTGTGGCCAAATTCATGGCACTTTATAAGAAGTTCATGGA    reads errors  (SEQ ID NO: 195)
       ----------------CCAAATCCATGGCACTTTAT--------------    6     1       (SEQ ID NO: 196)
       ----------------CCAAATTCATGGCACTTTATAAG-----------    1     0       (SEQ ID NO: 197)
       ----------------CCAAATTCATGGCACTTTACAAG-----------    1     1       (SEQ ID NO: 198)
```

FIG. 21C

AKR1A1 CDS miR-16

| | | reads | errors | |
|---|---|---|---|---|
| AGO | TAGCGTAGGCTACCGCCACATTGATTGTGCTGCTATCTACGGCAATGAG | | | (SEQ ID NO: 199) |
| | ---------------CCACATTGATCGTGCTGCTATCTACG-------- | 5 | 1 | (SEQ ID NO: 200) |
| | ---------------CCACATTGATCGTGCTGCTATCTAC--------- | 5 | 1 | (SEQ ID NO: 201) |
| | ---------------CCACATTGATCGTGCTGCTATC------------ | 3 | 1 | (SEQ ID NO: 202) |
| | ---------------CCACATTGATCGTGCTGCTATCT----------- | 2 | 1 | (SEQ ID NO: 203) |
| | ---------------CCACATTGATCGTGCTGCTATCTA---------- | 1 | 1 | (SEQ ID NO: 204) |

miR-16

| | | reads | errors | |
|---|---|---|---|---|
| TNRC6 | TAGCGTAGGCTACCGCCACATTGATTGTGCTGCTATCTACGGCAATGAG | | | (SEQ ID NO: 205) |
| | ---------------CCACATTGACTGTGCTGCTATCTA---------- | 5 | 1 | (SEQ ID NO: 206) |
| | ---------------CCACATTGATCGTGCTGCTAT------------- | 1 | 1 | (SEQ ID NO: 207) |
| | ---------------CCACATTGACTGTGCTGCTATCTACG-------- | 1 | 1 | (SEQ ID NO: 208) |

SEQUENCE LISTING

```
<160> NUMBER OF SEQ ID NOS: 208

<210> SEQ ID NO 1
<211> LENGTH: 8
<212> TYPE: PRT
<213> ORGANISM: Artificial Sequence
<220> FEATURE:
<223> OTHER INFORMATION: Synthetic sequence

<400> SEQUENCE: 1

Asp Tyr Lys Asp Asp Asp Asp Lys
1               5


<210> SEQ ID NO 2
<211> LENGTH: 8
<212> TYPE: PRT
<213> ORGANISM: Artificial Sequence
<220> FEATURE:
<223> OTHER INFORMATION: Synthetic sequence

<400> SEQUENCE: 2

Asp Tyr Lys Asp Glu Asp Asp Lys
1               5


<210> SEQ ID NO 3
<211> LENGTH: 9
<212> TYPE: PRT
<213> ORGANISM: Artificial Sequence
<220> FEATURE:
<223> OTHER INFORMATION: Synthetic sequence

<400> SEQUENCE: 3

Ala Trp Arg His Pro Gln Phe Gly Gly
1               5


<210> SEQ ID NO 4
<211> LENGTH: 13
<212> TYPE: PRT
<213> ORGANISM: Artificial Sequence
<220> FEATURE:
<223> OTHER INFORMATION: Synthetic sequence

<400> SEQUENCE: 4

Tyr Pro Tyr Asp Val Pro Asp Tyr Ala Ile Glu Gly Arg
1               5                   10


<210> SEQ ID NO 5
<211> LENGTH: 6
<212> TYPE: PRT
```

<213> ORGANISM: Artificial Sequence
<220> FEATURE:
<223> OTHER INFORMATION: Synthetic sequence

<400> SEQUENCE: 5

His His His His His His
1 5

<210> SEQ ID NO 6
<211> LENGTH: 11
<212> TYPE: PRT
<213> ORGANISM: Artificial Sequence
<220> FEATURE:
<223> OTHER INFORMATION: Synthetic sequence

<400> SEQUENCE: 6

Glu Gln Lys Leu Leu Ser Glu Glu Asp Leu Asn
1 5 10

<210> SEQ ID NO 7
<211> LENGTH: 31
<212> TYPE: DNA
<213> ORGANISM: Artificial Sequence
<220> FEATURE:
<223> OTHER INFORMATION: Synthetic sequence

<400> SEQUENCE: 7
atgaatcatg attttcaagc tcttgcatta g 31

<210> SEQ ID NO 8
<211> LENGTH: 48
<212> TYPE: DNA
<213> ORGANISM: Artificial Sequence
<220> FEATURE:
<223> OTHER INFORMATION: Synthetic sequence

<400> SEQUENCE: 8
ataagaatgc ggccgcttac agcattccat ttggtggtcc tccaatag 48

<210> SEQ ID NO 9
<211> LENGTH: 31
<212> TYPE: DNA
<213> ORGANISM: Artificial Sequence
<220> FEATURE:
<223> OTHER INFORMATION: Synthetic sequence

<400> SEQUENCE: 9
acgcgtcgac atggtcgggg aaatggaaac g 31

<210> SEQ ID NO 10
<211> LENGTH: 38
<212> TYPE: DNA
<213> ORGANISM: Artificial Sequence
<220> FEATURE:
<223> OTHER INFORMATION: Synthetic sequence

<400> SEQUENCE: 10
ataagaatgc ggccgcttag cctttcgttg ggaaagcc 38

<210> SEQ ID NO 11
<211> LENGTH: 37
<212> TYPE: DNA
<213> ORGANISM: Artificial Sequence
<220> FEATURE:
<223> OTHER INFORMATION: Synthetic sequence

<400> SEQUENCE: 11

-continued acgcgtcgac atgaacaagc tttacatcgg caacctc 37

<210> SEQ ID NO 12
<211> LENGTH: 40
<212> TYPE: DNA
<213> ORGANISM: Artificial Sequence
<220> FEATURE:
<223> OTHER INFORMATION: Synthetic sequence

<400> SEQUENCE: 12
ataagaatgc ggccgctcac ttcctccgtg cctgggcctg 40

<210> SEQ ID NO 13
<211> LENGTH: 37
<212> TYPE: DNA
<213> ORGANISM: Artificial Sequence
<220> FEATURE:
<223> OTHER INFORMATION: Synthetic sequence

<400> SEQUENCE: 13
acgcgtcgac atgatgaaca agctttacat cgggaac 37

<210> SEQ ID NO 14
<211> LENGTH: 40
<212> TYPE: DNA
<213> ORGANISM: Artificial Sequence
<220> FEATURE:
<223> OTHER INFORMATION: Synthetic sequence

<400> SEQUENCE: 14
ataagaatgc ggccgctcac ttgctgcgct gtgaggcgac 40

<210> SEQ ID NO 15
<211> LENGTH: 39
<212> TYPE: DNA
<213> ORGANISM: Artificial Sequence
<220> FEATURE:
<223> OTHER INFORMATION: Synthetic sequence

<400> SEQUENCE: 15
acgcgtcgac atgaacaaac tgtatatcgg aaacctcag 39

<210> SEQ ID NO 16
<211> LENGTH: 42
<212> TYPE: DNA
<213> ORGANISM: Artificial Sequence
<220> FEATURE:
<223> OTHER INFORMATION: Synthetic sequence

<400> SEQUENCE: 16
ataagaatgc ggccgcttac ttccgtcttg actgaggtgg tc 42

<210> SEQ ID NO 17
<211> LENGTH: 31
<212> TYPE: DNA
<213> ORGANISM: Artificial Sequence
<220> FEATURE:
<223> OTHER INFORMATION: Synthetic sequence

<400> SEQUENCE: 17
atgaatcatg attttcaagc tcttgcatta g 31

<210> SEQ ID NO 18
<211> LENGTH: 48
<212> TYPE: DNA

<213> ORGANISM: Artificial Sequence
<220> FEATURE:
<223> OTHER INFORMATION: Synthetic sequence

<400> SEQUENCE: 18
ataagaatgc ggccgcttac agcattccat ttggtggtcc tccaatag 48

<210> SEQ ID NO 19
<211> LENGTH: 31
<212> TYPE: DNA
<213> ORGANISM: Artificial Sequence
<220> FEATURE:
<223> OTHER INFORMATION: Synthetic sequence

<400> SEQUENCE: 19
acgcgtcgac atggtcgggg aaatggaaac g 31

<210> SEQ ID NO 20
<211> LENGTH: 38
<212> TYPE: DNA
<213> ORGANISM: Artificial Sequence
<220> FEATURE:
<223> OTHER INFORMATION: Synthetic sequence

<400> SEQUENCE: 20
ataagaatgc ggccgcttag cctttcgttg ggaaagcc 38

<210> SEQ ID NO 21
<211> LENGTH: 37
<212> TYPE: DNA
<213> ORGANISM: Artificial Sequence
<220> FEATURE:
<223> OTHER INFORMATION: Synthetic sequence

<400> SEQUENCE: 21
acgcgtcgac atgaacaagc tttacatcgg caacctc 37

<210> SEQ ID NO 22
<211> LENGTH: 40
<212> TYPE: DNA
<213> ORGANISM: Artificial Sequence
<220> FEATURE:
<223> OTHER INFORMATION: Synthetic sequence

<400> SEQUENCE: 22
ataagaatgc ggccgctcac ttcctccgtg cctgggcctg 40

<210> SEQ ID NO 23
<211> LENGTH: 37
<212> TYPE: DNA
<213> ORGANISM: Artificial Sequence
<220> FEATURE:
<223> OTHER INFORMATION: Synthetic sequence

<400> SEQUENCE: 23
acgcgtcgac atgatgaaca agctttacat cgggaac 37

<210> SEQ ID NO 24
<211> LENGTH: 40
<212> TYPE: DNA
<213> ORGANISM: Artificial Sequence
<220> FEATURE:
<223> OTHER INFORMATION: Synthetic sequence

<400> SEQUENCE: 24
ataagaatgc ggccgctcac ttgctgcgct gtgaggcgac 40

<210> SEQ ID NO 25
<211> LENGTH: 39
<212> TYPE: DNA
<213> ORGANISM: Artificial Sequence
<220> FEATURE:
<223> OTHER INFORMATION: Synthetic sequence

<400> SEQUENCE: 25
acgcgtcgac atgaacaaac tgtatatcgg aaacctcag 39

<210> SEQ ID NO 26
<211> LENGTH: 42
<212> TYPE: DNA
<213> ORGANISM: Artificial Sequence
<220> FEATURE:
<223> OTHER INFORMATION: Synthetic sequence

<400> SEQUENCE: 26
ataagaatgc ggccgcttac ttccgtcttg actgaggtgg tc 42

<210> SEQ ID NO 27
<211> LENGTH: 27
<212> TYPE: RNA
<213> ORGANISM: Artificial Sequence
<220> FEATURE:
<223> OTHER INFORMATION: Synthetic sequence

<400> SEQUENCE: 27
guaugccauu aacaaauuca uuaacaa 27

<210> SEQ ID NO 28
<211> LENGTH: 27
<212> TYPE: RNA
<213> ORGANISM: Artificial Sequence
<220> FEATURE:
<223> OTHER INFORMATION: Synthetic sequence
<220> FEATURE:
<221> NAME/KEY: modified_base
<222> LOCATION: (2)..(2)
<223> OTHER INFORMATION: s4u

<400> SEQUENCE: 28
guaugccauu aacaaauuca uuaacaa 27

<210> SEQ ID NO 29
<211> LENGTH: 27
<212> TYPE: RNA
<213> ORGANISM: Artificial Sequence
<220> FEATURE:
<223> OTHER INFORMATION: Synthetic sequence
<220> FEATURE:
<221> NAME/KEY: modified_base
<222> LOCATION: (4)..(4)
<223> OTHER INFORMATION: s4u

<400> SEQUENCE: 29
guaugccauu aacaaauuca uuaacaa 27

<210> SEQ ID NO 30
<211> LENGTH: 26
<212> TYPE: RNA
<213> ORGANISM: Artificial Sequence
<220> FEATURE:
<223> OTHER INFORMATION: Synthetic sequence
<220> FEATURE:
<221> NAME/KEY: modified_base
<222> LOCATION: (9)..(9)

<223> OTHER INFORMATION: s4u

<400> SEQUENCE: 30
guaugccaua acaaauucau uaacaa 26

<210> SEQ ID NO 31
<211> LENGTH: 27
<212> TYPE: RNA
<213> ORGANISM: Artificial Sequence
<220> FEATURE:
<223> OTHER INFORMATION: Synthetic sequence
<220> FEATURE:
<221> NAME/KEY: modified_base
<222> LOCATION: (10)..(10)
<223> OTHER INFORMATION: s4u

<400> SEQUENCE: 31
guaugccauu aacaaauuca uuaacaa 27

<210> SEQ ID NO 32
<211> LENGTH: 21
<212> TYPE: RNA
<213> ORGANISM: Artificial Sequence
<220> FEATURE:
<223> OTHER INFORMATION: Synthetic sequence

<400> SEQUENCE: 32
gaagagagca guugaagaau u 21

<210> SEQ ID NO 33
<211> LENGTH: 21
<212> TYPE: RNA
<213> ORGANISM: Artificial Sequence
<220> FEATURE:
<223> OTHER INFORMATION: Synthetic sequence

<400> SEQUENCE: 33
uucuucaacu gcucucuucu u 21

<210> SEQ ID NO 34
<211> LENGTH: 20
<212> TYPE: RNA
<213> ORGANISM: Artificial Sequence
<220> FEATURE:
<223> OTHER INFORMATION: Synthetic sequence

<400> SEQUENCE: 34
ccaauuggga gcaucuaaau 20

<210> SEQ ID NO 35
<211> LENGTH: 20
<212> TYPE: RNA
<213> ORGANISM: Artificial Sequence
<220> FEATURE:
<223> OTHER INFORMATION: Synthetic sequence

<400> SEQUENCE: 35
uuuagaugcu cccaauuggu 20

<210> SEQ ID NO 36
<211> LENGTH: 21
<212> TYPE: RNA
<213> ORGANISM: Artificial Sequence
<220> FEATURE:
<223> OTHER INFORMATION: Synthetic sequence

<400> SEQUENCE: 36
gggaagaauc uauggcaaau u 21

<210> SEQ ID NO 37
<211> LENGTH: 21
<212> TYPE: RNA
<213> ORGANISM: Artificial Sequence
<220> FEATURE:
<223> OTHER INFORMATION: Synthetic sequence

<400> SEQUENCE: 37
uuugccauag auucuucccu u 21

<210> SEQ ID NO 38
<211> LENGTH: 21
<212> TYPE: RNA
<213> ORGANISM: Artificial Sequence
<220> FEATURE:
<223> OTHER INFORMATION: Synthetic sequence

<400> SEQUENCE: 38
ggcaucaguu ugagaacuau u 21

<210> SEQ ID NO 39
<211> LENGTH: 21
<212> TYPE: RNA
<213> ORGANISM: Artificial Sequence
<220> FEATURE:
<223> OTHER INFORMATION: Synthetic sequence

<400> SEQUENCE: 39
uaguucucaa acugaugccu u 21

<210> SEQ ID NO 40
<211> LENGTH: 21
<212> TYPE: RNA
<213> ORGANISM: Artificial Sequence
<220> FEATURE:
<223> OTHER INFORMATION: Synthetic sequence

<400> SEQUENCE: 40
aaaucgaugu ccaccguaau u 21

<210> SEQ ID NO 41
<211> LENGTH: 21
<212> TYPE: RNA
<213> ORGANISM: Artificial Sequence
<220> FEATURE:
<223> OTHER INFORMATION: Synthetic sequence

<400> SEQUENCE: 41
uuacggugga caucgauuuu u 21

<210> SEQ ID NO 42
<211> LENGTH: 22
<212> TYPE: RNA
<213> ORGANISM: Artificial Sequence
<220> FEATURE:
<223> OTHER INFORMATION: Synthetic sequence

<400> SEQUENCE: 42
aacuauacaa ccuacuaccu ca 22

<210> SEQ ID NO 43
<211> LENGTH: 23
<212> TYPE: RNA

<213> ORGANISM: Artificial Sequence
<220> FEATURE:
<223> OTHER INFORMATION: Synthetic sequence

<400> SEQUENCE: 43
cacaaauucg gaucuacagg gua 23

<210> SEQ ID NO 44
<211> LENGTH: 22
<212> TYPE: RNA
<213> ORGANISM: Artificial Sequence
<220> FEATURE:
<223> OTHER INFORMATION: Synthetic sequence

<400> SEQUENCE: 44
cgccaauauu uacgugcugc ua 22

<210> SEQ ID NO 45
<211> LENGTH: 22
<212> TYPE: RNA
<213> ORGANISM: Artificial Sequence
<220> FEATURE:
<223> OTHER INFORMATION: Synthetic sequence

<400> SEQUENCE: 45
cacaaaccau uaugugcugc ua 22

<210> SEQ ID NO 46
<211> LENGTH: 22
<212> TYPE: RNA
<213> ORGANISM: Artificial Sequence
<220> FEATURE:
<223> OTHER INFORMATION: Synthetic sequence

<400> SEQUENCE: 46
uguaaaccau gaugugcugc ua 22

<210> SEQ ID NO 47
<211> LENGTH: 23
<212> TYPE: RNA
<213> ORGANISM: Artificial Sequence
<220> FEATURE:
<223> OTHER INFORMATION: Synthetic sequence

<400> SEQUENCE: 47
cuaccugcac uguaagcacu uug 23

<210> SEQ ID NO 48
<211> LENGTH: 23
<212> TYPE: RNA
<213> ORGANISM: Artificial Sequence
<220> FEATURE:
<223> OTHER INFORMATION: Synthetic sequence

<400> SEQUENCE: 48
cuaucugcac uagaugcacc uua 23

<210> SEQ ID NO 49
<211> LENGTH: 23
<212> TYPE: RNA
<213> ORGANISM: Artificial Sequence
<220> FEATURE:
<223> OTHER INFORMATION: Synthetic sequence

<400> SEQUENCE: 49
ucaguuuugc auagauuugc aca 23

<210> SEQ ID NO 50
<211> LENGTH: 23
<212> TYPE: RNA
<213> ORGANISM: Artificial Sequence
<220> FEATURE:
<223> OTHER INFORMATION: Synthetic sequence

<400> SEQUENCE: 50
ucaguuuugc auggauuugc aca 23

<210> SEQ ID NO 51
<211> LENGTH: 23
<212> TYPE: RNA
<213> ORGANISM: Artificial Sequence
<220> FEATURE:
<223> OTHER INFORMATION: Synthetic sequence

<400> SEQUENCE: 51
cuaccugcac uauaagcacu uua 23

<210> SEQ ID NO 52
<211> LENGTH: 23
<212> TYPE: RNA
<213> ORGANISM: Artificial Sequence
<220> FEATURE:
<223> OTHER INFORMATION: Synthetic sequence

<400> SEQUENCE: 52
cuaccugcac uaugagcacu uug 23

<210> SEQ ID NO 53
<211> LENGTH: 22
<212> TYPE: RNA
<213> ORGANISM: Artificial Sequence
<220> FEATURE:
<223> OTHER INFORMATION: Synthetic sequence

<400> SEQUENCE: 53
ucaacaucag ucugauaagc ua 22

<210> SEQ ID NO 54
<211> LENGTH: 22
<212> TYPE: RNA
<213> ORGANISM: Artificial Sequence
<220> FEATURE:
<223> OTHER INFORMATION: Synthetic sequence

<400> SEQUENCE: 54
ucagaccgag acaagugcaa ug 22

<210> SEQ ID NO 55
<211> LENGTH: 22
<212> TYPE: RNA
<213> ORGANISM: Artificial Sequence
<220> FEATURE:
<223> OTHER INFORMATION: Synthetic sequence

<400> SEQUENCE: 55
aacuauacaa ucuacuaccu ca 22

<210> SEQ ID NO 56
<211> LENGTH: 22
<212> TYPE: RNA
<213> ORGANISM: Artificial Sequence
<220> FEATURE:

<223> OTHER INFORMATION: Synthetic sequence

<400> SEQUENCE: 56
cuuccagucg aggauguuua ca 22

<210> SEQ ID NO 57
<211> LENGTH: 18
<212> TYPE: RNA
<213> ORGANISM: Artificial Sequence
<220> FEATURE:
<223> OTHER INFORMATION: Synthetic sequence

<400> SEQUENCE: 57
gaguguagga uguuuaca 18

<210> SEQ ID NO 58
<211> LENGTH: 22
<212> TYPE: RNA
<213> ORGANISM: Artificial Sequence
<220> FEATURE:
<223> OTHER INFORMATION: Synthetic sequence

<400> SEQUENCE: 58
acaggccggg acaagugcaa ua 22

<210> SEQ ID NO 59
<211> LENGTH: 23
<212> TYPE: RNA
<213> ORGANISM: Artificial Sequence
<220> FEATURE:
<223> OTHER INFORMATION: Synthetic sequence

<400> SEQUENCE: 59
cuaccugcac gaacagcacu uug 23

<210> SEQ ID NO 60
<211> LENGTH: 21
<212> TYPE: RNA
<213> ORGANISM: Artificial Sequence
<220> FEATURE:
<223> OTHER INFORMATION: Synthetic sequence

<400> SEQUENCE: 60
uucaguuauc acaguacugu a 21

<210> SEQ ID NO 61
<211> LENGTH: 23
<212> TYPE: RNA
<213> ORGANISM: Artificial Sequence
<220> FEATURE:
<223> OTHER INFORMATION: Synthetic sequence

<400> SEQUENCE: 61
ucauagcccu guacaaugcu gcu 23

<210> SEQ ID NO 62
<211> LENGTH: 21
<212> TYPE: RNA
<213> ORGANISM: Artificial Sequence
<220> FEATURE:
<223> OTHER INFORMATION: Synthetic sequence

<400> SEQUENCE: 62
aucugcacug ucagcacuuu a 21

<210> SEQ ID NO 63
<211> LENGTH: 22
<212> TYPE: RNA
<213> ORGANISM: Artificial Sequence
<220> FEATURE:
<223> OTHER INFORMATION: Synthetic sequence

<400> SEQUENCE: 63
agcccaaaag gagaauucuu ug 22

<210> SEQ ID NO 64
<211> LENGTH: 23
<212> TYPE: RNA
<213> ORGANISM: Artificial Sequence
<220> FEATURE:
<223> OTHER INFORMATION: Synthetic sequence

<400> SEQUENCE: 64
gcuuugacaa uacuauugca cug 23

<210> SEQ ID NO 65
<211> LENGTH: 21
<212> TYPE: RNA
<213> ORGANISM: Artificial Sequence
<220> FEATURE:
<223> OTHER INFORMATION: Synthetic sequence

<400> SEQUENCE: 65
ccuucugacu ccaaguccag u 21

<210> SEQ ID NO 66
<211> LENGTH: 23
<212> TYPE: RNA
<213> ORGANISM: Artificial Sequence
<220> FEATURE:
<223> OTHER INFORMATION: Synthetic sequence

<400> SEQUENCE: 66
uggaagacua gugauuuugu ugu 23

<210> SEQ ID NO 67
<211> LENGTH: 22
<212> TYPE: RNA
<213> ORGANISM: Artificial Sequence
<220> FEATURE:
<223> OTHER INFORMATION: Synthetic sequence

<400> SEQUENCE: 67
caacaaauca cagucugcca ua 22

<210> SEQ ID NO 68
<211> LENGTH: 21
<212> TYPE: RNA
<213> ORGANISM: Artificial Sequence
<220> FEATURE:
<223> OTHER INFORMATION: Synthetic sequence

<400> SEQUENCE: 68
uaaggcacgc ggugaaugcc a 21

<210> SEQ ID NO 69
<211> LENGTH: 21
<212> TYPE: RNA
<213> ORGANISM: Artificial Sequence
<220> FEATURE:
<223> OTHER INFORMATION: Synthetic sequence

<400> SEQUENCE: 69
cguguucaca gcggaccuug a 21

<210> SEQ ID NO 70
<211> LENGTH: 27
<212> TYPE: DNA
<213> ORGANISM: Artificial Sequence
<220> FEATURE:
<223> OTHER INFORMATION: Synthetic sequence

<400> SEQUENCE: 70
tctagtcgta tgccgtcttc tgcttgt 27

<210> SEQ ID NO 71
<211> LENGTH: 27
<212> TYPE: DNA
<213> ORGANISM: Artificial Sequence
<220> FEATURE:
<223> OTHER INFORMATION: Synthetic sequence

<400> SEQUENCE: 71
tctcctcgta tgccgtcttc tgcttgt 27

<210> SEQ ID NO 72
<211> LENGTH: 27
<212> TYPE: DNA
<213> ORGANISM: Artificial Sequence
<220> FEATURE:
<223> OTHER INFORMATION: Synthetic sequence

<400> SEQUENCE: 72
tctgatcgta tgccgtcttc tgcttgt 27

<210> SEQ ID NO 73
<211> LENGTH: 27
<212> TYPE: DNA
<213> ORGANISM: Artificial Sequence
<220> FEATURE:
<223> OTHER INFORMATION: Synthetic sequence

<400> SEQUENCE: 73
ttaagtcgta tgccgtcttc tgcttgt 27

<210> SEQ ID NO 74
<211> LENGTH: 27
<212> TYPE: DNA
<213> ORGANISM: Artificial Sequence
<220> FEATURE:
<223> OTHER INFORMATION: Synthetic sequence

<400> SEQUENCE: 74
tcacttcgta tgccgtcttc tgcttgt 27

<210> SEQ ID NO 75
<211> LENGTH: 59
<212> TYPE: DNA
<213> ORGANISM: Artificial Sequence
<220> FEATURE:
<223> OTHER INFORMATION: Synthetic sequence

<400> SEQUENCE: 75
aaatgttttt agattacttt ttcaactgta aataatgtac atttaatgtc acaagaaaa 59

<210> SEQ ID NO 76
<211> LENGTH: 32

<212> TYPE: DNA
<213> ORGANISM: Artificial Sequence
<220> FEATURE:
<223> OTHER INFORMATION: Synthetic sequence

<400> SEQUENCE: 76
attacttttt caactgtaaa caatgtacat tt 32

<210> SEQ ID NO 77
<211> LENGTH: 32
<212> TYPE: DNA
<213> ORGANISM: Artificial Sequence
<220> FEATURE:
<223> OTHER INFORMATION: Synthetic sequence

<400> SEQUENCE: 77
attacttttt caactgtaaa taatgtacac tt 32

<210> SEQ ID NO 78
<211> LENGTH: 32
<212> TYPE: DNA
<213> ORGANISM: Artificial Sequence
<220> FEATURE:
<223> OTHER INFORMATION: Synthetic sequence

<400> SEQUENCE: 78
attacttttt caactgtaaa taatgtacat tt 32

<210> SEQ ID NO 79
<211> LENGTH: 32
<212> TYPE: DNA
<213> ORGANISM: Artificial Sequence
<220> FEATURE:
<223> OTHER INFORMATION: Synthetic sequence

<400> SEQUENCE: 79
actttttcaa ctgtaaacaa tgtacattta at 32

<210> SEQ ID NO 80
<211> LENGTH: 32
<212> TYPE: DNA
<213> ORGANISM: Artificial Sequence
<220> FEATURE:
<223> OTHER INFORMATION: Synthetic sequence

<400> SEQUENCE: 80
attacttttt caactgtaaa taatgtacat ct 32

<210> SEQ ID NO 81
<211> LENGTH: 59
<212> TYPE: DNA
<213> ORGANISM: Artificial Sequence
<220> FEATURE:
<223> OTHER INFORMATION: Synthetic sequence

<400> SEQUENCE: 81
gtgactgacc atgcactata tttgtatata ttttatatgt tcatattgga ttgcgcctt 59

<210> SEQ ID NO 82
<211> LENGTH: 26
<212> TYPE: DNA
<213> ORGANISM: Artificial Sequence
<220> FEATURE:
<223> OTHER INFORMATION: Synthetic sequence

<400> SEQUENCE: 82

-continued cactatattt gtatacattt tatatg 26

<210> SEQ ID NO 83
<211> LENGTH: 27
<212> TYPE: DNA
<213> ORGANISM: Artificial Sequence
<220> FEATURE:
<223> OTHER INFORMATION: Synthetic sequence

<400> SEQUENCE: 83
cactatattt gtatacattt tatatgt 27

<210> SEQ ID NO 84
<211> LENGTH: 24
<212> TYPE: DNA
<213> ORGANISM: Artificial Sequence
<220> FEATURE:
<223> OTHER INFORMATION: Synthetic sequence

<400> SEQUENCE: 84
cactatattt gtatacattt tata 24

<210> SEQ ID NO 85
<211> LENGTH: 25
<212> TYPE: DNA
<213> ORGANISM: Artificial Sequence
<220> FEATURE:
<223> OTHER INFORMATION: Synthetic sequence

<400> SEQUENCE: 85
actatatttg tatacatttt atatg 25

<210> SEQ ID NO 86
<211> LENGTH: 32
<212> TYPE: DNA
<213> ORGANISM: Artificial Sequence
<220> FEATURE:
<223> OTHER INFORMATION: Synthetic sequence

<400> SEQUENCE: 86
cactatattt gtatatattt tatatgttca ca 32

<210> SEQ ID NO 87
<211> LENGTH: 42
<212> TYPE: DNA
<213> ORGANISM: Artificial Sequence
<220> FEATURE:
<223> OTHER INFORMATION: Synthetic sequence

<400> SEQUENCE: 87
tgtagaacac taattcataa tcactctaat taattgtaat ct 42

<210> SEQ ID NO 88
<211> LENGTH: 32
<212> TYPE: DNA
<213> ORGANISM: Artificial Sequence
<220> FEATURE:
<223> OTHER INFORMATION: Synthetic sequence

<400> SEQUENCE: 88
aacactaatt cataatcact ctaattaact gt 32

<210> SEQ ID NO 89
<211> LENGTH: 32
<212> TYPE: DNA
<213> ORGANISM: Artificial Sequence
<220> FEATURE:
<223> OTHER INFORMATION: Synthetic sequence

<400> SEQUENCE: 89
aacactaatt cataatcacc ctaattaatt gt 32

<210> SEQ ID NO 90
<211> LENGTH: 32
<212> TYPE: DNA
<213> ORGANISM: Artificial Sequence
<220> FEATURE:
<223> OTHER INFORMATION: Synthetic sequence

<400> SEQUENCE: 90
aacactaatt cataatcact ctaactaatt gt 32

<210> SEQ ID NO 91
<211> LENGTH: 32
<212> TYPE: DNA
<213> ORGANISM: Artificial Sequence
<220> FEATURE:
<223> OTHER INFORMATION: Synthetic sequence

<400> SEQUENCE: 91
aacactaatt cataatcact ctaattaatt gt 32

<210> SEQ ID NO 92
<211> LENGTH: 43
<212> TYPE: DNA
<213> ORGANISM: Artificial Sequence
<220> FEATURE:
<223> OTHER INFORMATION: Synthetic sequence

<400> SEQUENCE: 92
cgagtatgcc attaacaaat tcattaacaa ggacaagcgg cgg 43

<210> SEQ ID NO 93
<211> LENGTH: 23
<212> TYPE: DNA
<213> ORGANISM: Artificial Sequence
<220> FEATURE:
<223> OTHER INFORMATION: Synthetic sequence

<400> SEQUENCE: 93
ccactaacaa attcattaac aag 23

<210> SEQ ID NO 94
<211> LENGTH: 23
<212> TYPE: DNA
<213> ORGANISM: Artificial Sequence
<220> FEATURE:
<223> OTHER INFORMATION: Synthetic sequence

<400> SEQUENCE: 94
ccattaacaa attcactaac aag 23

<210> SEQ ID NO 95
<211> LENGTH: 23
<212> TYPE: DNA
<213> ORGANISM: Artificial Sequence
<220> FEATURE:
<223> OTHER INFORMATION: Synthetic sequence

<400> SEQUENCE: 95
ccattaacaa atccattaac aag 23

<210> SEQ ID NO 96
<211> LENGTH: 23
<212> TYPE: DNA
<213> ORGANISM: Artificial Sequence
<220> FEATURE:
<223> OTHER INFORMATION: Synthetic sequence

<400> SEQUENCE: 96
ccattaacaa attcattaac aag 23

<210> SEQ ID NO 97
<211> LENGTH: 23
<212> TYPE: DNA
<213> ORGANISM: Artificial Sequence
<220> FEATURE:
<223> OTHER INFORMATION: Synthetic sequence

<400> SEQUENCE: 97
ccattaacaa actcattaac aag 23

<210> SEQ ID NO 98
<211> LENGTH: 27
<212> TYPE: RNA
<213> ORGANISM: Artificial Sequence
<220> FEATURE:
<223> OTHER INFORMATION: Synthetic sequence

<400> SEQUENCE: 98
guaugccauu aacaaauuca uuaacaa 27

<210> SEQ ID NO 99
<211> LENGTH: 27
<212> TYPE: RNA
<213> ORGANISM: Artificial Sequence
<220> FEATURE:
<223> OTHER INFORMATION: Synthetic sequence

<400> SEQUENCE: 99
guaugccauu aacaaauuca uuaacaa 27

<210> SEQ ID NO 100
<211> LENGTH: 27
<212> TYPE: RNA
<213> ORGANISM: Artificial Sequence
<220> FEATURE:
<223> OTHER INFORMATION: Synthetic sequence

<400> SEQUENCE: 100
guaugccauu aacaaauuca uuaacaa 27

<210> SEQ ID NO 101
<211> LENGTH: 27
<212> TYPE: RNA
<213> ORGANISM: Artificial Sequence
<220> FEATURE:
<223> OTHER INFORMATION: Synthetic sequence

<400> SEQUENCE: 101
guaugccauu aacaaauuca uuaacaa 27

<210> SEQ ID NO 102
<211> LENGTH: 27
<212> TYPE: RNA
<213> ORGANISM: Artificial Sequence
<220> FEATURE:
<223> OTHER INFORMATION: Synthetic sequence

<400> SEQUENCE: 102
guaugccauu aacaaauuca uuaacaa 27

<210> SEQ ID NO 103
<211> LENGTH: 27
<212> TYPE: RNA
<213> ORGANISM: Artificial Sequence
<220> FEATURE:
<223> OTHER INFORMATION: Synthetic sequence

<400> SEQUENCE: 103
guaugcccac aucaaauucc acaucaa 27

<210> SEQ ID NO 104
<211> LENGTH: 27
<212> TYPE: DNA
<213> ORGANISM: Artificial Sequence
<220> FEATURE:
<223> OTHER INFORMATION: Synthetic sequence

<400> SEQUENCE: 104
gtatgccatt aacaaattca ttaacaa 27

<210> SEQ ID NO 105
<211> LENGTH: 52
<212> TYPE: DNA
<213> ORGANISM: Artificial Sequence
<220> FEATURE:
<223> OTHER INFORMATION: Synthetic sequence

<400> SEQUENCE: 105
ggggcccgct gcgtgccatc actcaaccat aacacttgat gccgtttctt tc 52

<210> SEQ ID NO 106
<211> LENGTH: 23
<212> TYPE: DNA
<213> ORGANISM: Artificial Sequence
<220> FEATURE:
<223> OTHER INFORMATION: Synthetic sequence

<400> SEQUENCE: 106
ccatcactca accacaacac ttg 23

<210> SEQ ID NO 107
<211> LENGTH: 23
<212> TYPE: DNA
<213> ORGANISM: Artificial Sequence
<220> FEATURE:
<223> OTHER INFORMATION: Synthetic sequence

<400> SEQUENCE: 107
ccatcactca accataacac ttg 23

<210> SEQ ID NO 108
<211> LENGTH: 23
<212> TYPE: DNA
<213> ORGANISM: Artificial Sequence
<220> FEATURE:
<223> OTHER INFORMATION: Synthetic sequence

<400> SEQUENCE: 108
ccatcaccca accataacac ttg 23

<210> SEQ ID NO 109

<211> LENGTH: 23
<212> TYPE: DNA
<213> ORGANISM: Artificial Sequence
<220> FEATURE:
<223> OTHER INFORMATION: Synthetic sequence

<400> SEQUENCE: 109
ccaccactca accataacac ttg 23

<210> SEQ ID NO 110
<211> LENGTH: 23
<212> TYPE: DNA
<213> ORGANISM: Artificial Sequence
<220> FEATURE:
<223> OTHER INFORMATION: Synthetic sequence

<400> SEQUENCE: 110
ccatcactca accataacac ctg 23

<210> SEQ ID NO 111
<211> LENGTH: 52
<212> TYPE: DNA
<213> ORGANISM: Artificial Sequence
<220> FEATURE:
<223> OTHER INFORMATION: Synthetic sequence

<400> SEQUENCE: 111
tgtctccagt acttgcctca ttctcatcat ccaaactgaa catttgtatc cc 52

<210> SEQ ID NO 112
<211> LENGTH: 23
<212> TYPE: DNA
<213> ORGANISM: Artificial Sequence
<220> FEATURE:
<223> OTHER INFORMATION: Synthetic sequence

<400> SEQUENCE: 112
cctcattctc atcacccaaa ctg 23

<210> SEQ ID NO 113
<211> LENGTH: 23
<212> TYPE: DNA
<213> ORGANISM: Artificial Sequence
<220> FEATURE:
<223> OTHER INFORMATION: Synthetic sequence

<400> SEQUENCE: 113
cctcactctc atcatccaaa ctg 23

<210> SEQ ID NO 114
<211> LENGTH: 23
<212> TYPE: DNA
<213> ORGANISM: Artificial Sequence
<220> FEATURE:
<223> OTHER INFORMATION: Synthetic sequence

<400> SEQUENCE: 114
cctcattctc atcatccaaa ctg 23

<210> SEQ ID NO 115
<211> LENGTH: 23
<212> TYPE: DNA
<213> ORGANISM: Artificial Sequence
<220> FEATURE:
<223> OTHER INFORMATION: Synthetic sequence

<400> SEQUENCE: 115
cctcattctc accatccaaa ctg 23

<210> SEQ ID NO 116
<211> LENGTH: 22
<212> TYPE: DNA
<213> ORGANISM: Artificial Sequence
<220> FEATURE:
<223> OTHER INFORMATION: Synthetic sequence

<400> SEQUENCE: 116
cccattctca tcatccaaac tg 22

<210> SEQ ID NO 117
<211> LENGTH: 53
<212> TYPE: RNA
<213> ORGANISM: Artificial Sequence
<220> FEATURE:
<223> OTHER INFORMATION: Synthetic sequence

<400> SEQUENCE: 117
ugucuccagu acuugccuca uucucaucau ccaaacugaa cauuuguauc cca 53

<210> SEQ ID NO 118
<211> LENGTH: 53
<212> TYPE: RNA
<213> ORGANISM: Artificial Sequence
<220> FEATURE:
<223> OTHER INFORMATION: Synthetic sequence

<400> SEQUENCE: 118
ugucuccagu acuugccuca ggcucagcag gcaaacugaa cauuuguauc cca 53

<210> SEQ ID NO 119
<211> LENGTH: 50
<212> TYPE: DNA
<213> ORGANISM: Artificial Sequence
<220> FEATURE:
<223> OTHER INFORMATION: Synthetic sequence

<400> SEQUENCE: 119
aagaagtgac acaaacctat acttcatatg ctgctttagt cacctgaaga 50

<210> SEQ ID NO 120
<211> LENGTH: 29
<212> TYPE: DNA
<213> ORGANISM: Artificial Sequence
<220> FEATURE:
<223> OTHER INFORMATION: Synthetic sequence

<400> SEQUENCE: 120
acacaaacct atacttcaca tgctgcttt 29

<210> SEQ ID NO 121
<211> LENGTH: 27
<212> TYPE: DNA
<213> ORGANISM: Artificial Sequence
<220> FEATURE:
<223> OTHER INFORMATION: Synthetic sequence

<400> SEQUENCE: 121
acacaaacct atacttcaca tgctgct 27

<210> SEQ ID NO 122
<211> LENGTH: 20
<212> TYPE: DNA

-continued

<213> ORGANISM: Artificial Sequence
<220> FEATURE:
<223> OTHER INFORMATION: Synthetic sequence

<400> SEQUENCE: 122
atacttcaca tgctgcttta 20

<210> SEQ ID NO 123
<211> LENGTH: 29
<212> TYPE: DNA
<213> ORGANISM: Artificial Sequence
<220> FEATURE:
<223> OTHER INFORMATION: Synthetic sequence

<400> SEQUENCE: 123
acacaaacct atacttcata cgctgcttt 29

<210> SEQ ID NO 124
<211> LENGTH: 28
<212> TYPE: DNA
<213> ORGANISM: Artificial Sequence
<220> FEATURE:
<223> OTHER INFORMATION: Synthetic sequence

<400> SEQUENCE: 124
acacaaacct atacttcaca tgctgctt 28

<210> SEQ ID NO 125
<211> LENGTH: 21
<212> TYPE: DNA
<213> ORGANISM: Artificial Sequence
<220> FEATURE:
<223> OTHER INFORMATION: Synthetic sequence

<400> SEQUENCE: 125
atacttcata tgctgcttca g 21

<210> SEQ ID NO 126
<211> LENGTH: 50
<212> TYPE: DNA
<213> ORGANISM: Artificial Sequence
<220> FEATURE:
<223> OTHER INFORMATION: Synthetic sequence

<400> SEQUENCE: 126
tttacccttg actgcccctt ctatgctgct tccaaaagtg atagtgtgtg 50

<210> SEQ ID NO 127
<211> LENGTH: 20
<212> TYPE: DNA
<213> ORGANISM: Artificial Sequence
<220> FEATURE:
<223> OTHER INFORMATION: Synthetic sequence

<400> SEQUENCE: 127
ccccttccat gctgcttcca 20

<210> SEQ ID NO 128
<211> LENGTH: 20
<212> TYPE: DNA
<213> ORGANISM: Artificial Sequence
<220> FEATURE:
<223> OTHER INFORMATION: Synthetic sequence

<400> SEQUENCE: 128
ccccttctac gctgcttcca 20

<210> SEQ ID NO 129
<211> LENGTH: 21
<212> TYPE: DNA
<213> ORGANISM: Artificial Sequence
<220> FEATURE:
<223> OTHER INFORMATION: Synthetic sequence

<400> SEQUENCE: 129
ccccttctac gctgcttcca a 21

<210> SEQ ID NO 130
<211> LENGTH: 23
<212> TYPE: DNA
<213> ORGANISM: Artificial Sequence
<220> FEATURE:
<223> OTHER INFORMATION: Synthetic sequence

<400> SEQUENCE: 130
ccccttctac gctgcttcca aaa 23

<210> SEQ ID NO 131
<211> LENGTH: 23
<212> TYPE: DNA
<213> ORGANISM: Artificial Sequence
<220> FEATURE:
<223> OTHER INFORMATION: Synthetic sequence

<400> SEQUENCE: 131
actgcccctt ctacgctgct tcc 23

<210> SEQ ID NO 132
<211> LENGTH: 27
<212> TYPE: RNA
<213> ORGANISM: Artificial Sequence
<220> FEATURE:
<223> OTHER INFORMATION: Synthetic sequence

<400> SEQUENCE: 132
guaugccauu aacaaauuca uuaacaa 27

<210> SEQ ID NO 133
<211> LENGTH: 27
<212> TYPE: RNA
<213> ORGANISM: Artificial Sequence
<220> FEATURE:
<223> OTHER INFORMATION: Synthetic sequence

<400> SEQUENCE: 133
guaugccauu aacaaauuca uuaacaa 27

<210> SEQ ID NO 134
<211> LENGTH: 27
<212> TYPE: RNA
<213> ORGANISM: Artificial Sequence
<220> FEATURE:
<223> OTHER INFORMATION: Synthetic sequence

<400> SEQUENCE: 134
guaugccauu aacaaauuca uuaacaa 27

<210> SEQ ID NO 135
<211> LENGTH: 27
<212> TYPE: RNA
<213> ORGANISM: Artificial Sequence
<220> FEATURE:

<223> OTHER INFORMATION: Synthetic sequence

<400> SEQUENCE: 135
guaugccauu aacaaauuca uuaacaa 27

<210> SEQ ID NO 136
<211> LENGTH: 27
<212> TYPE: RNA
<213> ORGANISM: Artificial Sequence
<220> FEATURE:
<223> OTHER INFORMATION: Synthetic sequence

<400> SEQUENCE: 136
guaugccauu aacaaauuca uuaacaa 27

<210> SEQ ID NO 137
<211> LENGTH: 27
<212> TYPE: RNA
<213> ORGANISM: Artificial Sequence
<220> FEATURE:
<223> OTHER INFORMATION: Synthetic sequence

<400> SEQUENCE: 137
guaugccauu aacaaauuca uuaacaa 27

<210> SEQ ID NO 138
<211> LENGTH: 27
<212> TYPE: RNA
<213> ORGANISM: Artificial Sequence
<220> FEATURE:
<223> OTHER INFORMATION: Synthetic sequence

<400> SEQUENCE: 138
guaugcccac aucaaauuca uuaacaa 27

<210> SEQ ID NO 139
<211> LENGTH: 27
<212> TYPE: RNA
<213> ORGANISM: Artificial Sequence
<220> FEATURE:
<223> OTHER INFORMATION: Synthetic sequence

<400> SEQUENCE: 139
guaugccauu aacaaauucc acaucaa 27

<210> SEQ ID NO 140
<211> LENGTH: 27
<212> TYPE: RNA
<213> ORGANISM: Artificial Sequence
<220> FEATURE:
<223> OTHER INFORMATION: Synthetic sequence

<400> SEQUENCE: 140
guaugcccac aucaaauucc acaucaa 27

<210> SEQ ID NO 141
<211> LENGTH: 59
<212> TYPE: DNA
<213> ORGANISM: Artificial Sequence
<220> FEATURE:
<223> OTHER INFORMATION: Synthetic sequence

<400> SEQUENCE: 141
ctcagtaaaa cattgccata cattaactct ccatttctgc attaacttca tttgctgga 59

<210> SEQ ID NO 142
<211> LENGTH: 59
<212> TYPE: DNA
<213> ORGANISM: Artificial Sequence
<220> FEATURE:
<223> OTHER INFORMATION: Synthetic sequence

<400> SEQUENCE: 142
ctcagtaaaa cattgccata caggaactct ccaggtctgc aggaacttca tttgctgga 59

<210> SEQ ID NO 143
<211> LENGTH: 59
<212> TYPE: DNA
<213> ORGANISM: Artificial Sequence
<220> FEATURE:
<223> OTHER INFORMATION: Synthetic sequence

<400> SEQUENCE: 143
ctccgtaaaa ccttgcccta ccttaactct ccctttctgc cttaacttcc tttgctgga 59

<210> SEQ ID NO 144
<211> LENGTH: 53
<212> TYPE: DNA
<213> ORGANISM: Artificial Sequence
<220> FEATURE:
<223> OTHER INFORMATION: Synthetic sequence

<400> SEQUENCE: 144
tgtctccagt acttgcctca ttctcatcat ccaaactgaa catttgtatc cca 53

<210> SEQ ID NO 145
<211> LENGTH: 53
<212> TYPE: DNA
<213> ORGANISM: Artificial Sequence
<220> FEATURE:
<223> OTHER INFORMATION: Synthetic sequence

<400> SEQUENCE: 145
tgtctccagt acttgcctca ggctcagcag gcaaactgaa catttgtatc cca 53

<210> SEQ ID NO 146
<211> LENGTH: 53
<212> TYPE: DNA
<213> ORGANISM: Artificial Sequence
<220> FEATURE:
<223> OTHER INFORMATION: Synthetic sequence

<400> SEQUENCE: 146
tgtctccagt acttgcctcc ttctcctcct cccaactgaa catttgtatc cca 53

<210> SEQ ID NO 147
<211> LENGTH: 23
<212> TYPE: DNA
<213> ORGANISM: Artificial Sequence
<220> FEATURE:
<223> OTHER INFORMATION: Synthetic sequence

<400> SEQUENCE: 147
cctcattctc atcatccaaa ctg 23

<210> SEQ ID NO 148
<211> LENGTH: 32
<212> TYPE: DNA
<213> ORGANISM: Artificial Sequence
<220> FEATURE:
<223> OTHER INFORMATION: Synthetic sequence

<400> SEQUENCE: 148
ccatacatta actctccatt tctgcattaa ct 32

<210> SEQ ID NO 149
<211> LENGTH: 78
<212> TYPE: DNA
<213> ORGANISM: Artificial Sequence
<220> FEATURE:
<223> OTHER INFORMATION: Synthetic sequence

<400> SEQUENCE: 149
taatttttaa gaattgagta atggtgtaga acactaattc ataatcactc taattaattg 60
taatctgaat aaagtgta 78

<210> SEQ ID NO 150
<211> LENGTH: 85
<212> TYPE: DNA
<213> ORGANISM: Artificial Sequence
<220> FEATURE:
<223> OTHER INFORMATION: Synthetic sequence

<400> SEQUENCE: 150
ggggcccgct gcgtgccatc actcaaccat aacacttgat gccgtttctt tcaatattta 60
tttccagagt ccggaggcag cagac 85

<210> SEQ ID NO 151
<211> LENGTH: 23
<212> TYPE: DNA
<213> ORGANISM: Artificial Sequence
<220> FEATURE:
<223> OTHER INFORMATION: Synthetic sequence

<400> SEQUENCE: 151
ccatcactca accataacac ttg 23

<210> SEQ ID NO 152
<211> LENGTH: 23
<212> TYPE: DNA
<213> ORGANISM: Artificial Sequence
<220> FEATURE:
<223> OTHER INFORMATION: Synthetic sequence

<400> SEQUENCE: 152
ccatcactca actataacac ttg 23

<210> SEQ ID NO 153
<211> LENGTH: 23
<212> TYPE: DNA
<213> ORGANISM: Artificial Sequence
<220> FEATURE:
<223> OTHER INFORMATION: Synthetic sequence

<400> SEQUENCE: 153
ccatcactca accataatac ttg 23

<210> SEQ ID NO 154
<211> LENGTH: 24
<212> TYPE: DNA
<213> ORGANISM: Artificial Sequence
<220> FEATURE:
<223> OTHER INFORMATION: Synthetic sequence

<400> SEQUENCE: 154
accatcactc aaccataaca cttg 24

<210> SEQ ID NO 155
<211> LENGTH: 29
<212> TYPE: DNA
<213> ORGANISM: Artificial Sequence
<220> FEATURE:
<223> OTHER INFORMATION: Synthetic sequence

<400> SEQUENCE: 155
atgccgtttc tttcaatatt tatttccag 29

<210> SEQ ID NO 156
<211> LENGTH: 22
<212> TYPE: DNA
<213> ORGANISM: Artificial Sequence
<220> FEATURE:
<223> OTHER INFORMATION: Synthetic sequence

<400> SEQUENCE: 156
ccatcactca accatacact tg 22

<210> SEQ ID NO 157
<211> LENGTH: 22
<212> TYPE: DNA
<213> ORGANISM: Artificial Sequence
<220> FEATURE:
<223> OTHER INFORMATION: Synthetic sequence

<400> SEQUENCE: 157
catcactcaa ccataacact tg 22

<210> SEQ ID NO 158
<211> LENGTH: 22
<212> TYPE: DNA
<213> ORGANISM: Artificial Sequence
<220> FEATURE:
<223> OTHER INFORMATION: Synthetic sequence

<400> SEQUENCE: 158
cctcactcaa ccataacact tg 22

<210> SEQ ID NO 159
<211> LENGTH: 24
<212> TYPE: DNA
<213> ORGANISM: Artificial Sequence
<220> FEATURE:
<223> OTHER INFORMATION: Synthetic sequence

<400> SEQUENCE: 159
gccatcactc aaccataaca cttg 24

<210> SEQ ID NO 160
<211> LENGTH: 22
<212> TYPE: DNA
<213> ORGANISM: Artificial Sequence
<220> FEATURE:
<223> OTHER INFORMATION: Synthetic sequence

<400> SEQUENCE: 160
ccatcatcaa ccataacact tg 22

<210> SEQ ID NO 161
<211> LENGTH: 85
<212> TYPE: DNA
<213> ORGANISM: Artificial Sequence
<220> FEATURE:

<223> OTHER INFORMATION: Synthetic sequence

<400> SEQUENCE: 161
ggggcccgct gcgtgccatc actcaaccat aacacttgat gccgtttctt tcaatattta 60
tttccagagt ccggaggcag cagac 85

<210> SEQ ID NO 162
<211> LENGTH: 23
<212> TYPE: DNA
<213> ORGANISM: Artificial Sequence
<220> FEATURE:
<223> OTHER INFORMATION: Synthetic sequence

<400> SEQUENCE: 162
ccatcactca accacaacac ttg 23

<210> SEQ ID NO 163
<211> LENGTH: 23
<212> TYPE: DNA
<213> ORGANISM: Artificial Sequence
<220> FEATURE:
<223> OTHER INFORMATION: Synthetic sequence

<400> SEQUENCE: 163
ccatcactca accataacac ttg 23

<210> SEQ ID NO 164
<211> LENGTH: 23
<212> TYPE: DNA
<213> ORGANISM: Artificial Sequence
<220> FEATURE:
<223> OTHER INFORMATION: Synthetic sequence

<400> SEQUENCE: 164
ccatcaccca accataacac ttg 23

<210> SEQ ID NO 165
<211> LENGTH: 23
<212> TYPE: DNA
<213> ORGANISM: Artificial Sequence
<220> FEATURE:
<223> OTHER INFORMATION: Synthetic sequence

<400> SEQUENCE: 165
ccaccactca accataacac ttg 23

<210> SEQ ID NO 166
<211> LENGTH: 23
<212> TYPE: DNA
<213> ORGANISM: Artificial Sequence
<220> FEATURE:
<223> OTHER INFORMATION: Synthetic sequence

<400> SEQUENCE: 166
ccatcactca accataacac ctg 23

<210> SEQ ID NO 167
<211> LENGTH: 23
<212> TYPE: DNA
<213> ORGANISM: Artificial Sequence
<220> FEATURE:
<223> OTHER INFORMATION: Synthetic sequence

<400> SEQUENCE: 167
ccatcactca accataacac tcg 23

<210> SEQ ID NO 168
<211> LENGTH: 23
<212> TYPE: DNA
<213> ORGANISM: Artificial Sequence
<220> FEATURE:
<223> OTHER INFORMATION: Synthetic sequence

<400> SEQUENCE: 168
tttctttcaa tatttatttc cag 23

<210> SEQ ID NO 169
<211> LENGTH: 23
<212> TYPE: DNA
<213> ORGANISM: Artificial Sequence
<220> FEATURE:
<223> OTHER INFORMATION: Synthetic sequence

<400> SEQUENCE: 169
tttctttcaa tatttattcc cag 23

<210> SEQ ID NO 170
<211> LENGTH: 22
<212> TYPE: DNA
<213> ORGANISM: Artificial Sequence
<220> FEATURE:
<223> OTHER INFORMATION: Synthetic sequence

<400> SEQUENCE: 170
ccatcaccaa ccataacact tg 22

<210> SEQ ID NO 171
<211> LENGTH: 22
<212> TYPE: DNA
<213> ORGANISM: Artificial Sequence
<220> FEATURE:
<223> OTHER INFORMATION: Synthetic sequence

<400> SEQUENCE: 171
catcactcaa ccacaacact tg 22

<210> SEQ ID NO 172
<211> LENGTH: 20
<212> TYPE: DNA
<213> ORGANISM: Artificial Sequence
<220> FEATURE:
<223> OTHER INFORMATION: Synthetic sequence

<400> SEQUENCE: 172
ccatcactca accacaacac 20

<210> SEQ ID NO 173
<211> LENGTH: 85
<212> TYPE: DNA
<213> ORGANISM: Artificial Sequence
<220> FEATURE:
<223> OTHER INFORMATION: Synthetic sequence

<400> SEQUENCE: 173
ggggcccgct gcgtgccatc actcaaccat aacacttgat gccgtttctt tcaatattta 60
tttccagagt ccggaggcag cagac 85

<210> SEQ ID NO 174
<211> LENGTH: 23
<212> TYPE: DNA

<213> ORGANISM: Artificial Sequence
<220> FEATURE:
<223> OTHER INFORMATION: Synthetic sequence

<400> SEQUENCE: 174
ccatcactca accataacac ttg 23

<210> SEQ ID NO 175
<211> LENGTH: 26
<212> TYPE: DNA
<213> ORGANISM: Artificial Sequence
<220> FEATURE:
<223> OTHER INFORMATION: Synthetic sequence

<400> SEQUENCE: 175
ctgccatcac tcaaccataa cacttg 26

<210> SEQ ID NO 176
<211> LENGTH: 20
<212> TYPE: DNA
<213> ORGANISM: Artificial Sequence
<220> FEATURE:
<223> OTHER INFORMATION: Synthetic sequence

<400> SEQUENCE: 176
ccatcactca accataacac 20

<210> SEQ ID NO 177
<211> LENGTH: 23
<212> TYPE: DNA
<213> ORGANISM: Artificial Sequence
<220> FEATURE:
<223> OTHER INFORMATION: Synthetic sequence

<400> SEQUENCE: 177
tttctttcaa tatttatttc cag 23

<210> SEQ ID NO 178
<211> LENGTH: 50
<212> TYPE: DNA
<213> ORGANISM: Artificial Sequence
<220> FEATURE:
<223> OTHER INFORMATION: Synthetic sequence

<400> SEQUENCE: 178
tttacccttg actgcccctt ctatgctgct tccaaaagtg atagtgtgtg 50

<210> SEQ ID NO 179
<211> LENGTH: 20
<212> TYPE: DNA
<213> ORGANISM: Artificial Sequence
<220> FEATURE:
<223> OTHER INFORMATION: Synthetic sequence

<400> SEQUENCE: 179
ccccttccat gctgcttcca 20

<210> SEQ ID NO 180
<211> LENGTH: 20
<212> TYPE: DNA
<213> ORGANISM: Artificial Sequence
<220> FEATURE:
<223> OTHER INFORMATION: Synthetic sequence

<400> SEQUENCE: 180
ccccttctac gctgcttcca 20

<210> SEQ ID NO 181
<211> LENGTH: 21
<212> TYPE: DNA
<213> ORGANISM: Artificial Sequence
<220> FEATURE:
<223> OTHER INFORMATION: Synthetic sequence

<400> SEQUENCE: 181
ccccttctac gctgcttcca a 21

<210> SEQ ID NO 182
<211> LENGTH: 23
<212> TYPE: DNA
<213> ORGANISM: Artificial Sequence
<220> FEATURE:
<223> OTHER INFORMATION: Synthetic sequence

<400> SEQUENCE: 182
ccccttctac gctgcttcca aaa 23

<210> SEQ ID NO 183
<211> LENGTH: 23
<212> TYPE: DNA
<213> ORGANISM: Artificial Sequence
<220> FEATURE:
<223> OTHER INFORMATION: Synthetic sequence

<400> SEQUENCE: 183
actgcccctt ctacgctgct tcc 23

<210> SEQ ID NO 184
<211> LENGTH: 50
<212> TYPE: DNA
<213> ORGANISM: Artificial Sequence
<220> FEATURE:
<223> OTHER INFORMATION: Synthetic sequence

<400> SEQUENCE: 184
tttacccttg actgcccctt ctatgctgct tccaaaagtg atagtgtgtg 50

<210> SEQ ID NO 185
<211> LENGTH: 24
<212> TYPE: DNA
<213> ORGANISM: Artificial Sequence
<220> FEATURE:
<223> OTHER INFORMATION: Synthetic sequence

<400> SEQUENCE: 185
ccccttctat gctgcttcca aaag 24

<210> SEQ ID NO 186
<211> LENGTH: 20
<212> TYPE: DNA
<213> ORGANISM: Artificial Sequence
<220> FEATURE:
<223> OTHER INFORMATION: Synthetic sequence

<400> SEQUENCE: 186
ccccttctac gctgcttcca 20

<210> SEQ ID NO 187
<211> LENGTH: 22
<212> TYPE: DNA
<213> ORGANISM: Artificial Sequence
<220> FEATURE:

<223> OTHER INFORMATION: Synthetic sequence

<400> SEQUENCE: 187
ccccttccat gctgcttcca aa 22

<210> SEQ ID NO 188
<211> LENGTH: 50
<212> TYPE: DNA
<213> ORGANISM: Artificial Sequence
<220> FEATURE:
<223> OTHER INFORMATION: Synthetic sequence

<400> SEQUENCE: 188
ttggaagcgt ttgtggccaa attcatggca ctttataaga agttcatgga 50

<210> SEQ ID NO 189
<211> LENGTH: 21
<212> TYPE: DNA
<213> ORGANISM: Artificial Sequence
<220> FEATURE:
<223> OTHER INFORMATION: Synthetic sequence

<400> SEQUENCE: 189
ccaaattcac ggcactttat a 21

<210> SEQ ID NO 190
<211> LENGTH: 22
<212> TYPE: DNA
<213> ORGANISM: Artificial Sequence
<220> FEATURE:
<223> OTHER INFORMATION: Synthetic sequence

<400> SEQUENCE: 190
ccaaattcat ggcactttac aa 22

<210> SEQ ID NO 191
<211> LENGTH: 21
<212> TYPE: DNA
<213> ORGANISM: Artificial Sequence
<220> FEATURE:
<223> OTHER INFORMATION: Synthetic sequence

<400> SEQUENCE: 191
ccaaatccat ggcactttat a 21

<210> SEQ ID NO 192
<211> LENGTH: 20
<212> TYPE: DNA
<213> ORGANISM: Artificial Sequence
<220> FEATURE:
<223> OTHER INFORMATION: Synthetic sequence

<400> SEQUENCE: 192
ccaaatccat ggcactttat 20

<210> SEQ ID NO 193
<211> LENGTH: 21
<212> TYPE: DNA
<213> ORGANISM: Artificial Sequence
<220> FEATURE:
<223> OTHER INFORMATION: Synthetic sequence

<400> SEQUENCE: 193
ccaaattcat ggcactttat a 21

<210> SEQ ID NO 194
<211> LENGTH: 24
<212> TYPE: DNA
<213> ORGANISM: Artificial Sequence
<220> FEATURE:
<223> OTHER INFORMATION: Synthetic sequence

<400> SEQUENCE: 194
ccaaattcat ggcactttat aata 24

<210> SEQ ID NO 195
<211> LENGTH: 50
<212> TYPE: DNA
<213> ORGANISM: Artificial Sequence
<220> FEATURE:
<223> OTHER INFORMATION: Synthetic sequence

<400> SEQUENCE: 195
ttggaagcgt ttgtggccaa attcatggca ctttataaga agttcatgga 50

<210> SEQ ID NO 196
<211> LENGTH: 20
<212> TYPE: DNA
<213> ORGANISM: Artificial Sequence
<220> FEATURE:
<223> OTHER INFORMATION: Synthetic sequence

<400> SEQUENCE: 196
ccaaatccat ggcactttat 20

<210> SEQ ID NO 197
<211> LENGTH: 23
<212> TYPE: DNA
<213> ORGANISM: Artificial Sequence
<220> FEATURE:
<223> OTHER INFORMATION: Synthetic sequence

<400> SEQUENCE: 197
ccaaattcat ggcactttat aag 23

<210> SEQ ID NO 198
<211> LENGTH: 23
<212> TYPE: DNA
<213> ORGANISM: Artificial Sequence
<220> FEATURE:
<223> OTHER INFORMATION: Synthetic sequence

<400> SEQUENCE: 198
ccaaattcat ggcactttac aag 23

<210> SEQ ID NO 199
<211> LENGTH: 49
<212> TYPE: DNA
<213> ORGANISM: Artificial Sequence
<220> FEATURE:
<223> OTHER INFORMATION: Synthetic sequence

<400> SEQUENCE: 199
tagcgtaggc taccgccaca ttgattgtgc tgctatctac ggcaatgag 49

<210> SEQ ID NO 200
<211> LENGTH: 26
<212> TYPE: DNA
<213> ORGANISM: Artificial Sequence
<220> FEATURE:
<223> OTHER INFORMATION: Synthetic sequence

<400> SEQUENCE: 200
ccacattgat cgtgctgcta tctacg 26

<210> SEQ ID NO 201
<211> LENGTH: 25
<212> TYPE: DNA
<213> ORGANISM: Artificial Sequence
<220> FEATURE:
<223> OTHER INFORMATION: Synthetic sequence

<400> SEQUENCE: 201
ccacattgat cgtgctgcta tctac 25

<210> SEQ ID NO 202
<211> LENGTH: 22
<212> TYPE: DNA
<213> ORGANISM: Artificial Sequence
<220> FEATURE:
<223> OTHER INFORMATION: Synthetic sequence

<400> SEQUENCE: 202
ccacattgat cgtgctgcta tc 22

<210> SEQ ID NO 203
<211> LENGTH: 23
<212> TYPE: DNA
<213> ORGANISM: Artificial Sequence
<220> FEATURE:
<223> OTHER INFORMATION: Synthetic sequence

<400> SEQUENCE: 203
ccacattgat cgtgctgcta tct 23

<210> SEQ ID NO 204
<211> LENGTH: 24
<212> TYPE: DNA
<213> ORGANISM: Artificial Sequence
<220> FEATURE:
<223> OTHER INFORMATION: Synthetic sequence

<400> SEQUENCE: 204
ccacattgat cgtgctgcta tcta 24

<210> SEQ ID NO 205
<211> LENGTH: 49
<212> TYPE: DNA
<213> ORGANISM: Artificial Sequence
<220> FEATURE:
<223> OTHER INFORMATION: Synthetic sequence

<400> SEQUENCE: 205
tagcgtaggc taccgccaca ttgattgtgc tgctatctac ggcaatgag 49

<210> SEQ ID NO 206
<211> LENGTH: 24
<212> TYPE: DNA
<213> ORGANISM: Artificial Sequence
<220> FEATURE:
<223> OTHER INFORMATION: Synthetic sequence

<400> SEQUENCE: 206
ccacattgac tgtgctgcta tcta 24

<210> SEQ ID NO 207
<211> LENGTH: 21

-continued

```
<212> TYPE: DNA
<213> ORGANISM: Artificial Sequence
<220> FEATURE:
<223> OTHER INFORMATION: Synthetic sequence

<400> SEQUENCE: 207

ccacattgat cgtgctgcta t                                            21


<210> SEQ ID NO 208
<211> LENGTH: 26
<212> TYPE: DNA
<213> ORGANISM: Artificial Sequence
<220> FEATURE:
<223> OTHER INFORMATION: Synthetic sequence

<400> SEQUENCE: 208

ccacattgac tgtgctgcta tctacg                                       26
```

METHODS FOR IDENTIFYING RNA SEGMENTS BOUND BY RNA-BINDING PROTEINS OR RIBONUCLEOPROTEIN COMPLEXES

This application asserts priority of U.S. Provisional Application Ser. No. 61/137,265 filed on Jul. 28, 2008. The specification of U.S. Provisional Application Ser. No. 61/137,265 is hereby incorporated by reference in its entirety.

BACKGROUND OF THE INVENTION

Understanding global gene expression at the level of the whole cell requires detailed knowledge of the contributions of transcription, pre-mRNA processing, mRNA turnover, and translation. Although the sum total of these regulatory processes in each cell accounts for its unique expression profile, few methods are available to independently assess each process en masse. DNA arrays are well suited for profiling the steady-state levels of mRNA globally (i.e., the transcriptome). However, because of posttranscriptional events affecting mRNA stability and translation, the expression levels of many cellular proteins do not directly correlate with steady-state levels of mRNAs.

RNA binding proteins (RBPs) and ribonucleoprotein complexes (RNPs), such as microRNA-containing RNPs, are essential regulators of virtually all cellular activities, ranging from development, metabolism and migration to reaction to cellular stress. These proteins do so by binding to coding and non-coding RNAs at specific regions on an RNA transcript. The proteins regulate the rate of transcription, modification, splicing, nuclear export, transport, stability and translation. RNA binding proteins and RNPs recognize canonical binding motifs on a given transcript and cooperate and compete with other RBPs and RNPs in controlling its fate or metabolic rate.

A number of diseases are associated with, or caused by, deregulation or mutations in these proteins. Notable examples among autoimmune disease include systemic lupus erythematosis, primary biliary cirrhosis (PBC) and Sjogren's syndrome, and among neurologic disease include the paraneoplastic neurologic antigens Nova and Hu, and the Fragile X mental retardation FMR1 protein, the spinal muscular atrophy SMN protein, the myotonic dystrophy CELF proteins, and the spinocerebellar ataxia SCA1 protein.

Understanding the role RBPs and RNPs play in disease and normal biology, particularly in the brain, requires methods to identify the set of RNAs to which the RBPs and RNPs bind in vivo. Identifying binding motifs on the RNAs offer ways for targeted therapy. However, the targets of RBPs and RNPs involved in normal and abhorrent cellular processes and systems, including disease states such as autoimmune and genetic diseases have been difficult to identify.

Accordingly, the present invention provides methods for identifying binding sites on RNA transcripts that interact with RBPs and RNPs.

BRIEF DESCRIPTION OF DRAWINGS

The patent or application file contains at least one drawing executed in color. Copies of this patent or patent application publication with color drawing(s) will be provided by the Office upon request and payment of the necessary fee.

In the left panels a ratio of 1 indicates no bias for a specific nucleotide, a ratio larger than 1 indicates a nucleotide that is preferentially mutated. In the right panels, white indicates relatively high mutation frequency towards a particular nucleotide. In general, transitions are more frequent than other mutations. The experimental conditions were: 254 nm CLIP—generates mutations preferably on Gs, probably due to depurination (left panel). G nucleotides are targeted for mutation approximately twice as often as the other nucleotides. The reverse transcriptase preferentially incorporates A instead of the G nucleotide (shown by the matrix in the right panel). Treatment of cells with 6SG (middle two panels) results in a marked preference for mutations at G, about one order of magnitude compared to the other nucleotides. Interestingly RT/PCR reaction on crosslinked RNA results in a preferred incorporation of an A instead of the G. This preference is more pronounced relative to that observed in the 254 nm crosslinked sample. 4SU treatment of cells and subsequent UV crosslinking results in an about 30-fold increased mutation preference for thymidines. After RT/PCR these positions are almost always sequenced as cytidines. B same analysis as in a for the five individual proteins described in this study, IGF2BP1-3, C Quaking, and Pumilio 2. The mutational biases for these proteins are comparable. T is almost exclusively targeted for mutation, and is preferentially sequenced as C. D The increase in T to C transitions after 4SU-protein crosslinking can be rationalized by structural changes in donor/acceptor properties of 4SU after crosslinking to proximal amino acid side chains and subsequent incorporation of the nucleotides in the reverse transcription; R representing a side chain.

Figure 11A:
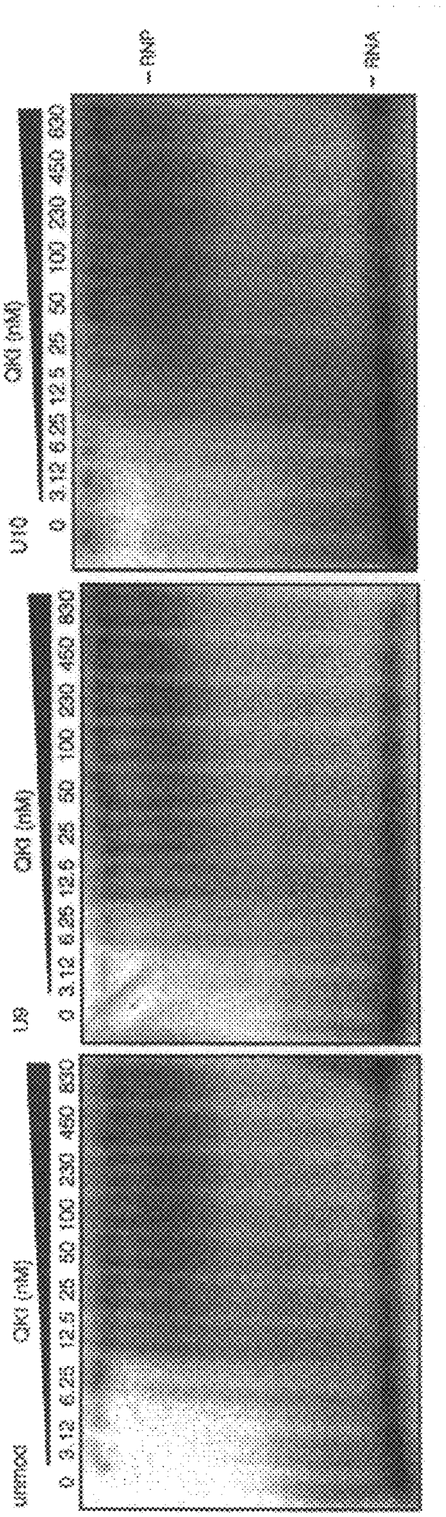
Figure 11B:
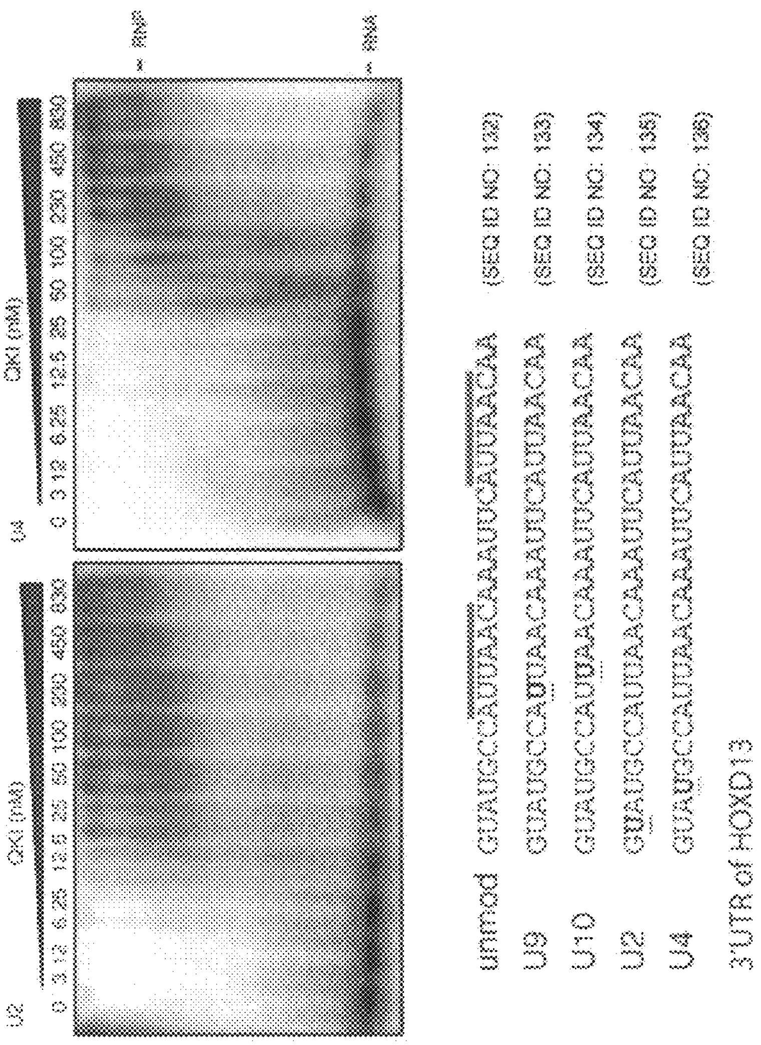

FIG. 11: Electrophoretic mobility shift assay (EMSA) to analyze binding of recombinant QKI to synthetic oligoribonucleotides with a sequence derived from a cluster identified by QKI PURE-CLIP. A-B Incorporation of 4SU into different positions (bold and underlined) of the oligoribonucleotides does not have a significant effect on the affinity of QKI to the RNA. C Mutation of either one of the QKI binding sites (marked with red bars in the RNA-sequence) results in decreased affinity of QKI to the RNA. Mutation of both binding sites leads to complete loss of affinity of QKI to the RNA.

Figure 12A:
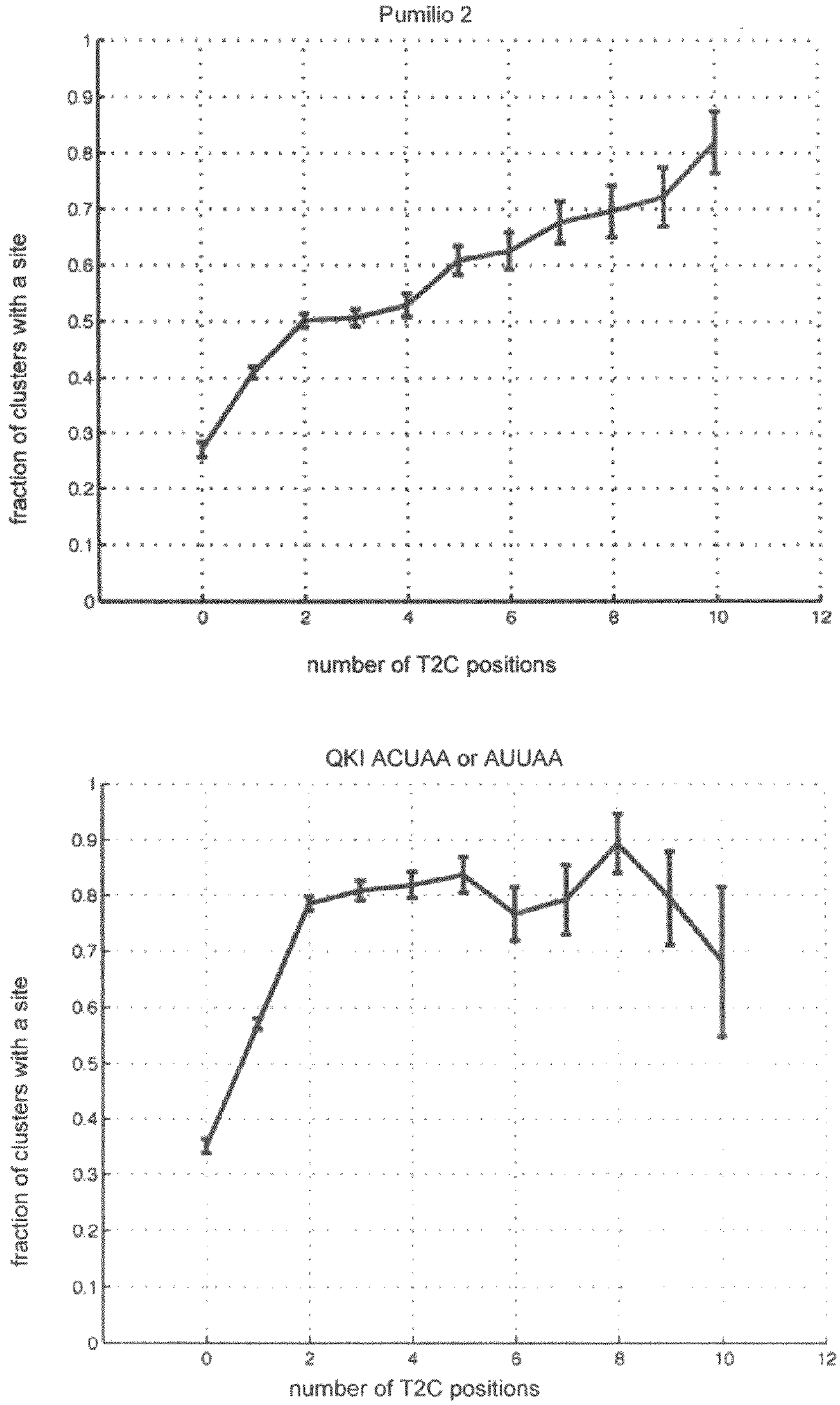
Figure 12B:
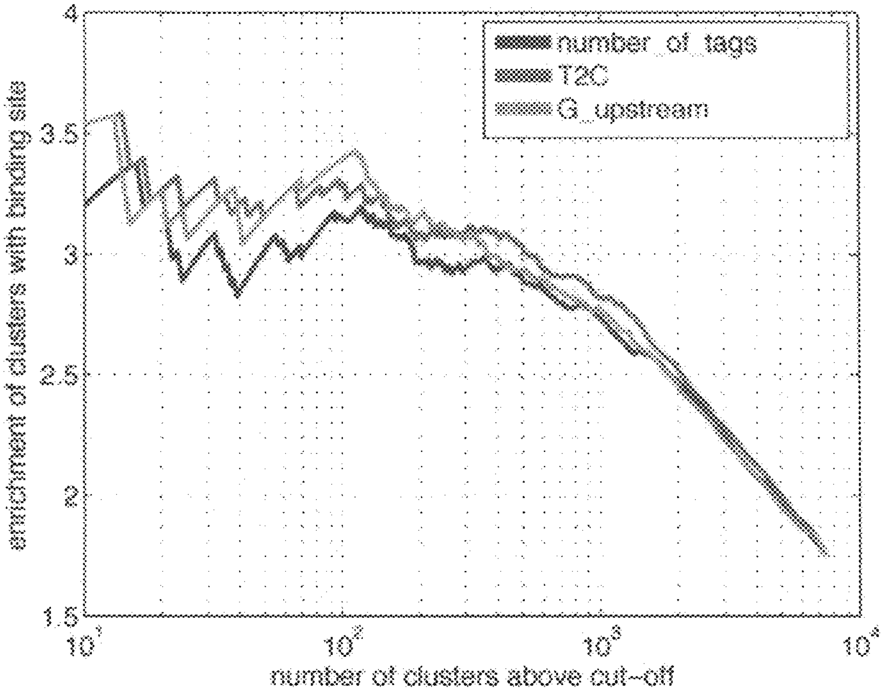
Figure 12C:
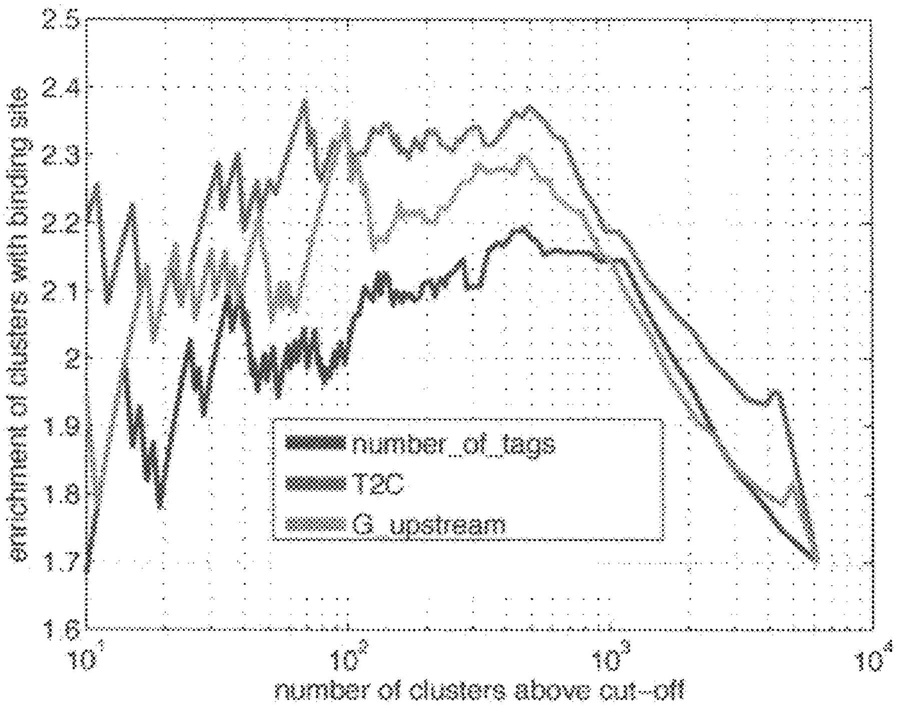

FIG. 12: Presence of the PUM2 and QKI recognition sequences in clusters generated by PURE-CLIP from cell lines stably overexpressing the respective protein. A Fraction of clusters with the recognition element for PUM2 (left panel) and QKI (right panel) versus the number of distinct crosslinking sites within a cluster indicated by a T to C change. The fraction of sites containing the recognition motif rises with the number of crosslinking sites. Enrichment of clusters containing the PUM2-recognition motif B and QKI recognition motifs C versus the total number of clusters above a given cut-off on a particular property as indicated in the figure (G_upstream: number of sequence reads with a G at position-1; T2C: number of sequence reads with a T to C mutation; number_of_tags: total number of sequence reads in the cluster). For each cut-off on a given property, an enrichment of binding sites was calculated, which is defined as the fraction of clusters with at least one binding site above the given cut-off divided by the fraction of clusters with no T to C mutation that have at least one binding site. Cut-off increases from right to left. The best signal can be obtained by sorting according to the frequency of crosslinking events. The enrichment is higher for Pumilio because the consensus motif is longer and thus appears less frequently in the background set.

Figure 13A:
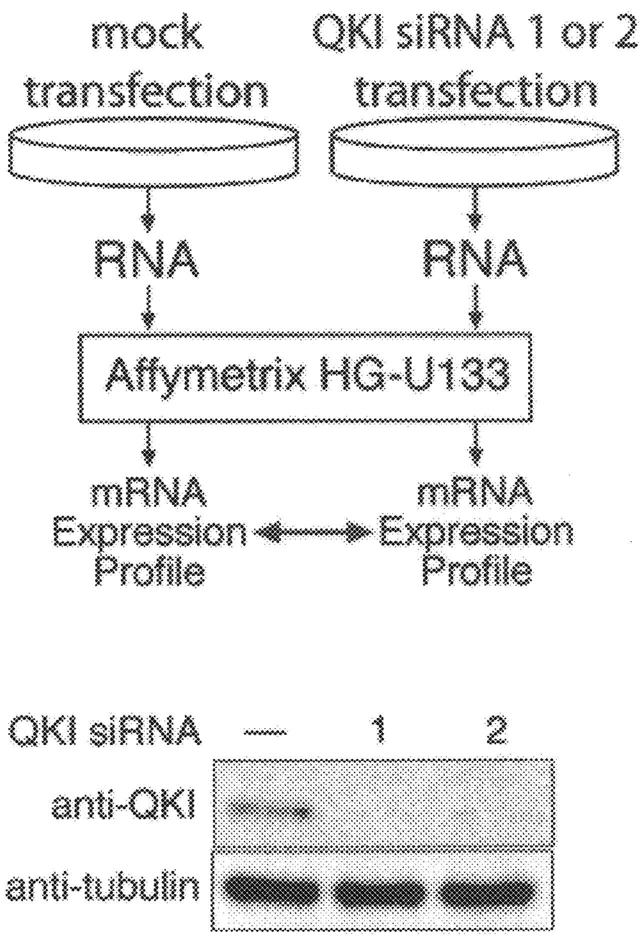
Figure 14A:
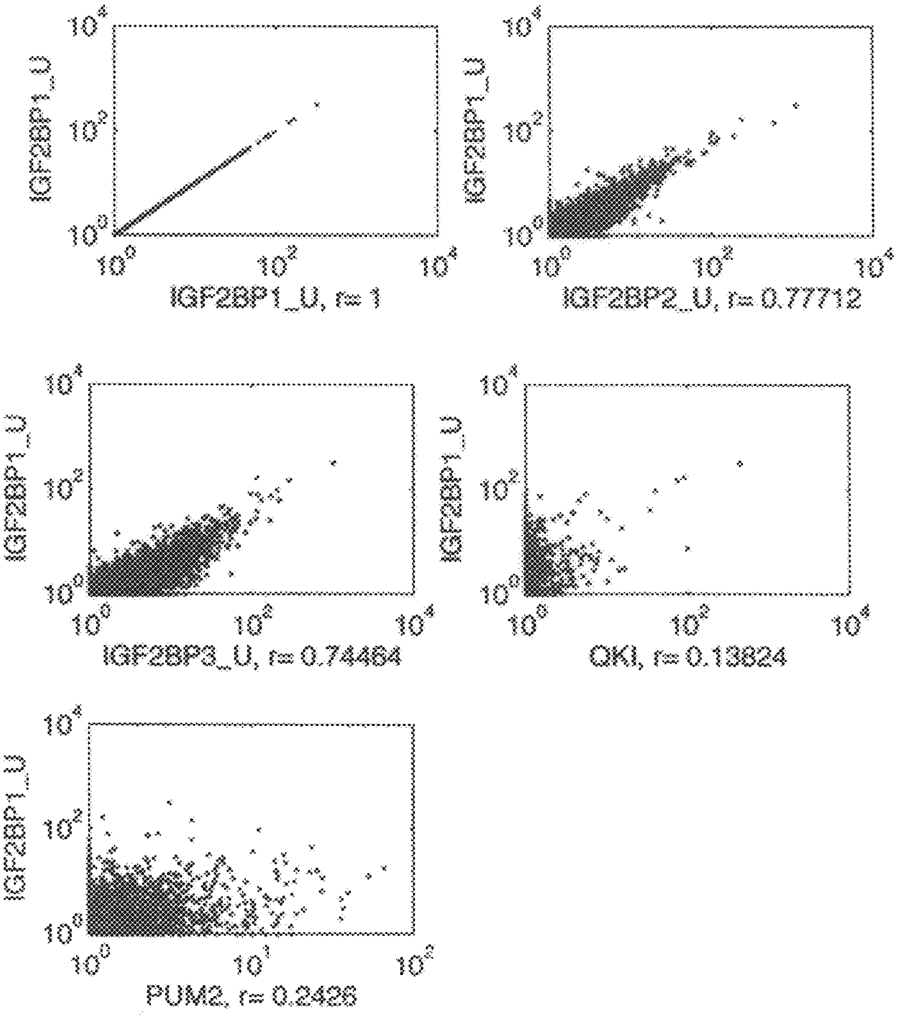
Figure 14B:
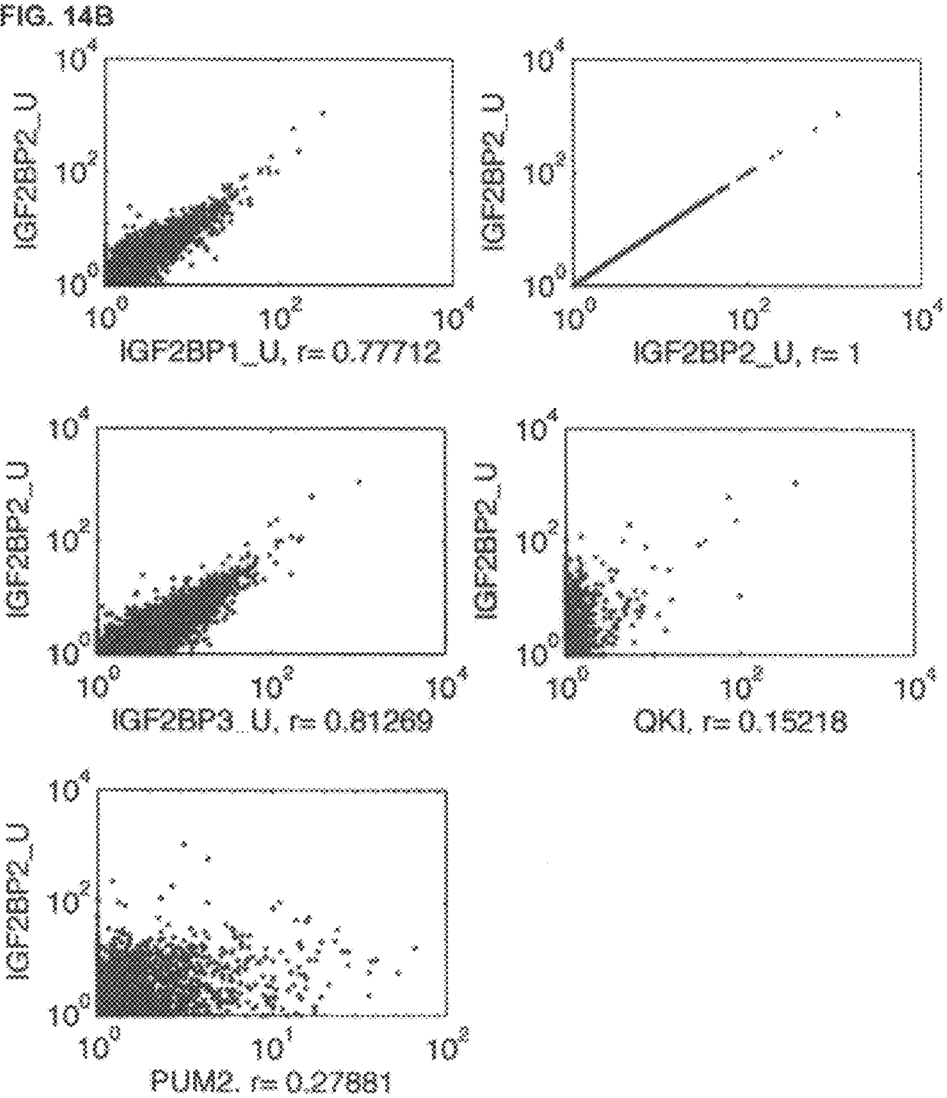
Figure 14:
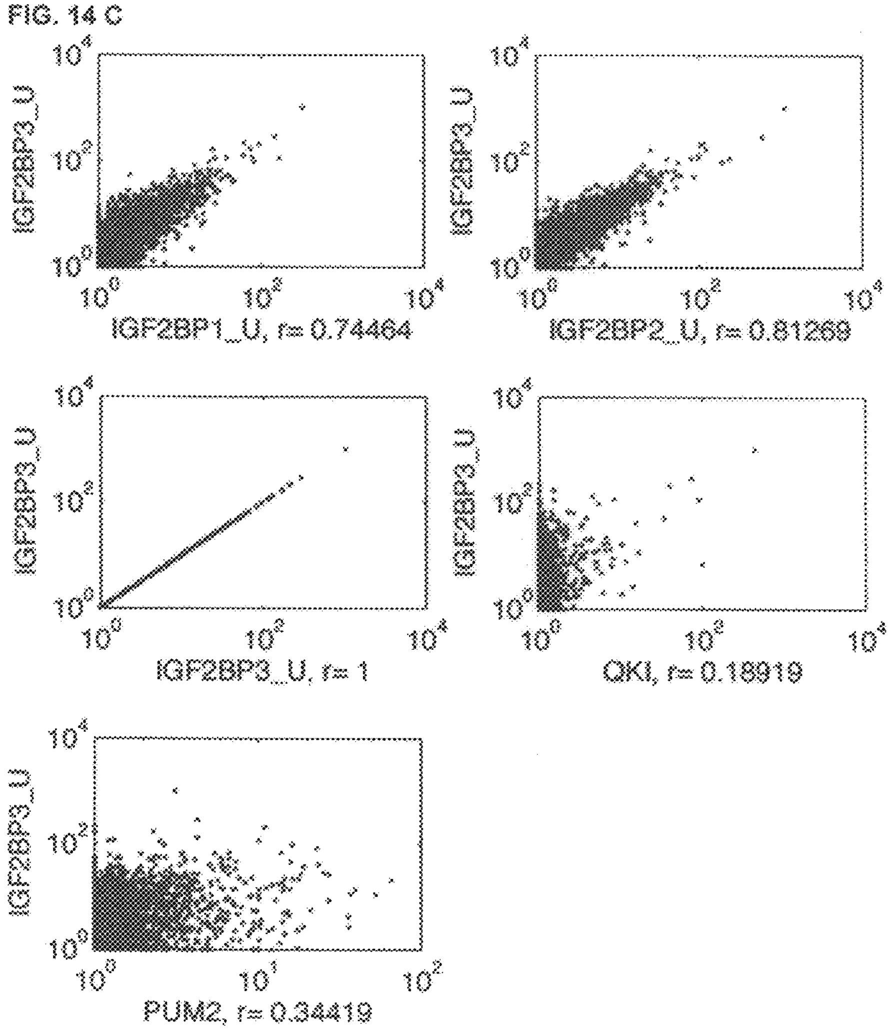
Figure 14D:
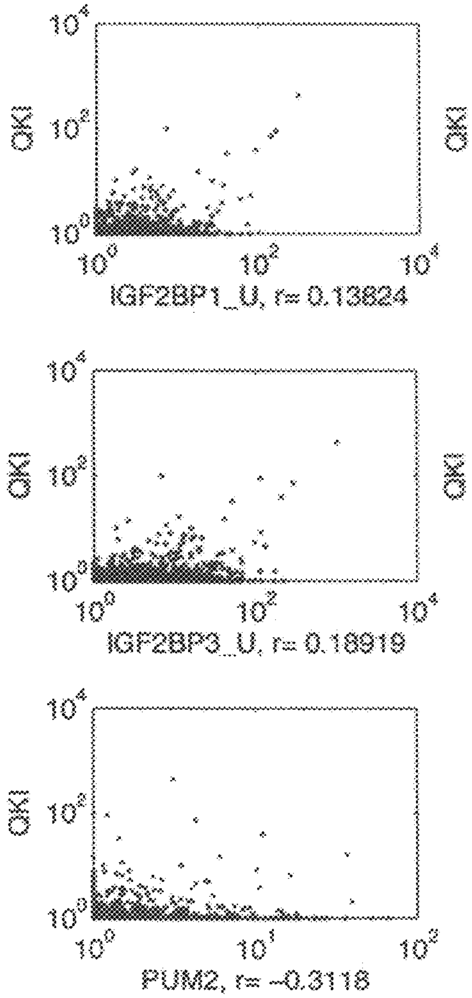
Figure 14E:
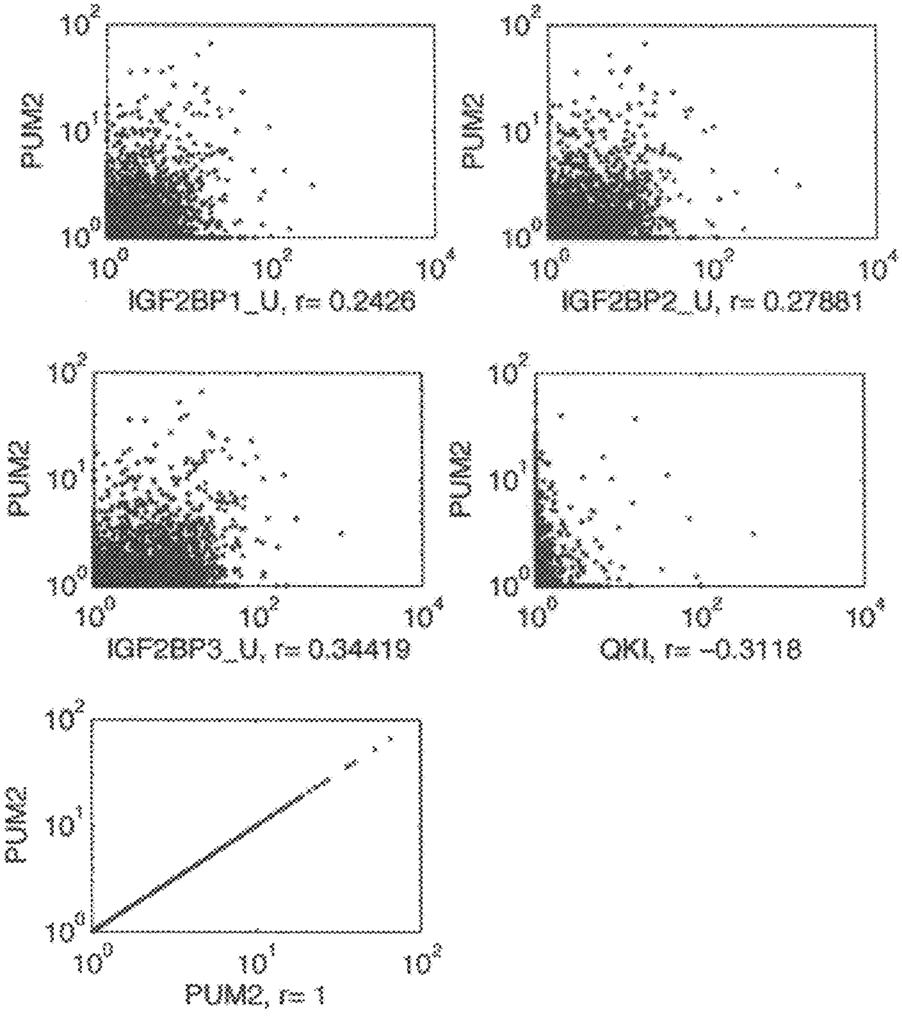
Figure 15A:
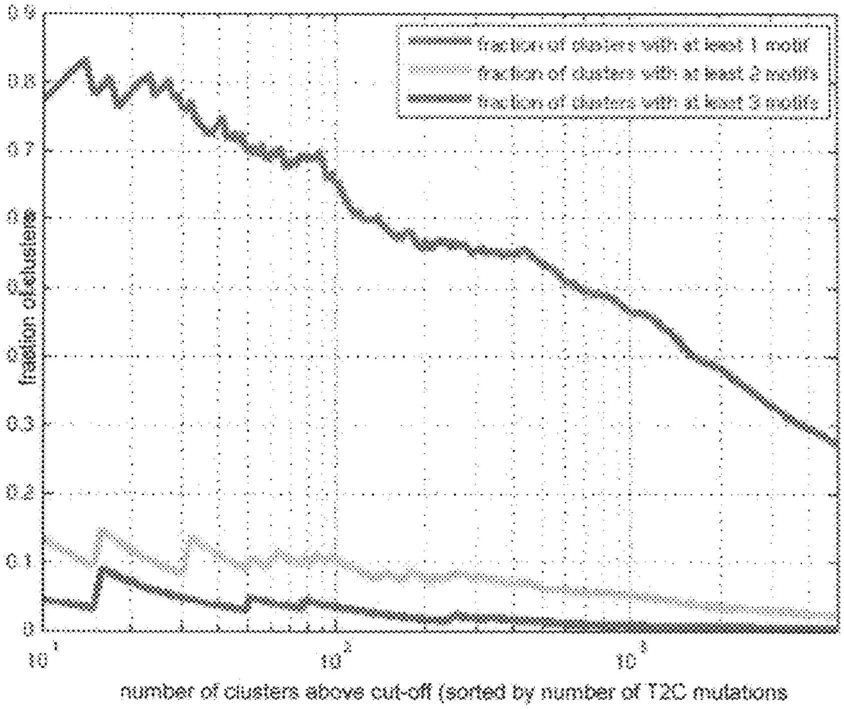
Figure 15B:
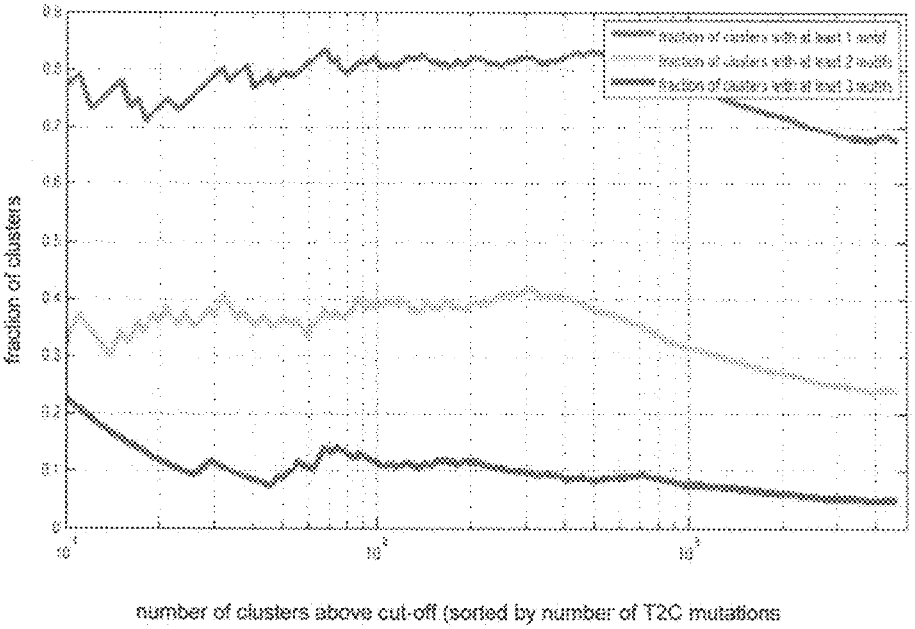
Figure 15D:
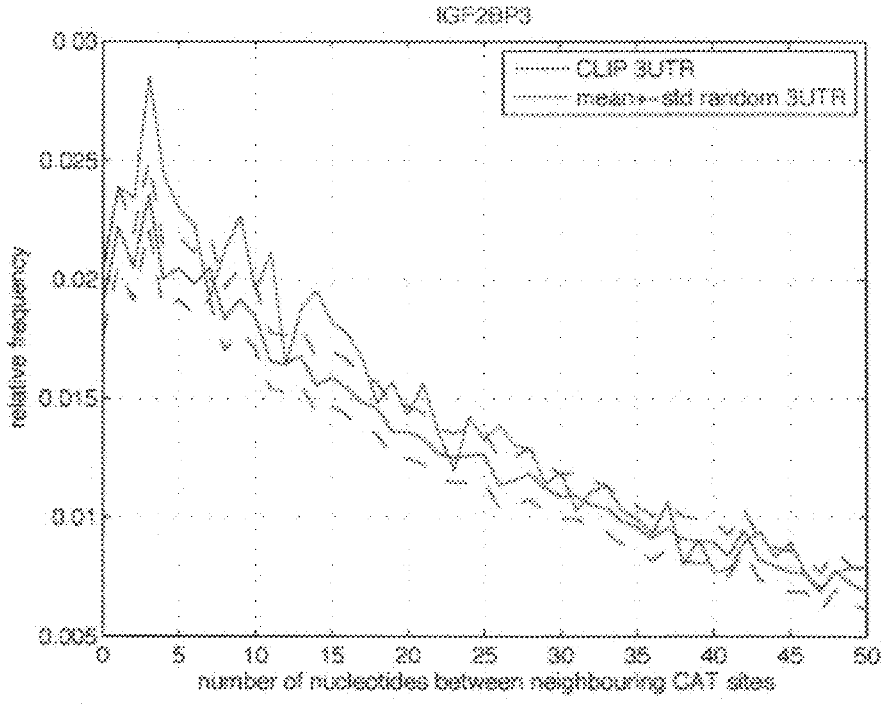

FIG. 13: QKI reduces the abundance of target transcripts identified by PURE-CLIP. A Experimental setup: mRNA expression level of mock-transfected cells and cells transfected with QKI siRNA 1 and siRNA 2 (for sequences, see Methods section) was recorded with Affymetrix Human Genome U133 Plus2.0 microarrays. B The effect of QKI knockdown on transcript stability on transcripts not bound (black lines) by QKI or bound by QKI (red lines), as determined by PURE-CLIP, was compared after subtraction of possible off-target effects caused by guide and passenger strands of either siRNA. Shown are the cumulative distribution function (top panel) and the probability density function (bottom panel) of expression changes of transcripts bound and not bound by QKI.

FIG. 14A-E: Correlation plot comparing the number of sequence reads per gene normalized by the expression of the corresponding genes as determined by DGEX for each RBP from PURE-CLIP from HEK293-cells expressing tagged IGF2BP1, -2, -3, Quaking, and Pumilio 2. Only genes with at least 10 DGEX tags are shown. Normalization is necessary to remove the background correlation due to the correlation of expression levels in the different experiments. Sequence clusters obtained from IGF2BP1-3 show a high correlation coefficient (~0.75), indicating that they have very similar binding specificity. PUM2 and QKI have different specificities as indicated by the lower correlation coefficients.

FIG. 15A-D: Clustering of IGF2BP1-3 binding sites. The most frequent distance between two consecutive CAT sites is 3 nts and pairs of CAT sites within a distance of 3-6 nts are significantly enriched in PURE-CLIPped clusters compared to what would be expected by chance.

Figure 16A:
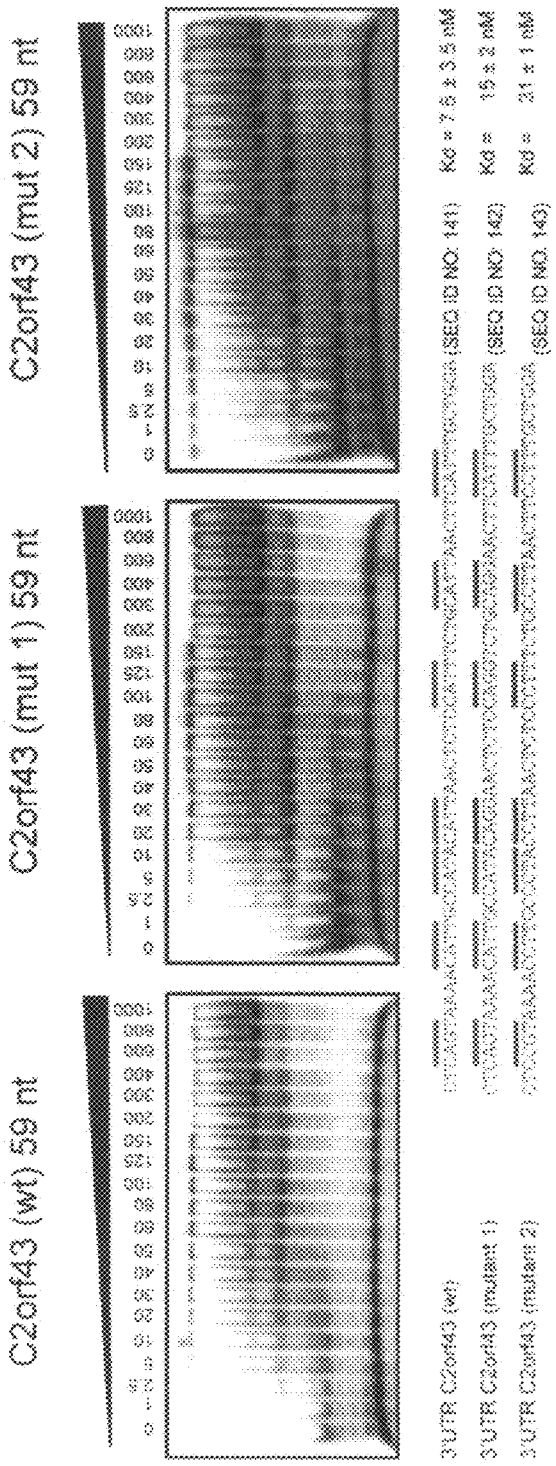
Figure 16B:
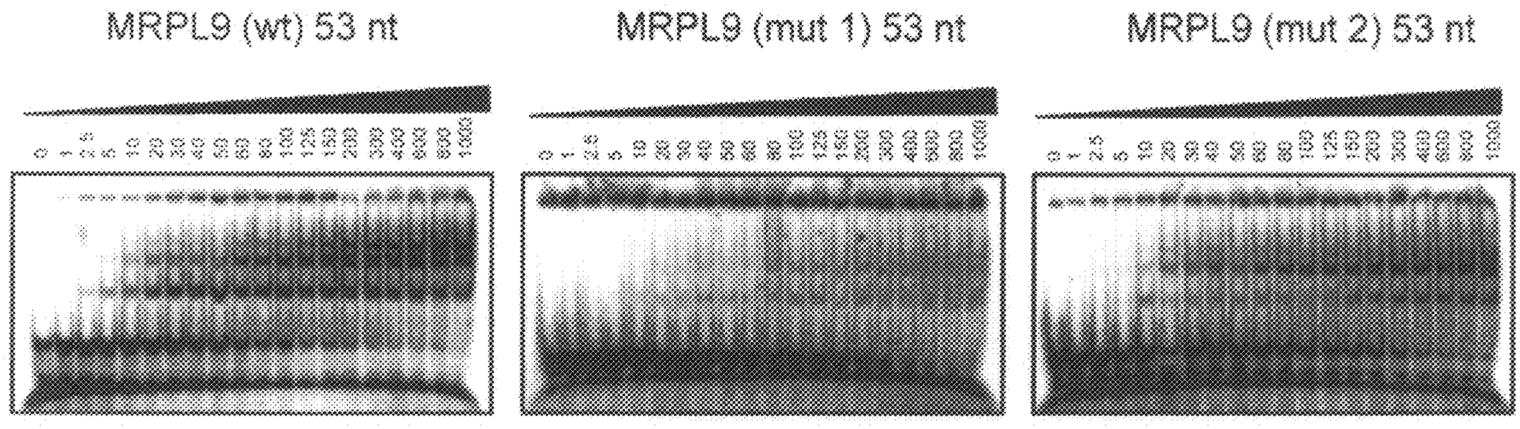
Figure 16C:
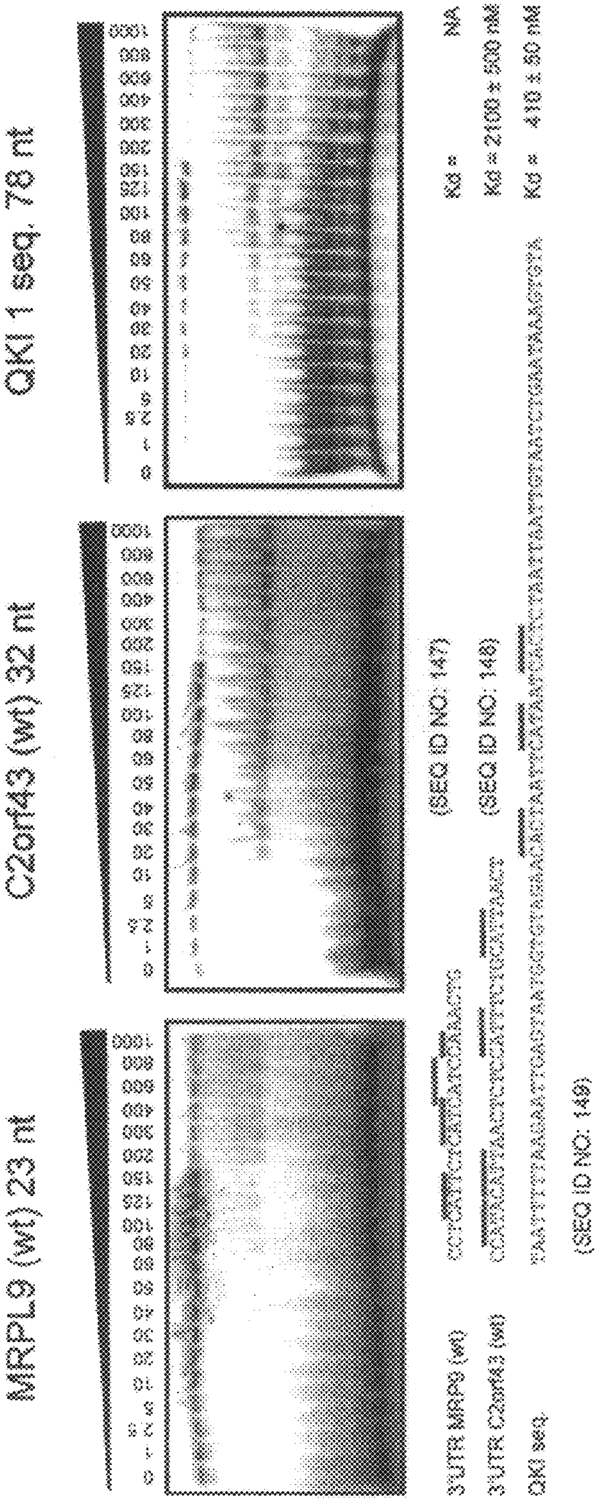
Figure 17A:
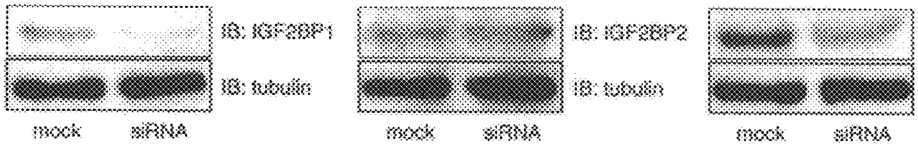
Figure 17B:
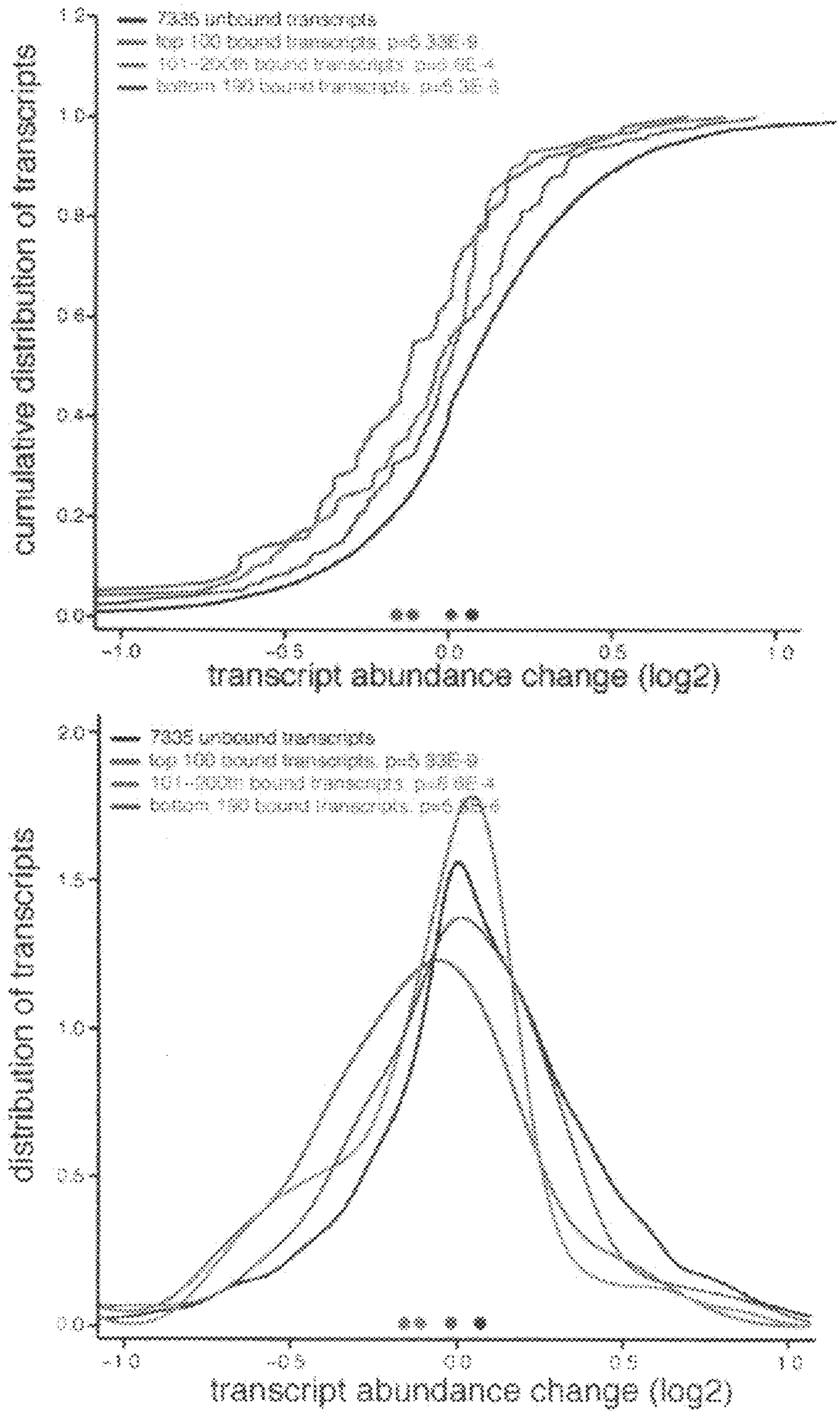
Figure 17C:
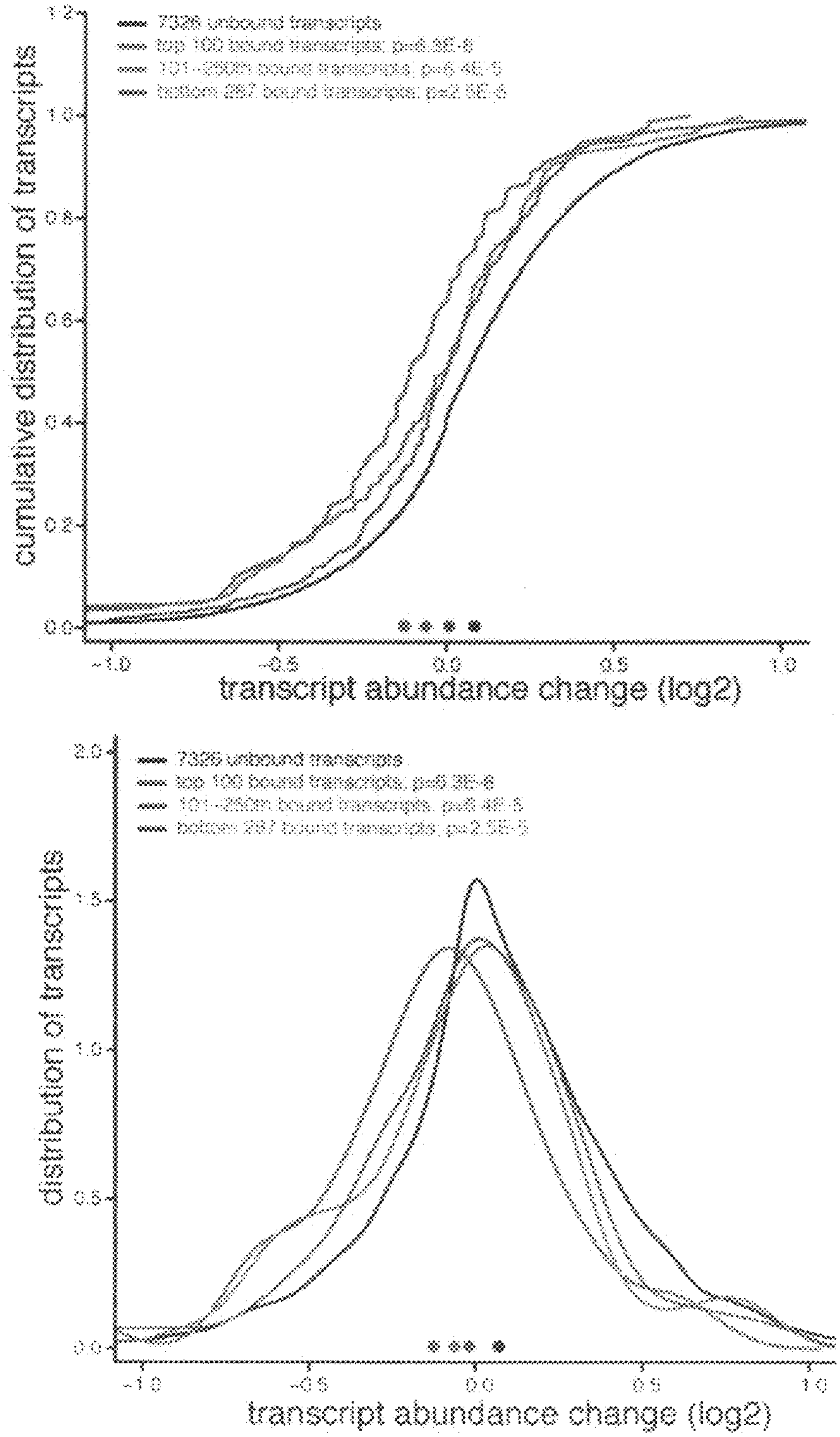
Figure 17D:
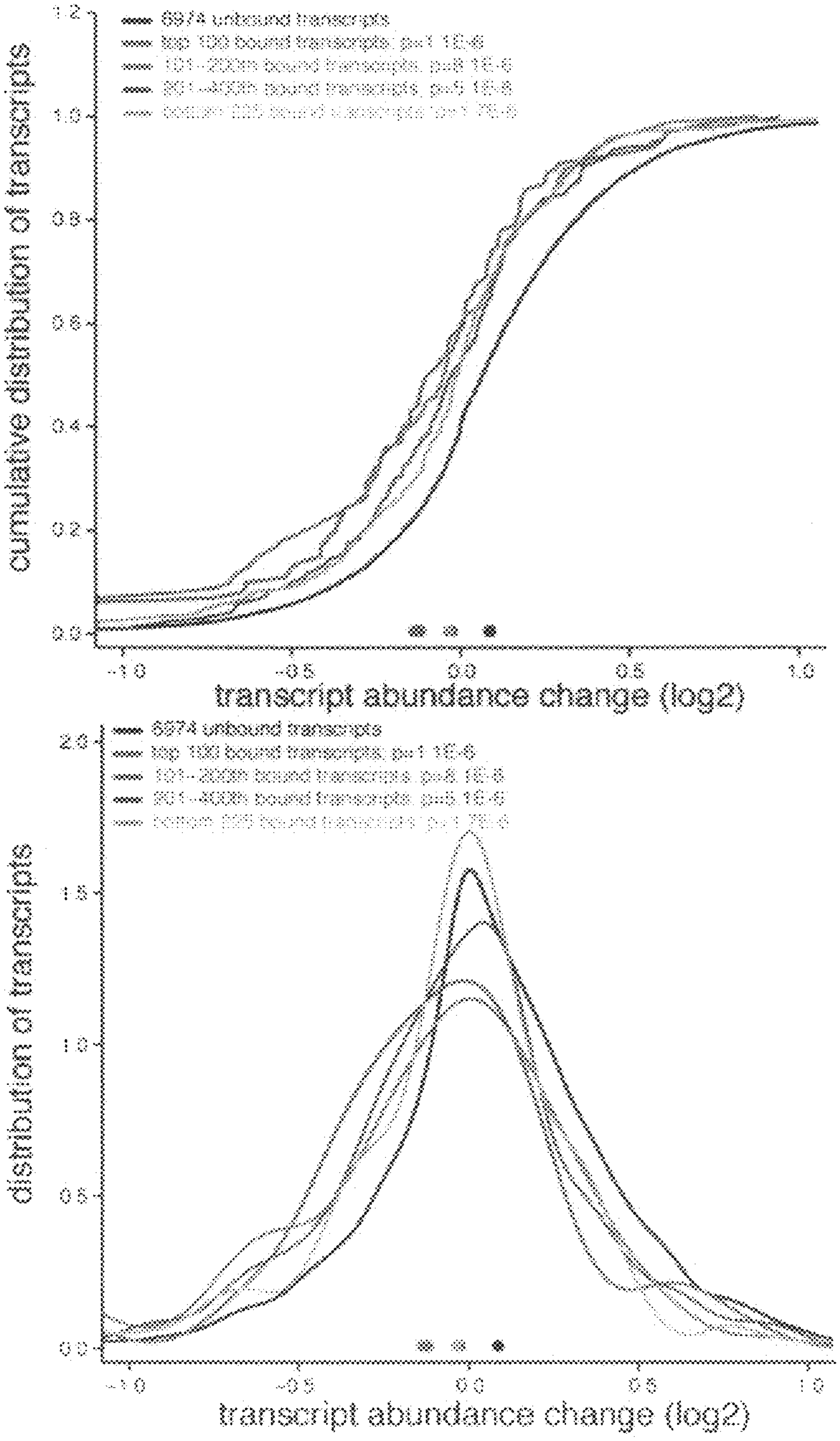

FIG. 16A-C: EMSA to analyze binding of recombinant IGF2BP2 to synthetic oligoribonucleotides with sequences derived from clusters identified by IGF2BP2-CLIP. Sequences used for the EMSA are shown beneath the autoradiograms. Bold red lines denote the recognition element of IGF2BP2, bold blue lines mutated sequences.

FIG. 17: IGF2BP1-3 stabilize target transcripts identified by PURECLIP. A siRNAs targeting IGF2BP1, -2 and -3 were transfected into HEK293 cells. Shown is a Western Blot confirming the reduction of IGF2BP 1-3 levels 72 hrs after siRNA transfection. B The effect of IGF2BP1-3 knockdown on transcript stability of transcripts that are not bound (black line) by IGF2BP1 or bound by IGF2BP1 (colored lines; transcripts are divided into bins of the indicated size after sorting of the transcripts according to the T to C mutation frequency of the sequence clusters mapping to them), as determined by PURE-CLIP, was compared after subtraction of possible off-target effects caused by guide and passenger strands of either siRNA. Shown are the cumulative distribution function (top panel) and the probability density function (bottom panel) of expression changes of bound and not bound transcripts. IGF2BP1 knockdown significantly stabilizes the transcripts that were found to directly interact with IGF2BP1. C Same as B, for IGF2BP2. D Same as B, for IGF2BP3.

Figure 18B:
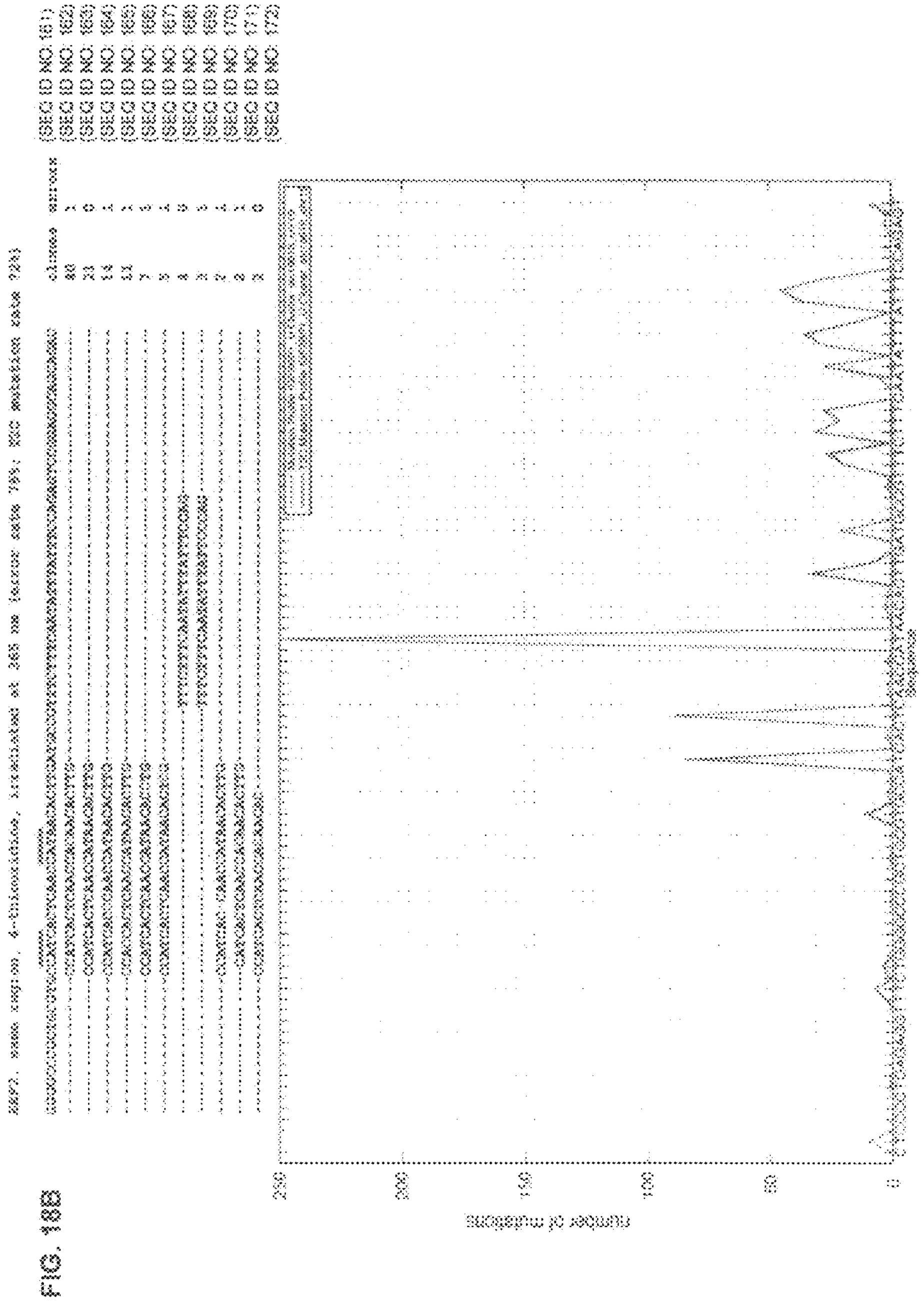
Figure 18C:
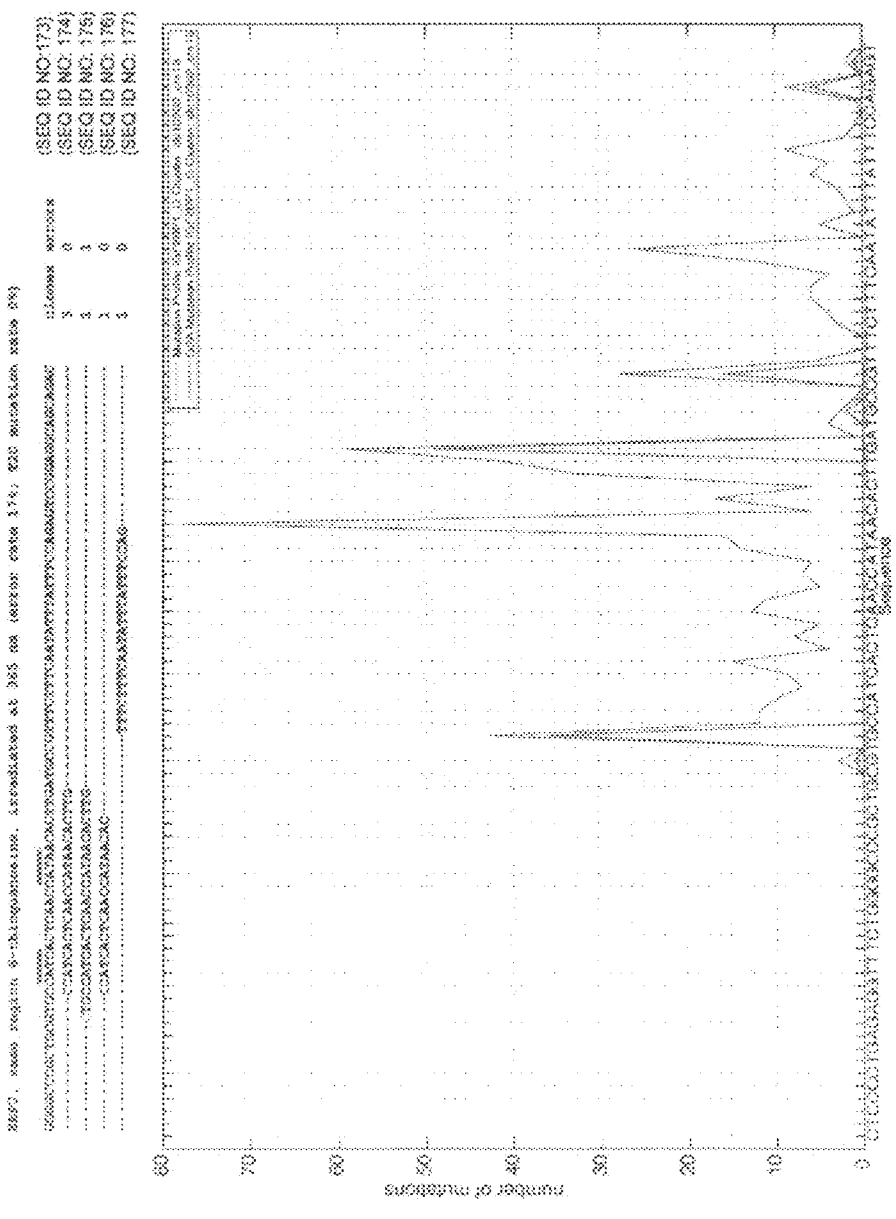

FIG. 18: Alignment of sequences from immunoprecipitation and crosslinking experiments with IGF2BP1 against nucleotides 2784-2868 of the human EEF2-transcript (NM_001961). Nucleotides marked in red show the T to C changes, all other mismatches are marked in orange. Due to space limitations, not all tags with clone count one are shown. A Alignment of sequences obtained from UV crosslinking at 254 nm. Lower panel: Profile for G to A mutations(red) and for any mutation(blue) f B Alignment of sequences obtained after incorporation of 4SU into the transcript and crosslinking at 365 nm. Lower panel: mutational profile for T to C mutations (red) and for any mutation (blue) By far the highest number of T to C mutations occur in the last T of the CAT motif Note that the total number of mutations is much higher than in A and C. C Alignment of sequences obtained after incorporation of 6SG into the transcript and crosslinking at 365 nm. Lower panel: as in A.

Figure 19:
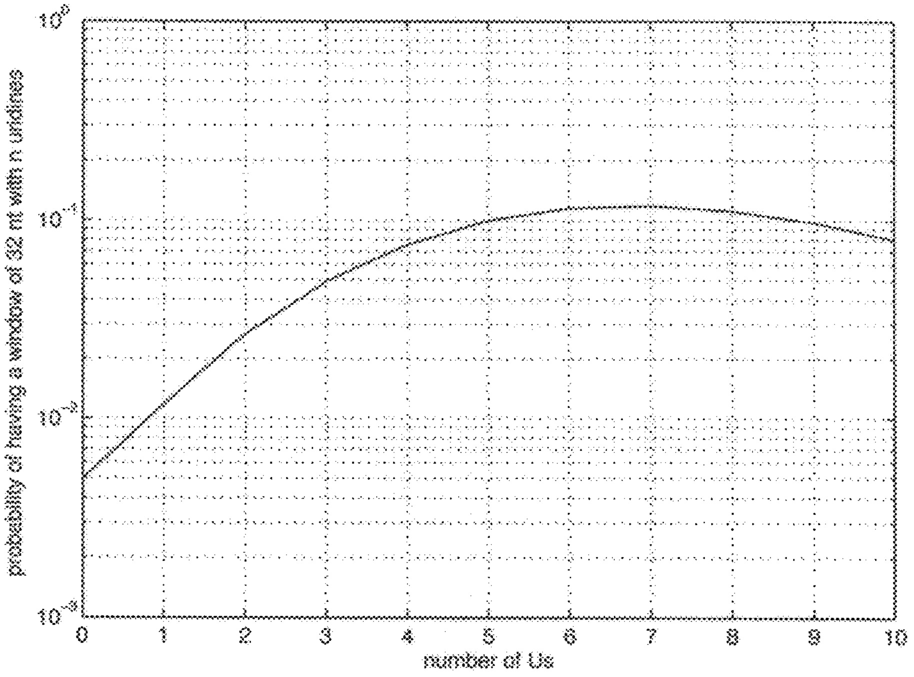

FIG. 19: Fraction of the entire transcriptome (RefSeq sequences) containing the indicated number of uridines in a given 32-nt window. The largest fraction of the transcriptiome contains 7 uridines per 32 nt.

Figures 20A, 20B:
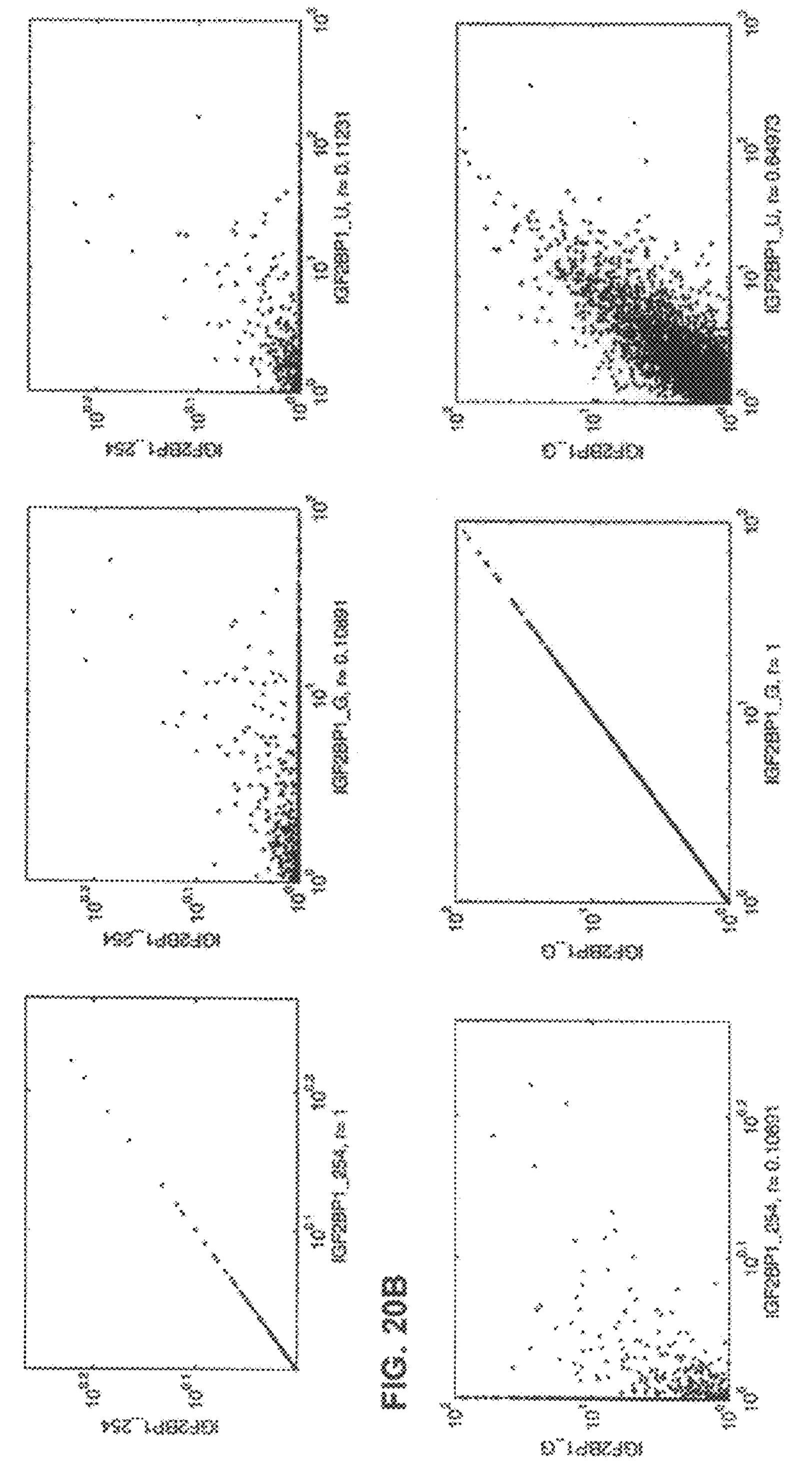
Figure 20C:
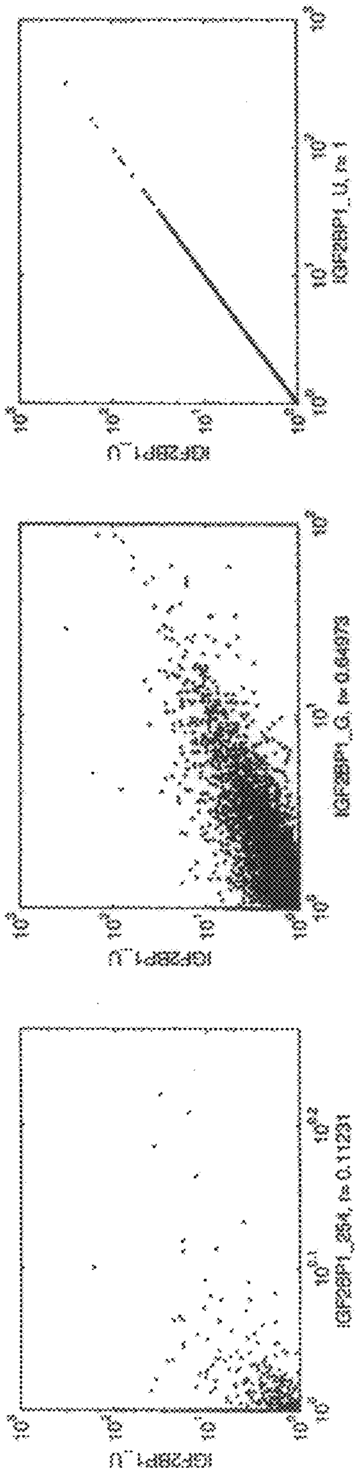

FIG. 20A-C: Correlation plots as in supplementary FIG. 7 for IGF2BP1 CLIP with 254 nm UV (IGF2BP1_254) (FIG. 20A), PURE-CLIP (IGF2BP1_U) (FIG. 20C) and 6SG-CLIP (IGF2BP1_G) (FIG. 20B) after irradiation at UV 365 nm. In the 254 nm CLIP library, due to low RNA yield, all tags were used to calculate the correlation. The Spearman correlation coefficient calculated shows a very weak correlation between the sequence clusters obtained by PURE-CLIP and those obtained by 254 nm UV CLIP (r=0.1), at least partially due to the low enrichment of target RNAs in the 254 nm CLIP library. PURECLIP with the nucleoside analogues 6SG and 4SU showed a good correlation of 0.65.

FIG. 21: AGO and TNRC6 bind to similar regions on the target transcripts. Alignments of AGO PURE-CLIP and TNRC6 PURE-CLIP cDNA sequence reads relative to regions in A the 3' UTRs of OGT (RefSeq transcript NM_181672.1), B the CDS of RFC3 (RefSeq transcript NM_002915.3) and C the CDS of AKR1A1 (RefSeq transcript NM_006066.2). Red bars indicate 8 nt seed complementary sequences and nucleotides marked in red indicate T to C mutations diagnostic of position of crosslinking FIG. 22: Classification of some types of miRNA/mRNA matches examined in the present study: A Strong sites; B Weak sites; C Atypical sites.

Figure 23:
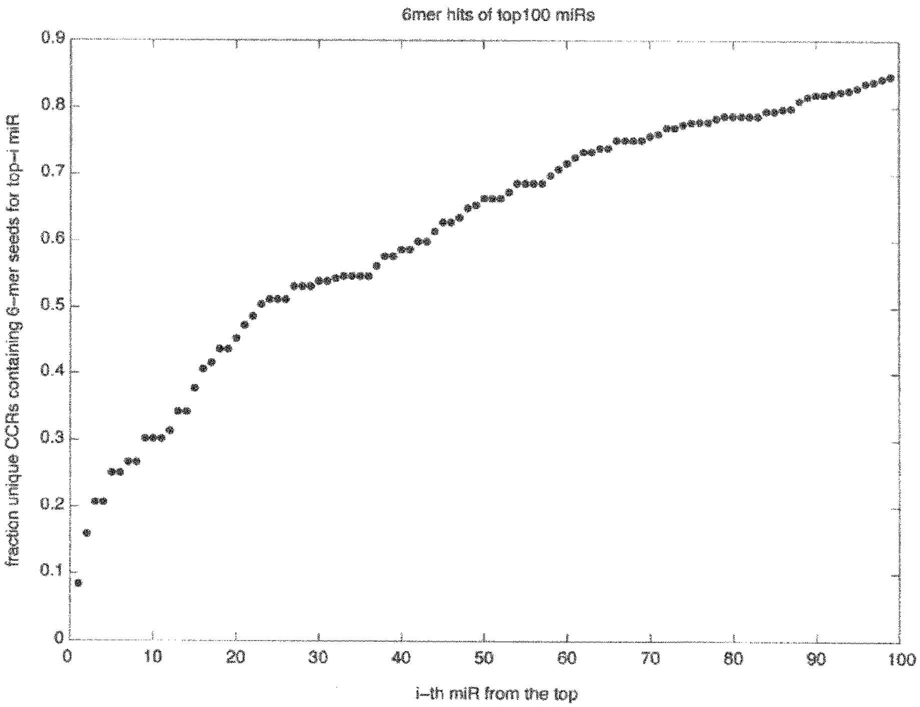

FIG. 23: Fraction of the CCRs containing at least one 6-mer from the top 100 most abundant miRNAs. Plotted is the fraction of CCRs containing 6-mer seed complementary sequences for the first to the i-th miR from the top.

Figure 1C:
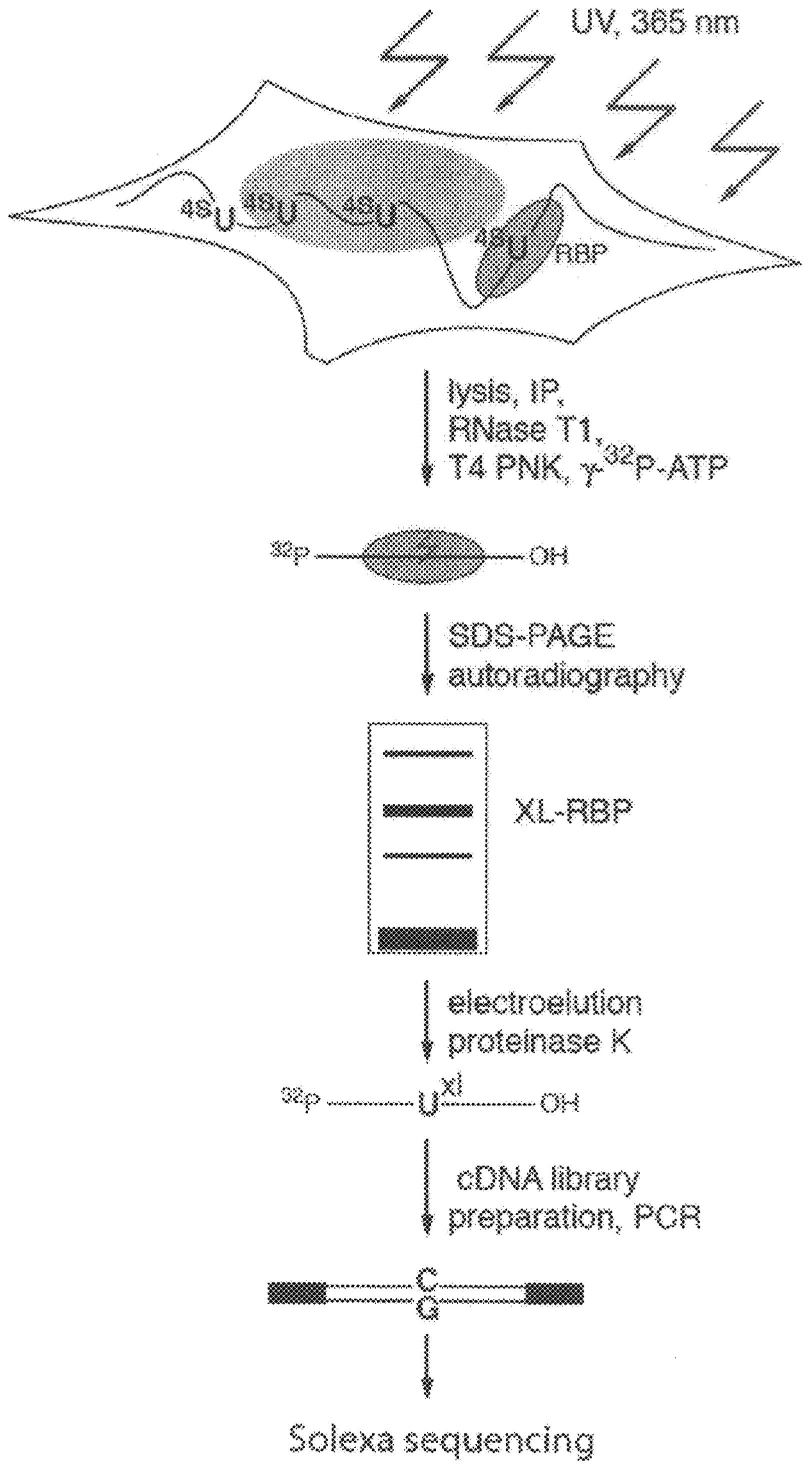
FIG. 1. PURE-CLIP methodology. A Structure of photoreactive nucleosides. B Incorporation of photoreactive nucleosides to enable UV 365 nm crosslinking of RNA to RNA-binding IGF2BP1 protein. Upper panels show phosphorimages of SDS protein gels resolving 5'-32P-labeled RNA-FLAG/HA-IGF2BP1 immunoprecipitates (IPs) prepared from lysates from cells that were cultured in media in the absence or presence of 100 μM photoreactive nucleoside for 12 hrs and crosslinked with 365 nm UV. For comparison, a sample prepared from cells crosslinked at 254 nm, was included. Lower panels show immunoblots probed with an anti-HA antibody confirming uniform gel loading. C Illustration of the method. 4SU-labeled transcripts are crosslinked to RBPs and partially digested RNA-protein complexes are immunopurified and size-fractionated. RNA molecules are recovered and converted to a cDNA library and deep sequenced.
Figure 24A:
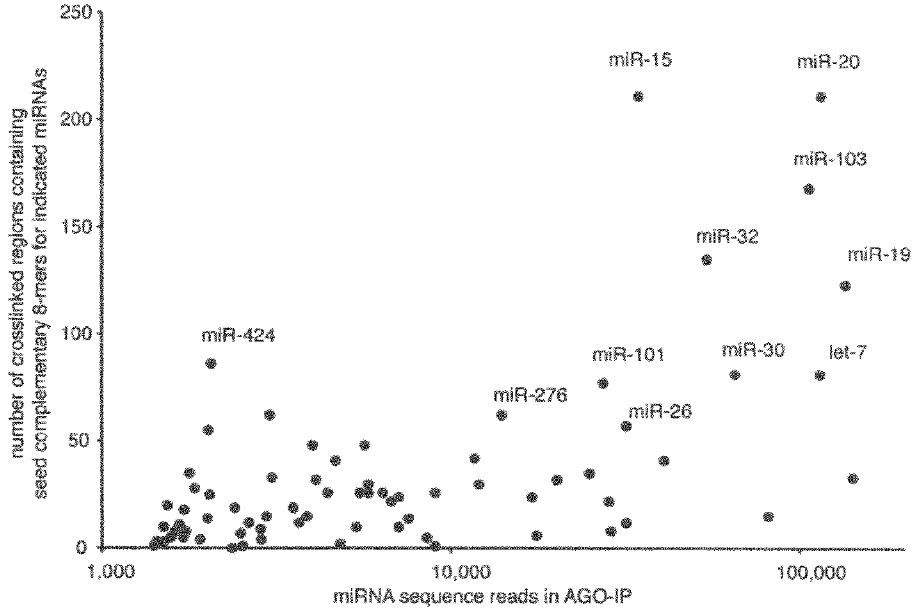
Figure 24B:
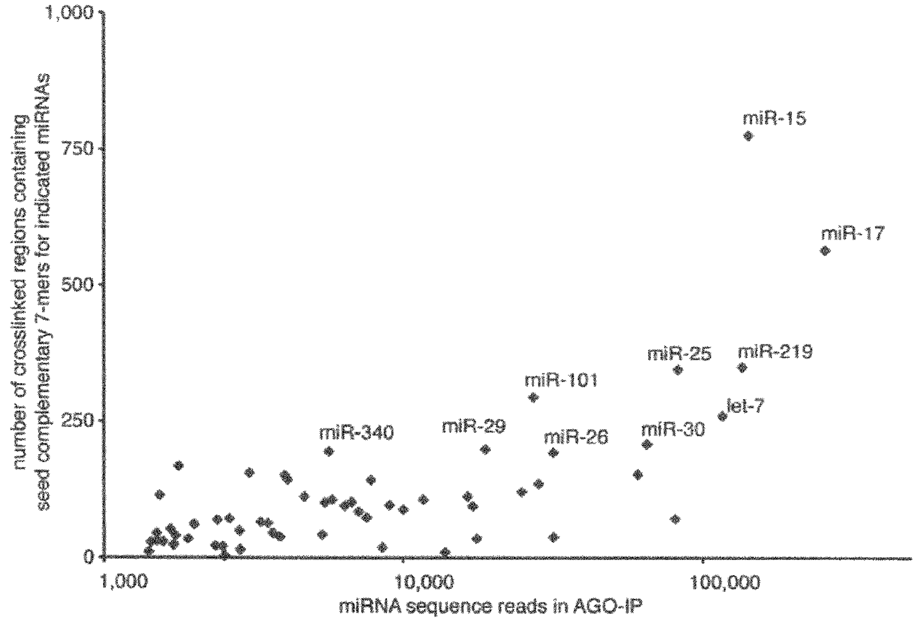

FIG. 24A-B: Correlation between occurrence of 8-mer (upper panel) and 7-mer (lower panel) seed matches in the CCRs and the abundance of the corresponding miRNA seeds (see also FIG. 1*c*. The grouping of miRNAs in 8-mer and 7-mer seed groups is shown in.

Figure 25:
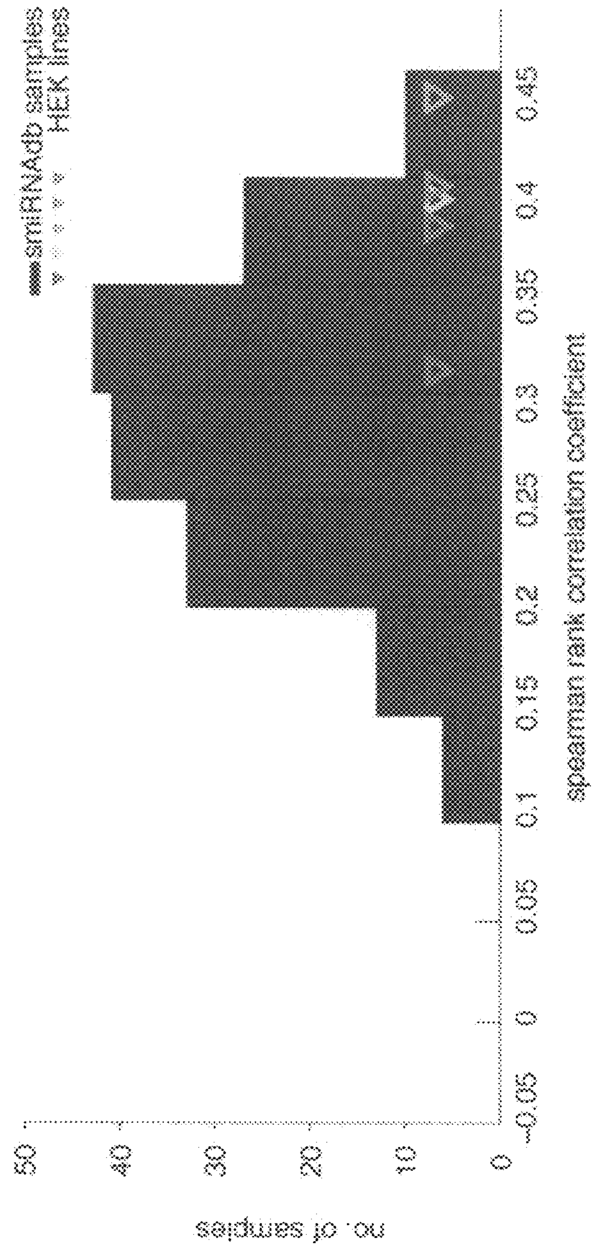

FIG. 25: Spearman correlation between the number of 7-mer (2-8) seed matches in the CCRs and the experimentally determined counts of corresponding miRNA seeds in various miRNA samples from the smiRNAdb database and in a HEK293 data set obtained in this study. Triangles indicate different HEK293 samples.

Figure 26:
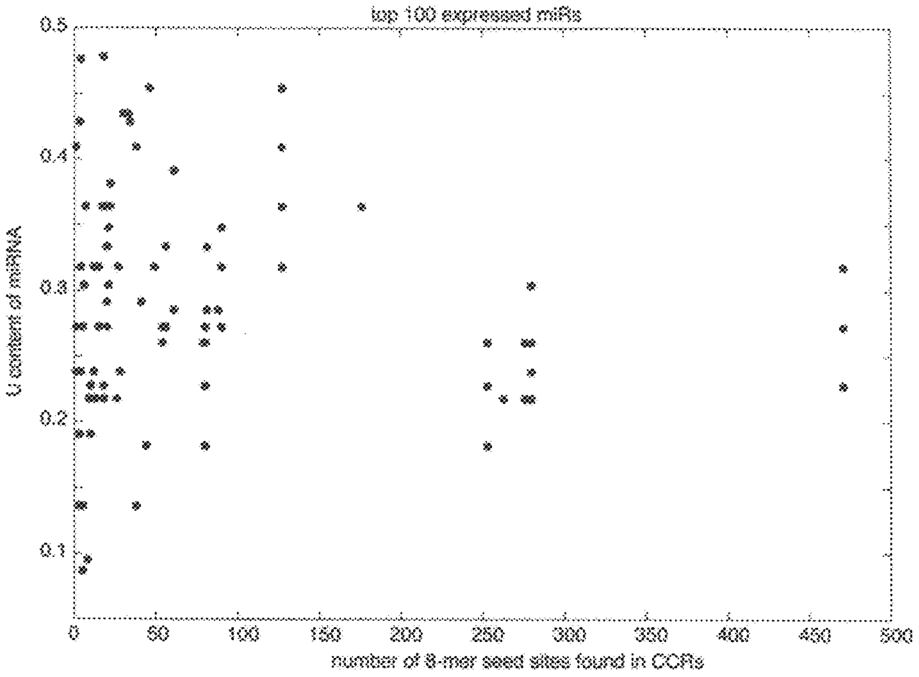

FIG. 26: U content of the top 100 miRNAs depending on the number of CCRs containing their 8-mer seed sequence complementary sequences.

Figure 27:
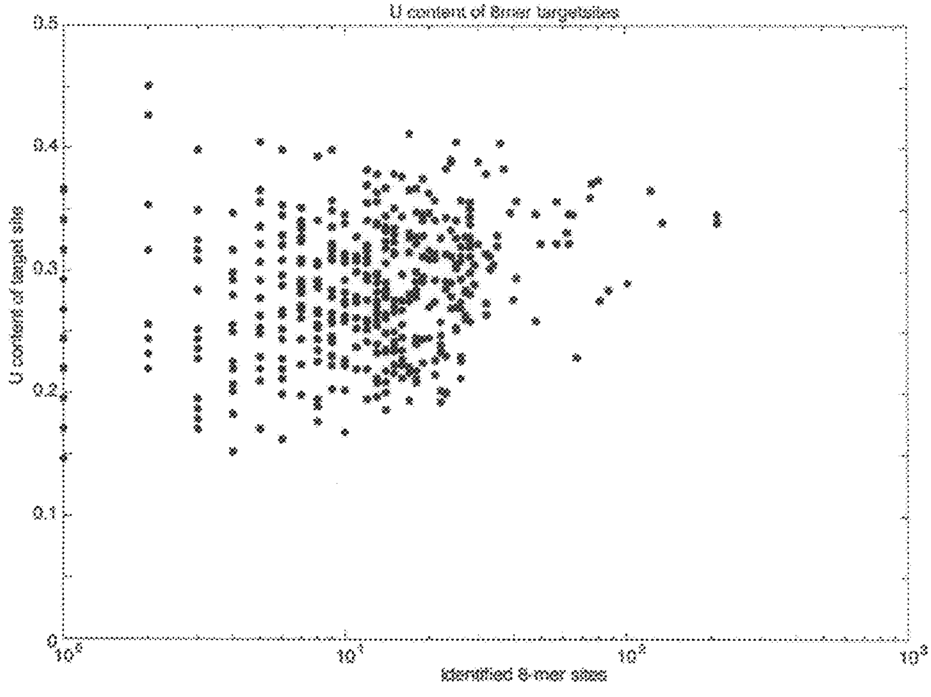

FIG. 27: U content of the CCRs containing 8-mer seed sequence complementary sites for the top 100

FIG. 28A-D: The most down-regulated and the most up-regulated transcripts in an experiment and determine whether they are depleted/enriched in seed matches for tha antagonize miRNAs. Background is depletion/enrichment in the down-/up-regulated transcripts of motifs that have the same approximate frequency across the entire set of transcripts. All miRNAs are assumed to have U at position 1. p-values for 4 types of seeds, indicated below, were tested. Two of the antisense oligoribonucleotides did not seem to have inhibited their cognate miRNAs (miR-10a and miR-27a).

FIG. 29: Binding sites for highly expressed miRNAs co-occur in the crosslinked regions. A Number of pairs of non-overlapping seed (2-8) matches for the top20 miRNAs in the crosslinked regions (red arrow) and in control regions (100 sets of di-nucleotide shuffled crosslinked regions). Only the experimental set shows enrichment of miRNA pairs. B Number of co-occurring pairs of miRNA seed matches in the AGO crosslinked regions and the shuffled control regions for 20 randomly chose miRNAs. C Number of co-occurring pairs of miRNA seed matches in the AGO crosslinked regions for 100 sets of 20 randomly chosen miRNAs. D Heat map representation of miRNA seed match co-occurrence. The scale indicates the absolute number of co-occurring pairs. The miR-17 seed co-ocurs with miR-19/miR-130/miR-301/miR-30/miR-15/miR-16. miR-16 has also the tendency to co-occur with itself.

Figure 30:
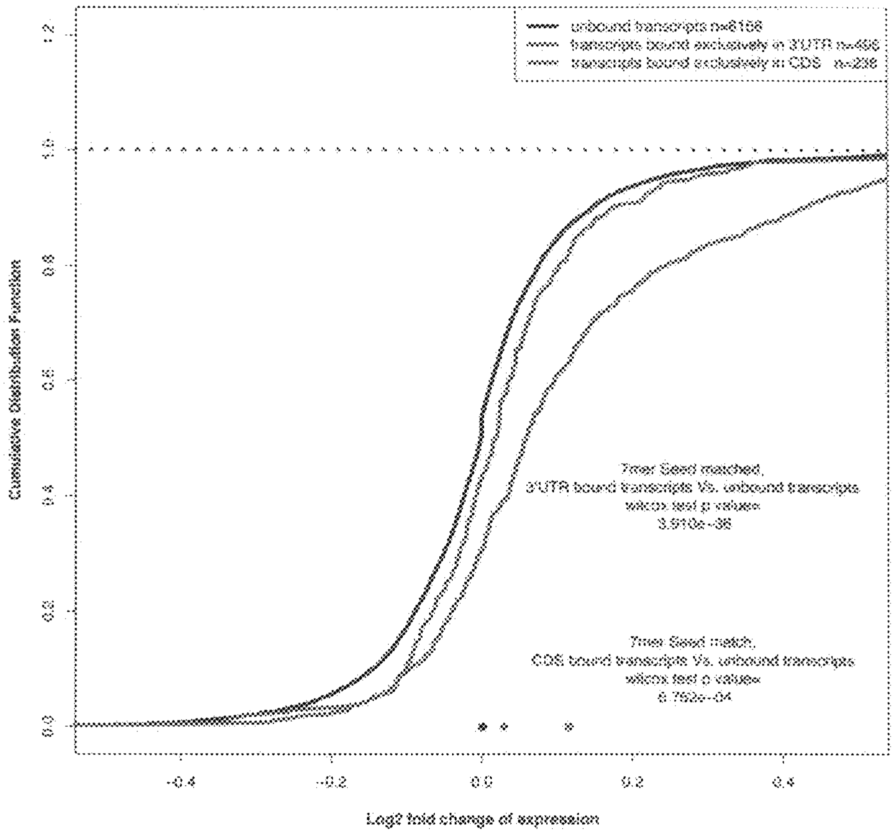

FIG. 30: AntagomiR vs Mock Transfected; Comparison of Log 2 Fold changes of expression for CDS, 3' UTR bound transcripts. Transcripts containing CCRs were categorized according to the presence of 7-mer seed complementary matches in the CDS or in the 3'UTR and distributions of stability changes upon miRNA inhibition are shown. The p-values indicate the significance of the difference between the changes of target versus non-target transcripts, as given by the Wilcoxon rank-sum test.

Figure 31A:
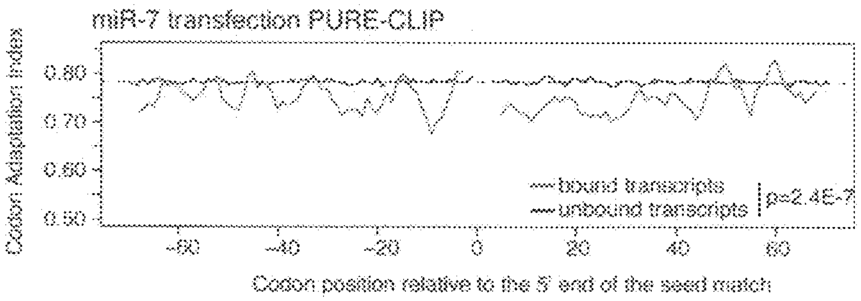
Figure 31B:
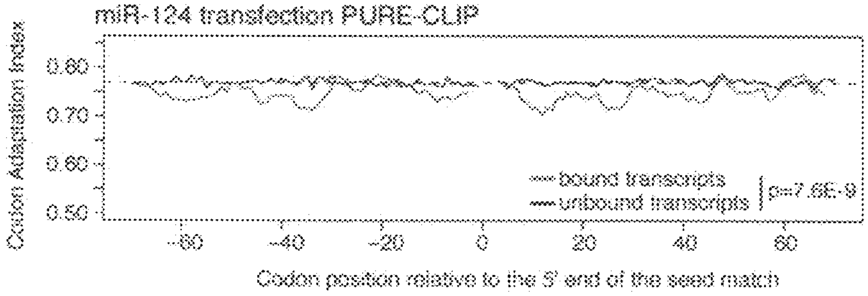

FIG. 31: Codon adaptation index (CAI) for CCRs found in the CDS for the A miR-7 and B miR-124 transfection experiments. The red and the black lines indicate the CAI for CLIPed and unCLIPed transcripts, respectively.

Figure 32A:
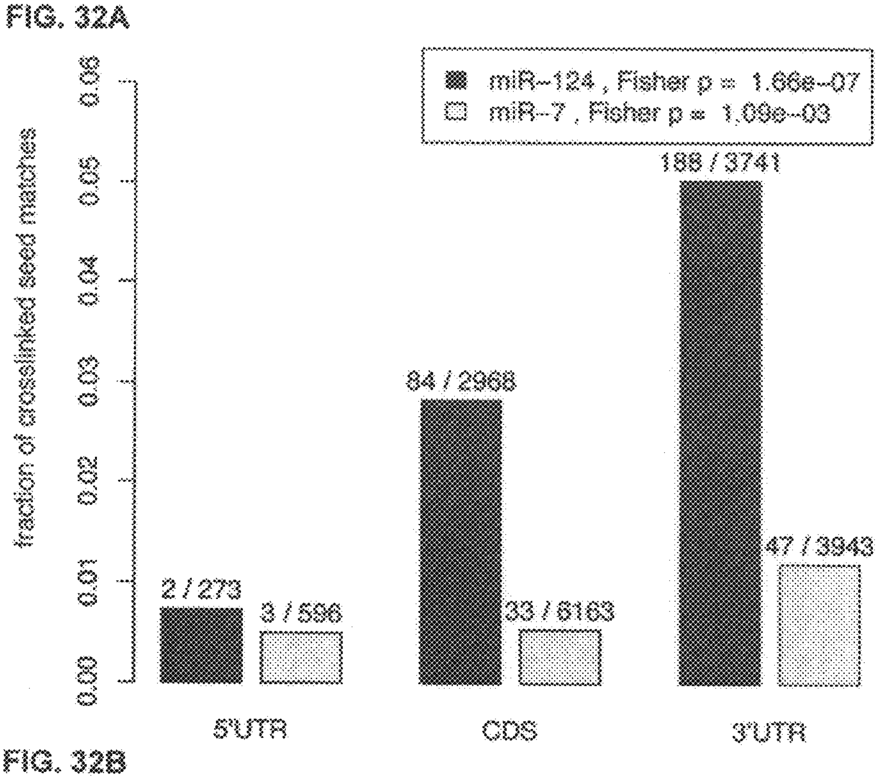
Figure 32B:
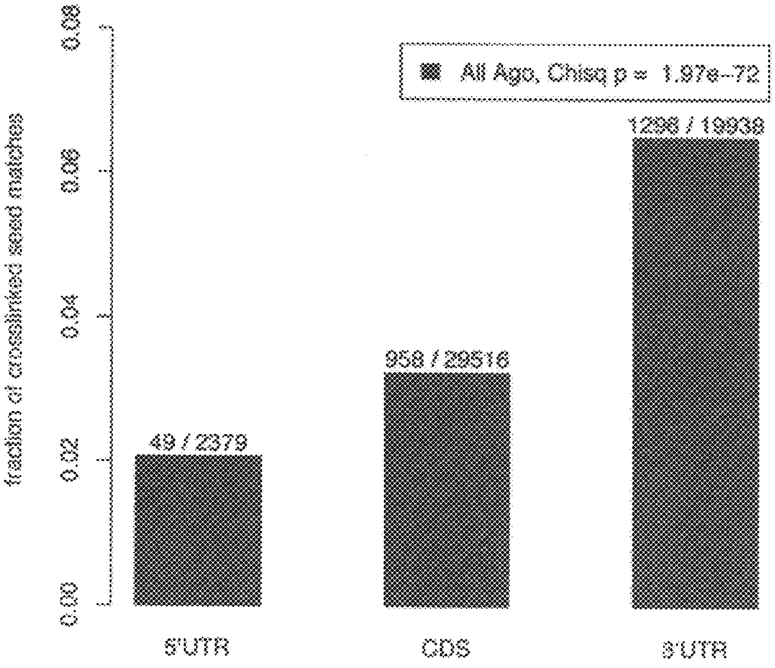

FIG. 32: Seed complementary sequences in the 3'UTR are more efficiently crosslinked than seed complementary regions in the CDS. A Fraction of crosslinked seed matches (1-7 or 2-8) for miR-124 (dark bars) and miR-7 (light bars). B Fraction of crosslinked seed matches for miR-15, miR-16, miR-19, and let-7.

Figure 33A:
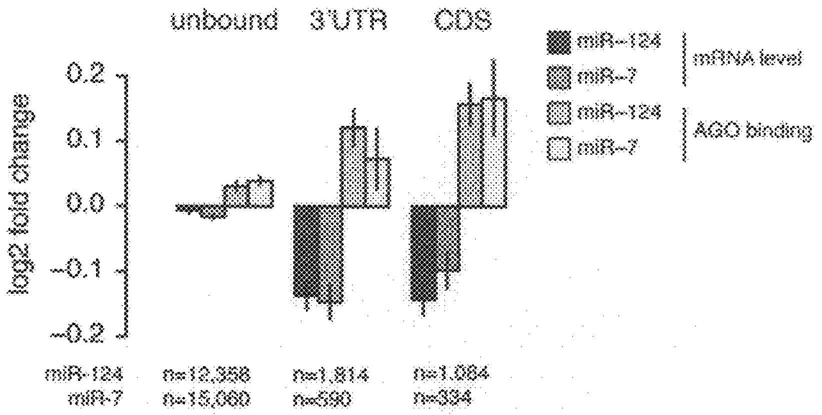
Figure 33B:
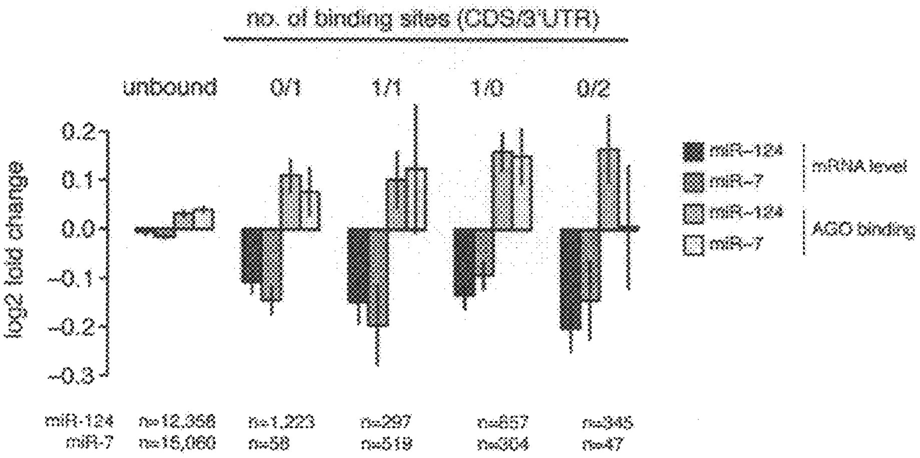
Figure 33C:
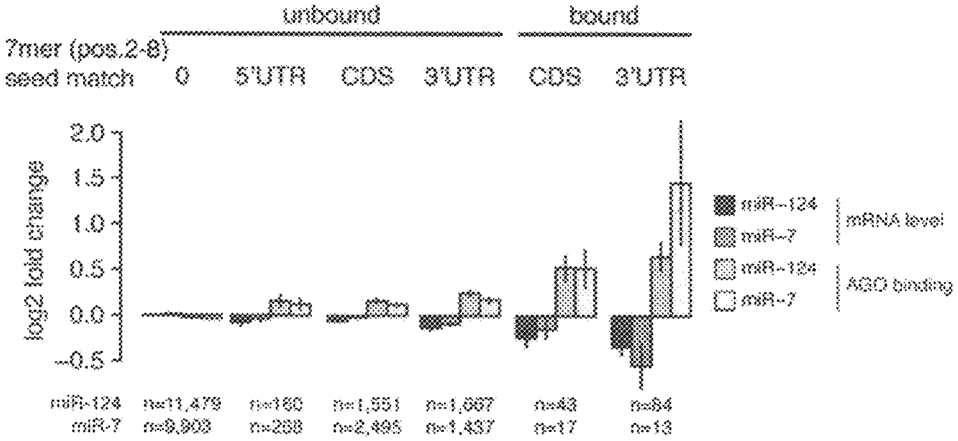

FIG. 33: Properties of AGO-PURE-CLIP sequence read clusters obtained after miR-124 and miR-7 transfection. A Transcripts with PURE-CLIP sequence read clusters identified after miR-124 and miR-7 transfection are bound by AGO2 and destabilized. Transcript stability (dark grey bars) was determined as in FIG. 3 by comparison of mRNA-abundance of mock transfected and miR-124 and miR-7 transfected HEK293 cells overexpressing AGO2. AGO2 binding (light grey bars) was determined by comparing the changes in transcripts co-immunoprecipitated by AGO2 of mock transfected and miR-124 and miR-7 transfected HEK293 cells. Transcripts containing PURE-CLIP sequence read clusters were categ6iv616zed according to the region of binding of AGO2 (CDS/3'UTR). B Same as in A. Transcripts were categorized in more detail according to the number and region of sequence read clusters identified. C Same as in A. Transcripts containing a miR-124 and miR-7 seed sequence but that did not contain PURE-CLIP sequence read clusters were compared to transcripts containing PURE-CLIP sequence read clusters with miR-124 and miR-7 seed complementary sequences and categorized according to region.

Figure 34A:
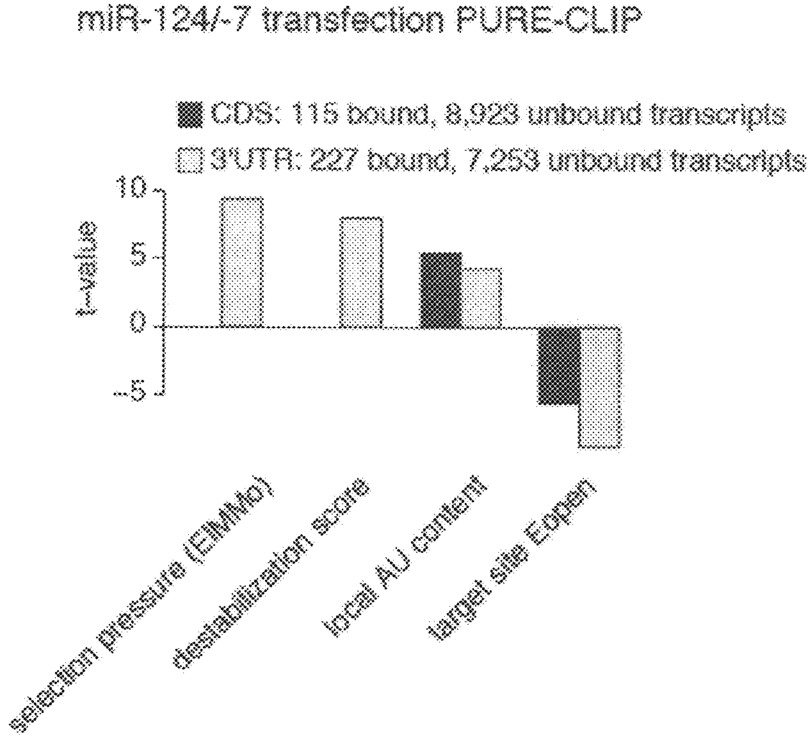
Figure 34B:
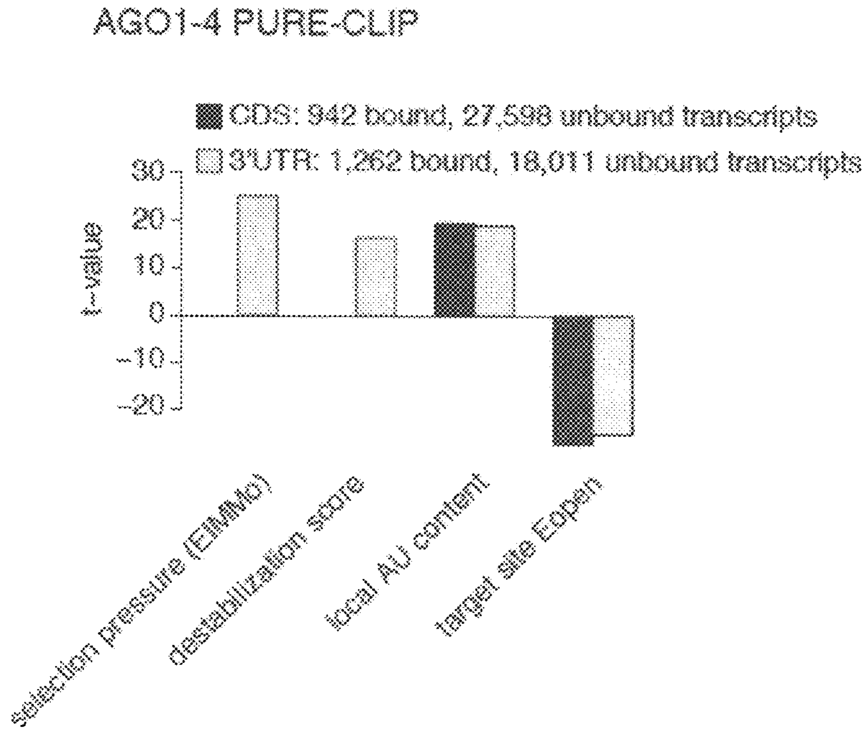

FIG. 34: The sequence context defines a functional miRNA binding site in the UTR as well as in the CDS. Four different criteria were compared for crosslinked transcripts containing 7-mer seed matches for A miR-124 and miR-7 and B the miR-15, miR-19, miR-20, and let-7 miRNA families in the AGO1-4 PURE-CLIP experiment compared to non-crosslinked transcripts containing the same 7-mer seed matches.

Figure 35A:
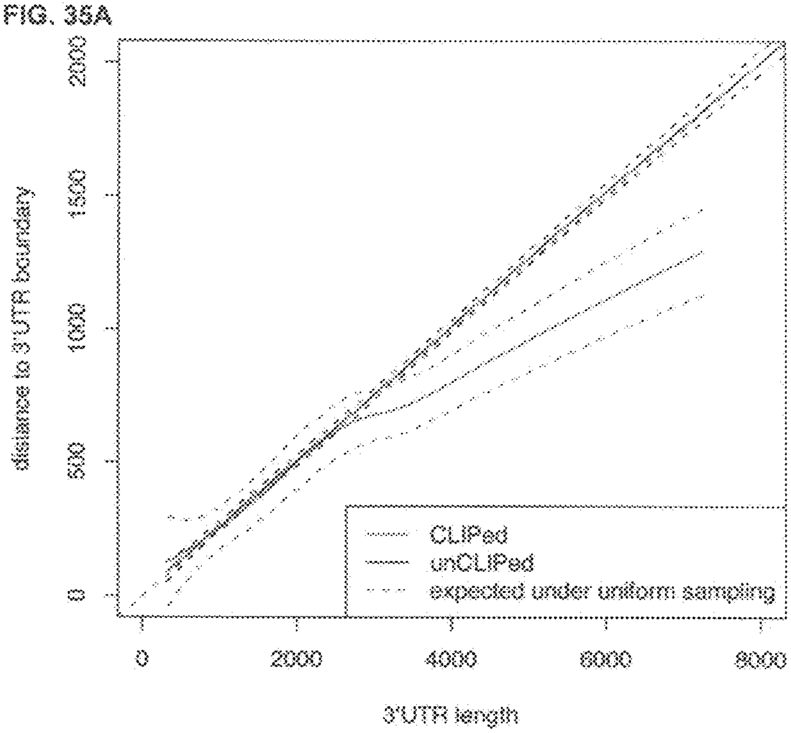
Figure 35B:
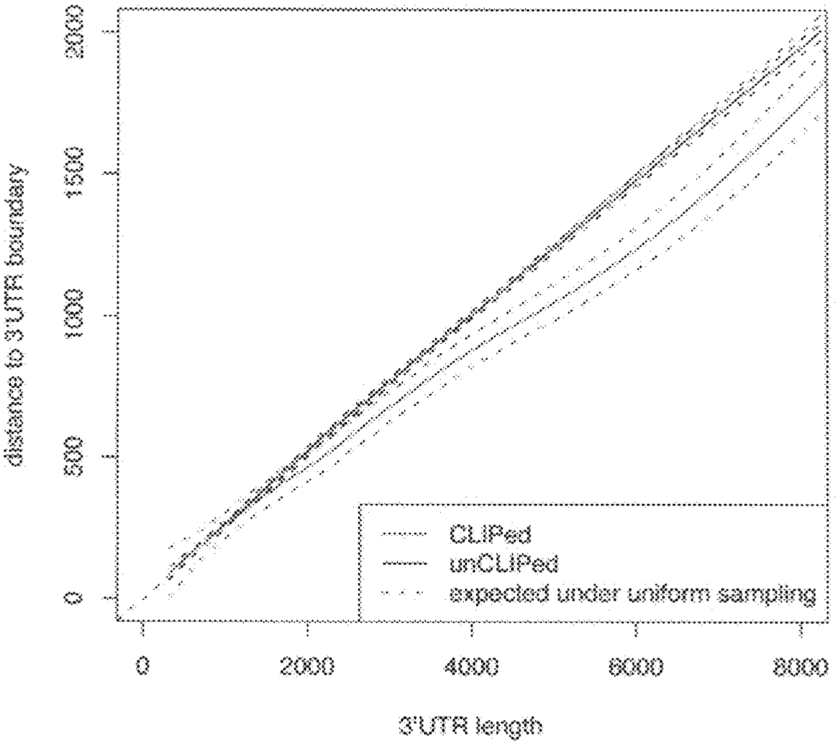

FIG. 35: In 3'UTRs longer than 3,000 nts the crosslinked sites distribute preferentially near to the boundaries of the UTR. Distance of crosslinked regions with 7-mer seed matches regions falling in the 3'UTR from the region boundaries (stop codon and polyA signal, respectively) to (A) miR-124 and miR-7 (red line) (B) and 7-mer seed matches to the miR-15, miR-16, miR-19 and let-7 seed groups (red line) (see Supplementary Methods) compared to non-crosslinked seed-matches (black lines).

Figure 36A:
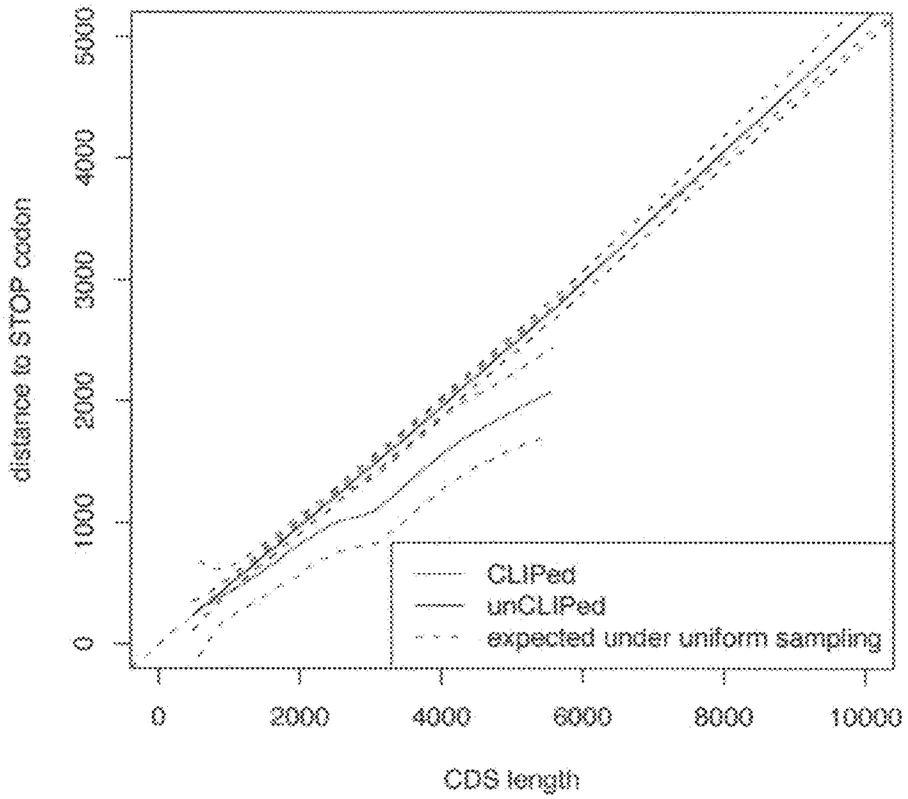
Figure 36B:
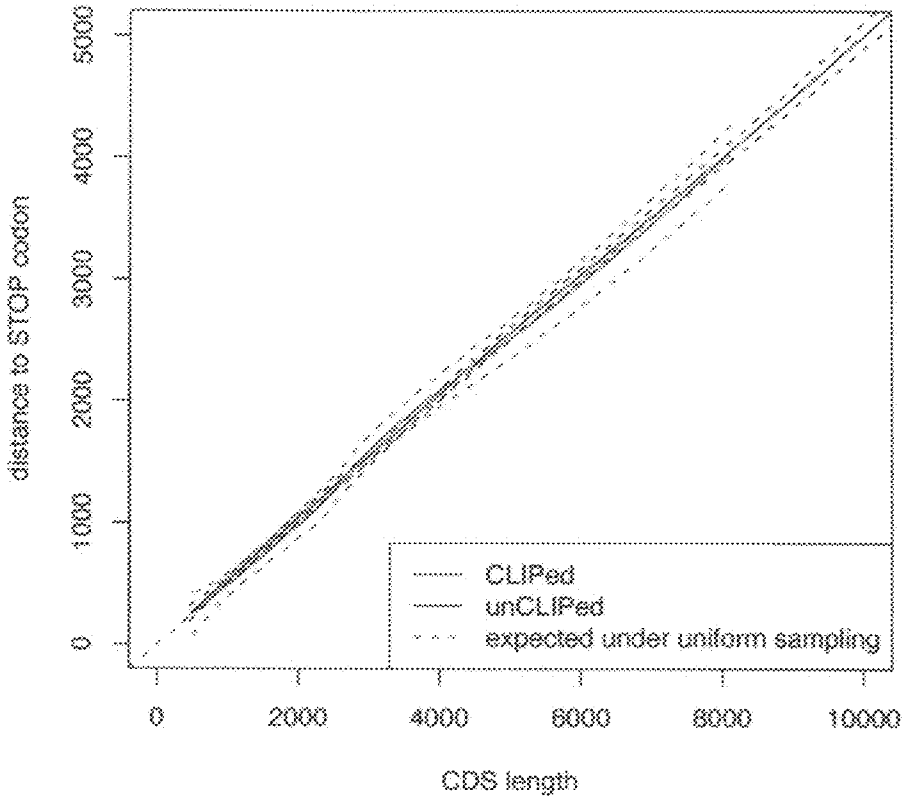

FIG. 36: Distance of crosslinked regions falling in the CDS from the stop codon of 7-mer seed matches of (A) miR-124 and miR-7 (red line) or (B) and 7-mer seed matches of the miR-15, miR-16, miR-19 and let-7 seed groups (red line) (see Supplementary Methods) compared to non-crosslinked seed-matches (black lines). Only for the miR-124 and miR-7 transfection experiments the crosslinked sites in the CDS distribute significantly nearer to the stop-codon.

Figure 37:
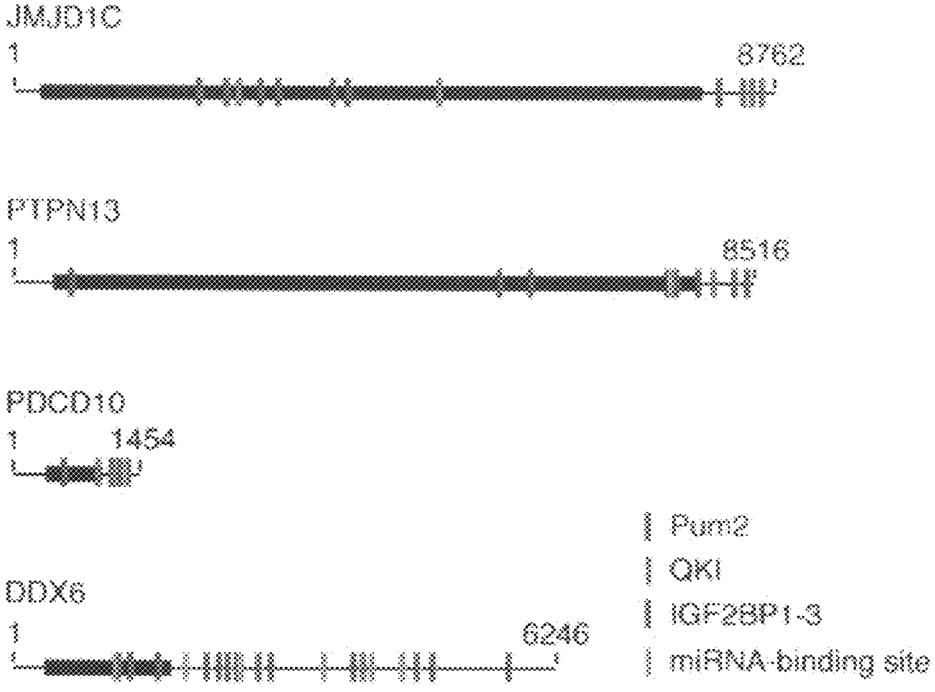

FIG. 37: Co-targeting of transcripts by several RNA-binding proteins. Experimentally defined binding sites are color-coded. Bold and thin black lines indicate ORF and UTRs, respectively.

DETAILED DESCRIPTION OF THE INVENTION

The inventors have surprisingly discovered a powerful method to identify, on a transcriptome-wide level, the target sites of any given RNA-binding protein (RBP) or ribonucleoprotein complex (RNP) with nucleotide resolution. The discovery is based, in part, on using a photoreactive nucleoside that is incorporated into nascent mRNA and is effectively crosslinked to the interacting moieties at long-range UV light in vivo.

The inventors discovered that the photoreactive nucleoside undergoes a structural change upon crosslinking, and is subsequently identified as a mutation in cDNA that is prepared from the modified mRNA. The mutated cDNA can then be analyzed by exploiting the mutation, thereby providing a means of distinguishing UV-crosslinked target sites from background RNA fragments that were captured but not initially crosslinked to the moiety. Such an analysis dramatically increases the recovery of target sites that were crosslinked, reduces the risk of scoring false positives of target sites, and allows for extraction of sequence information of the target site. The inventive methods described herein are also useful for determining the regulation of interactions on the target sites and for binding assays using recombinantly expressed proteins.

In one embodiment, the present invention includes methods for identifying RNA transcripts that associate with a given binding moiety, and also for identifying the region(s) on RNA transcripts which recognize, interact and/or bind to binding moieties. Such a region on an RNA transcript is termed an "RNA protein binding site." The present invention particularly includes methods for identifying the region(s) on RNA transcripts which recognize, interact and/or bind to binding moieties in vivo. In this specification, "in vivo" refers to a living cultured cell as well as cells in intact organs and intact animals.

As used herein the term "binding moiety" refers to any substantially protein entity that binds to an "RNA protein binding site." Examples of binding moieties include, but are not limited to, proteins, protein complexes, or portions or fragments thereof, including protein domains, regions, sections and the like. Proteins include one or more RNA-binding proteins (RBP), RNA-associated proteins or combinations thereof. In addition to protein, a protein complex may comprise, for example, nucleic acid components in ribonucleoprotein complexes (RNP), e.g., miRNA, piRNA, siRNA, endo-siRNA, snoRNA, snRNA, tRNA, rRNA or combinations thereof. In RNP complexes, RNA guides and participates in target RNA binding. Binding moieties also include RNA helicases, e.g. MOV10, and proteins containing nuclease motifs, e.g. SND1.

As used herein, the term "RNA protein binding site" or "binding site" refers to that portion, region, position or location on an RNA transcript in which at least one interaction with a binding moiety occurs. Such interaction may include at least one direct base-pairing between the RNA transcript and the binding moiety. A binding site or sites of an RNA transcript may be found at a structured or unstructured region of the RNA transcript. It is also contemplated that more than one binding site may exist for any one RNA transcript. Further, binding sites of RNA transcripts may involve noncontiguous nucleotides of the RNA transcript. Such binding sites are contemplated when structure, such as, for example, a stem loop, is involved in binding.

The method includes introducing a photoreactive nucleoside into living cells wherein the living cells incorporate the photoreactive nucleoside into RNA transcripts during transcription. The RNA transcripts, into which a photoreactive nucleoside is incorporated, are termed "modified RNA transcripts."

A "photoreactive nucleoside" refers to a modified nucleoside that contains a photochromophore and is capable of photocrosslinking with a binding moiety. Preferably, the photoreactive group will absorb light in a spectrum of the wavelength that is not absorbed by the binding moiety or the non-modified portions of the RNA.

In one embodiment, the photoreactive nucleoside is a thiouridine analog. Thiouridine analogs include 2-thiouridine; 4-thiouridine; and 2,4-di-thiouridine. The thiouridine analogs can optionally be substituted at the 5 and/or 6 position. The substituents can be, for example, methyl, ethyl, halo, nitro, $NR^1R^2$ and $OR^3$. $R^1$, $R^2$ and $R^3$ independently represent hydrogen, methyl or ethyl.

In another embodiment, the photoreactive nucleoside is a thioguanosine analog. Thioguanosine analogs include 6-thioguanosine.

In yet another embodiment, the photoreactive nucleoside includes a detectable "label" covalently attached to the nucleoside in order to facilitate use of detection systems, such as luminescence-based systems. Examples of labeled nucleosides include nucleosides modified with biotin and nucleosides modified with suitable haptens such as digoxigenin. Preferred nucleoside analogs for incorporation of a detectable label into RNA include biotin-16-UTP (biotin-16-uridine-5'triphosphate, Roche) and digoxigenin-11-dUTP (an analog of dTTP, 2'-deoxyuridine-5'-triphosphate, coupled to digoxigenin via an 11-atom spacer arm). Fluorescein, Cy3, and Cy5 can be linked to dUTP for direct labeling. Cy3.5 and Cy7 are available as avidin or anti-digoxigenin conjugates for secondary detection of biotin- or digoxigenin-labelled probes. Suitable fluorescence-labeled nucleosides include fluorescein-isothiocyanate-dUTP, cyanine-3-dUTP, and cyanine-5-dUTP.

Accordingly, in one embodiment, the modified nucleoside can be detected by fluorescence (Fluorescein, Rhodamingreen or Cy5). In another example, the nucleoside is detected by an antibody reaction (Digoxigenin, Fluorescein). In yet another example, the nucleoside can be detected by the specific interaction with Streptavidin (Biotin) and a nucleoside that carries a reactive group which can be linked to a label chemically (Aminopentinyl-C7-deaza-dATP).

Any label that can be attached to the nucleoside are suitable. Such labels include radioactive labels, enzymes (that need a reaction with a substrate to be detected), specific binding pair components (such as avidin, streptavidin, and/or biotin), biocytin, iminobiotin, colloidal dye substances, fluorochromes (rhodamin, etc.), reducing substances (eosin, erythrosine, etc.), digoxigenin, metals (ruthenium), metal sols or other particulate sols (selenium, carbon, etc.), dansyl lysine, infra red dyes, coumarines (amino methyl coumarine), antibodies, protein A, protein G, etc. Preferably, the label is biotin, avidin, streptavidin, digoxigenin, or a functional equivalent thereof.

As referred to herein, the "living cell or cells" may be part of a cell culture, a cell extract, cell line, whole tissue, a whole organ, tissue extract, or tissue sample, such as, for example, a biopsy or progenitor cells as from bone marrow or stem cells. The living cell can be from a healthy source or from a diseased source, such as, for example, a tumor, a tumor cell, a cell mass, diseased tissue, tumor cell extract, a pre-cancerous lesion, polyp, or cyst or taken from fluids of such sources. The cells can be any kind of cells, for example, cells from bacteria and yeast, animals, especially mammalian cells, and plants.

Once RNA transcripts have been produced, or at a time at which transcription should have produced transcripts within the living cell or cells, the living cell or cells comprising the modified RNA transcripts are then irradiated. The irradiation is at a wavelength which is significantly absorbed by the photoreactive nucleoside such that covalent cross-links are formed between the modified RNA transcript and a binding moiety and the RNA is not damaged. The minimum wavelength can be 300 nm, preferably 320 nm, and more preferably 340 nm. The maximum wavelength can be 410 nm, preferably 390 nm, and more preferably 380 nm. Any combination of minimum and maximum wavelength values can be used to describe a suitable range. The optimal wavelength is approximately 365 nm for a thiouridine analog. The optimal wavelength for a thioguanosine analog is approximately 310 nm.

Irradiation forms covalent cross-links between the modified RNA transcript and a binding moiety spatially located close enough to said modified RNA transcript to undergo cross-linking. The part or parts of a modified RNA transcript which are in close enough contact to have undergone cross-linking with a binding moiety can be considered binding sites. Thus, binding sites are covalently cross-linked to binding moieties. (For example, see FIG. 1.)

Covalent cross-linking allows the use, in some embodiments of the present invention, of rigorous purification schemes, such as, for example, immuno-precipitation and separating complexes on SDS-PAGE. In some embodiments, the covalent bond enables partial cleavage of RNA molecules without affecting their protein binding by the use of nucleases.

Next, modified RNA transcripts, or portions thereof, which are not covalently cross-linked upon irradiation to one or more binding moieties are removed. The resulting constructs are termed "cross-linked segments." These "cross-linked segments" include the portion of the modified transcript that comprises the binding site as well as at least the portion of the binding moiety that was subject to cross linking. The binding site therefore contains at least one photoreactive nucleoside through which the binding site is cross-linked to the binding moiety. The "cross-linked segments" also may include additional nucleotides of the modified RNA transcript that are not bound to the binding moiety. These portions are termed "flanking segments."

In one embodiment, the "cross-linked segments" are formed by harvesting and lysing the cells to form a soluble extract of the cells; and treating the extract with a nuclease. The nuclease trims the regions of the modified transcripts that are not cross-linked to binding moieties. It is contemplated, in one embodiment, that the nuclease would remove, or trim, all of the portion of a modified transcript that is not cross-linked to a binding moiety. However, since trimming can occur in various places on a modified RNA transcript which are not cross-linked to binding moieties, the population of "cross-linked segments" may include "cross-linked segments" with various species of "flanking segments."

Preferably, the nuclease is ribonuclease-T1 (*Aspergillus*). Ribonuclease-T1 cleaves the modified RNA transcript at 3' phosphates of guanine residues, producing terminal guanosine 3' phosphates. The characteristic of cleaving the modified RNA transcript at 3' phosphates of guanine residues assists in identifying valid binding sites from noise. This characteristic is especially important for RNA segments below a size of 20-nt, when the frequency for mapping shorter RNA segments to multiple genomic location increases dramatically. It is contemplated that other nucleases may also be employed either alone or in combination with Ribonuclease T1, as well as any other method known in the art that is suited to digest protected RNAs, for example, such as RNase A (which may be isolated from bovine pancreas or from pancreas of other mammalian species, for example); RNase I (which may be isolated from *E. coli*); or RNase T2 (which is the broad specificity RNase from *Aeromonas*).

Next, the cross-linked segments are isolated to generate "isolated cross-linked segments." In one embodiment, isolation is effected by immunoprecipitation ("IP"). Other suitable isolation means with which immunoprecipitation may be combined with or substituted by include use of SDS-PAGE, protein tags, gel filtration, sucrose gradients, etc., with a caveat that the purification scheme preferably does not include conditions that would damage nucleic acids (such conditions as alkaline hydrolysis of RNA).

In IP, a biological sample (e.g., the soluble extract) is contacted with a specific binding molecule, e.g., a molecule that interacts specifically with the part of the "cross-linked segments" and attaches or adheres the molecules to a substrate. The examples of specific binding molecules include antibodies and fragments of antibodies that comprise at least one hypervariable region.

IP is usually carried out with the specific binding molecule on a solid support. Solid supports are known in the art. Examples include any type of solid support, such as any type of bead, plate, column, fiber or array. The molecule that specifically interacts with the "cross-linked segments" may be attached, in one embodiment, to the substrate using any known method, including chemical or physical attachment in some embodiments, as known in the art. Examples of IP methods include protein A/sepharose beads, protein G/sepharose beads, and magnetic beads such as Dynabeads. Techniques for performing IP are known to those skilled in the art (see, for example, Current Protocols in Molecular Biology (1998) Ausubel, et al, eds.).

In one embodiment, the IP is effected by epitope-tagging the binding moiety. A variety of epitopes may be used. Such epitopes may be naturally-occurring amino acid sequences found in nature, artificially constructed sequences, or modified natural sequences. In one embodiment, an artificial epitope sequence with the eight amino acid FLAG marker peptide (Asp-Tyr-Lys-Asp-Asp-Asp-Asp-Lys) (SEQ ID NO: 1) can be used with antibodies recognizing the epitope readily available (Brewer et al., *Bioprocess Technol.* 2:239-266 (1991); Kunz et al., *J. Biol. Chem.* 267:9101-9106 (1991)).

Additional artificial epitope tags include an improved FLAG tag having the sequence Asp-Tyr-Lys-Asp-Glu-Asp-Asp-Lys (SEQ ID NO: 2), a nine amino acid peptide sequence Ala-Trp-Arg-His-Pro-Gln-Phe-Gly-Gly (SEQ ID NO: 3) referred to as the "Strep tag" (Schmidt et al, *J. Chromatography* 676:337-345), poly-histidine sequences, e.g., a poly-His of six residues which is sufficient for binding to IMAC beads, an eleven amino acid sequence from human c-myc recognized by monoclonal antibody 9E10, or an epitope represented by the sequence Tyr-Pro-Tyr-Asp-Val-Pro-Asp-Tyr-Ala-Ile-Glu-Gly-Arg (SEQ ID NO: 4) derived from an influenza virus hemagglutinin (HA) subtype, recognized by the monoclonal antibody 12CA5. Also, the Glu-Glu-Phe sequence recognized by the anti-alpha-tubulin monoclonal antibody YL1/2 has been used as an affinity tag for purification of recombinant proteins (Stammers et al., *FEBS Lett.* 283:298-302 (1991)).

Another commonly used artificial epitope is a poly-His sequence having six histidine residues (His-His-His-His-His-His) (SEQ ID NO: 5). Naturally occurring epitopes include the eleven amino acid sequence from human c-myc recognized by the monoclonal antibody 9E10 (Glu-Gln-Lys-Leu-Leu-Ser-Glu-Glu-Asp-Leu-Asn) (SEQ ID NO: 6) (Manstein et al. (1995) Gene 162:129-134). Another useful epitope is the tripeptide Glu-Glu-Phe which is recognized by the monoclonal antibody YL 1/2 against alpha-tubulin.

Preferably, magnetic beads, such as Dynabeads, are used as the substrate. The beads can be easily collected by a magnet. Preferably, precipitate, i.e., the isolated "cross-linked segments," are washed.

As before isolation, the population of "isolated cross-linked segments" comprises "cross-linked segments" of various lengths having differing portions of modified RNA transcripts which are not cross-linked to binding moieties. In one embodiment, the "cross-linked segments" may optionally be treated again with a nuclease to further trim the regions of the modified transcripts that are not cross-linked to binding moieties. In one embodiment, the nuclease would cut off any remaining piece of a modified transcript that is not cross-linked to a binding moiety. However, typically, a population of "isolated cross-linked segments" of various lengths remains.

In one embodiment, the "isolated cross-linked segments" can be separated on the basis of length from other species in a sample. For example, the "isolated cross-linked segments" can be radiolabeled on the 5' end of the modified transcript and separated by SDS-PAGE gel electrophoresis, and/or further separated by Western blotting. Such separation means are useful for separating the isolated cross-linked segments from isolated segments that were not crosslinked to the binding moiety. The use of these separation techniques is known to those skilled in the art, and is described in, for example, *Methods in Enzymology: Guide to Molecular Cloning Techniques* (1987) Berger and Kimmel, eds. A protein of optimal length is then eluted from the gel. The optimal length is that length of a known binding moiety.

In a preferred embodiment, the binding moieties are removed from the "isolated cross-linked segments" to generate "isolated segments." The protein components of the binding moieties are removed by digesting the binding moieties with a protease. Preferably, digestion is effected by Proteinase K or a homologous enzyme. Proteinase K is capable of efficiently digesting protein binding moieties, liberating RNA and yielding products that can be used for ligation and amplification.

Other examples of classes of proteases or their homologues include: Aspartyl proteases, caspases, thiol proteases, Insulinase family proteases, zinc binding proteases, Cytosol Aminopeptidase family proteases, Zinc carboxypeptidases Neutral Zinc Metallopeptidases, extracellular matrix metalloproteinases, matrixins, Prolyl oligopeptidases, Aminopeptidases, Proline Dipeptidases, Methionine aminopeptidases, Serine Carboxypeptidases, Cathepsins, Subtilases, Proteasome A-type Proteases, Proteosome B-type Proteases, Trypsin Family Serine Proteases, Subtilase Family Serine Proteases, Peptidases, and Ubiquitin carboxyl-terminal hydrolases.

The "isolated cross-linked segments" and/or the "isolated segments" are then reverse transcribed to generate cDNA transcripts. Note that although it is preferred to remove the binding moiety before reverse transcription (i.e., to reverse transcribe the isolated segments), it is also possible to reverse transcribe the isolated cross-linked segments (i.e., the segments to which a whole or partial binding moiety is attached).

The introduction of the photoreactive nucleoside yields a mutation in the cDNA transcript when the isolated crosslinked segment is reverse transcribed. For example, the thiouridine analog is reverse transcribed to a deoxyguanosine instead of the deoxyadenosine that is normally incorporated into the reverse transcribed cDNA by Watson-Crick base pairing.

The thioguanosine analog is reverse transcribed to a deoxythymidine instead of the deoxycytidine normally incorporated by Watson-Crick base-pairing. Therefore, the mutation within the cDNA transcript is located within a binding site.

The cDNA transcripts are then amplified, thereby generating cDNA amplicons. When the thiouridine analog is reverse transcribed to produce the mutation of a deoxyguanosine instead of the deoxyadenosine, as described above, the respective cDNA transcripts, when amplified, will include a mutation wherein the expected deoxythymidine is replaced with a deoxycytidine in the amplicons.

When the thioguanosine analog is reverse transcribed to produce the mutation of a deoxythymidine instead of the deoxycytidine, as described above, the respective cDNA transcripts, when amplified, will include a mutation wherein the expected deoxyguanosine is replaced by a deoxyadenosine in the amplicons.

The reverse transcription and amplification can be performed by methods known in the art. For example, the reverse transcription to generate cDNA transcripts and amplification can be achieved using linker ligation and RT-PCR thereby generating amplified cDNA transcripts.

In one embodiment, to prepare cDNA from the "isolated cross-linked segments" and/or the "isolated segments" (i.e., the isolated small RNAs), first synthetic oligonucleotide adapters of known sequence are ligated to the 3' and 5' ends of the small RNA pool using T4 RNA ligases. The adapters introduce primer-binding sites for reverse transcription and PCR amplification.

Along with the "isolated cross-linked segments" and/or the "isolated segments," the small RNA pool typically comprises contaminants resulting from the nuclease digests of very abundant transcripts and non-coding RNAs such as ribosomal RNAs. If desired, non-palindromic restriction sites present within the adapter/primer sequences can be used for generation of concatamers to increase the read length for conventional sequencing or longer size range 454 sequencing.

As will be appreciated by those in the art, the attachment, or joining, of the adapter sequence to the "isolated cross-linked segments" and/or the "isolated segments" can be done in a variety of ways. For example, the adapter sequence can be attached either on the 3' or 5' ends, or in an internal position of "isolated cross-linked segments" and/or the "isolated segments."

In one embodiment, precautions can be taken to prevent circularization of 5' phosphate/3' hydroxyl small RNAs during adapter ligation. For example, chemically pre-adenylated 3' adapter deoxyoligonucleotides, which are blocked at their 3' ends to avoid their circularization, can be used. The use of pre-adenylated adapters eliminates the need for ATP during ligation, and thus minimizes the problem of adenylation of the pool RNA 5' phosphate that leads to circularization. Additionally, a truncated form of T4 RNA ligase 2, Rnl2(1-249), or an improved mutant, Rnl2(1-249)K227Q, can be used to minimize adenylate transfer from the 3' adapter 5' phosphate to the 5' phosphate of the small RNA pool and subsequent pool RNA circularization. See also International Patent Application No. PCT/US2008/001227, published as WO 2008/094599, which is incorporated herein by reference in its entirety.

The length of the adapter sequences will vary. In a preferred embodiment, adapter sequences range from about 6 to about 500 nucleotides in length, preferably from about 8 to about 100, and most preferably from about 10 to about 25 nucleotides in length.

The cDNA amplicons are then sequenced. The sequencing can be performed by any known means. In a preferred embodiment, the sequencing method will generate sequences of amplicons of at least about 20 nucleotides in length.

For example, the amplicons can be sequenced using Solexa massive parallel sequencing which yields 30 million sequences of 32, 36 or 72 nucleotides in length per library and sequencing reaction. Solexa sequencing can also be carried out conveniently at a smaller scale processing a larger sample number, i.e. yielding about 1.5-4 million reads per sample. The larger sets are obtained, if a full sequencing plate is used. (See M. Hafner, P. Landgraf, J. Ludwig, A. Rice, T. Ojo, C. Lin, D. Holoch, C. Lim, T. Tuschl, Identification of microRNAs and other small regulatory RNAs using cDNA library sequencing, *Methods,* 2008, 44:3-12.) Alternatively, the amplicons can be sequenced using pyrosequencing (454 sequencing, Roche), which provides up to 400,000 sequences of up to 250 nt in length for a single read. Data management and sequence analysis from small RNA cDNA libraries is best carried out in collaboration with an experienced computational biology laboratory.

Next, the amplicons are assessed in order to identify those that include the portion of the RNA transcript that binds to the binding moiety in vivo.

In one embodiment, first unique sequences (i.e., nonredundant sequences) are identified and counted. Preferably, by various steps, the amplicons are filtered to remove irrelevant sequences (i.e., irrelevant amplicons). For example, the amplicon sequences can be filtered in accordance with any or all for the following rules:

The selected amplicons should have sufficient length to enable identification by means of sequencing or hybridization.

The selected amplicons should not have highly repetitive portion(s) within their sequence.

The selected amplicons should avoid sequences that may interfere with the manipulation of RNA and DNA while performing the invention (e.g. they should not have recognition sites for restriction endonuleases used during the manipulation process).

For example, the amplicons are narrowed to those more likely to include the portion of the RNA transcript that binds to the binding moiety in vivo. For example, in one embodiment, amplicons which are shorter than a certain number are removed, for example, less than 20 nucleotides or less than 15 nucleotides. Additionally, amplicons that do not map to a portion of the reference sequence being studied and/or amplicons that do not map to a portion of a known RNA sequence can be removed. Further, amplicons which contain highly repetitive portion(s) within their sequence (e.g., many multiples of TATA or GCGC) can be removed. Such sequences are referred to as "low entropic sequences."

A "reference sequence" refers to any known sequence with which to compare an amplicon sequence. The reference sequence may be derived from a genomic sequence, a transcriptome sequence, an expressed sequence tags (EST) database, a sequence from which the RNA transcript was extracted, a known sequence library, a synthetic nucleotide sequence, a randomized RNA sequence, or a known RNA sequence. Typically, the human genomic sequence is being studied.

Next, the amplicons with overlapping sequences are "clustered." "Clustering" refers to grouping together and aligning overlapping sequences.

In one embodiment, the quantities of amplicons in a particular cluster are then counted. For example, overlapping amplicon sequences, which differ by length simply because of a different point of digestion by a nuclease, can be counted as a cluster. For example, if ribonuclease-T1 is used, then a set of overlapping amplicons that differ by length because they extend to the next guanosine site are considered a cluster. Accordingly, in one embodiment, aligning the sequences of the amplicons includes determining which amplicons have the characteristic that, when aligned with the reference sequence, the reference sequence has a guanosine one nucleotide upstream from the 5' end of the amplicons.

In another embodiment, aligning sequences occurs without narrowing down the amplicons in quantity before analyzing the amplicons.

The greater the quantity of amplicons in a particular cluster, the more likely that those amplicons include an RNA sequence expressed in vivo as opposed to being merely noise. (For example, see FIG. 2.) (See P. Berninger, D. Gaidatzis, E. van Nimwegen, M. Zavolan, Computational analysis of small RNA cloning data, Methods, 2008, 44, 13-21.)

Noise is the low frequency amplicon counts that are due to random degradation or RNA turnover products present as background in cross-linked RNA recovered from IP or gels. In one embodiment, noise is detected by the absence of a deoxythymidine to deoxycytidine mutation when using a thiouridine analog, such as 4-thiouridine, as the photoreactive nucleoside or by the absence of a deoxyguanosine to deoxyadenosine mutation when using a thioguanosine analog, e.g., 6-thioguanosine, as the photoreactive nucleoside. Noise can also be detected by the absence of very sharp "peaks" on a given transcript. Noise is seen as a random distribution of amplicons along a transcript.

In a further embodiment, aligning the sequences of the amplicons includes determining which amplicons have a mutation (preferably, a mismatch mutation) when compared to the reference sequence. For example, aligning the sequences of the amplicons may include determining which amplicons have a mutation wherein a deoxythymidine of the reference sequence is replaced by a deoxycytidine in the amplicons, when a thiouridine analog, such as 4-thiouridine, is used as the photoreactive nucleoside.

As another example, aligning the sequences of the amplicons may include determining which amplicons have a mutation wherein a deoxyguanosine of the reference sequence is replaced by a deoxyadenosine in the amplicons when using a thioguanosine analog, e.g., 6-thioguanosine, as photoreactive nucleoside. In one embodiment, such amplicons that are determined to have a mismatch mutation when compared to the reference sequence are considered "valid amplicons."

In a preferred embodiment, the aligning the sequences of the amplicons includes determining which amplicons have at least one mismatch mutation when compared to the reference sequence. In another preferred embodiment, the step of aligning the sequences of the amplicons includes determining which amplicons have only one mismatch mutation when compared to the reference sequence.

A "mismatch" as used herein refers to a nucleic acid base that is any other nucleic acid base located on an amplicon at a specific position compared to the nucleic acid base that is aligned to the reference sequence. For example, at Position 1 on the amplicon is a thymidine, and on the reference sequence that is aligned, at Position 1, the mismatch can be Adenosine, Guanosine, or Cytosine. The mismatch between the amplicon and reference sequence may be due to deletions, insertions, substitutions, or frameshift mutations in the amplicon or reference sequence.

The sequences of the amplicons are then analyzed to determine the specific location on an RNA transcript that a given binding moiety binds in vivo, i.e., to determine the binding site. In this method, the amplicons are further narrowed down to find "valid amplicons." A "valid amplicon" as used herein refers to an amplicon that is not noise, as described above.

A "valid amplicon" includes those having a mutation resulting from the introduction of the photoreactive nucleoside. For example, one method by which to find "valid amplicons" is to use the deoxythymidine to deoxycytidine mutation. Clustered amplicons with only a single mutation with respect to the "reference sequence," i.e., the deoxythymidine to deoxycytidine mutation, are located. It is considered that the mutation occurred upon reverse transcription as described above. Such amplicons are considered to be "valid."

Another method by which to find "valid amplicons" is to use the deoxyguanosine to deoxyadenosine mutation. Clustered amplicons with only a single mutation with respect to the "reference sequence," i.e., the deoxyguanosine to deoxyadenosine mutation, are located. It is considered that the mutation occurred upon reverse transcription, as described above. Such amplicons are also considered to be "valid."

Preferably, these "valid amplicons" are assessed in view of the total number of sequences that aligned to the region at issue, i.e., the total amplicons in a particular cluster. The total number of aligned sequences includes those sequences that have the mutation and those that do not have the mutation. The greater the percentage of the total aligned amplicons that show the mutation, the greater is the probability that the amplicons showing the mutation are "valid amplicons."

When assessing the percentage, it is preferable to take into account the quantity of total aligned amplicons i.e., the total amplicons in a particular cluster. For example, a low percentage (e.g., 1% to 49%) is adequate to demonstrate a "valid amplicon" if the total quantity of aligned sequences is large (20 amplicons or more); and a high percentage (e.g., 50% to 100%) is adequate to demonstrate a "valid amplicon" if the total quantity of aligned sequences is small (19 amplicons or less. At least 10% of the sequences have to show the mutation to indicate a "valid amplicon."

Another method by which to further validate "valid amplicons" is to use the property of ribonuclease-T1 to cleave the modified RNA transcript at 3' phosphates of guanine residues. The modified transcripts were treated with ribonuclease-T1 to remove all or part of the modified RNA transcripts which was not covalently cross-linked to the binding moiety. In particular, it is determined which amplicon sequences have the characteristic that, when aligned with the "reference sequence" (i.e., in a particular cluster), the "reference sequence" has a guanosine one nucleotide upstream from the 5' end of the amplicons. Such amplicons are also considered to be "valid amplicons."

Preferably, an amplicon is considered to be a "valid amplicon" if it is considered to be valid by both the method of using the mutation and the method of using the cleaving property of ribonuclease-T1.

Once "valid amplicons" have been identified, they are further analyzed in view of the "reference sequence" to determine the presence of a consensus motif or sequence within a binding site. The binding site can be part of coding transcript or non-coding transcript of RNA.

For example, the deoxythymidine to deoxycytidine mutation and/or the deoxyguanosine to deoxyadenosine mutation in the amplicon is used as an anchor for comparing the sequence surrounding the mutation to the "reference sequence." Such surrounding sequence is termed "sequence window."

In one embodiment, the "sequence window" includes the mutation plus at least one nucleotide on either side of the mutation. Preferably, the number of nucleotides on either side of the mutation ranges from about 5 to about 20 nucleotides. In another embodiment, the mutation is at the center of the sequence window.

Figure 3A:
FIG. 3. RNA recognition sites of QKI protein. A Domain structure of QKI protein. B Phosphorimage of SDS polyacrylamide gel resolving radiolabeled RNA crosslinked to FLAG/HA-QKI IPs from non-irradiated or UV-irradiated 4SU-labeled cells. The lower panel shows the anti-HA immunoblot controlling for uniform gel loading. C Two alignments of PURE-CLIP cDNA sequence reads to the corresponding regions of the 3'UTRs of the Refseq CTNNB1 and HOXD13 transcripts, respectively. Red bars indicate the QKI recognition motif and red-letter nucleotides indicate T to C sequence changes. D Weblogo of the QKI recognition motif generated by PhyloGibbs analysis of the top 100 sequence read clusters. E Analysis of the T to C positional mutation frequency for PURE-CLIP clusters anchored at the recognition motif AUUAAY (left panel) and ACUAAY (right panel) from all motif-containing clusters. The dashed line represents the average T to C mutation frequency within the clusters. F Sequences of synthetic 4SU-labeled oligoribonucleotides with QKI recognition motifs, derived from a sequence read cluster aligning to the 3'UTR of HOXD13 (see c). G Phosphorimage of SDS polyacrylamide gel resolving 5'-32P-RNA-labeled recombinant QKI protein after crosslinking with oligoribonucleotides shown in f. H Assessment of mutational biases of 4SU labeling before and after crosslinking. The oligoribonucleotide U2 (sequence is shown in F) was crosslinked to recombinant QKI (red line) or sequenced before crosslinking (black line). The position-dependent mutation rate is shown for the two libraries and was obtained from analysis of 500 clones per library. I Stabilization of QKI44 bound transcripts upon siRNA knockdown. Two distinct siRNA duplexes (1 and 2) were used for QKI knockdown and transcript stability changes relative to mock transfection were derived from Affymetrix microarray analysis. Distributions of changes upon siRNA transfection for QKI PURE-CLIP target transcripts versus non-targeted messages are shown. The p-values indicate the significance of the difference between the changes of target versus non-target transcripts, as given by the Wilcoxon rank-sum test.
Figure 3B:
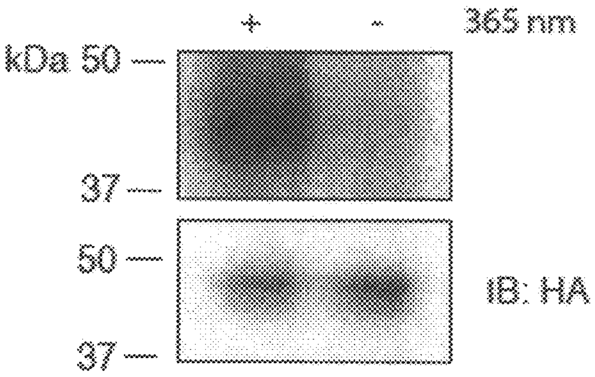
Figure 3:
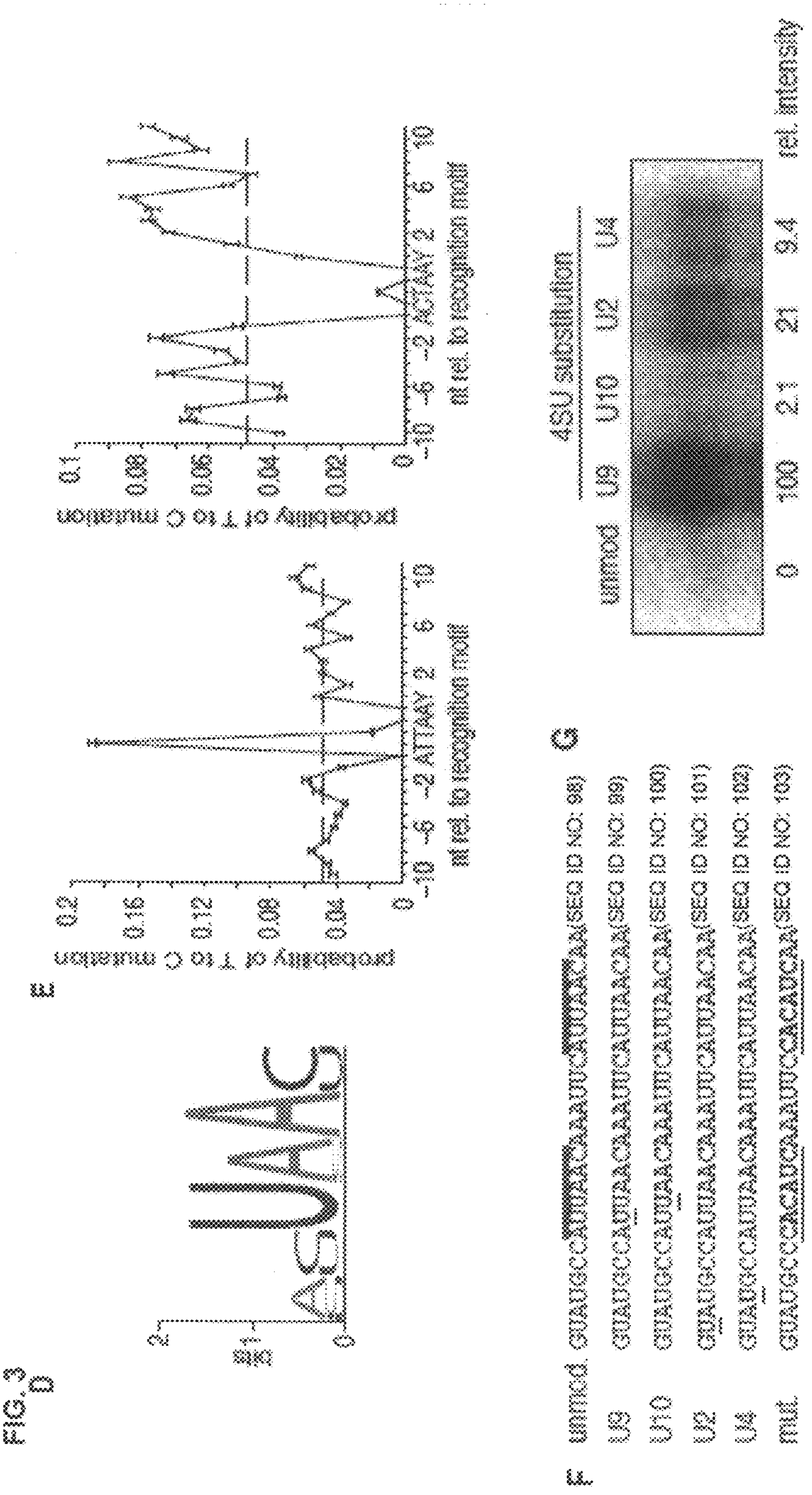
Figure 3:
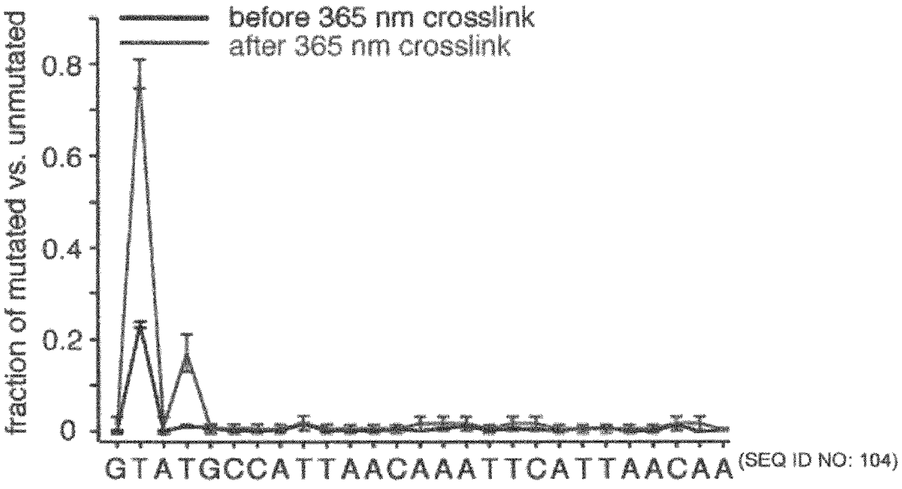
Figure 3:
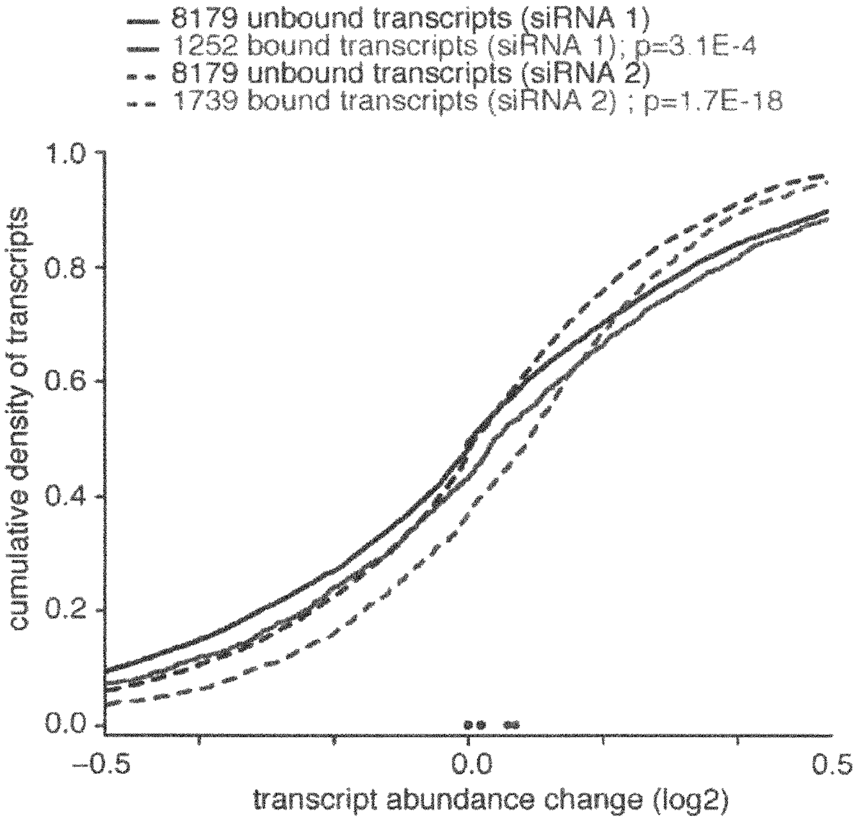

As an illustration, see FIG. 3 for the alignment of amplicons against Pum2-targeted transcript. The Pum2 motif contains the mutated deoxythymidine in the recognition element TGTANATA (the underlined T is mutated in every valid amplicon).

As is known in the art, a number of different programs and algorithms may be used to identify whether an amplicon has sequence identity or similarity to a known sequence. Sequence identity and/or similarity is determined using standard techniques known in the art, including, but not limited to, the local sequence identity algorithm of Smith & Waterman, Adv. Appl. Math., 2:482 (1981), by the sequence identity alignment algorithm of Needleman & Wunsch, J. Mol. Biol., 48:443 (1970), by the search for similarity method of Pearson & Lipman, Proc. Natl. Acad. Sci. U.S.A., 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res., 12:387-395 (1984), preferably using the default settings, or by inspection. All references cited in this paragraph are incorporated by reference in their entirety.

In one embodiment, motif searches are conducted for the extracted sequences by computational means known in the art. Examples of methods used in conducting motif searches (i.e., consensus sequence searches) include CONSENSUS, multiple expectation maximization for motif elicitations (MEME) program, Gibbs sampling, PhyloGibbs sampling, Motif Discovery scan program (MDScan), or AlignACE (Roth, F. P., Hughes, J. D., Estep, P. W. & Church, G. M. Finding DNA regulatory motifs within unaligned noncoding sequences clustered by whole-genome mRNA quantitation. *Nat Biotechnol* 16, 939-45 (1998)). For example, the MEME program finds conserved ungapped short motifs within a group of related, unaligned sequences (Bailey and Gribskov, 1998, J Comput Biol, 5:211-21). MDScan, for example, is used to identify sequence motifs from a set of identified genomic regions (Liu X S et al. (2002) *Nat. Biotechnol.,* 20(8):835-9). In another embodiment, more than one algorithm may be used to identify motifs for the extracted sequences.

In one embodiment, the analysis of the amplicon sequences can further include identifying a feature required for interaction of the binding site and the binding moiety. For example, evaluation of the consensus sequence of the binding site can reveal a structure, such as a stem loop, that may be required or involved in binding to the binding moiety. Additionally, the property of the ribonuclease-T1 cleavage can further be used to validate the sequences, as described above.

Once the consensus motif of the binding site has been identified using the methods described above, it can be utilized for various clinical or research applications. For example, the binding site can be sequenced using patient DNA to identify mutations, deletion or insertions that may link a genetic alteration in an important, regulatory RNA segment to a disease condition. It is known that RNA binding proteins are essential regulators of proteins by binding to coding and non-coding RNAs and regulating their transcription, modification, splicing, nuclear export, transport and translation. Consequently, understanding the binding site on the RNA and the identity of the bound RNA binding proteins offer ways to targeted therapy. For example, an RNA binding protein known to affect the stability or translation of a gene can be utilized as a drug target for the regulation of the targets of the gene.

In one embodiment, the present invention is kit for identifying a binding site on an RNA transcript. The kit comprises a thiouridine analog, as described above, or thiouridine analog-supplemented tissue culture medium; reagents for nuclease digestion, as described above; reagents for immunoprecipitation, as described above; and adapters and primers for small RNA cloning.

EXAMPLES

Example 1

Oligonucleotides

The following oligodeoxynucleotides were used for PCR and cloning of the listed genes (restriction site are underlined);

```
Pum2:
                                   (SEQ ID NO: 7)
5'-ATGAATCATGATTTTCAAGCTCTTGCATTAG,
                                   (SEQ ID NO: 8)
ATAAGAATGCGGCCGCTTACAGCATTCCATTTGGTGGTCCTCCAATAG;

QKI:
                                   (SEQ ID NO: 9)
ACGCGTCGACATGGTCGGGGAAATGGAAACG,
                                  (SEQ ID NO: 10)
ATAAGAATGCGGCCGCTTAGCCTTTCGTTGGGAAAGCC;

IGF2BP1:
                                  (SEQ ID NO: 11)
ACGCGTCGACATGAACAAGCTTTACATCGGCAACCTC,
                                  (SEQ ID NO: 12)
ATAAGAATGCGGCCGCTCACTTCCTCCGTGCCTGGGCCTG;
```

-continued

```
IGF2BP2:
                                  (SEQ ID NO: 13)
ACGCGTCGACATGATGAACAAGCTTTACATCGGGAAC,
                                  (SEQ ID NO: 14)
ATAAGAATGCGGCCGCTCACTTGCTGCGCTGTGAGGCGAC;

IGF2BP3:
                                  (SEQ ID NO: 15)
ACGCGTCGACATGAACAAACTGTATATCGGAAACCTCAG,
                                  (SEQ ID NO: 16)
ATAAGAATGCGGCCGCTTACTTCCGTCTTGACTGAGGTGGTC;
```

Plasmids

Plasmids pENTR4 IGF2BP1, -2, -3, QKI, and PUM2 were generated by PCR amplification of respective coding sequences (CDS) followed by restriction digest and ligation into pENTR4 (Invitrogen). Primer sequences are listed under DNA oligonucleotides in Suppl. Material. pENTR4 IGF2BP1, -2, and -3 were recombined into pFRT/TO/FLAG/HA-DEST destination vector using GATEWAY LR recombinase according to manufacturer's protocol (Invitrogen), which allow for inducible expression of stably transfected FLAG/HA-tagged protein in Flp-In T-REx HEK293 cells (Invitrogen) from the TO/CMV promoter. Whereas pENTR4 QKI and pENTR4 QKI were recombined into pFRT/FLAG/HA-DEST, which only allows constitutive expression in Flp-In T-REx HEK293 cells. Plasmids for overexpression of N-terminally His-tagged IGF2BP1, -2, and -3 were generated by ligation of CDS into pET16 (Novagen). The plasmids described in this study can be obtained from Addgene.

Recombinant Protein Expression pET16 IGF2BP1, -2, and -3 plasmid were transformed in *E. coli* STAR(DE3) (Invitrogen). Cells were grown in LB supplemented with 50 μg/ml ampicillin at 37° C. to $A_{600}$=0.5. Culture was cooled to 25° C. for induction of soluble protein by addition of IPTG to a final concentration of 1 mM. Incubation was continued at 25° C. for 3 h before cells were harvested and resuspended in 8 ml/g cells of lysis buffer (25 mM Tris-HCl, pH 7.5, 0.5 M NaCl, 5 mM imidazole, and complete EDTA-free protease inhibitor cocktail (Roche)) All following steps were carried out at 4° C. Cells resuspended in lysis buffer were sonicated to complete lysis. Insoluble material was removed by centrifugation at 12,000×g. Supernatant was incubated with 250 μl/10 ml cell supernatant HIS-Select Cobalt Affinity Gel (Sigma) for 1 h. The affinity gel was washed three times with 10 gel volumes of lysis buffer and His-tagged proteins were eluted in 4 gel volumes of 25 mM Tris-HCl, pH7.5, 0.5 M NaCl, and 250 mM imidazole.

Cell Lines and Cell Culture

HEK293 T-REx Flp-In cells (Invitrogen) were grown in D-MEM high glucose (1×) with 10% (v/v) fetal bovine serum, 1% (v/v) 2 mM L-glutamine, 1% (v/v) 10,000 U/ml penicillin/10,000 μg/ml streptomycin, 100 μg/ml zeocin and 15 μg/ml blasticidin. Cell lines stably expressing FLAG/HA-tagged proteins were generated by co-transfection of pFRT/TO/FLAG/HA or pFRT/FLAG/HA constructs with pOG44 (Invitrogen). Cells were selected by exchanging zeocin with 100 μg/ml hygromycin. Expression of FLAG/HA-IGF2BP1, -2, -3 was induced by addition of 250 ng/ml doxycycline 15-20 h before crosslink.

UV 254 nm or UV 365 nm Crosslinking

For UV crosslink, cells were washed once with ice-cold PBS while still attached to the plate. PBS was removed completely and cells were irradiated with 254 nm UV light, or 365 nm UV light for cells treated with nucleoside analogues (0.15 $J/cm^2$) using a UV Stratalinker 2400 (Stratagene). After UV treatment, 5 ml of ice-cold PBS was added per plate immediately. Cells were scraped off the plate and collected by centrifugation in 15 ml Falcon tubes (Sorvall legend RT, 2000 rpm, 10 min, 4° C.).

Cell Lysis and Partial RNase T1 Digestion

The pellets of 365 nm UV-crosslinked cells (ca. 3 ml cell pellet for about 20 15 cm cell culture dishes) were resuspended in approximately 3 cell pellet volumes of NP40 lysis buffer (50 mM HEPES, pH 7.5, 150 mM KCl, 2 mM EDTA, 1 mM NaF, 0.5% (v/v) NP40, 0.5 mM DTT, complete EDTA-free protease inhibitor cocktail (Roche)) and passively incubated on ice for 10 min. The cell lysate was cleared by centrifugation in 13 ml polypropylene tubes (Sorvall SS34, 13,000 rpm, 10 min, 4° C.) and the supernatant was passed through a 0.5 μm Supor membrane syringe filter (Pall). RNase T1 (Fermentas) was added to the cleared cell lysates to a final concentration of 1 U/μl and incubated in a water bath at 22° C. for 15 min and subsequently cooled for 5 min on ice before addition of antibody-conjugated magnetic beads (see below).

Immunoprecipitation and Recovery of Crosslinked Target RNA Fragments

Preparation of Magnetic Beads

Conjugation of antibodies to magnetic beads was performed the same day as the immunoprecipitation (IP). Dynabeads Protein G magnetic particles (Invitrogen) were resuspended by vortexing and an aliquot (10 μl for per ml cell lysate) was transferred to an Eppendorf tube. Beads were collected with the Dynal MPC-S magnetic particle concentrator (Invitrogen) for removal of the supernatant. Beads were washed twice with 1 ml of citrate-phosphate buffer (pH 5.0, 4.7 g/l citric acid, 9.2 g/l $Na_2HPO_4$) and resuspended in twice the volume of citrate-phosphate buffer relative to the original volume of bead suspension. 0.25 μg of anti-FLAG M2 monoclonal antibody (Sigma) per ml suspension was added and incubated on a rotating wheel at room temperature for 40 min. Beads were then washed twice with 1 ml of citrate-phosphate buffer to remove unbound antibody and resuspended again in twice the volume of citrate-phosphate buffer relative to the original volume of bead suspension.

Immunoprecipitation (IP), Further RNase T1 Digestion, and Dephosphorylation

A typical IP for an average expressed RNA-binding protein requires about 10 ml crosslinked and partially RNase T1 digested lysate (see above). 10 μl of freshly prepared antibody-conjugated magnetic beads per ml of cell lysate were added and incubate in 15 ml centrifugation tubes on a rotating wheel for 1 h at 4° C. Magnetic beads were collected on a magnetic particle collector (Invitrogen). Manipulations of the following steps were carried out in 1.5 ml centrifugation tubes. The supernatant was removed from the bead-bound material, which was washed 3 times with 1 ml of IP Wash Buffer (50 mM HEPES-KOH, pH 7.5, 300 mM KCl, 0.05% (v/v) NP40, 0.5 mM DTT, complete EDTA-free protease inhibitor cocktail (Roche)). Beads were resuspended in one volume (here and in following steps volume refers to volume of used bead suspension) of IP Wash Buffer. RNase T1 (Fermentas) was added to obtain a final concentration of 100 U/μl, and the bead suspension was incubated in a water bath at 22° C. for 15 min, and subsequently cooled for 5 min on ice. Beads were washed 3 times with 1 ml of High-Salt Wash Buffer (50 mM HEPES-KOH, pH 7.5, 500 mM KCl, 0.05% (v/v) NP40, 0.5 mM DTT, complete EDTA-free protease inhibitor cocktail (Roche)) and resuspended in one volume of Dephosphorylation Buffer (50 mM Tris-HCl, pH 7.9, 100 mM NaCl, 10 mM $MgCl_2$, 1 mM DTT). Calf Intestinal Alkaline Phosphatase (NEB) was added to obtain a final concentration of 0.5 U/μl, and the suspension was incubated for 10 min at 37° C. Beads were washed twice with 1 ml of Phosphatase Wash Buffer (50 mM Tris-HCl, pH 7.5, 20 mM EGTA, 0.5% (v/v) NP40) and twice with 1 ml of Polynucleotide Kinase (PNK) Buffer (50 mM Tris-HCl, pH 7.5, 50 mM NaCl, 10 mM $MgCl_2$, 5 mM DTT). Beads were resuspended in one volume of Polynucleotide Kinase Buffer.

Radiolabeling of RNA Segments Crosslinked to Immunoprecipitated Proteins

To the bead suspension described above, γ-$^{32}$P-ATP (GE Healthcare, formerly Amersham Biosciences) was added to a final concentration of 0.5 μCi/μl and T4 Polynucleotide Kinase (NEB) to 1 U/μl. The suspension was incubated for 30 min at 37° C. Thereafter, non-radioactive ATP (Fermentas) was added to obtain a final concentration of 100 μM and the incubation was continued for another 5 min at 37° C. The magnetic beads were then washed 5 times with 800 μl of PNK Buffer and resuspended in 70 μl of SDS-PAGE Loading Buffer (10% glycerol (v/v), 50 mM Tris, pH 6.8, 2 mM EDTA, 2% SDS (w/v), 100 mM DTT, 0.1% Bromophenol blue).

SDS-PAGE and Electroelution of Crosslinked RNA-Protein Compounds from Gel Slices The radiolabeled bead suspension was denatured for 5 min at 95° C., and the supernatant, which was separated from the magnetic beads, was loaded in 2 wells of a NuPAGE Novex 4-12% BT Midi 1.0 gel (Invitrogen) next to well loaded with 5 μl of Precision Plus Protein Dual Color Standard (BioRad). The gel was run for 1 h at 200 V in NuPAGE MOPS SDS Running Buffer (Invitrogen). To detect radiolabeled bands, the gel was covered in Saran plastic wrap and analyzed by phosphorimaging. The radioactive band migrating at the expected molecular weight of the target protein and any other distinct molecular size bands, were excised from the gel and electroeluted in a D-Tube Dialyzer Midi with a molecular cut-off of 3.5 kD (Novagen). The electroelution was performed at 100 V for 2 h in SDS Running Buffer (25 mM Tris base, 192 mM glycine, 0.1% (w/v) SDS). The eluate (approx. 400 μl) was transferred to an Eppendorf tube.

Proteinase K Digestion

An equal volume of 2× Proteinase K Buffer (100 mM Tris-HCl, pH 7.5, 150 mM NaCl, 12.5 mM EDTA, 2% (w/v) SDS) with respect to the electroeluate was added, followed by the addition of Proteinase K (Roche) to a final concentration of 1.2 mg/ml, and and incubation for 30 min at 55° C. The RNA was recovered by acidic phenol/chloroform extraction. One volume of acidic phenol:chloroform:isoamyl alcohol (25:24:1) was added to the proteinase K digest and vortexed. Phases were separated by centrifugation in a tabletop centrifuge (13,000 rpm, 5 min). The upper aqueous phase was transferred to a new tube, extracted once with an equal volume of chloroform. The RNA was then precipitated from the aqueous phase after adding 1/10 volume of 3 M NaCl, 2 μl of 10 mg/ml GlycoBlue (Ambion) and 3 volumes of absolute ethanol. After incubation of at least 1 h on ice or overnight at −20° C., the precipitated RNA was collected by centrifugation (13,000 rpm, 20 min, 4° C.), and the pellet was dried and resuspended in 30 μl of sterile water.

cDNA Library Preparation and Deep Sequencing

The recovered RNA was carried through a cDNA library preparation protocol originally described for cloning of small regulatory RNA (Hafner, Methods, 2008). The first step, 3' adapter ligation, was carried out as described on a 20-μl scale using 10.5 μl of the recovered RNA. UV 254 nm crosslinked RNAs were processed using standard adapter sets, followed by PCR to introduce primers compatible with 454 sequencing; UV 365 nm crosslinked sample RNAs were processed using Solexa sequencing adapter sets. Depending on the amount of RNA recovered, fast migrating 5'-adapter-3'- adapter products without inserts may be detected after amplification of the cDNA. In such case, the expected longer PCR products was excised from a 3% NuSieve low-melt agarose, eluted from the gel pieces with the Illustra GFX-PCR purification kit (GE Healthcare) and directly submitted for Solexa sequencing. 454 pyrosequencing was carried out by Agnes Viale at the Sequencing core facility at Memorial Sloan Kettering Cancer Center, New York. Solexa sequencing was performed by Scott Dewell at the Genomics Resource Center of Rockefeller University.

2-D Electrophoresis

2-D electrophoresis begins with 1-D electrophoresis but then separates the molecules by a second property in a direction 90 degrees from the first. The two dimensions that proteins can be separated into using this technique can be, for example, isoelectric point, protein complex mass in the native state, and protein mass.

Example 2

PURE-CLIP

Human embryonic kidney (HEK) 293 cells stably expressing FLAG/HA-tagged IGF2BP1-3, QKI, and PUM2 (Landthaler et al., 2008, incorporated herein by reference in its entirety) were grown overnight in medium supplemented with 100 μM 4-thiouridine (4SU). Living cells were irradiated with 365 nm UV light (0.15 $J/cm^2$) n a Stratalinker 2400 (Stratagene). Cells were harvested and lysed in 3 cell pellet volumes of NP40 lysis buffer (50 mM HEPES-KOH, pH 7.5, 150 mM KCl, 2 mM EDTA, 1 mM NaF, 0.5% (v/v) NP40, 0.5 mM DTT, complete EDTA-free protease inhibitor cocktail (Roche)). The cell lysate was cleared by centrification at 13,000×g.

RNase T1 (Fermentas) was added to the cleared cell lysates to a final concentration of 1 U/μl and the reaction mixture was incubated at 22° C. for 15 min and subsequently cooled on ice before addition of antibody-conjugated magnetic beads. FLAG/HA-tagged AGO proteins were immunoprecipitated with anti-FLAG antibodies bound to Protein G Dynabeads. RNase T1 (Fermentas) was added to obtain a final concentration of 100 U/μl to the immunoprecipitate, and the bead suspension was incubated in a water bath at 22° C. for 15 min, and subsequently cooled for 5 min on ice. Beads were washed 3 times with wash buffer (50 mM HEPES-KOH, pH 7.5, 500 mM KCl, 0.05% (v/v) NP40, 0.5 mM DTT, complete EDTA-free protease inhibitor cocktail (Roche)) and resuspended in one volume of dephosphorylation buffer (50 mM Tris-HCl, pH 7.9, 100 mM NaCl, 10 mM MgCl2, 1 mM DTT). Calf intestinal alkaline phosphatase (NEB) was added to obtain a final concentration of 0.5 U/μl, and the suspension was incubated for 10 min at 37° C.

Beads were washed twice with phosphatase wash buffer (50 mM Tris-HCl, pH 7.5, 20 mM EGTA, 0.5% (v/v) NP40) and twice with polynucleotide kinase (PNK) Buffer (50 mM Tris-HCl, pH 7.5, 50 mM NaCl, 10 mM MgCl2, 5 mM DTT). The crosslinked RNA segments were radiolabeled on the magnetic beads with γ-32P-ATP and 1 U/μl T4 PNK (NEB). After incubation for 30 min at 37° C., non-radioactive ATP (Fermentas) was added to a final concentration of 100 μM and the incubation was continued for another 5 min.

The magnetic beads were then washed 5 times with PNK Buffer, resuspended in 70 μl of SDS-PAGE loading buffer, and incubated for 5 min at 95° C. The protein-RNA complexes were separated on a SDS-PAGE. The gel was analyzed by phosphorimaging. The radioactive band migrating at the expected molecular weight of AGO proteins was excised from the gel and electroeluted. The electroeluate was proteinase K digested. The RNA was recovered by acidic phenol/chloroform extraction followed by a chloroform extraction and an ethanol precipitation. The recovered RNA was carried through a small RNA cDNA library preparation protocol as described for cloning of small RNAs (Hafner et al., 2008) and Solexa sequenced.

The extracted sequence reads were mapped to the human genome (hg18) and human mRNAs. Transfection of siRNAs and mRNA profiling by array analysis were described previously (Landthaler et al., 2008).

Example 3

Figure 8A:
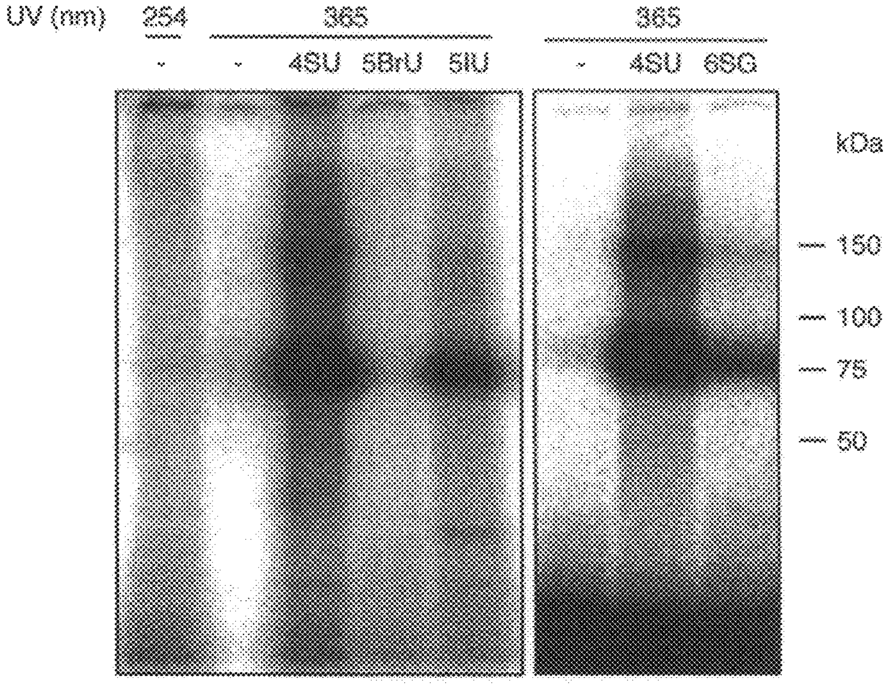
FIG. 8: A Full-size phosphorimages of a 4-12% gradient SDSpolyacrylamide gel from which a detail was shown in FIG. 1*b*. 5'-32P-Labeled RNA-FLAG/HA-IGF2BP1 immunoprecipitates (IPs) prepared from lysates from cells that were cultured in media in the absence or presence of 100 μM photoreactive nucleoside for 12 hrs and crosslinked with 365 nm UV. For comparison, a sample prepared from cells crosslinked at 254 nm, was included. The nucleoside analogues were 4-thiouridine (4SU), 5-bromouridine (5BrU), 5-iodouridine (5IU), and 6-thioguanosine. B Full-size phosphorimages of 5'-32P-labeled and crosslinked IPs for indicated RNA-binding protein as described in FIGS. 2A, 3A, and 4A.
Figure 8B:
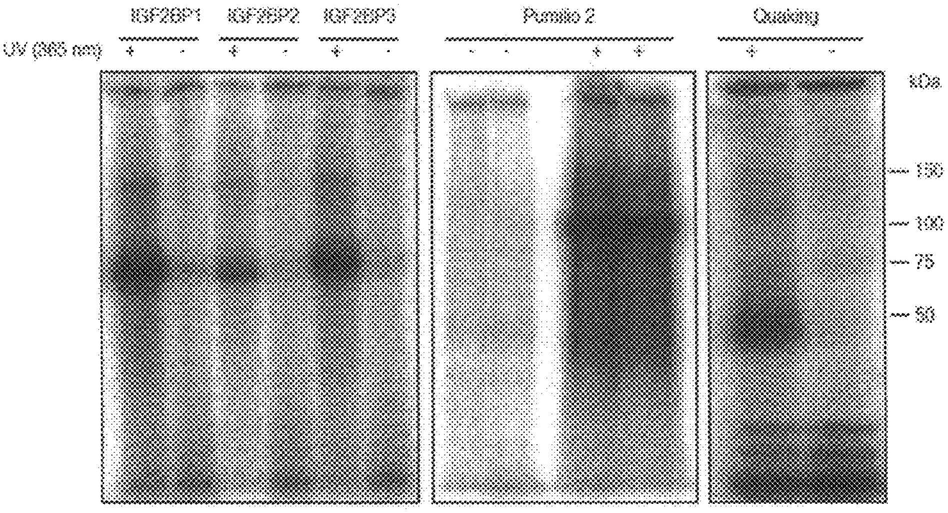
Figure 9A:
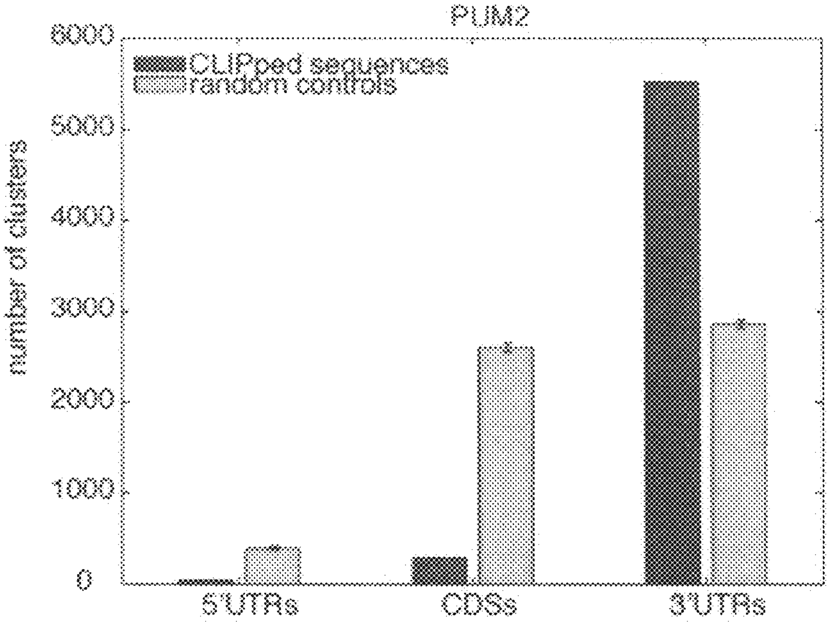
FIG. 9A-E: Analysis of the transcript regional preferences of IGF2BP1-3, PUM2 and QKI. For each protein, the number of exonic sequence read clusters annotated as derived from the 5'UTR, CDS or 3'UTR of a target transcript is shown (green bars). Yellow bars show the location distribution of the clusters if the RBPs would bind without regional preference to the target transcript.
Figure 9B:
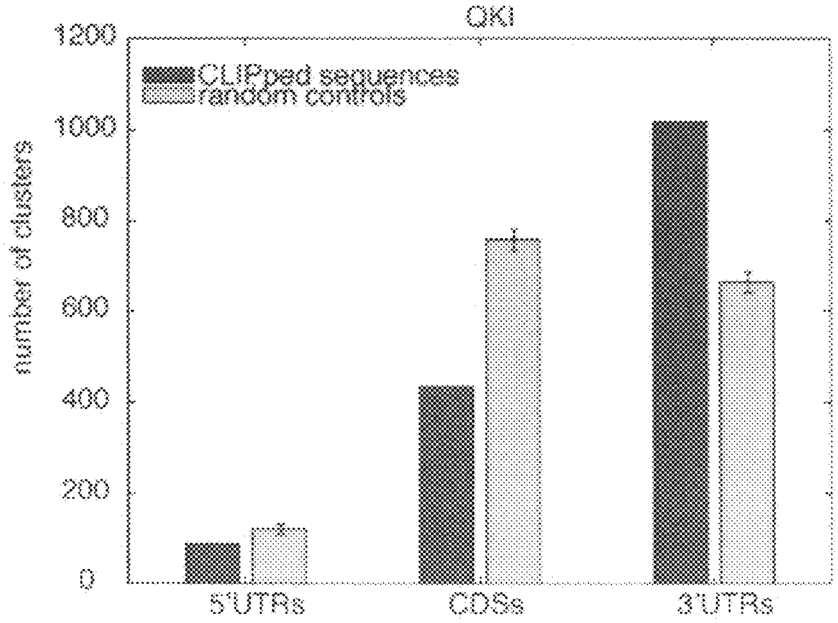
Figure 9C:
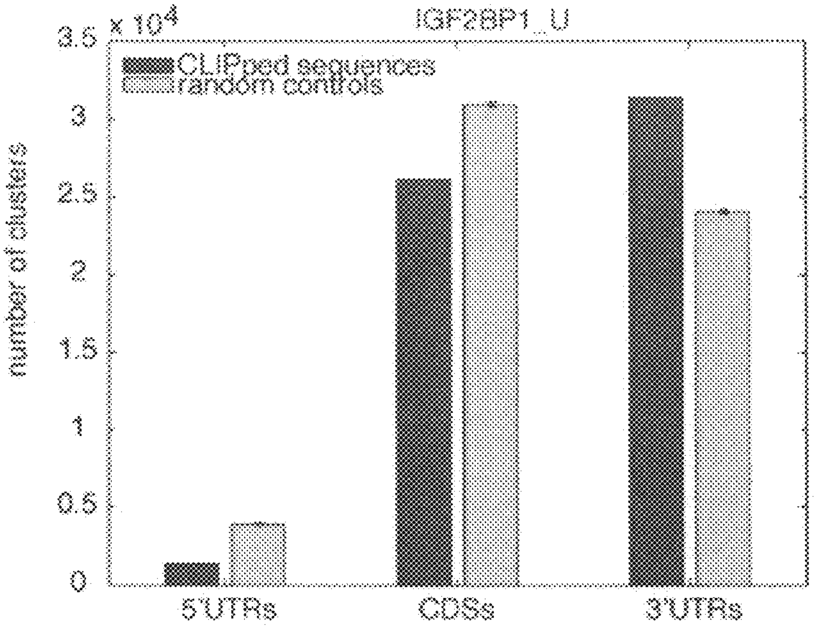
Figure 9D:
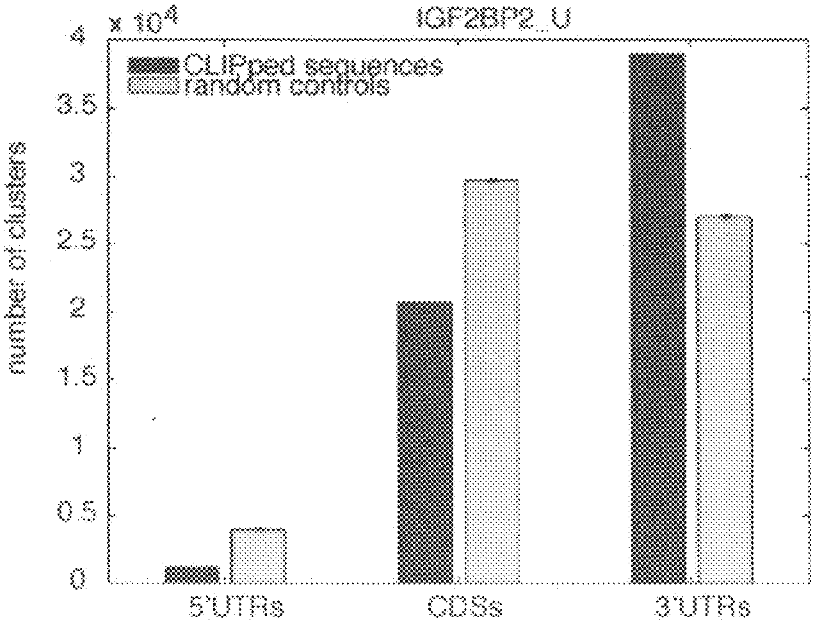
Figure 9E:
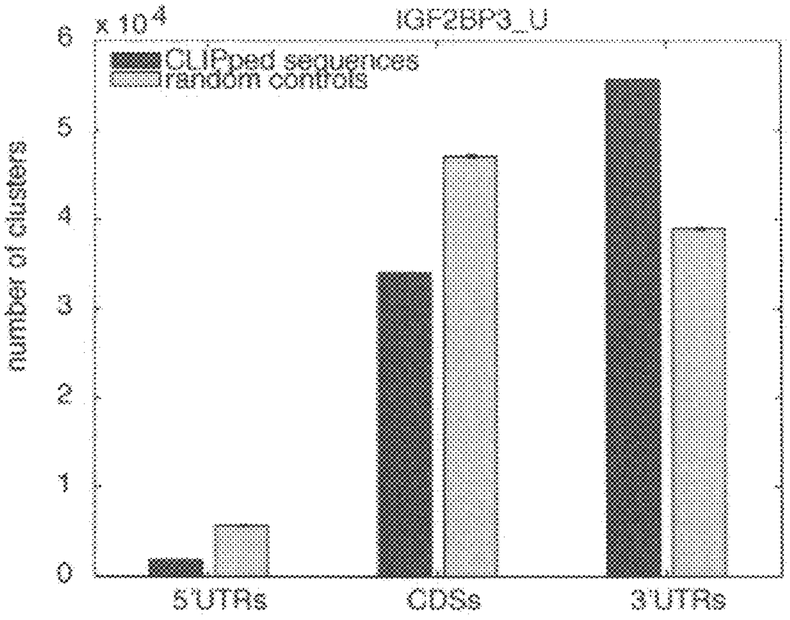

Application of Photoreactive Nucleosides to Cultured Cells Enhances UV Crosslinking Between RNA and RBP Incorporation of modified photoreactive nucleoside analogues into RNA facilitates UV crosslinking to RBPs (Meisenheimer and Koch, 1997), as shown previously for in vitro transcribed site-specifically labeled RNAs (Kirino and Mourelatos, 2008; Moore and Query, 1998). Several of these photoreactive nucleosides are excitable by longer wavelength UV (>300 nm) and are readily taken up by cells, where they are incorporated into nascent transcripts without noticeable toxicity and then can be used for in vivo crosslinking (Bezerra and Favre, 1990; Favre et al., 1986; Wagenmakers et al., 1980). We applied a subset of these nucleoside analogues (FIG. 1A) to cultured cells expressing the FLAG/HA-tagged RBP IGF2BP1. Live cells were UV-irradiated at 365 nm. The crosslinked RNA-protein complexes were isolated by immunoprecipitation, and the covalently bound RNA was partially digested with RNase T1 and radiolabeled. Separation of the radiolabeled RNPs by denaturing SDS gel electrophoresis indicated that 4SU-labeled RNA crosslinked most efficiently to IGF2BP1. Compared to unmodified UV 254 nm crosslinking, the nucleoside analogues enhanced RNA recovery between 100- and 1000-fold (FIG. 1B and FIG. 8). It is important to note that we did not optimize either short or long wavelength UV exposure to define the limits of crosslinking, but used standard laboratory UV crosslinking equipment at their high intensity settings and a time-window selected to minimize overheating and denaturation of cellular proteins.

Based on our initial analysis we selected 4SU as crosslinker. However, before we proceeded with analysis of IGF2BP proteins, for which the consensus binding sites were not known, we studied human Pumilio 2 (PUM2), a member of the well-studied Pufprotein family (FIG. 9A-E) with well defined consensus motifs (Wang et al., 2002; Wickens et al., 2002).

Example 4

Identification of Pumilio2 mRNA Targets and its RRE

Figure 2A:
FIG. 2. RNA recognition sites of PUM2 protein. A Domain structure of PUM2 protein. B Phosphorimage of SDS polyacrylamide gel resolving radiolabeled RNA crosslinked to FLAG/HA-PUM2 IPs from non-irradiated or UV-irradiated 4SU-labeled cells. The lower panel shows the anti-HA immunoblot controlling for uniform gel loading. C Two alignments of PURE-CLIP cDNA sequence reads to corresponding regions in the 3'UTR of ELF1 and HES1 Refseq transcripts, respectively. Sequence reads are shown in the order of their abundance. Red bars indicate the PUM2 recognition motif and red-letter nucleotides indicate T to C sequence changes. D Weblogo of the PUM2 recognition motif generated by PhyloGibbs analysis of the top 100 sequence read clusters. E Analysis of the T to C positional mutation frequency for PURE-CLIP clusters anchored at the 8-nt recognition motif from all motif-containing clusters. The dashed line represents the average T to C mutation frequency within the clusters.
Figure 2B:
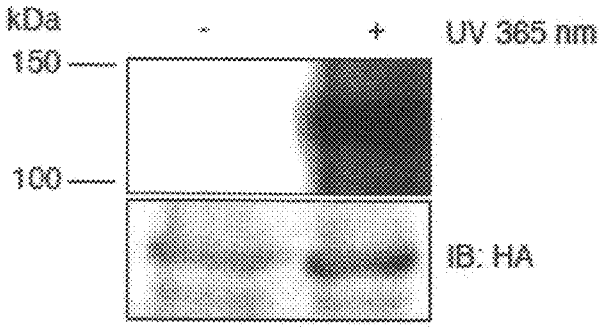

PUM2 protein, similar to IGF2BP1, readily crosslinked to 4SU-containing transcripts (FIG. 2B and FIG. 8B), and the crosslinked segments were converted into a cDNA library (FIG. 1C) and Solexa sequenced to obtain about 10 million reads (Hafner et al., 2008). The sequence reads were annotated by alignment against the human genome and EST databases. Sequence reads mapping to one unique position in the genome with up to one mismatch were used to build sequence clusters (FIG. 2C and Supplementary Methods). We identified 7,523 clusters mapping to about 3,000 unique transcripts, 93% of which were found within the 3'UTR, in agreement with previously published work characterizing the *C. elegans* members of this protein family (Wickens et al., 2002) (FIG. 9). All sequence clusters with information on the annotation and mapping are available online at the RNA regulatory networks-Zavolan lab website.

Figure 2D:
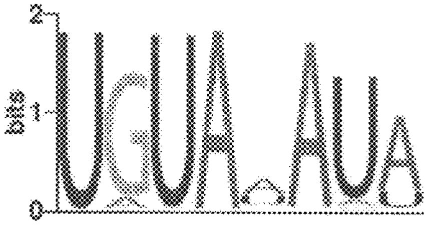
Figure 2E:
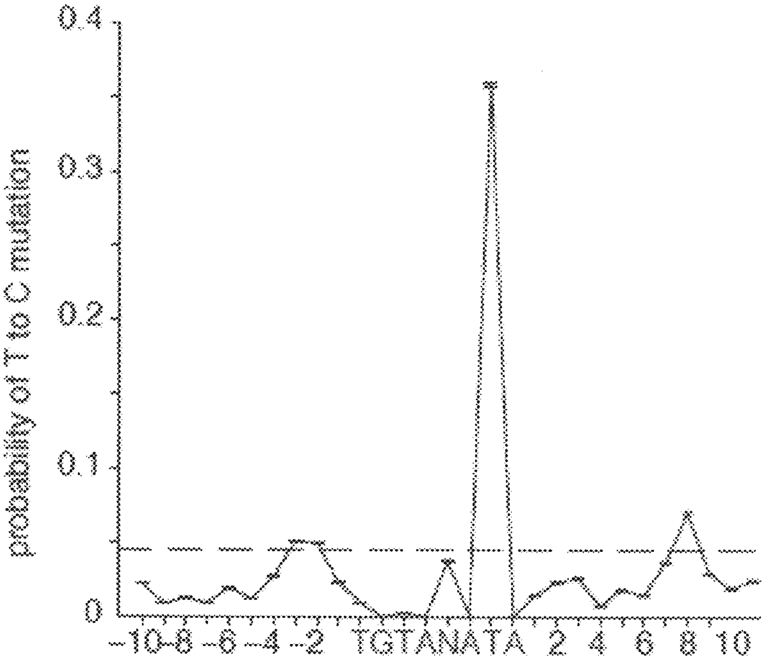

The PUM2 RNA recognition element, UGUANAUA (Galgano et al., 2008; Gerber et al., 2006; Gupta et al., 2008; Zamore et al., 1997), was readily identified by a PhyloGibbs analysis (Siddharthan et al., 2005) from the top 100 sequence read clusters annotated as mRNA (FIG. 2D).

About 71% of the clustered sequence reads showed a thymidine (T) to cytidine (C) alteration, with the T corresponding to U7 of the RRE mutated at higher frequency compared to the Ts corresponding to U1 and U3 (FIG. 2E), which are bound tightly in the PUM2 RNA binding site and for which the local amino acid environment probably does not allow efficient crosslinking. The 71% conversion frequency of a uridine residue to cytidine within sequence reads mapping to mRNA transcripts was unexpected, and suggested that crosslinked 4SU residues encountered during reverse transcription caused the sequence change, and that within the consensus motif, certain residues were preferably crosslinking 4SU residues in immediate vicinity of the binding site were also found to participate in crosslinking, indicating that our method can capture PUM2 binding sites that have a nucleotide other than U at position 7.

Example 5

Identification of QKI RNA Targets and its RRE

To further validate our method, we investigated the RBP Quaking (QKI) for which neither the RNA recognition element nor the target mRNAs have been so far defined, though an ACUAAY motif was determined by SELEX (Galarneau and Richard, 2005). The QKI protein contains one heterogeneous nuclear ribonucleoprotein K homology (KH) domain (FIG. 3A), embedded in the context of a larger protein domain involved in signal transduction (Chen and Richard, 1998). Mice with reduced expression of QKI show dysmyelination and develop rapid tremors or "quaking" 10 days after birth (Ebersole et al., 1996). The precise molecular function of QKI and its presumably deregulated mRNA targets responsible for the mutant phenotype are unknown. QKI has been implicated in post-transcriptional regulation including pre-mRNA splicing, mRNA export, mRNA stability and protein translation (Chenard and Richard, 2008). FLAG/HA-tagged QKI was 4SU-crosslinked to RNA (FIG. 3B, FIG. 8B), and the isolated RNA was converted into a cDNA library and Solexa sequenced.

PhyloGibbs analysis of the top 100 clusters aligning to sequences annotated as mRNA (FIG. 3C) yielded the sequence AYUAAY as the RNA recognition element (FIG. 3D), similar to the sequence motif ACUAAY identified by SELEX from randomized RNA sequences (Galarneau and Richard, 2005). We found that close to 75% of the more than 6,000 sequence clusters were derived from intronic sequences, supporting the hypothesis that QKI is a splicing regulator (Wu et al., 2002). 70% of the remaining, exonic, clusters fall into 3'UTRs. Together, all of the identified sites map to about 2,500 protein-coding transcripts. This analysis shows that our protocol was not only able to isolate RNA segments from mature transcripts accumulating in the cytoplasm but also segments present in presumably nuclear-localized pre-mRNAs. T to C mutation analysis of the clustered sequence reads showed that T corresponding to position 2 in AUUAAY was frequently sequenced as C whereas the T corresponding to position 3 in AUUAAY or ACUAAY remained unaltered (FIG. 3E). Crosslinking of 4SU residues in immediate vicinity to the consensus binding site was sufficient for exposing the motif with C at position 2.

Example 6

T to C Mutations Define the Crosslinking Sites

Figure 11C:
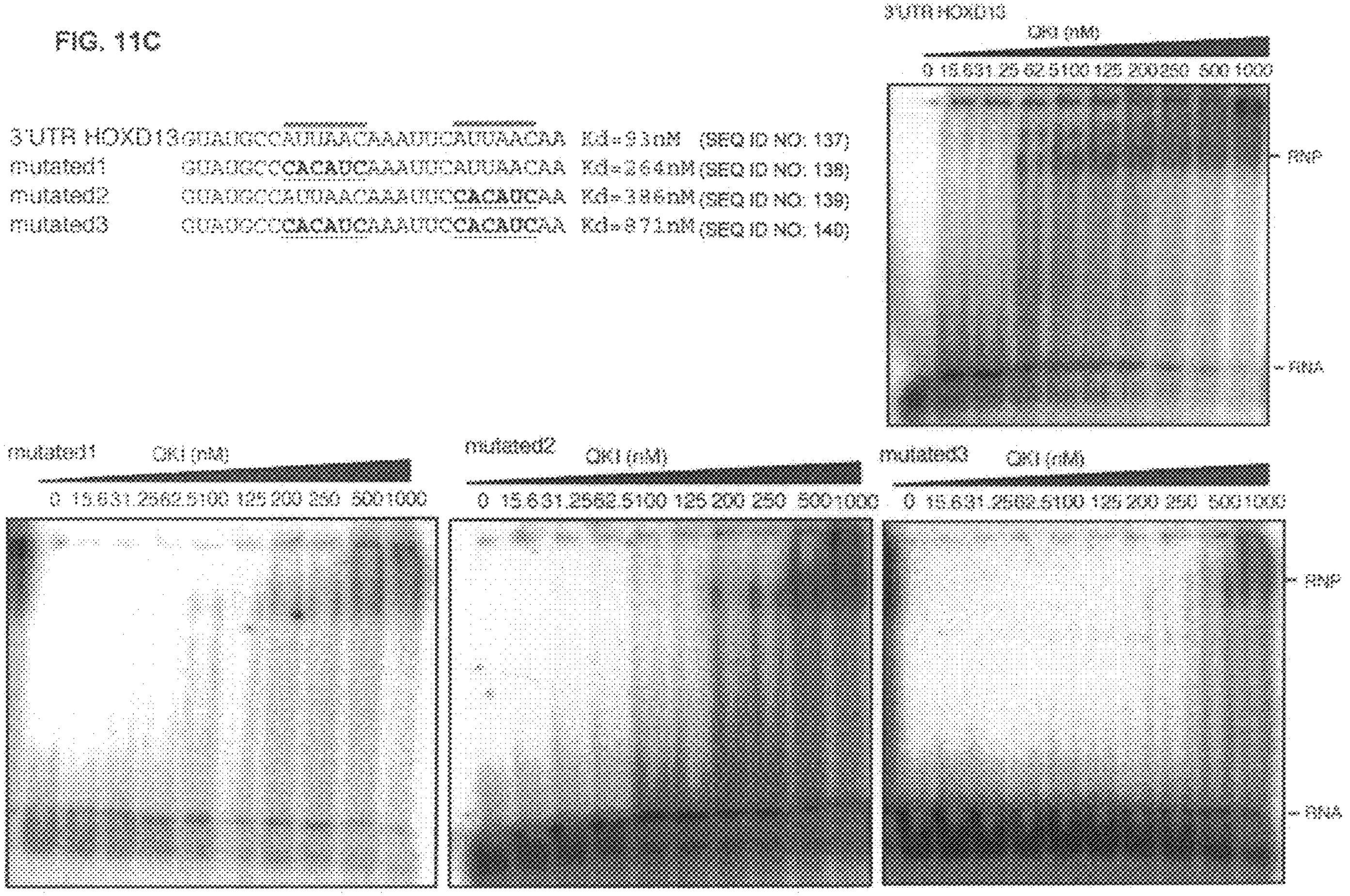

To better understand the cytidine sequence conversion after sequencing of crosslinked RNA segments, we subjected synthetic 4SU-containing oligoribonucleotides together with recombinant QKI to UV 365 nm crosslinking (FIGS. 3F, G). Oligoribonucleotide U9 with a 4SU substitution at position 2 of the recognition element crosslinked approximately 50-times more efficiently than oligonucleotide U10 with a modification at position 3 (FIG. 3G). RNA-binding to recombinant QKI protein was unaffected by 4SU incorporation at U9 or U10 as determined by gel-shift analysis (FIG. 11A-B), whereas regular mutation of the recognition element weakened the binding (FIG. 11C). The position-dependent crosslinking results suggest that the local amino acid environment of the protein RNA-binding site influences crosslinking efficiency and that T to C changes in the cDNA identify crosslink sites.

Figure 10A:
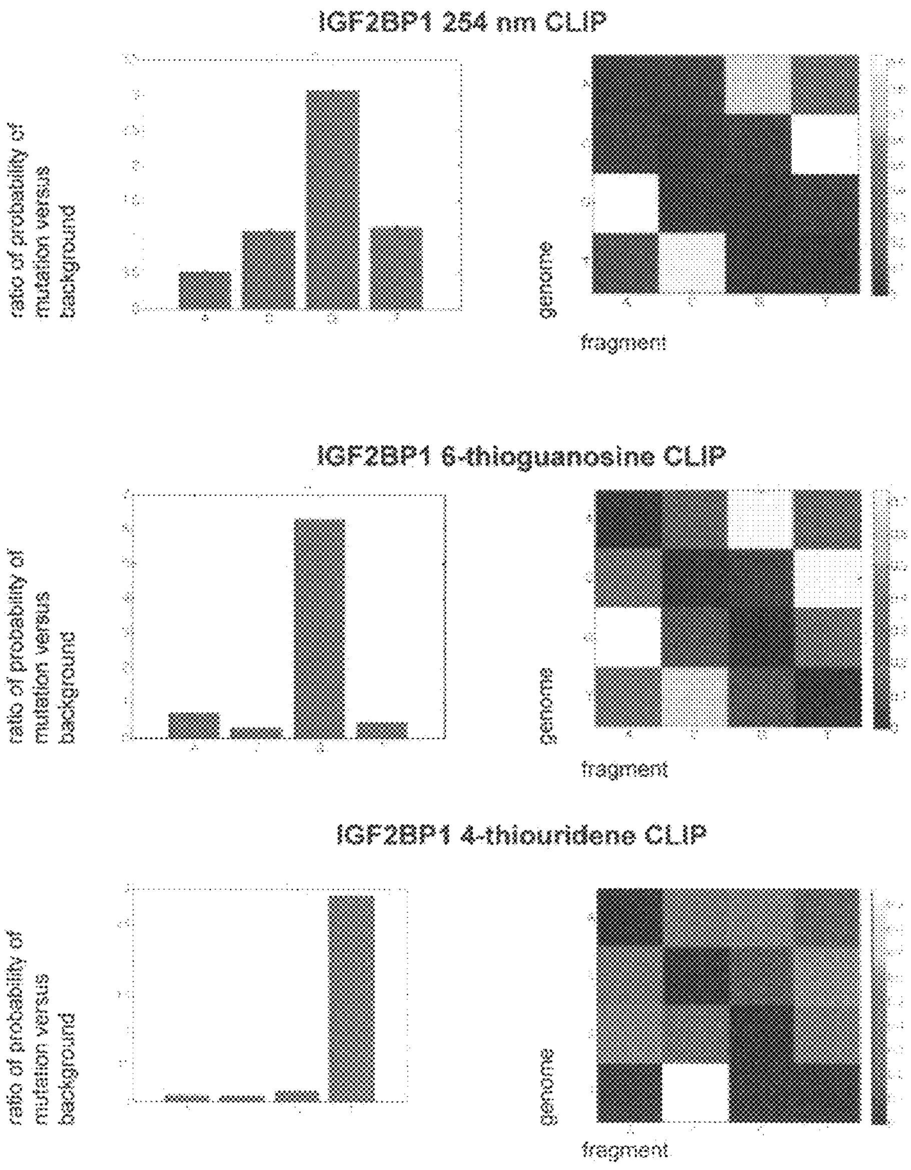
FIG. 10: Analysis of mutations observed in the clustered sequence reads relative to the genomic regions. A) Comparison of the mutational pattern of traditional CLIP for HEK293 cells stably expressing FLAG/HA-tagged IGF2BP1 and that observed with PURE-CLIP for cells fed with 6SG and 4SU. For each experimental condition we show two panels: the left one showing the mutation frequency at each of the four nucleotides relative to the frequency of occurrence of these nucleotides in all sequence reads; and the right one showing for each of the four nucleotides, the frequency of mutation towards each of the three others.
Figure 10B:
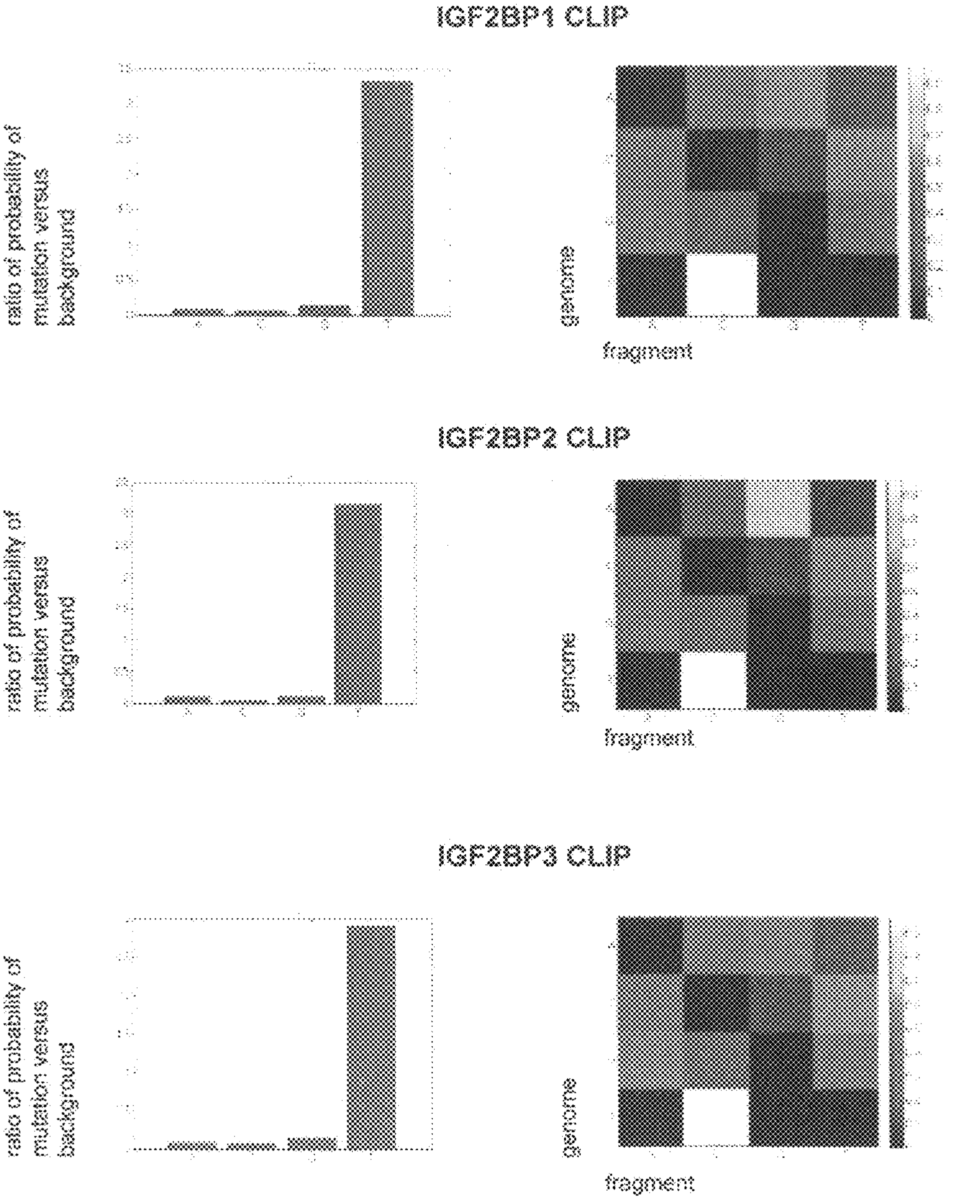
Figure 10C:
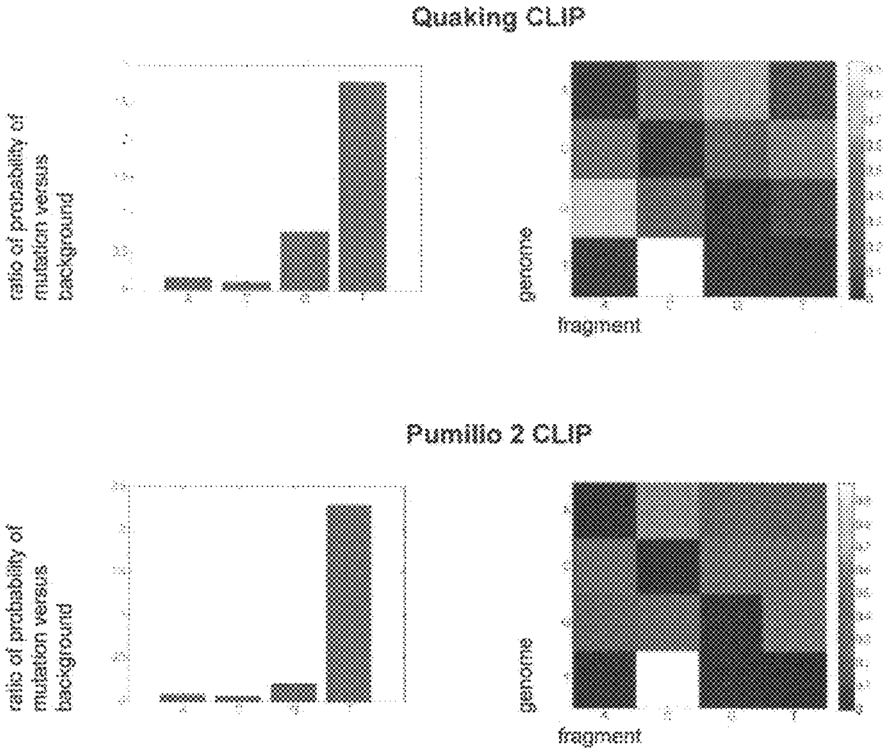
Figure 10D:
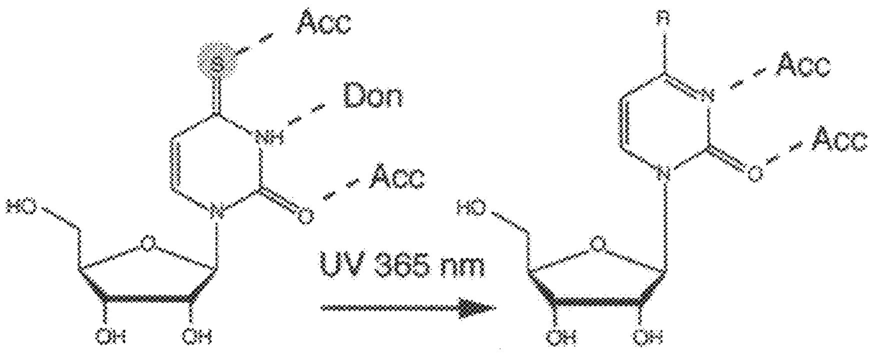

When we sequenced a library prepared from a synthetic 4SU-labeled oligoribonucleotide crosslinked to recombinant QKI protein, approximately 80% of the sequence reads derived from the crosslinked RNA oligonucleotide showed a T to C change at the modified position compared to about 20% of the sequence reads obtained from non-crosslinked RNA (FIG. 3H). A likely explanation for the 4-fold increase in T to C transition is a chemical structural change of 4SU upon crosslinking to an amino acid side chain, resulting in a modified base with altered hydrogen bond donor/acceptor properties preferentially directing the incorporation of deoxyguanosine rather than deoxyadenosine during reverse transcription (FIG. 10D). At the doses of 4SU applied to cultured cells, about 1 out of 50 uridines will be substituted by 4SU, and the average T to C conversion of a 40-nt sequence reads derived from non-crosslinked sequences, the background, is estimated to be near 4%. Clusters of sequence reads with average T to C conversion above this threshold, irrespective of the number of sequence reads, most certainly represent crosslinking sites, unless polymorphisms or errors in the genome assembly occur. Nonetheless, such problems cannot have a high prevalence, because we found that in the case of PUM2 and QKI, the binding motifs are strongly enriched around the positions with high T to C mutation frequency, something that would not be expected if these positions were in fact polymorphic or part of an incorrect assembly (FIG. 12). Therefore, the ability to separate signal from noise by focusing on clusters with a high frequency of T to C mutations rather than clusters with the largest number of reads, represents a major enhancement of our method over conventional CLIP, and we therefore termed our method PURE-CLIP (Photoreactive-Uridine-Enhanced Crosslinking and Immunoprecipitation).

To assess whether the transcripts identified by PURE-CLIP are regulated by QKI, the protein was knocked down using siRNAs and the mRNA levels of QKI knockdown cells were compared to that of mock-transfected cells using microarray analysis. The mRNA levels of transcripts identified by PURE-CLIP were significantly increased, indicating that QKI protein negatively regulated bound mRNAs, consistent with its proposed function as being a repressor protein (FIG. 3I and FIG. 13) (Chenard and Richard, 2008).

Example 7

Identification of IGF2BP RNA Targets and its RRE

Figure 4B:
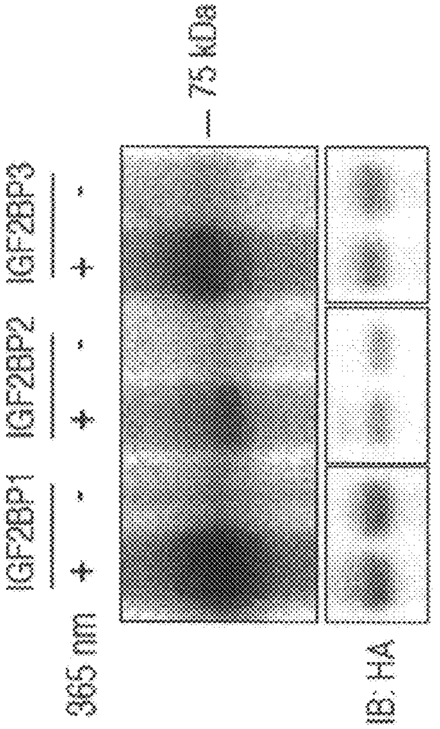
FIG. 4. RNA recognition sites of the IGF2BP protein family. A Domain structure of IGF2BP1 to 3 proteins. B Phosphorimage of SDS polyacrylamide gel resolving radiolabeled RNA crosslinked to FLAG/HA-IGF2BP1-3 IPs from non-irradiated or UVirradiated 4SU-labeled cells. The lower panel shows the Western blot with an anti-HA antibody to visualize the amount of FLAG/HA-IGF2BP1-3 proteins present in the FLAG IPs. C Two alignments of IGF2BP1 PURE-CLIP cDNA sequence reads to the corresponding regions of the 3' UTRs of CTNNB1 and HOXD13 Refseq transcripts, respectively. Red bars indicate the 4-nt IGF2BP1 recognition motif and nucleotides marked in red indicate sequence changes. D Weblogo of the IGF2BP1-3 recognition motifs generated by PhyloGibbs analysis of the top 100 sequence read clusters. E Analysis of the T to C positional mutation frequency for PURE-CLIP clusters anchored at the 4-nt recognition motif from all motif-containing clusters. The dashed line represents the average T to C mutation frequency within the clusters. F Phosphorimage of native polyacrylamide gels resolving complexes of recombinant IGF2BP2 protein with a wild-type (left panel) and a mutated synthetic target oligoribonucleotide (right panel). Sequences and dissociation constants (Kd) are indicated. G Destabilization of IGF2BP1-3 bound transcripts upon siRNA knockdown. A cocktail of three siRNA duplexes targeting IGF2BP1, 2, and 3, respectively, and a mock transfection were performed to obtain the changes in transcript stability by Affymetrix microarray analysis. Distributions of transcript level changes for IGF2BP1-3 PURE-CLIP target transcripts versus non-targeted messages are shown. IGF2BP1-3 target sequences were ranked and divided into the indicated bins. The destabilization effect is strongest for the highest ranking transcripts. The p-values indicate the significance of the difference between the changes of target versus non-target transcripts, as given by the Wilcoxon rank-sum test and are corrected for multiple testing.
Figure 4A:
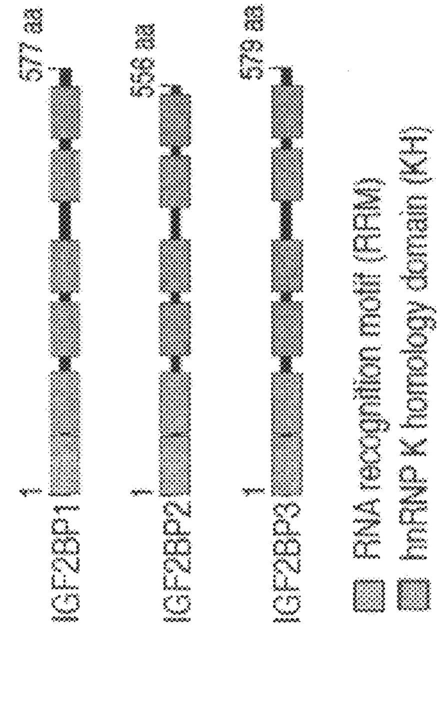
Figure 4:
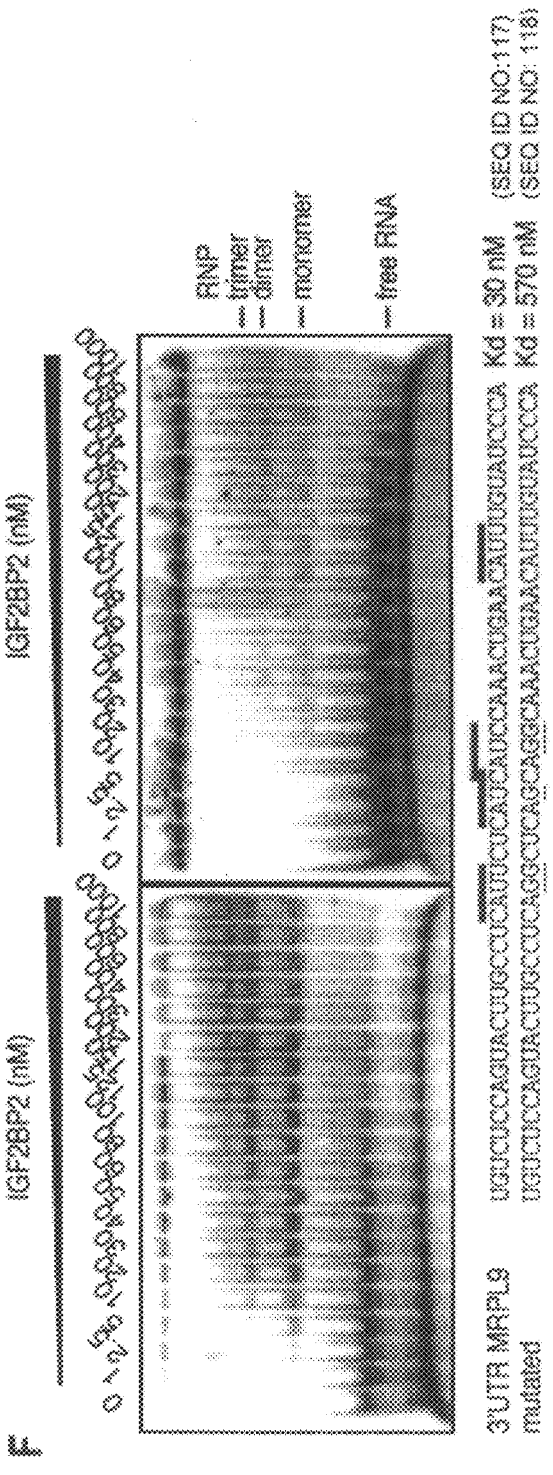

We then applied PURE-CLIP to study the insulin-like growth factor 2 mRNA-binding proteins 1, 2, and 3 (IGF2BP1-3), comprising a family of highly conserved proteins that play a role in cell polarity and cell proliferation (Yisraeli, 2005). They are predominantly expressed in the embryo but are re-expressed in various cancers (Boyerinas et al., 2008; Dimitriadis et al., 2007). IGF2BP2 has also recently been associated with type-2 diabetes (Diabetes Genetics Initiative of Broad Institute of Harvard and MIT et al., 2007; Scott et al., 2007). The IGF2BPs regulate mRNA stability, transport and translation (Yisraeli, 2005). They contain six canonical RNA-binding domains, two RNA recognition motifs (RRMs) and four KH domains (FIG. 4A). RRMs recognize several nucleotides of single-stranded RNA (Clery et al., 2008), but target recognition for this six-domaincontaining protein family appears complex, and so far, only a small number of coding and non-coding RNAs have been shown to interact with IGF2BPs without precise localization or definition of its RREs (Yisraeli, 2005).

We crosslinked FLAG/HA-tagged IGF2BP1, 2, and 3 to 4SU-labeled RNA (FIG. 4B and FIG. 8B) and analyzed the bound RNA by Solexa sequencing. The three IGF2BPs recognized a highly similar set of target transcripts (FIG. 14A-E), suggesting similar and redundant functions consistent with the high degree of sequence similarity between family members. PhyloGibbs analysis of the clusters derived from mRNAs (FIG. 4C) yielded the sequence CAUH (H=A, U, or C) as the only consensus recognition element (FIG. 4D). In total, we identified over 100,000 sequence clusters recognized by the IGF2BP family that map to about 8,400 protein-coding transcripts. The annotation of the clusters was predominantly exonic (ca. 90%), and there was a slight preference for binding in the 3'UTR compared to the coding sequence (CDS) (FIG. 9A-E). The mutation frequency of all sequence tags containing the element CAUH showed that the crosslinked residue was positioned inside the motif, or immediately around it (FIG. 4E). The consensus motif CAUH was generally found repeated in targeted transcripts, predominantly within a distance of three to five nucleotides (FIG. 15A-D). Furthermore, in vitro binding assays showed that nucleotide changes of the CAUH motif decreased the binding affinity (FIG. 4F and FIG. 16A-C), emphasizing the importance of the consensus motif. Nevertheless, mutation of an RRE did not fully abolish binding, suggesting that the sequence environment around the RRE, e.g. its high overall CA-content and likely the multiplicity of binding sites, also contribute to binding (FIG. 16A-C).

Figure 4G:
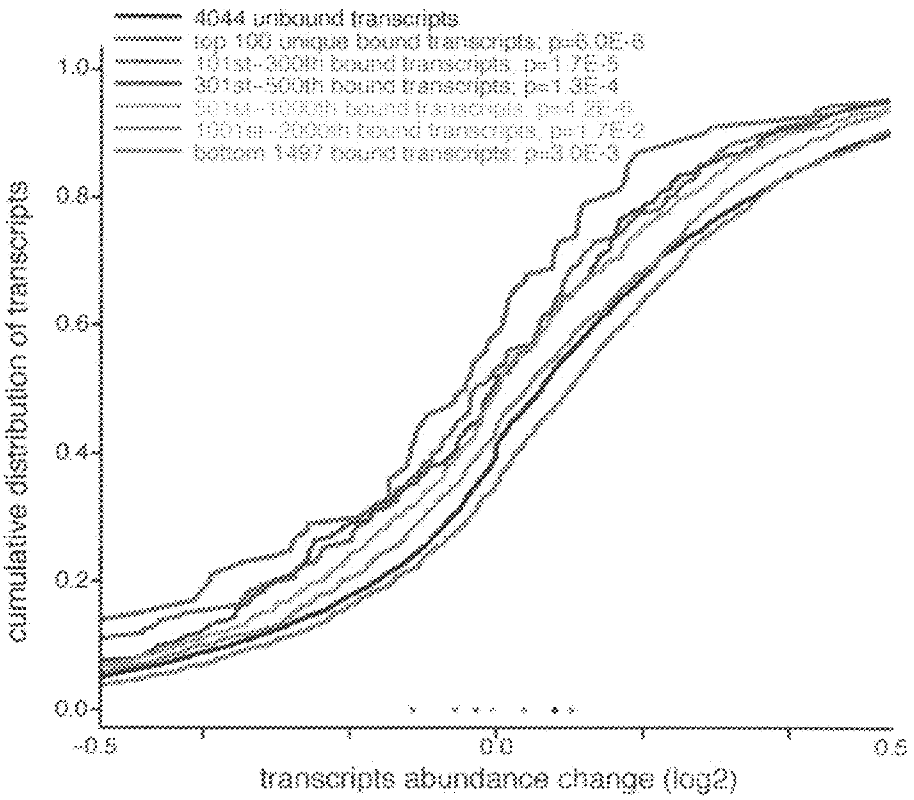

To test whether binding of the IGF2BPs affects the stability of their interacting mRNAs, as reported previously for some targets, we simultaneously depleted all three IGF2BP members using siRNAs (FIG. 17) and compared the cellular RNA from knockdown and mock-transfected cells on microarrays. Transcripts identified by CLIP showed a decrease in their mRNA levels in IGF2BP depleted cells, indicating that the IGF2BP proteins stabilize their target mRNAs. In addition, the top mRNAs, ranked according to the total number of T to C mutations were most destabilized (FIG. 4G). This indicates that the ranking criterion that we derived based on the analysis of PUM2 and QKI data generalizes to other RBPs. For comparison to conventional CLIP and deep-sequencing HITS-CLIP (Licatalosi et al., 2008; Ule et al., 2003), we also sequenced cDNA libraries prepared from UV 254 nm crosslinking and then compared the sequence clusters derived from these experiments with those of PURE-CLIP (FIG. 18). UV 254 nm crosslinking identified the identical segments of a target RNA, yet, the crosslinking site was not readily deduced, because the sequence reads making up the cluster had a mutation rate lower than 1% with a weak G to A bias in the mutation frequency that might be more difficult to exploit (FIG. 18). This can lead to problems separating signal from noise and deducing binding sites from analysis of clusters simply ranked by number of sequence reads.

Example 8

Identification of miRNA Targets by AGO and TNRC6 PURE-CLIP

To test our approach on ribonucleoprotein complexes, we selected the protein components mediating miRNA-guided target RNA recognition. In animal cells, miRNAs recognize their target mRNAs through base-pairing interactions between 6-8 nucleotides at the 5' end of the miRNA, the so called "seed", and complementary sequences thought to reside mainly in the 3'UTR of mRNAs. Computational methods to predict miRNA binding sites in several organisms mostly rely on the interaction of the miRNA seed region with its target mRNA 3'UTR- and evolutionary conservation of the target site (Gaidatzis et al., 2007; Grimson et al., 2007; Grun et al., 2005; John et al., 2004; Krek et al., 2005; Lewis et al., 2005). miRNA target sites are located in the 3'UTRs of mRNAs (Brennecke et al., 2005; Grimson et al., 2007; Wightman et al., 1993). There are also individual examples of target mRNAs that are efficiently repressed by miRNA-binding sites in the 5' UTR and the coding sequence (CDS) (Kloosterman et al., 2004; Lytle et al., 2007; Tay et al., 2008). We isolated mRNA fragments bound by miRNPs from HEK293 cell lines stably expressing FLAG/HA-tagged AGO and TNRC6 family proteins (Landthaler et al., 2008).

Figure 5:
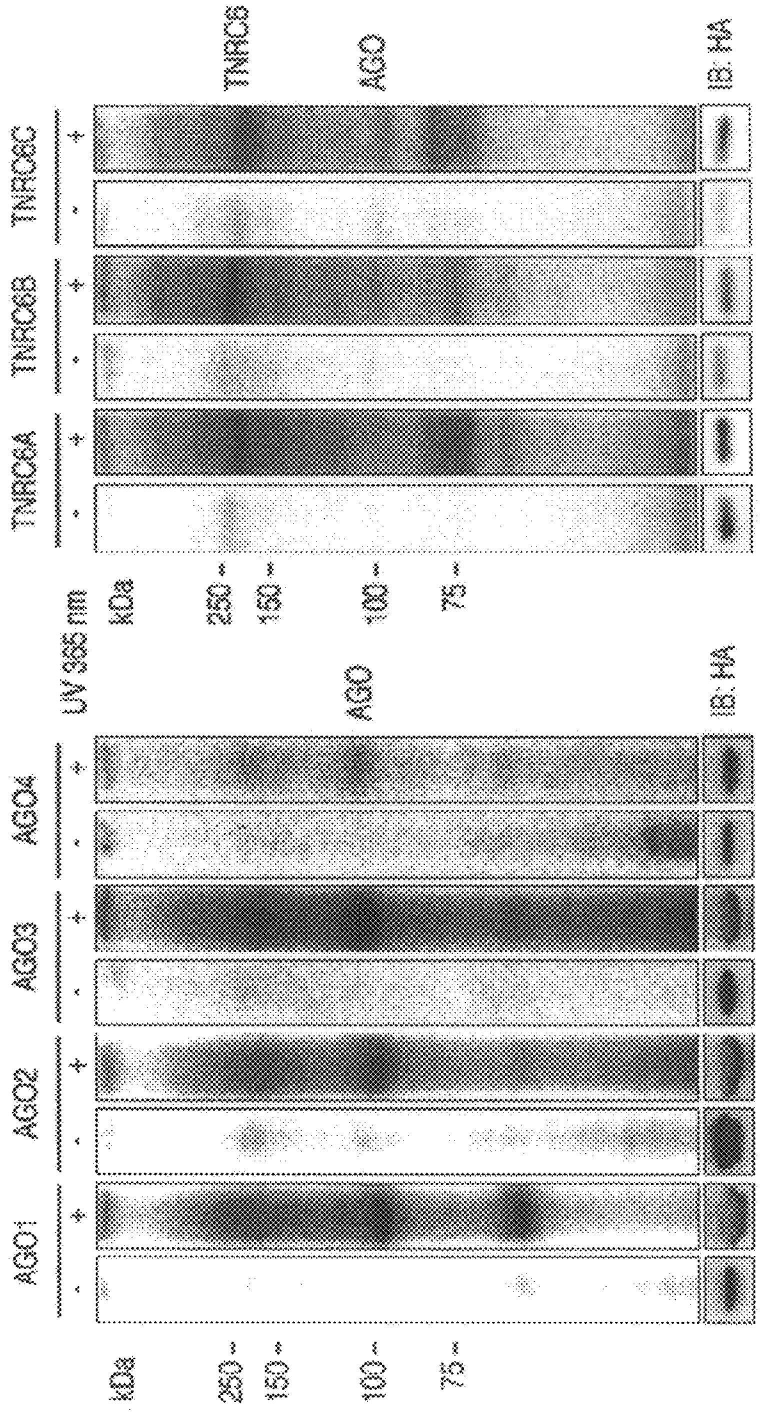
FIG. 5. AGO protein family and TNRC6 family PURE-CLIP. A Phosphorimage of SDS polyacrylamide gel resolving the FLAG/HA-AGO1-4 and FLAG/HA-TNRC6A-C immunoprecipitates prepared from UV 365 nm irradiated and non-irradiated 4SU-treated cells. The covalently attached RNA present in the immunoprecipitates was 5'-32P-labeled before SDS-PAGE. The lower panel shows the immunoblot with an anti-HA antibody to detect FLAG/HA-AGO1-4 and FLAG/HA-TNRC6 proteins present in IPs. B Alignments of AGO PURE-CLIP cDNA sequence reads relative to the 3' UTRs of PAG1 (NM_018440) and OGT (NM_181672), respectively. Red bars indicate the 8 nt miR-103 seed complementary sequence and nucleotides marked in red indicate T to C mutations diagnostic of position of crosslinking. C miRNA profiles of FLAG/HA-AGO2 HEK293 cell lysates and profiles obtained from analysis of the FLAG-immunoprecipitates (IPs) of FLAG/HA-AGO1-4 HEK293 cell lines not treated with 4SU compared to the miRNA profile obtained from PURE-CLIP for the AGO proteins. The profiles were determined by small RNA cDNA library sequencing for the untreated IPs and from the sequence reads mapped to miRNAs for the AGO-PURE-CLIP. The color code represents relative frequencies determined by sequencing. miRNAs marked in red letters were inhibited for the transcriptome-wide characterization of the destabilization effect of miRNA binding. D Analysis of the T to C positional mutation frequency for sequence reads derived from PURE-CLIP annotated as miRNA (black trace). The red trace represents the conditional probability of finding a U at that position of the miRNA. The dashed line represents the mean conditional probability.

The AGO IPs revealed two prominent RNA-crosslinked full-length proteins of 100 and 180 kDa size, representing AGO, and likely TNRC6 and/or DICER1 protein, respectively (Landthaler et al., 2008) (FIG. 5A). The TNRC6 IPs showed one prominent RNAcrosslinked protein band of 180 kDa size, and several smaller proteins, one of which likely represents AGO (Landthaler et al., 2008). The RNA recovered from the AGO-band in the AGO-IP and from the TNRC6-band in the TNRC6-IP was converted into cDNA libraries and Solexa sequenced.

We clustered overlapping, uniquely-mapped reads that were at least 20 nts long into clusters, and we retained for further analyses those clusters that contained at least five sequence reads and had a content of more than 20% crosslinked sequences (based on the T to C transition, indicative of crosslinking) We removed all clusters that were present at a tenfold higher level in the cDNA libraries derived from PURE-CLIP for the completely unrelated IGF2BP protein family, and therefore constitute background sequences. Finally, we selected sequence regions that were centered over the predominant crosslinking site from each cluster, and extended them 20 nt in both directions to allow for accommodation of the various positions at which target RNA crosslinking was observed (see below). We refer to those 41-nt sequences as crosslinkcentered regions (CCRs).

The AGO experiments yielded on average about 4,000 clusters that overlapped, supporting our earlier observation that AGO1 through 4 bound similar sets of transcripts (Landthaler et al., 2008). We therefore combined all sequence reads obtained from the individual AGO experiments and identified 17,319 clusters of sequence reads using the cut-offs defined above (FIG. 5B)). Note that a large number of additional clusters that were not present in the individual AGO1-4 cluster sets, because of the condition that a cluster is made up by at least 5 sequence reads, were created. The clusters mapped to 4,647 transcripts with defined GeneIDs, corresponding to 21% of the 22,466 unique HEK293 transcripts we identified by Solexa sequencing of oligoT-purified total RNA (digital gene expression, DGE, Illumina).

The individual TNRC6 experiments yielded on average about 600 clusters that were similar to each other, also consistent with our observation that TNRC6 family proteins bind similar sets of transcripts (Landthaler et al., 2008). We therefore combined all sequence reads obtained by the different TNRC6 experiments, yielding 1,865 clusters. Although they had similar numbers of mRNA-annotated sequence reads, the TNRC6 libraries had a higher proportion of sequence reads that were shorter than 20 nts and were not considered for construction of clusters. For this reason we identified fewer clusters in the TNRC6 dataset compared to the AGO dataset. An analysis of the TNRC6 CCRs showed that the crosslinked positions of 26% of the CCRs were virtually indistinguishable from those obtained for AGO (at least 75% overlap between the 41-nt AGO- and TNRC6-derived CCRs) (FIG. 21). We showed previously that AGO and TNRC6 protein family members bound to a large extent the same transcripts (Landthaler et al., 2008). Here we find that when AGO and TNRC6 bind to the same transcripts they also bind to the same site. We speculate that the TNRC6 protein acts like a lid covering the solvent-accessible side of the AGO miRNA-target RNA complex (Wang et al., 2008a) in order to stabilize the interaction with the target mRNA.

Example 9 miRNA Profiles from AGO PURE-CLIP are Similar to the HEK293 miRNA Profile

Figure 5C:
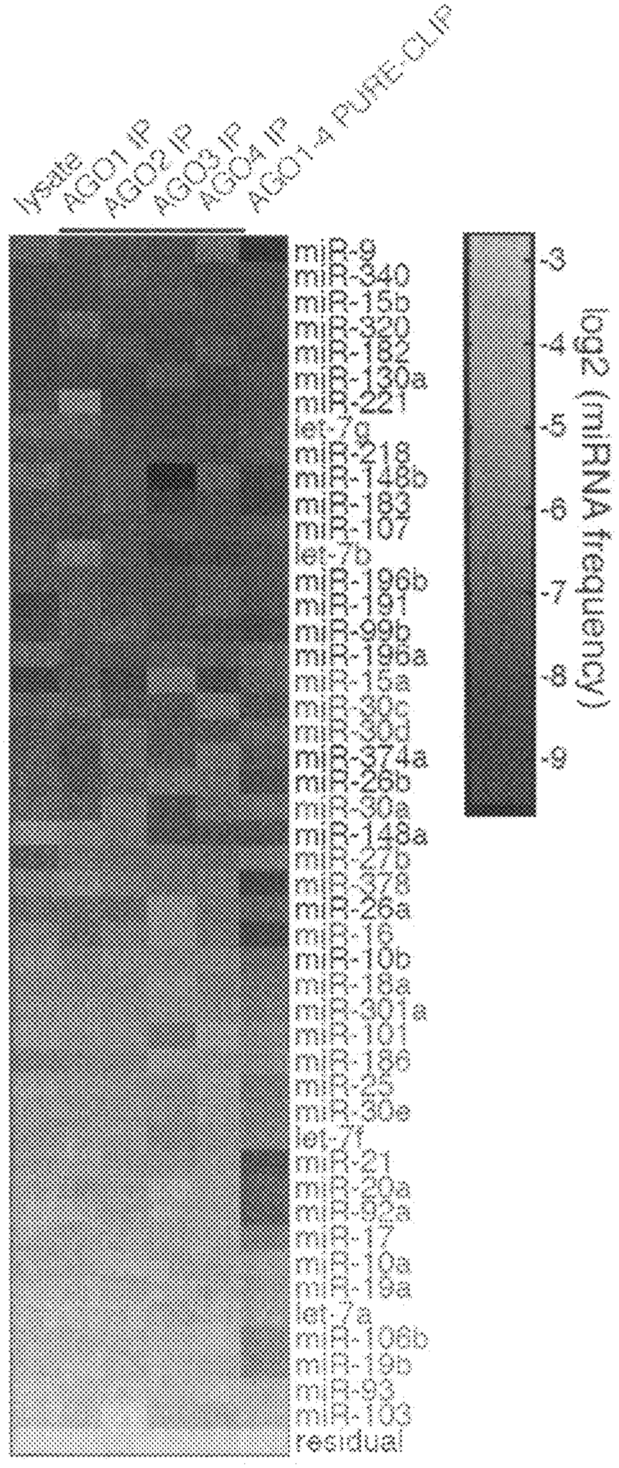
Figure 5D:
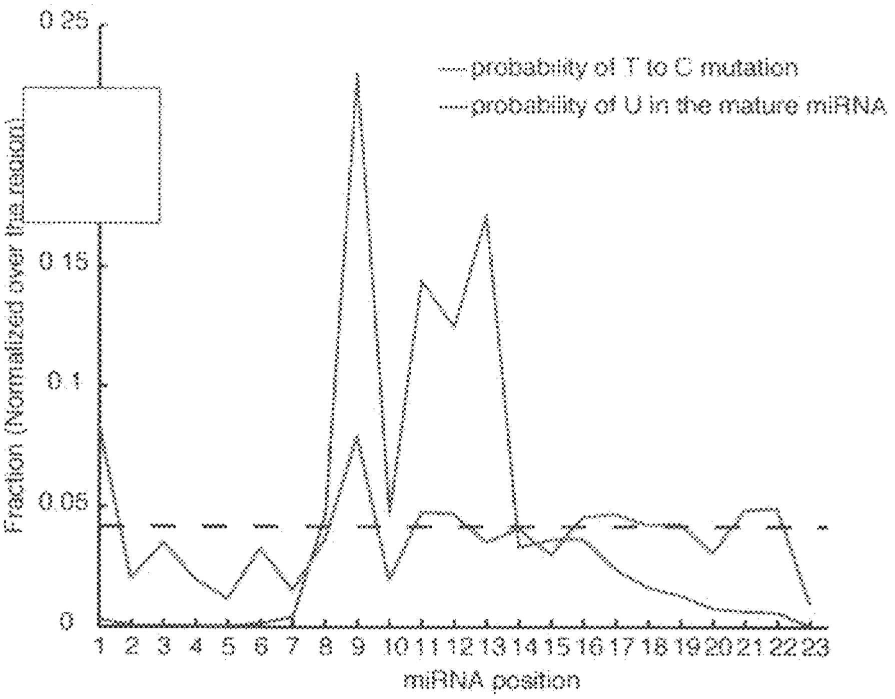

To relate CCRs to the endogenously expressed miRNAs, we determined the miRNA profiles in cell lysate as well as AGO1-4 IPs of non-crosslinked FLAG/HA-AGO expressing HEK293 cells by Solexa sequencing as well as the miRNA profiles from miRNAs in the PURE-CLIP experiments. The non-crosslinked miRNA profiles were highly similar (FIG. 5C) and supported our observation that AGO1 to 4 crosslinked to similar transcript sites. The most abundant miRNAs in our HEK293 cells were miR-103 (7% of miRNA sequence reads), miR-93 (6.5%), and miR-19b (5.5%), showing that HEK293 cells differ from other systems such as muscle, liver or brain, in that they do not have a clearly dominant miRNA, which could yield a strong sequence signature in the mRNAs. The top 25 expressed miRNAs account for 72%, and the top 100 account for 95% of the total of miRNA sequence reads; the residual 5% correspond to 457 distinct miRNAs and miRNA*. We restricted the subsequent computational analysis of miRNA target sites to the top 100 miRNAs and their sequence families, and the experimental inhibition analysis of miRNAs for assessment of endogenous miRNA binding on mRNA stability to the top 25 most abundant miRNAs.

miRNA profiles from combined AGO1- to 4 PURE-CLIP experiments were constructed from a total of 2.4 M sequence reads mapping to the miRNA precursor sequences from the latest version of Rfam (v9.1) (Gardner et al., 2009). The vast majority of sequence reads derived from prototypical miRNAs (Landgraf et al., 2007) displayed T to C conversion near or above 50%. Five of the 100 most abundant miRNAs in HEK293 cells lack uridines at position 8-13, yet only 2 of those miRNAs, miR-374a and b, revealed T to C transitions at background level, because uridines at residues 14 and higher can still be crosslinked. The T to C conversion was predominantly concentrated within positions 8 to 13 (FIG. 5D), residing in the singlestranded region of the AGO protein ternary complex (Wang et al., 2008a). Position 1, though predominantly a U, was not crosslinking, presumably because its binding pocket protein environment was not amenable to crosslinking. The miRNA profile derived from AGO-PURE-CLIP miRNA sequence reads was comparable to non-crosslinked miRNA profiles (FIG. 5C), even though one would expect that the uridine composition would have an influence on the miRNA profile. Very interestingly, we noted that many of the more recent additions of miRNAs to Rfam returned with sequence reads devoid of crosslinking evidence despite their presence of uridines at positions 8 to 13, indicating that those precursor sequences and their corresponding miRNAs are unlikely to represent an AGO protein associated RNAs. AGO-PURE-CLIP therefore might represent a novel means for miRNA functional annotation.

Example 10 mRNAs Interacting with AGOs Contain miRNA Seed Complementary Sequences

Figure 6A:
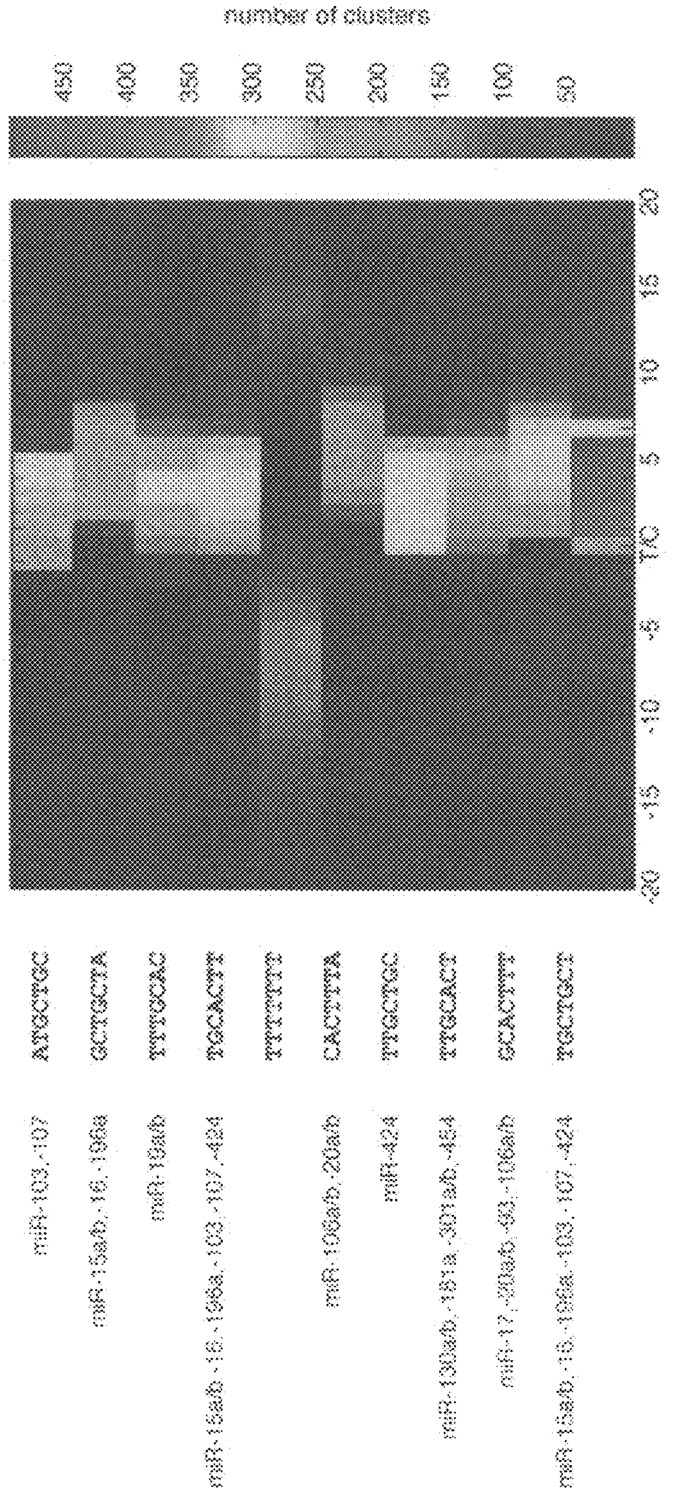
FIG. 6. AGO-PURE CLIP identifies miRNA seed complementary sequences in HEK293 cells. A Identification and position of the 10 most significantly enriched 7-mer sequences within pure-clip clusters B Analysis of the T to C positional mutation frequency for PURE-CLIP clusters anchored at the 7mer seed complementary sequence (pos. 2-8 of the miRNA) from all sequence read clusters containing seed complementary sequences to the top 100 expressed miRNAs in HEK293 cells. The dashed line represents the average T to C mutation frequency within the clusters. C miRNAs bind their targets predominantly with their seed sequence. Occurrence of a 4-nt complementary sequence relative to the beginning of the miRNA was counted in the 41-nt crosslink centered clusters (CCRs). The top 100 expressed miRNAs in HEK293 cells were used for this plot. D Analysis of the positional distribution of CCRs. The number of clusters annotated as derived from the 5' UTR, CDS or 3' UTR of target transcripts is shown (green bars). Yellow bars show the location distribution of the crosslinked regions expected if the AGO proteins would bind without regional preference to the target transcript.
Figure 6B:
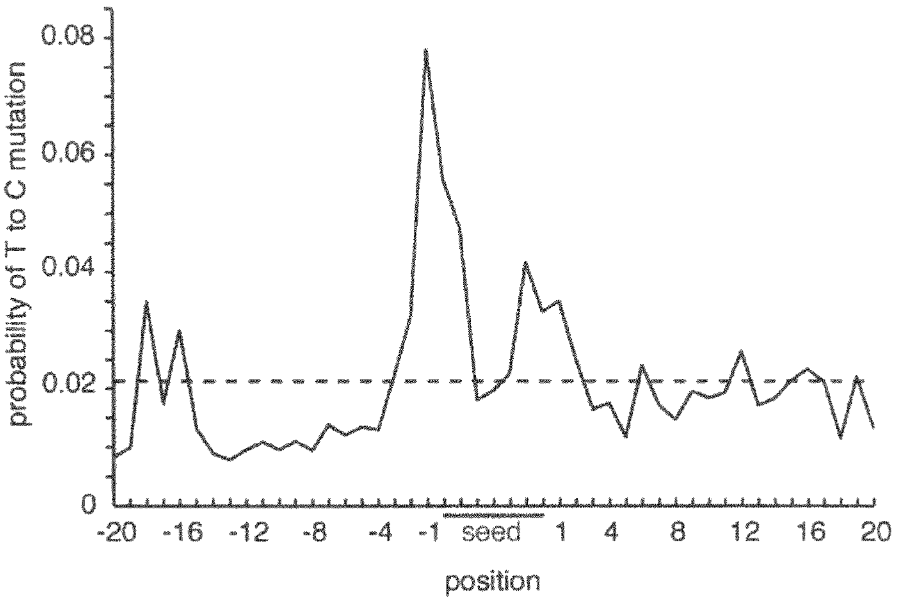

Animal miRNAs were shown to primarily recognize their target mRNAs based on sequence complementarity between the 5' end (the so-called seed region) of the miRNA (see illustrations in FIG. 22), particularly the 7-nt segment from position 2 to 8 of the miRNA, and the target mRNA (Brennecke et al., 2005; Gaidatzis et al., 2007; Grimson et al., 2007; Grun et al., 2005; Krek et al., 2005; Lai, 2002; Lewis et al., 2005; Stark et al., 2003). Independent of any pairing models, we first determined the enrichment of all 16,384 theoretically possible 7-mers within the 17,319 CCRs from the AGO experiments, relative to random sequences with the same dinucleotide composition. The most significantly enriched 7-mers corresponded to the reverse complement of the seed regions 2-8 of the most abundant HEK293 miRNAs, and they were most frequently positioned 1-2 nt downstream of the predominant crosslinking site within CCRs (FIG. 6A). This places the crosslinking site near the centre of the AGO-miRNA-target RNA ternary complex, where the target RNA is proximal to the PIWI/RNase H domain of AGO (Wang et al., 2008a). To further examine the positional dependence of target RNA crosslinking, we anchored the CCRs containing seed complements (defined as A opposite miRNA pos. 1 and match pos. 2-8) of the top 100 expressed miRNAs and plotted the position-dependent frequency of finding a crosslinked position (FIG. 6B). This identified two additional crosslinking regions, which in structural terms correspond to the unpaired 5' and 3' ends of the target RNA exiting from the AGO ternary complex. This indicates that the 41-nt windows centered on the predominant crosslink position cover the miRNA-complementary sites.

Figure 22A:
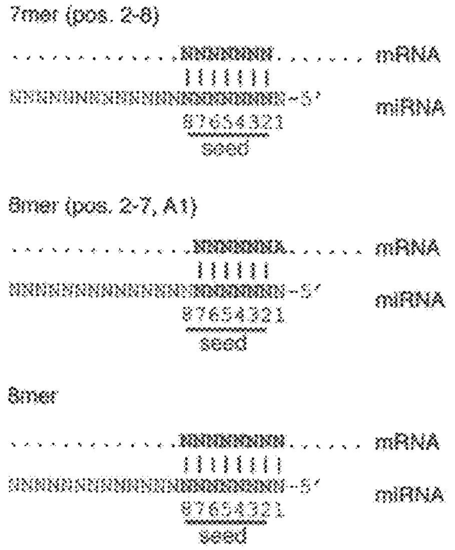
Figure 22B:
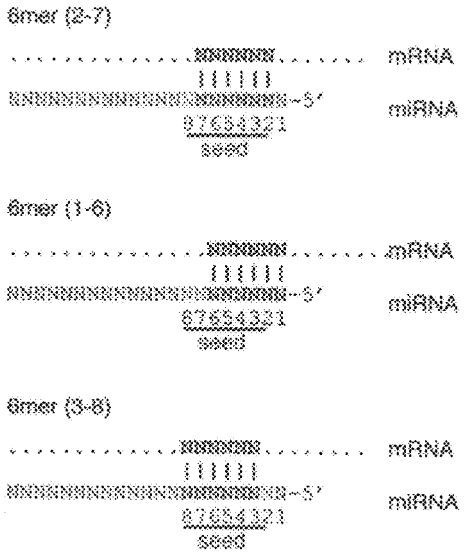
Figure 22C:
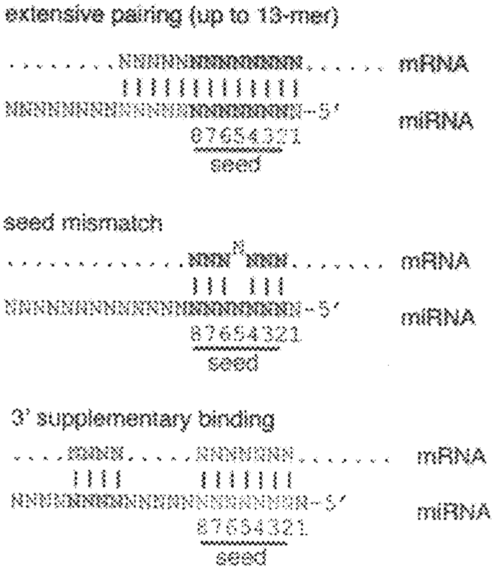

We then analyzed the occurrence of miRNA-complementary sequences in CCRs. We found 57 CCRs that had long matches (more than 12 nucleotides) to one of the top 100 miRNAs. The most significant enrichment relative to sequences with the same dinucleotide composition was generally obtained with 8-mers that were complementary to miRNA seed regions (defined as above), and a total of 14,809 of the 17,319 CCRs (85%) contained at least one 6-mer miRNA seed-complementary region (FIG. 23). 6-mers still showed some degree of excess conservation in comparative genomics studies (Gaidatzis et al., 2007; Lewis et al., 2005), and thus these results suggest that the majority of the CCRs represent bona fide miRNA binding sites. Furthermore, the number of miRNA seed complements counted for all known miRNAs over all CCRs correlated well with the expression levels of miRNA families found in HEK293 cells, and less well with miRNA profiles of other tissue samples (FIGS. 22-23). We also evaluated whether uridine sequence biases due to the use of 4SU were detectable for the most frequently isolated mRNA target segments. We found no obvious connection between the nucleotide composition of the top 100 most abundant miRNAs and the number of seed complementary sites found in the CCRs (FIG. 26). While the CCRs themselves had a slightly higher U-content (approximately 30% U) as would be expected around miRNA-binding sites, there was no apparent connection between the probability of finding seed complementary sites and the U content of a CCR (Grimson et al., 2007) (FIG. 27).

Example 11

Figure 6C:
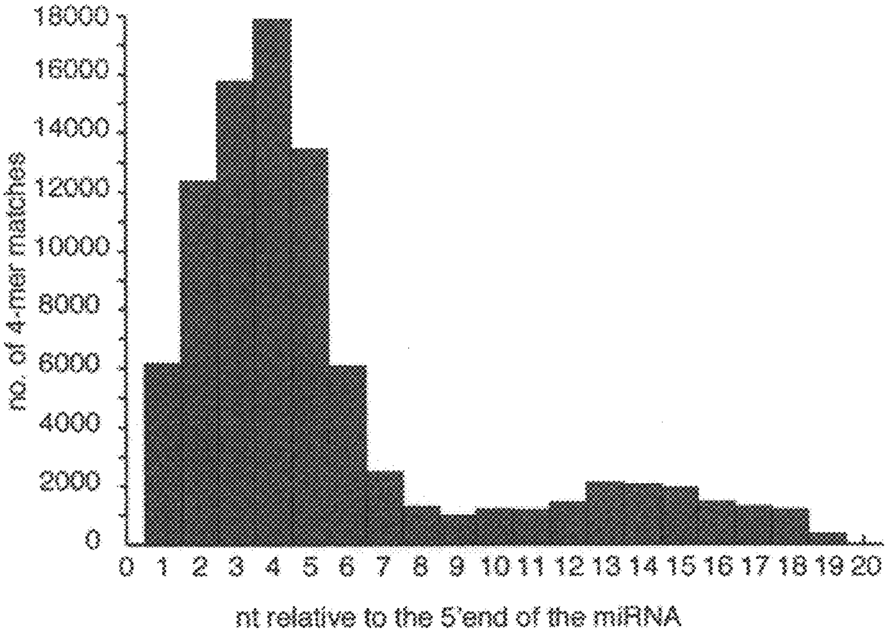

Limited Extent of Non-Canonical and 3'End Pairing of miRNAs to their mRNA Targets Structural and biochemical studies of *Thermus thermophilus* AGO indicated that small bulges and mismatches can be accommodated in the seed pairing region within the target RNA strand (Wang et al., 2008b). We therefore searched for putative non-seed miRNA binding sites, which we defined as binding sites that contained 2 blocks, discontinuous in either the miRNA and/or target, with a total of at least 6 matched nucleotides. We only considered such non-seed putative sites if they were significantly enriched in CCRs compared to dinucleotide randomized sequences. We identified 891 CCRs with mismatches and 256 with bulges in the seed region. Mismatches occurred most frequently across from pos. 5 of the miRNA as G-U or U-G wobbles, U-U mismatches and A-G mismatches, with the A residing in the miRNA. Therefore, it appears that only a small fraction of the miRNA targets that we isolated (less than 6.6%), contained bulges or loops in the seed-region. Another contribution to the specificity of miRNA-target RNA interactions was proposed to be contiguous base-pairing of sequences in the miRNA 3' half and the target mRNAs (Brennecke et al., 2005; Grimson et al., 2007). We examined the occurrence of 4-nt complementary segments to any of the top 100 miRNAs in the CCRs that contained a match to the 7-mer seed sequences of these miRNAs, and detected a small peak in the frequency for segments corresponding to positions 13-18 of these miRNAs (FIG. 6C).

Figure 6D:
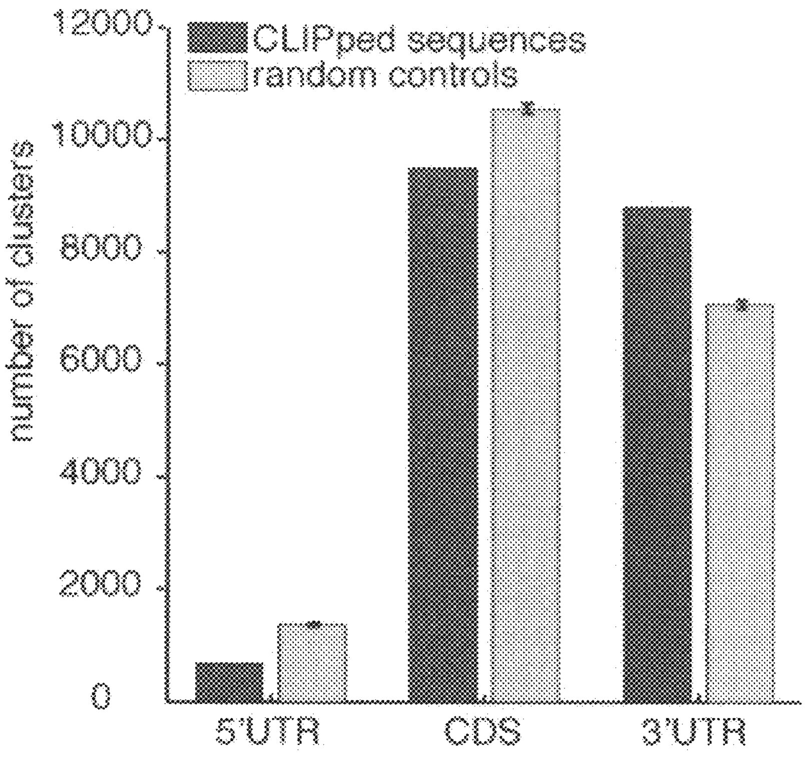

Example 12 miRNA Binding in CDS and 3'UTR Differentially Destabilizes mRNA Targets miRNAs are predominantly localized to the cytoplasm although a smaller fraction can be detected in nuclear extracts (Hwang et al., 2007; Meister et al., 2004; Pena et al., 2009; Robb et al., 2005; Weinmann et al., 2009). Our CCRs correspond to 84% exonic, 14% intronic, and 2% not assigned transcribed regions. This distribution is consistent with the predominant cytoplasmic function of miRNAs. Of the exonic CCRs, 50% distributed to the CDS, 46% to the 3' UTR, and 4% to the 5' UTR of mRNAs, with a specific enrichment in the 3'UTRs relative to what is expected based on the relative lengths of different transcript regions (FIG. 6D). The identification of such a large number of miRNA binding sites within the CDS was unexpected, because miRNA are believed to predominantly act on 3' UTRs (Bartel, 2009), with a few reports providing evidence for miRNA-binding to 5' UTR or CDS (Forman et al., 2008; Lytle et al., 2007; Orom et al., 2008; Tay et al., 2008). In order to determine if CCR-containing transcripts were indeed subject to miRNA-dependent regulation, we inhibited 25 of the most abundant miRNAs in HEK293 cells (FIG. 5C) with a cocktail of 2'-O-methyl-modified antisense oligoribonucleotides (FIG. 7A and see FIG. 28A-C for the efficiency of the individual antisense oligoribonucleotide). The change in relative mRNA abundance before and after miRNA inhibition was recorded by Affymetrix whole transcriptome array analysis.

Figure 28A:
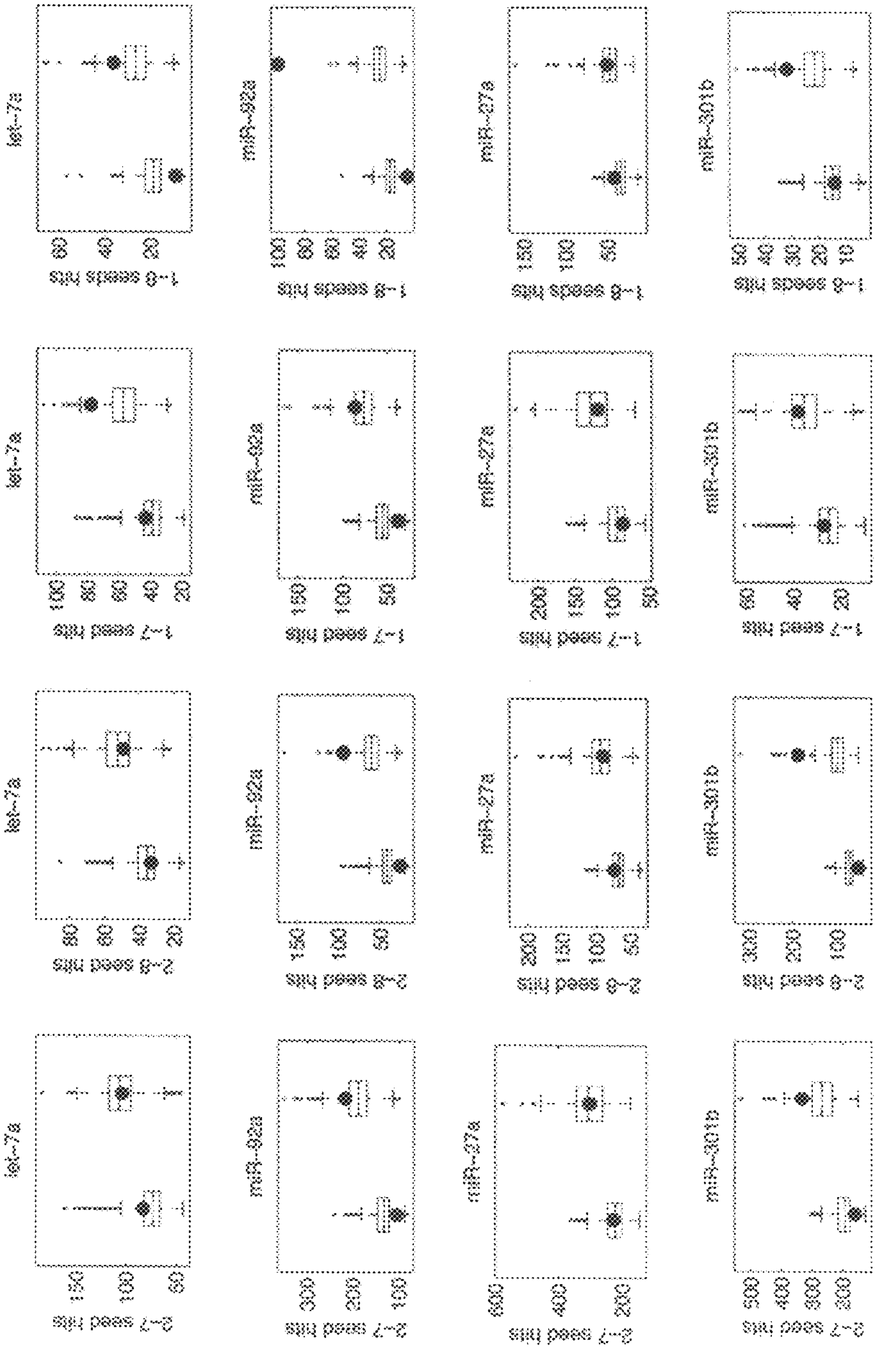
Figure 28B:
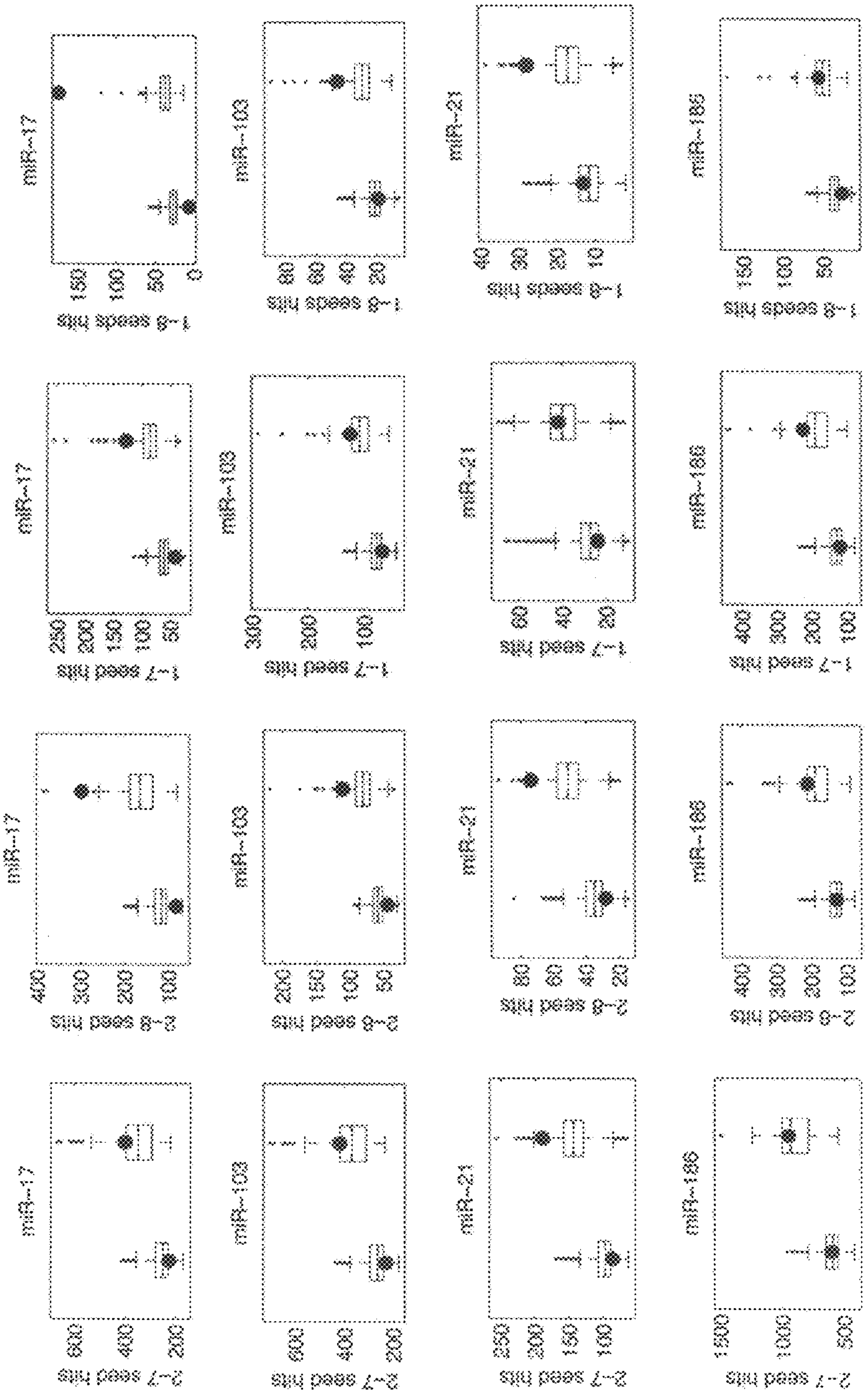
Figure 28C:
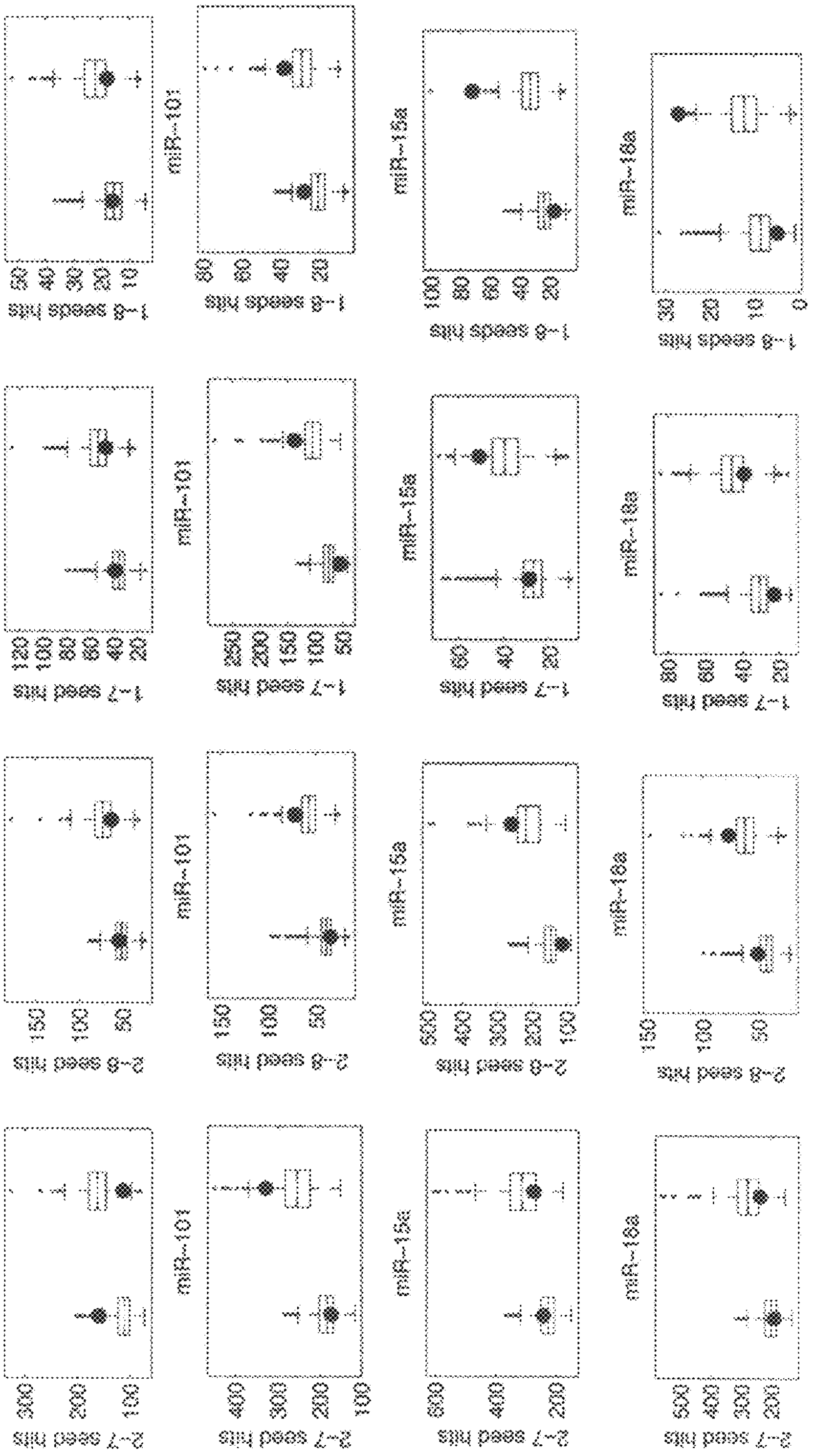
Figure 28D:
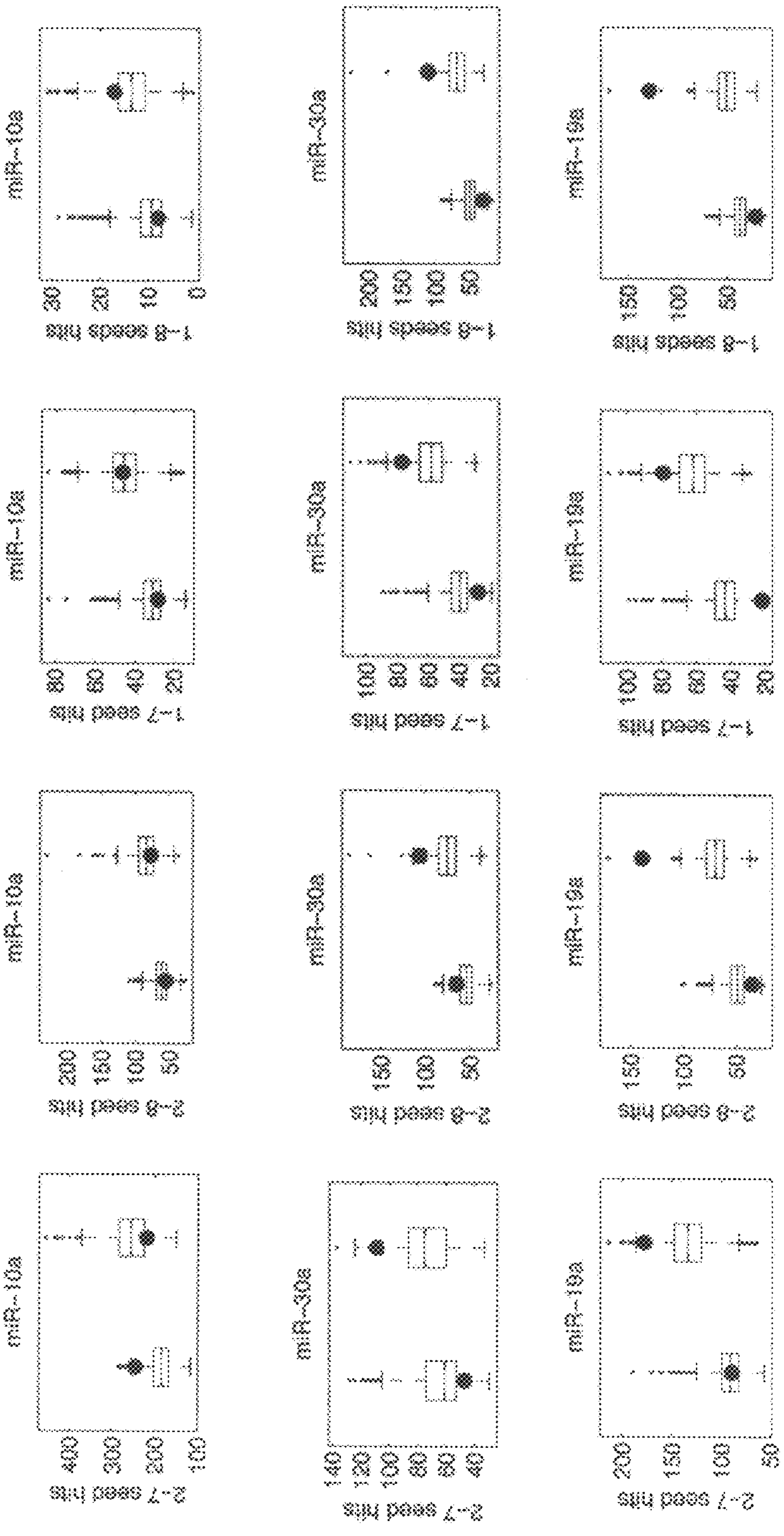
Figure 29A:
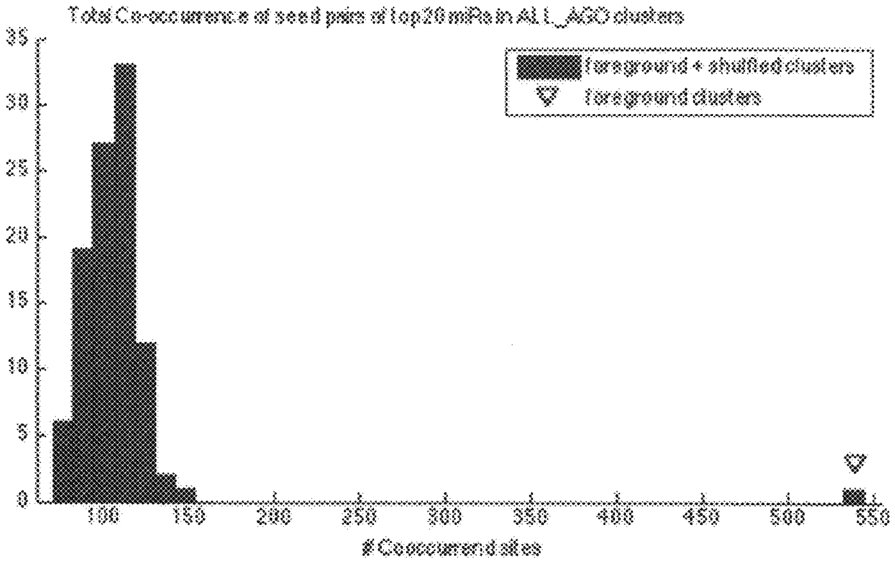
Figure 29B:
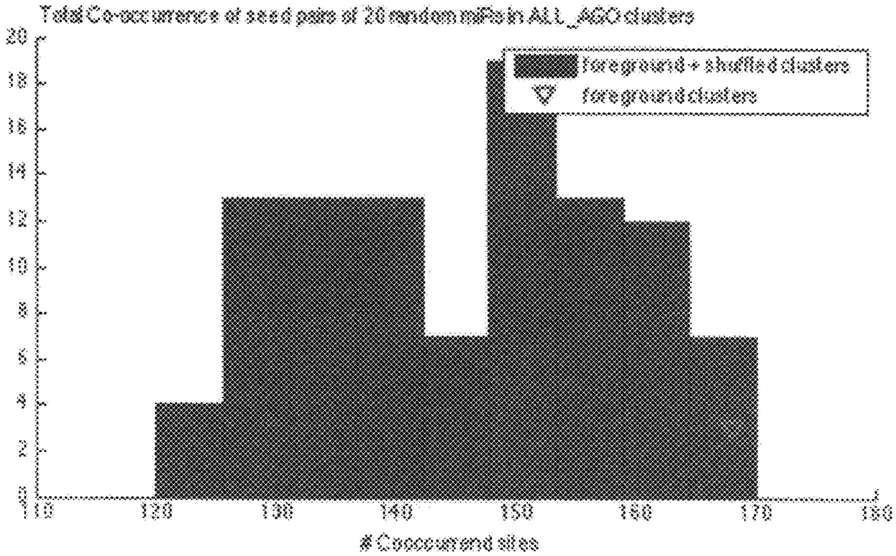
Figure 29C:
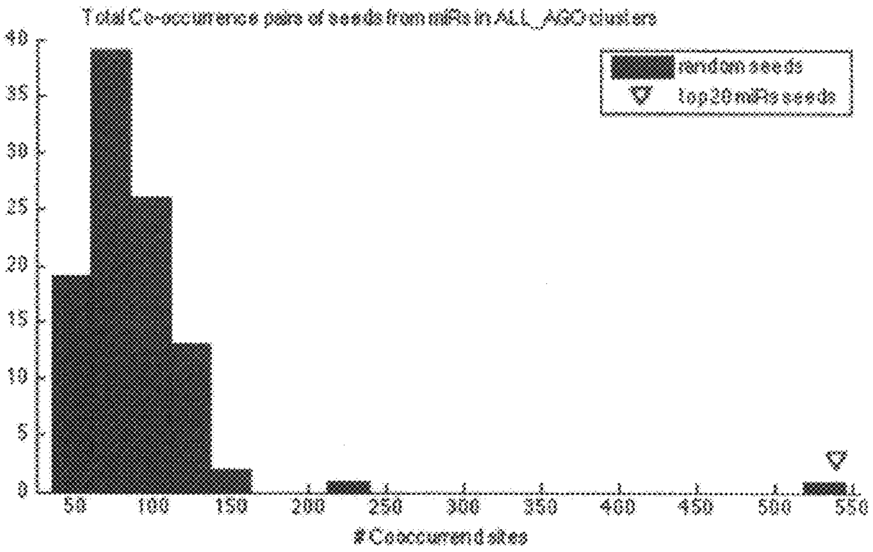
Figure 29D:
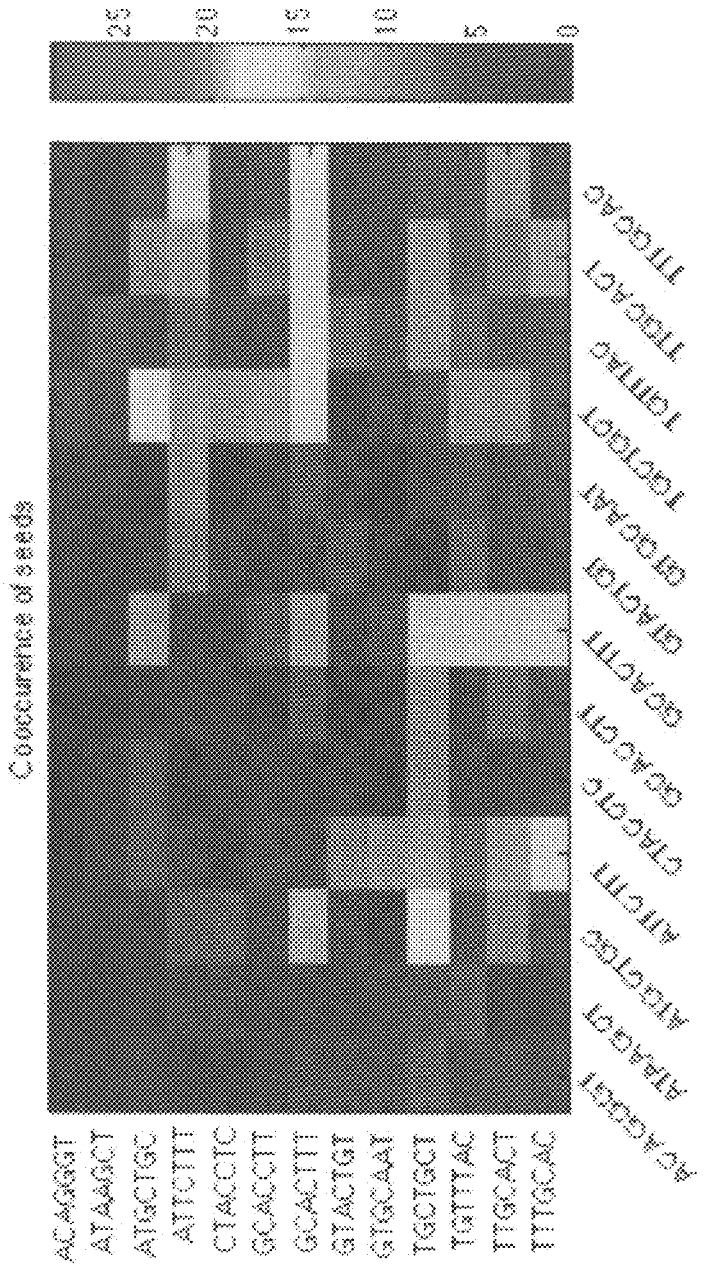

Regarding FIG. 28A-C:

Let-7a: Marginal.
2-7 seed let-7a: down p=0.223, up p=0.436
2-8 seed let-7a: down p=0.357, up p=0.364
1-7 seed let-7a: down p=0.292, up p=0.027
1-8 seeds let-7a: down p=0.013, up p=0.076
MiR-92a: Worked.
2-7 seed miR-92a: down p=0.029, up p=0.164
2-8 seed miR-92a: down p=0.010, up p=0.003
1-7 seed miR-92a: down p=0.023, up p=0.242
1-8 seeds miR-92a: down p=0.001, up p=0.000
MiR-27a: Didn't Work.
2-7 seed miR-27a: down p=0.429, up p=0.474
2-8 seed miR-27a: down p=0.281, up p=0.433
1-7 seed miR-27a: down p=0.301, up p=0.396
1-8 seeds miR-27a: down p=0.169, up p=0.392
MiR-301b: Worked.
2-7 seed miR-301b: down p=0.073, up p=0.049
2-8 seed miR-301b: down p=0.032, up p=0.002
1-7 seed miR-301b: down p=0.359, up p=0.378
1-8 seeds miR-301b: down p=0.414, up p=0.042
MiR-17: Worked.
2-7 seed miR-17: down p=0.227, up p=0.223
2-8 seed miR-17: down p=0.010, up p=0.001
1-7 seed miR-17: down p=0.027, up p=0.006
1-8 seeds miR-17: down p=0.000, up p=0.000
MiR-103: Worked.
2-7 seed miR-103: down p=0.137, up p=0.244
2-8 seed miR-103: down p=0.067, up p=0.019
1-7 seed miR-103: down p=0.208, up p=0.204
1-8 seeds miR-103: down p=0.337, up p=0.015
MiR-21: Marginal.
2-7 seed miR-21: down p=0.184, up p=0.013
2-8 seed miR-21: down p=0.150, up p=0.010
1-7 seed miR-21: down p=0.280, up p=0.408
1-8 seeds miR-21: down p=0.344, up p=0.013
MiR-186: Didn't Work Well.
2-7 seed miR-186: down p=0.438, up p=0.455
2-8 seed miR-186: down p=0.496, up p=0.258
1-7 seed miR-186: down p=0.330, up p=0.131
1-8 seeds miR-186: down p=0.088, up p=0.335
MiR-378: Marginal.
2-7 seed miR-378: down p=0.008, up p=0.013
2-8 seed miR-378: down p=0.377, up p=0.238
1-7 seed miR-378: down p=0.337, up p=0.261
1-8 seeds miR-378: down p=0.443, up p=0.224
MiR-101: Marginal.
2-7 seed miR-101: down p=0.341, up p=0.014
2-8 seed miR-101: down p=0.281, up p=0.091
1-7 seed miR-101: down p=0.039, up p=0.042
1-8 seeds miR-101: down p=0.094, up p=0.107

MiR-15a: Worked.

2-7 seed miR-15a: down p=0.325, up p=0.292

2-8 seed miR-15a: down p=0.033, up p=0.109

1-7 seed miR-15a: down p=0.370, up p=0.081

1-8 seeds miR-15a: down p=0.108, up p=0.001

MiR-18: Worked.

2-7 seed miR-18a: down p=0.374, up p=0.223

2-8 seed miR-18a: down p=0.175, up p=0.102

1-7 seed miR-18a: down p=0.093, up p=0.229

1-8 seeds miR-18a: down p=0.099, up p=0.002

MiR-10a: Didn't Work.

2-7 seed miR-10a: down p=0.023, up p=0.202

2-8 seed miR-10a: down p=0.298, up p=0.339

1-7 seed miR-10a: down p=0.328, up p=0.472

1-8 seeds miR-10a: down p=0.345, up p=0.207

MiR-30a: Worked.

2-7 seed miR-30a: down p=0.092, up p=0.013

2-8 seed miR-30a: down p=0.134, up p=0.011

1-7 seed miR-30a: down p=0.037, up p=0.046

1-8 seeds miR-30a: down p=0.012, up p=0.001

MiR-19a: Worked.

2-7 seed miR-19a: down p=0.463, up p=0.010

2-8 seed miR-19a: down p=0.037, up p=0.001

1-7 seed miR-19a: down p=0.001, up p=0.063

1-8 seeds miR-19a: down p=0.009, up p=0.000

Figure 7A:
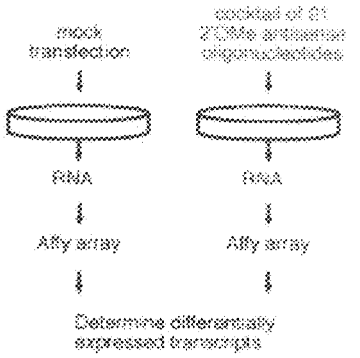
FIG. 7. mRNAs targeted by AGO proteins according to PURE-CLIP are destabilized. A Illustration of the experiment to determine alterations in mRNA expression level between mock-transfected cells and cells transfected with a cocktail of 21 2'-O-methyl (2'OMe) antisense oligoribonucleotides. mRNA expression was measured using microarrays. The cocktail of 24 2'OMe modified antisense oligoribonucleotides, inhibited 25 of the top 50 expressed miRNAs in HEK293 cells (miRNAs marked red in FIG. 5C). B Transcripts containing CCRs were categorized according to the presence of n-mer seed complementary matches and distributions of stability changes upon miRNA inhibition are shown. The p-values indicate the significance of the difference between the changes of target versus non-target transcripts, as given by the Wilcoxon rank-sum test and corrected for multiple testing. C Transcripts were categorized according to number of CCRs found. D Transcripts were categorized according to positional distribution of CCRs. Only transcripts containing CCRs binding exclusively to the indicated region are used. E Codon adaptation index (CAI) for transcripts containing seed complementary regions in the CDS for the miR-15, miR-19, miR-20, and let-7 miRNA families. The red and the black lines indicate the CAI for transcripts bound and unbound by AGO proteins. F LOESS regression of transcript abundance (log 2 of sequence counts in mRNA sequencing experiment) against fold change of expression (log 2) after transfection of the antisense cocktail versus mock transfection.
Figure 7B:
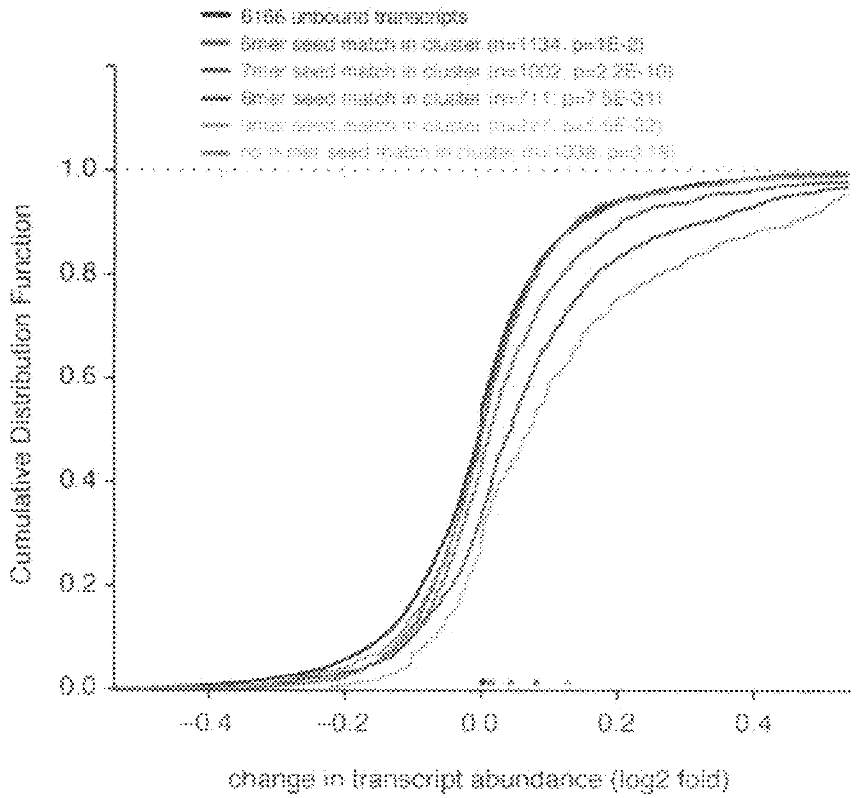

First, we examined the change in stability for target RNAs that contain at least one CCR, as a function of the length of the seed-complementary region (FIG. 7B). Consistent with previous studies (Crimson et al., 2007), the magnitude of the destabilization effects dropped from 9-mer, to 8-mer to 7-mer to 6-mer matches. Transcripts harboring CCRs that did not contain a 6-mer match to the antagonized miRNAs were not significantly stabilized, suggesting only limited regulation of transcripts with no canonical seed site.

Figure 7C:
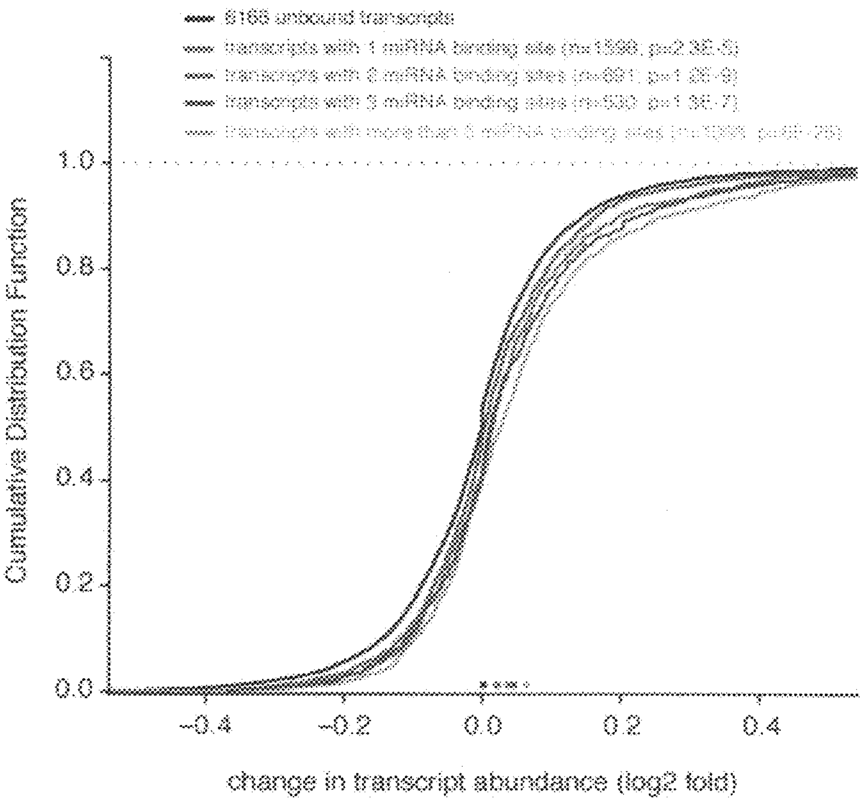
Figure 7D:
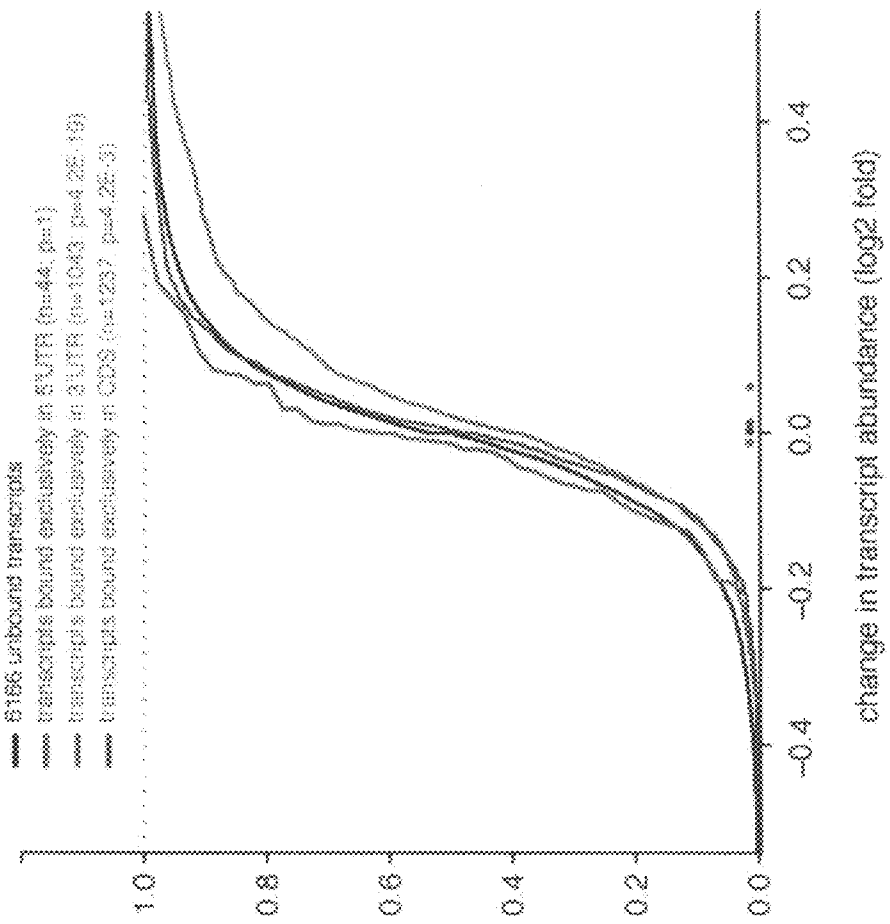

Second, we examined the change in stability of CCR-containing transcripts as a function of the number of binding sites, and found that transcripts containing more than one CCR were more efficiently destabilized than transcripts containing a single CCR (FIG. 7C). We also found that multiple binding sites for highly expressed miRNAs can co-occur within a single CCR (FIG. 27). Both of these findings were supported by previous observations (Grimson et al., 2007).

Figure 7E:
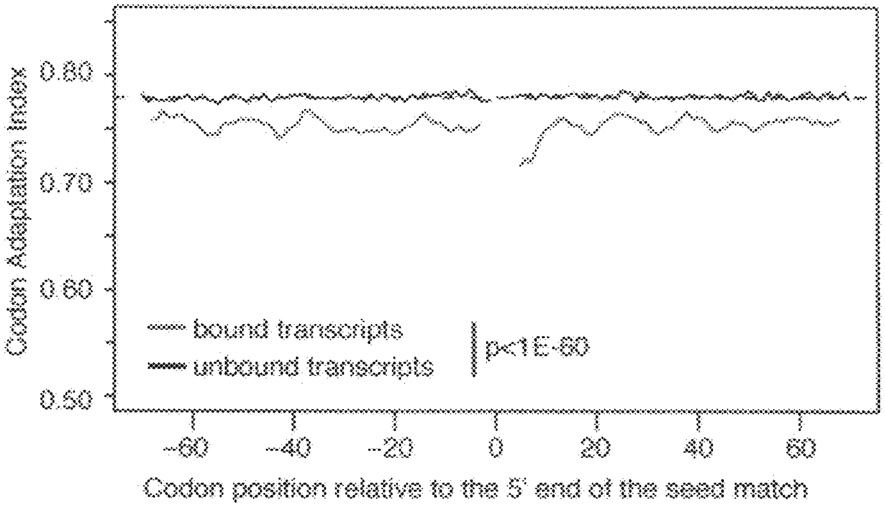

Third, we asked whether transcripts harboring CCRs exclusively in the CDS exhibited a similar level of regulation compared to transcripts with CCRs exclusive to the 3'UTRs; the number of 5'UTR-localized seed-match-containing CCRs was too small to allow for a statistically significant analysis of miRNA-dependent regulation. Transcripts with sites exclusively in the CDS were subject to a statistically significant miRNAdependent destabilization, albeit a lot less pronounced compared to the destabilizing effect caused by sites located in the 3'UTR (FIG. 7D), independent of whether they contained extensive seed matches to abundant miRNAs or not (FIG. 30). It was recently reported that miRNA targeting in the CDS was enhanced by inserting rare codons upstream of the miRNA-binding site, presumably by stalling the ribosomes and increasing the lifetime of miRNA-target-RNA interactions (Gu et al., 2009). We therefore examined the codon usage around crosslinked seed matches by calculating the codon adaptation index (Sharp and Li, 1987) and found that it was different from the average codon usage around non-crosslinked seed matching CDS regions. The bias in codon usage extended at least 70 codons up- as well as downstream of the crosslinked seed matches (FIG. 7E). It is conceivable that this bias led to a reduced translational efficiency and higher stability of interaction between the CDS of these transcripts and miRNA-AGO complexes. In summary, the miRNA inhibition studies provided evidence that CCRs represent functionally active sites and that the magnitude of miRNA-induced mRNA destabilization depends on the strength of base-pairing between miRNA and transcript, the number of interaction sites, and the position of these sites within the transcript.

Figure 7F:
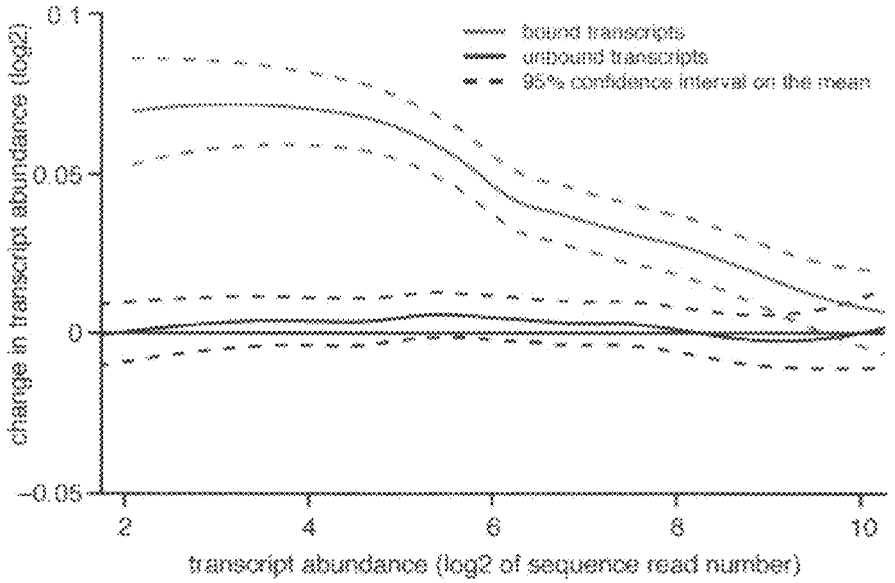

The abundance of mRNA species within cells varies over several orders of magnitude (Bishop et al., 1974). We determined the relative abundance of HEK293 transcripts by DGE profiling. Based on 3.9 M reads annotated as mRNA, we detected 22,466 expressed transcripts with expression levels varying over 5 orders of magnitude. When we related the expression level of CCR-containing transcripts with the magnitude of transcript stabilization after miRNA inhibition, we found that miRNAs preferentially act on transcripts with low and medium expression levels (FIG. 7F). Highly expressed mRNAs appear to avoid miRNA regulation (Farh et al., 2005; Sood et al., 2006; Stark et al., 2005), at least for those miRNAs expressed in HEK293 cells.

Example 13 miR-7 and miR-124 Transfection to Identify their Targets by PURE-CLIP

Earlier studies that revealed the destabilizing roles of miRNAs were carried out by transfection of individual cell-type specific miRNAs into cellular systems devoid of these particular miRNAs (Baek et al., 2008; Burchard et al., 2009; Lim et al., 2005; Selbach et al., 2008). To allow for a comparison to such studies, we transfected miRNA duplexes corresponding to the deeply conserved miR-7 and miR-124 into HEK293 cells stably expressing FLAG/HA-AGO2 and performed PURE-CLIP. Before transfection, these miRNAs were only present in trace amounts in HEK293 cells, less than 0.2% of total miRNA abundance. We found 1,866 unique sequence read clusters in the miR-7 and 10,929 in the miR-124 transfection experiments. The CCRs isolated from miR-7 and miR-124 transfection experiments were enriched for the seed sequences of the transfected miRNA duplexes. These CCRs were predominantly exonic (87 and 88%, respectively), 28% mapped to the CDS, 57 and 59%, respectively, to the 3'UTR of mRNAs and only 3 and 2%, respectively, to the 5'UTR. miR-7 and miR-124 binding sites that were located in the CDS for miR-7 and -124 were also embedded in regions with unusual codon bias, similar to the binding sites of endogenous miRNA target sites (FIG. 31).

The change in mRNA stability was analyzed after miRNA duplex transfection by Affymetrix whole genome microarrays (Hausser et al., submitted). We observed that transcripts containing miR-7- or miR-124-specific CCRs were destabilized upon miRNA delivery, especially for transcripts with CCRs located in the 3'UTR (FIG. 32-33). Therefore, analysis of data obtained with endogenous or transfected miRNAs yielded similar insights into miRNA targets and their regulation.

miRNA-target interactions are predominantly driven by seed interactions, however, not every seed-complementary sequence in the HEK293 transcriptome represented an experimental miRNA target site. We therefore tested whether CCRs and non-crosslinked seed-complementary sites differ in the ElMMo selection pressure (Gaidatzis 2007), the TargetScanS mRNA stability scores (Grimson et al., 2007), as well as the sequence and structural elements around the miRNA seed complementary site. The feature that distinguished most CCR sites from non-crosslinked sites was the free energy required to resolve local secondary structure involving the miRNA-binding region. The free energy for CCRs was on average 25% lower than that of non-crosslinked sites (FIG. 34). This difference in the stability of the secondary structure for CCRs is also associated with a 6% increase in the A/U content from within 100 nts around the seedpairing site. These properties hold for seed-complementary regions located in the CDS as well as in the 3'UTRs. Compared to non-crosslinked sites, CCRs are under stronger evolutionary selection (ElMMo) and in sequence contexts favoring degradation (TargetScanS).

We also compared our large datasets to computationally predicted interactions that involved at least a 7-mer subsequence (1-7 or 2-8) of miRNA seed regions and 3'UTRs of mRNAs. The rate of crosslinking of high-confidence target sites predicted by ElMMo (Gaidatzis et al., 2007) for the most abundant endogenous miRNA families (miR-15, miR-19, miR-103, miR-20 and let-7, see Supplementary Methods) and miR-7 and -124 was 8 to 15%. On the other hand, similar proportions (8-15%) of the seed-containing CCR were among low-confidence ElMMO predictions. Similar numbers were obtained using the TargetScanS (Grimson et al., 2007) target prediction tool. The apparent over-prediction of miRNA target sites may have several reasons, e.g. binding to other mRNA-binding proteins or the involvement of the putative target sites in RNA secondary structure, interactions that may change as a function of cellular context.

Consistent with the hypothesis that some of the predicted target sites may function in different cellular contexts that were not covered in our experiments. Consistent with this hypothesis, we found that high-confidence predicted target sites that were crosslinked resided in transcripts with higher expression (25-60% higher average expression depending on the experiment in HEK293 cells compared to high-confidence predicted target sites that were not crosslinked.

Finally, the relative position of CCRs is non-random. The CCRs containing 7-mer or 8-mer sites that are complementary to endogenous miRNAs as well as to miR-7 and miR-124 and residing in transcripts with relatively long 3'UTRs (more than 3 kb) were preferentially located near the stop codon or the polyA tail (FIG. 35). The CCRs located in the CDS showed a bias towards positions near the stop codon for the transfected miR-7 and 124, but not for the endogenous miRNAs (FIG. 36), again possibly reflecting a bias for highly efficient targeting sites in transfection experiments.

Example 14

Posttranscriptional Gene Regulation is a Complex Interplay Between RBPs and their Targets Maturation, localization, decay and translational regulation of mRNAs involves RBPs that form RNP complexes with their RNA targets (Komili and Silver, 2008; Martin and Ephrussi, 2009; Moore and Proudfoot, 2009). The human genome encodes several hundred RBPs, many of which consist of multiple repeats of a small set of RNA-binding domains that generate the diverse structural requirements for target RNA recognition (Lunde et al., 2007). Two of the most abundant domains are the RRM and KH domains, both of which recognize about 3- to 5-nucleotide (nt) long single-stranded RNA sequence motifs. Proteins containing these domains are involved in all aspects of posttranscriptional gene regulation and are also linked to a number of diseases (Keene, 2007).

Pumilio proteins represent another conserved group of RBPs repressing translation and/or enhancing mRNA decay and their RRMs comprise 8-10 nt of single-stranded RNA (Wickens et al., 2002). Furthermore miRNAs, hundreds of which are encoded in mammalian genomes (Landgraf et al., 2007), function in the context of AGO and TNRC6 proteins to destabilize target mRNAs and/or repress their translation, and they require 6-8 nt complementarity between the miRNA 5' end (seed) and their mRNA targets (Bartel, 2009; Filipowicz et al., 2008). Collectively, it is this dynamic association of RBPs and miRNPs with mRNAs that constitutes the code for posttranscriptional gene regulation, which we aim to elucidate. Until now, one of the limitations towards this goal was the lack of methods that directly identify RBP mRNA targets and binding sites with a clear separation of “true” versus “false” sites, while avoiding possible reorganization of RBP27 and RNP-target-RNA networks in the process (Mili et al., 2008).

Example 15

PURE-CLIP Allows High-Resolution Mapping of RBP and miRNA Target Sites

Utilizing 4SU effectively separates true binding sites from background. We showed that growing cultured cells in tissue culture medium supplemented by a photoreactive nucleoside enabled effective long-wavelength UV crosslinking of RNA to interacting proteins, thereby freezing even transient or low affinity interactions by covalent bond formation. We concentrated on the application of 4SU after it became apparent that the crosslink sites in isolated RNAs were revealed upon sequencing by a prominent transition from T to C in the cDNA prepared from the isolated crosslinked RNA segments. Regular UV 254 crosslinking in the absence of photoreactive nucleosides not only yielded less RNA in our hands, but more importantly, the location of the crosslink was not readily apparent by a mutational pattern. Studies using conventional 254 nm CLIP have not reported exploitable incidences of deletions and mutations (Chi et al., 2009; Licatalosi et al., 2008; Ule et al., 2003). A recent publication that focused on RBPs interacting exclusively with one RNA, the U3 snoRNA, showed that there was an increased incidence of deletions and substitutions around the single binding site (Granneman et al., 2009), however it remains unclear whether these mutations can be exploited on a transcriptome-wide level. Our identification of 4SU crosslink sites by frequent T to C transitions was unexpected and points to a distinct structural change of the crosslinked nucleobase likely resembling a cytidine analog that directs the reverse transcriptase to incorporate its cognate nucleotide partner distinct from the starting nucleotide. Standard UV 254 crosslinking, which occurs by a different mechanism, presumably yields base structures unable to induce a specific sequence change at scorable frequency. Irrespective of the UV crosslinking method applied, one must assume that amino-acid-modified nucleotides represent a severe block for reverse transcription, and that non-crosslinked RNA, always present as background after purification of crosslinked RNA segments, has a significant advantage over crosslinked RNA. It is therefore important to have a method that now provides an easy means to separate signal from noise.

In order to decipher with high-resolution crosslink sites by sequencing, they have to fall into the 32- to 36-nt Solexa sequencing read windows. This was accomplished by stringent RNase T1 digestion of the immunopurified RNPs to recover RBAs within a 20-40 nt RNA size window. Overdigestion of the RNA to size fragments too small to map uniquely to the genome was not a serious issue, because RNase T1 only cleaves after guanosines and the crosslinked RBP or miRNP also protects the bound target RNA. Nevertheless, it is useful to point out that some clusters of sequence reads arising from regions devoid of guanosines over a longer distance from the crosslinking sites must have received T to C transition scores similar to background in the current analysis pipeline. Using less specific nucleases, such as RNase A, may remedy the detection of these subsets of clusters, however, fine-tuning of RNase treatment may be technically more challenging.

Finally, the PURE-CLIP approach allows the definition of binding sites of cytoplasmic as well as nuclear localized proteins and RNPs, as shown by the identification of intronic clusters of sequence reads, reaching up to 70% for QKI. This is an important finding and indicates that the method is suitable to also study emerging new RNA regulatory processes closely linked to transcription (Kapranov et al., 2007).

Example 15

Context Dependence in 4SU Crosslink Sites

The crosslinking efficiency of 4SU appears to be context-dependent and affected by the local amino acid environment of the RBP. Therefore, the number of sequence reads for a given binding site is a complicated sum of not only the cellular abundance of target mRNAs and the affinity and association and dissociation rates of the RBP, but also the sequence composition affecting crosslinking efficiency. Nevertheless, by the depth of sequencing one can accomplish today, it is feasible to identify the majority of binding sites at a transcriptome level. An increasing understanding of copy numbers of RNA transcripts and RBPs and miRNAs inside cells, combined with further biochemical binding studies, will eventually yield a more quantitative description of RNA recognition processes.

Certain extreme types of binding sites or sequence environment may be difficult to be fully covered by using solely 4SU. To assess the possible magnitude of this potential problem, we determined that only about 0.4% of 32-nt long sequence segments present in the entire transcriptome are actually devoid of uridines, or in other words, an 8-kb long mRNA would on average contain only one 32 nt long U-less segment (FIG. 19). To provide a means to resolve such unlikely situations, the use of other photoreactive nucleosides, such as 6SG, was explored. We found that IGF2BP1 sites identified by use of 6SG overlapped substantially with those from using 4SU, despite of the fact that the environment of IGF2BP1 binding sites was strongly depleted for guanosine (FIG. 20A-C). Furthermore, the sites of crosslinking using 6SG were enriched for G to A transitions, pointing to an interesting structural change in 6SG upon crosslinking presumably mimicking an adenosine analog. The only drawback for using 6SG is its higher cytotoxicity noticeable above 100 μM at exposure longer than 24 hrs in culture medium (Melvin et al., 1978), which is at the threshold of the concentrations we have used in our studies. We therefore recommend to first use 4SU and then possibly resort to use 6SG when sequence contexts were encountered that are avoiding uridines over long sequence regions.

Example 16 miRNA Target Identification

When applying PURE-CLIP to isolate mRNA segments bound by endogenously expressed or additionally co-transfected miRNAs, we were surprised by the extent of binding sites present in the CDS, approaching nearly 50%. miRNA inhibition experiments showed that miRNA binding at these sites also caused mRNA destabilization, albeit to a lesser extent than binding sites located in the 3'UTR. The CDS miRNA binding sites showed an increased incidence of rare codon usage, presumably reducing translational efficiency and opening a window for transient miRNP binding. Similar observations were made previously using artificially designed reporter systems (Gu et al., 2009). A broad distribution of binding sites across CDS and 3'UTR were also seen for IGF2BP or QKI protein binding sites, however for PUM2 protein, which has a consensus site length similar to miRNAs, the sites were almost exclusively restricted to 3'UTRs. The reason for this striking difference is unclear, presumably different biochemical mechanisms and evolutionary selection of target RNA regulation must be at play.

High-resolution knowledge of the crosslinking site allows us to narrowly define the miRNA binding regions for matching the site with the most likely miRNA endogenously co-expressed with its targets, and assess non-canonical miRNA binding modes. This approach is distinct from relying on matching predicted miRNA binding sites to a broad peak of clusters (Chi et al., 2009). We were able to explain the majority of PURE-CLIP binding sites by conventional miRNA-mRNA seed-pairing interactions (Grimson et al., 2007), yet found that about 6% of miRNA target sites might best be explained by accepting bulges or mismatches in the seed pairing region, similar to the interaction between let-7 and its target lin-41 (Vella et al., 2004) and those recently observed in biochemical and structural studies of *T. thermophilus* AGO protein (Wang et al., 2008a).

Finally, mutational analysis of miRNAs in AGO PURE-CLIP also showed the expected T to C transition, but not for all sequences currently proposed to be miRNAs. In part, these differences are due to the absence of U within the regions of the miRNA effectively crosslinking to AGO proteins, but others do not show such biases and therefore likely represent RNAs that were misclassified as miRNAs. Consequently, we now have a new method that is able to validate putative miRNAs acquired from deep sequencing approaches. It is important to note that all of our PURE-CLIP libraries, also those unrelated to AGO or TNRC6 proteins contain between 10 and 30% miRNAs, yet only AGO libraries do contain T to C changes in their sequence reads. This is further testament for the importance of separating signal from noise using crosslinking approaches to isolate and identify bound RNA segments.

Example 17

Implications for the mRNA Ribonucleoprotein Code

It was surprising to discover that each of the examined RBP or miRNPs control a substantial (one to seven thousand) fraction of transcripts out of the possible 20,000 detectable in HEK293 cells. These numbers illustrate that transcripts are mostly under combinatorial control, and that simple regulatory networks cannot be deduced from solely determining binding sites for a single RBP. This discovery also implies that highresolution mapping at a nucleotide level of RBP RNA interaction is imperative as many of these sites are adjacent to each other. It will therefore be critical to expand the PURECLIP approaches to all other RBPs and also transiently interacting RNA-binding factors, such as helicases, nuclease or polymerases, to ultimately enable us to understand how the sum or a particular combination of these interactions ultimately controls the fate of each mRNA. To assess the impact of post-transcriptional regulation, we can now begin to interpret the rapidly emerging data on genetic variation between individuals and how these variations contribute to complex genetic diseases.

Example 18

Supplementary Methods

Oligonucleotides and siRNA Duplexes

The following oligodeoxynucleotides were used for PCR and cDNA cloning into pENTR4 (Invitrogen), restriction site are underlined:

```
PUM2,
                                        (SEQ ID NO: 17)
ATGAATCATGATTTTCAAGCTCTTGCATTAG,
                                        (SEQ ID NO: 18)
ATAAGAATGCGGCCGCTTACAGCATTCCATTTGGTGGTCCTCCAATAG;

QKI,
                                        (SEQ ID NO: 19)
ACGCGTCGACATGGTCGGGGAAATGGAAACG,
                                        (SEQ ID NO: 20)
ATAAGAATGCGGCCGCTTAGCCTTTCGTTGGGAAAGCC;

IGF2BP1,
                                        (SEQ ID NO: 21)
ACGCGTCGACATGAACAAGCTTTACATCGGCAACCTC,
                                        (SEQ ID NO: 22)
ATAAGAATGCGGCCGCTCACTTCCTCCGTGCCTGGGCCTG;

IGF2BP2,
                                        (SEQ ID NO: 23)
ACGCGTCGACATGATGAACAAGCTTTACATCGGGAAC,
                                        (SEQ ID NO: 24)
ATAAGAATGCGGCCGCTCACTTGCTGCGCTGTGAGGCGAC;

IGF2BP3,
                                        (SEQ ID NO: 25)
ACGCGTCGACATGAACAAACTGTATATCGGAAACCTCAG,
                                        (SEQ ID NO: 26)
ATAAGAATGCGGCCGCTTACTTCCGTCTTGACTGAGGTGGTC.
```

The following oligoribonucleotides were used for QKI protein in vitro binding and crosslinking studies and were purchased from Dharmacon:

```
GUAUGCCAUUAACAAAUUCAUUAACAA,        (SEQ ID NO: 27)

G(4sU)AUGCCAUUAACAAAUUCAUUAACAA,    (SEQ ID NO: 28)

GUA(4sU)GCCAUUAACAAAUUCAUUAACAA,    (SEQ ID NO: 29)

GUAUGCCA(4sU)AACAAAUUCAUUAACAA,     (SEQ ID NO: 30)

GUAUGCCAU(4sU)AACAAAUUCAUUAACAA,    (SEQ ID NO: 31)
4sU, 4-thiouridine.
```

The following siRNA duplexes (sense/antisense) were used for knockdown experiments and synthesized on a modified ABI 392 RNA/DNA synthesizer using Dharmacon synthesis reagents.

```
QKI duplex 1,
                          (SEQ ID NO: 32)
5'GAAGAGAGCAGUUGAAGAAUU,
                          (SEQ ID NO: 33)
UUCUUCAACUGCUCUCUUCUU;

QKI duplex 2,
                          (SEQ ID NO: 34)
CCAAUUGGGAGCAUCUAAAUdT,
```

-continued

```
                          (SEQ ID NO: 35)
UUUAGAUGCUCCCAAUUGGUdT;

IGF2BP1,
                          (SEQ ID NO: 36)
GGGAAGAAUCUAUGGCAAAUU,
                          (SEQ ID NO: 37)
UUUGCCAUAGAUUCUUCCCUU;

IGF2BP2,
                          (SEQ ID NO: 38)
GGCAUCAGUUUGAGAACUAUU,
                          (SEQ ID NO: 39)
UAGUUCUCAAACUGAUGCCUU;

IGF2BP3,
                          (SEQ ID NO: 40)
AAAUCGAUGUCCACCGUAAUU,
                          (SEQ ID NO: 41)
UUACGGUGGACAUCGAUUUUU.
```

2'-O-Methyl Oligoribonucleotides and miRNA Duplexes

The following sequences were chemically synthesized on an ABI394 RNA/DNA synthesizer using 5'silyl/2'orthoester chemistry (Dharmacon):

```
anti-let-7a:
                          (SEQ ID NO: 42)
AACUAUACAACCUACUACCUCA-NH2;

anti-miR-10a:
                          (SEQ ID NO: 43)
CACAAAUUCGGAUCUACAGGGUA-NH2;

anti-miR-15a:
                          (SEQ ID NO: 44)
CGCCAAUAUUUACGUGCUGCUA;

anti-miR-15b:
                          (SEQ ID NO: 45)
CACAAACCAUUAUGUGCUGCUA;

anti-miR-16:
                          (SEQ ID NO: 46)
UGUAAACCAUGAUGUGCUGCUA;

anti-miR-17-5p:
                          (SEQ ID NO: 47)
CUACCUGCACUGUAAGCACUUUG;

anti-miR-18a:
                          (SEQ ID NO: 48)
CUAUCUGCACUAGAUGCACCUUA-NH2;

anti-miR-19a:
                          (SEQ ID NO: 49)
UCAGUUUUGCAUAGAUUUGCACA;

anti-miR-19b:
                          (SEQ ID NO: 50)
UCAGUUUUGCAUGGAUUUGCACA;

anti-miR-20a:
                          (SEQ ID NO: 51)
CUACCUGCACUAUAAGCACUUUA;

anti-miR-20b:
                          (SEQ ID NO: 52)
CUACCUGCACUAUGAGCACUUUG;

anti-miR-21:
                          (SEQ ID NO: 53)
UCAACAUCAGUCUGAUAAGCUA;

anti-miR-25:
                          (SEQ ID NO: 54)
UCAGACCGAGACAAGUGCAAUG;
```

-continued

```
anti-miR-27:
                                        (SEQ ID NO: 55)
AACUAUACAAUCUACUACCUCA;

anti-miR-30a:
                                        (SEQ ID NO: 56)
CUUCCAGUCGAGGAUGUUUACA-NH2;

anti-miR-30b/c:
                                        (SEQ ID NO: 57)
GAGUGUAGGAUGUUUACA-NH2;

anti-miR-92b:
                                        (SEQ ID NO: 58)
ACAGGCCGGGACAAGUGCAAUA;

anti-miR-93:
                                        (SEQ ID NO: 59)
CUACCUGCACGAACAGCACUUUG;

anti-miR-101:
                                        (SEQ ID NO: 60)
UUCAGUUAUCACAGUACUGUA;

anti-miR-103:
                                        (SEQ ID NO: 61)
UCAUAGCCCUGUACAAUGCUGCU;

anti-miR-106b:
                                        (SEQ ID NO: 62)
AUCUGCACUGUCAGCACUUUA-NH2;

anti-miR-186:
                                        (SEQ ID NO: 63)
AGCCCAAAAGGAGAAUUCUUUG;

anti-miR-301:
                                        (SEQ ID NO: 64)
GCUUUGACAAUACUAUUGCACUG;

anti-miR-378:
                                        (SEQ ID NO: 65)
CCUUCUGACUCCAAGUCCAGU;
-NH2; indicates C6 aminolinker
(Dharmacon).

miR-7/miR-7* duplex,
                                        (SEQ ID NO: 66)
5'-UGGAAGACUAGUGAUUUUGUUGU,
                                        (SEQ ID NO: 67)
5'-CAACAAAUCACAGUCUGCCAUA;

miR-124/miR124* duplex,
                                        (SEQ ID NO: 68)
5'-UAAGGCACGCGGUGAAUGCCA,
                                        (SEQ ID NO: 69)
5'-CGUGUUCACAGCGGACCUUGA.
```

Plasmids

Plasmids pENTR4 IGF2BP1, 2, 3, QKI, AGO1-4, TNRC6A-C and PUM2 were generated by PCR amplification of the respective coding sequences (CDS) followed by restriction digest with SalI and NotI and ligation into pENTR4 (Invitrogen). pENTR4 IGF2BP1, -2, and -3 were recombined into pFRT/TO/FLAG/HA-DEST destination vector (Invitrogen) using GATEWAY LR recombinase according to manufacturer's protocol (Invitrogen) to allow for doxycycline-inducible expression of stably transfected FLAG/HA-tagged protein in Flp-In T-REx HEK293 cells (Invitrogen) from the TO/CMV promoter. pENTR4 QKI and pENTR4 PUM2 were recombined into pFRT/FLAG/HA4 DEST for constitutive expression in Flp-In T-REx HEK293 cells.

Plasmids for bacterial expression of N-terminally His6-tagged IGF2BP1, 2, and 3 in *E. coli* were generated by ligation of CDS into pET16 (Novagen). The plasmid for bacterial expression of N-terminally His6-tagged QKI was generated by LR recombination of pENTR4 QKI with pDEST17 (Invitrogen). The plasmids described in this study can be obtained from Addgene.

Antibodies

Polyclonal rabbit antibodies against IGF2BP1, 2, and 3 were generated by injection of synthetic peptides corresponding to positions aa 561-573, 264-275, and 567-579, respectively. Rabbit anti-QKI (BL1040) was purchased from Bethyl Laboratories.

Recombinant Protein Expression and Purification pET16 IGF2BP1, -2, and -3 and pDEST17-QKI plasmids, encoding an N-terminal His6-tag, were transformed in *E. coli* STAR(DE3) (Invitrogen). Cells were grown in LB medium supplemented with 50 μg/ml ampicillin at 37° C. to A600=0.6. The cells were cooled to 25° C., protein synthesis was induced by addition of IPTG to a final concentration of 1 mM, cells were harvested 3 h later. The cell pellet was resuspended in 10 ml lysis buffer (50 mM Tris-HCl pH 8.0, 300 mM KCl, 5 mM MgCl2, 0.1% Triton X-100, and complete EDTA-free protease inhibitor (Roche)) per gram cell pellet. All the following steps were carried out at 4° C. Cells were resuspended in lysis buffer and incubated with 1 mg/ml lysozyme for 30 min and sonicated to reduce viscosity. Insoluble material was removed by centrifugation at 12,000×g for 20 min. For His-tag affinity selection, the supernatant was incubated with 250 μl HIS-Select Cobalt Affinity Gel (Sigma) per 10 ml cell supernatant for 1 h. The gel was washed three times with 10 gel volumes of wash buffer (50 mM Tris-HCl, pH 8.0, 300 mM KCl, 5 mM MgCl2, 1 mM DTT, 0.1% Triton X-100, 25 mM imidazol, and complete EDTA-free protease inhibitor (Roche)). His-tagged proteins were eluted in 3 gel volumes of elution buffer (50 mM Tris-HCl pH 8.0, 300 mM KCl, 5 mM MgCl2, 1 mM DTT, 0.1% Triton X-100, 250 mM imidazol, and complete EDTA-free protease inhibitor (Roche)). The eluted proteins were applied to a Heparin column equilibrated in 20 mM Tris-HCl pH 7.8, 5 mM MgCl2, 100 mM KCl, 1 mM DTT, 0.1% Triton X-100, 10% glycerol. Proteins were eluted with a KCl gradient (0.5-1.5 M) in 20 mM Tris-HCl, pH 7.8, 5 mM MgCl2, 1 mM DTT, 0.1% Triton X-100, 10% glycerol. His6-IGF2BP1, -2, and -3 eluted at 550 to 650 mM KCl and His6-QKI at 1.1 M KCl.

Electrophoretic Mobility-Shift Analysis

Radiolabeled RNA (100 pM) was incubated with recombinant His6-IGF2BP2 protein at indicated concentrations and 100 ng tRNA in 20 μl of 20 mM Tris-HCl, pH 7.8, 140 mM KCl, 2 mM MgCl2 and 0.1% Triton X-100 at 30° C. for 1 h. After addition of 6 μl loading dye (40% glycerol, bromophenol blue in binding buffer), the solution was loaded onto a native 6% acrylamide gel containing 0.5×TBE, running at 200 V for 1 h at room temperature, using 0.5×TBE as running buffer.

Radiolabeled RNA (1 nM) was incubated with recombinant His6-QKI protein at various concentrations and 100 ng tRNA in 20 μl of 20 mM HEPES-KOH, pH 7.4, 330 mM KCl, 10 mM MgCl2, 0.1 mM EDTA and 0.01% IGEPAL CA630 (Sigma). After addition of 6 μl loading dye (40% glycerol, bromophenol blue in binding buffer), the solution was loaded onto a native 10% acrylamide gel containing 0.5×TBE, running at 200 V for 2 h at room temperature, using 0.5×TBE as running buffer. The protein-bound RNA and the free RNA were quantified using a phosphorimager.

Cell Lines and Culture Conditions

HEK293 T-REx Flp-In cells (Invitrogen) were grown in D-MEM high glucose (1×) with 10% (v/v) fetal bovine serum, 1% (v/v) 2 mM L-glutamine, 1% (v/v) 10,000 U/ml penicillin/10,000 μg/ml streptomycin, 100 μg/ml zeocin and 15 μg/ml blasticidin. Cell lines stably expressing FLAG/HA-tagged proteins were generated by co-transfection of pFRT/TO/FLAG/HA or pFRT/FLAG/HA constructs with pOG44 (Invitrogen). Cells were selected by exchanging zeocin with 100 μg/ml hygromycin. Expression of FLAG/HA-IGF2BP1, -2, -3 was induced by addition of 250 ng/ml doxycycline 15 to 20 hrs before crosslinking SiRNA Transfection and mRNA Affymetrix Array Analysis siRNA transfections of HEK293 T-REx Flp-In cells were performed in 6-well format using Lipofectamine RNAiMAX (Invitrogen) as described by the manufacturer. Total RNA of transfected cells was extracted using TRIZOL following the instructions of the manufacturer. The RNA was further purified using the RNeasy purification kit (Qiagen). 2 μg of purified total RNA was used in the One-Cycle Eukaryotic Target Labeling Assay (Affymetrix) according to manufacturer's protocol. Biotinylated cRNA targets were cleaned up, fragmented, and hybridized to Human Genome U133 Plus 2.0 Array (Affymetrix). For details of the analysis, see Bioinformatics section.

miRNA Duplex Transfection and mRNA Affymetrix Array Analysis miRNA duplexes and 2'-O-methyl oligoribonucletide transfections of HEK293 TREx Flp-In cells were carried out using Lipofectamine RNAiMAX (Invitrogen). Total RNA was isolated by TRIZOL RNA extraction. The RNA was further purified and Human Genome U133 Plus 2.0 Array (Affymetrix) analyses were performed as described previously (Landthaler et al., 2008).

miRNA RNA Profiling miRNAs were extracted from FLAG/HA-AGO immunoprecipitates as described in Meister et al. (Meister et al., 2004). miRNAs from immunoprecipitate and total RNA were cloned and Solexa-sequenced (Hafner et al., 2008) using following bar-coded 5' adapters:

```
                                    (SEQ ID NO: 70)
AGO1-IP: TCTAGTCGTATGCCGTCTTCTGCTTGT

                                    (SEQ ID NO: 71)
AGO2-IP: TCTCCTCGTATGCCGTCTTCTGCTTGT

                                    (SEQ ID NO: 72)
AGO2-IP: TCTGATCGTATGCCGTCTTCTGCTTGT

                                    (SEQ ID NO: 73)
AGO3-IP: TTAAGTCGTATGCCGTCTTCTGCTTGT

                                    (SEQ ID NO: 74)
Lysate: TCACTTCGTATGCCGTCTTCTGCTTGT
```

UV 254 and 365 nm Crosslinking

For UV crosslinking, cells were washed once with ice-cold PBS while still attached to the plates. PBS was removed completely and cells were irradiated on ice with 254 nm UV light (0.15 J/cm2), or 365 nm UV light for cells treated for 14 hrs with 100 μM nucleoside analogues (0.15 J/cm2) in a Stratalinker 2400 (Stratagene), equipped with light bulbs for the appropriate wavelength. Cells were scraped off with a rubber policeman in 1 ml PBS per plate and collected by centrifugation at 500×g for 5 min.

Cell Lysis and First Partial RNase T1 Digestion

The pellets of UV365-crosslinked cells were resuspended in 3 cell pellet volumes of NP40 lysis buffer (50 mM HEPES, pH 7.5, 150 mM KCl, 2 mM EDTA, 1 mM NaF, 0.5% (v/v) NP40, 0.5 mM DTT, complete EDTA-free protease inhibitor cocktail (Roche)) and incubated on ice for 10 min. The typical scale of such an experiment was 3 ml of cell pellet. The cell lysate was cleared by centrifugation at 13,000×g. RNase T1 (Fermentas) was added to the cleared cell lysates to a final concentration of 1 U/μl and the reaction mixture was incubated in a water bath at 22° C. for 15 min and subsequently cooled for 5 min on ice before addition of antibody-conjugated magnetic beads.

Immunoprecipitation and Recovery of Crosslinked Target RNA Fragments

Preparation of Magnetic Beads

10 μl of Dynabeads Protein G magnetic particles (Invitrogen) per ml cell lysate were washed twice with 1 ml of citrate-phosphate buffer (4.7 g/l citric acid, 9.2 g/l Na2HPO4, pH 5.0) and resuspended in twice the volume of citrate-phosphate buffer relative to the original volume of bead suspension. 0.25 μg of anti-FLAG M2 monoclonal antibody (Sigma, F9291) per ml suspension was added and incubated at room temperature for 40 min. Beads were then washed twice with 1 ml of citrate-phosphate buffer to remove unbound antibody and resuspended again in twice the volume of citrate-phosphate buffer relative to the original volume of bead suspension.

Immunoprecipitation (IP), Second RNase T1 Digestion, and Dephosphorylation

10 μl of freshly prepared antibody-conjugated magnetic beads per ml of partial RNase T1 treated cell lysate were added and incubated in 15 ml centrifugation tubes on a rotating wheel for 1 h at 4° C. Magnetic beads were collected on a magnetic particle collector (Invitrogen). Manipulations of the following steps were carried out in 1.5 ml Eppendorf tubes. The supernatant was removed from the bead-bound material. Beads were washed 3 times with 1 ml of IP wash buffer (50 mM HEPES-KOH, pH 7.5, 300 mM KCl, 0.05% (v/v) NP40, 0.5 mM DTT, complete EDTA-free protease inhibitor cocktail (Roche)) and resuspended in one volume of IP wash buffer. RNase T1 (Fermentas) was added to obtain a final concentration of 100 U/μl, and the bead suspension was incubated in a water bath at 22° C. for 15 min, and subsequently cooled for 5 min on ice. Beads were washed 3 times with 1 ml of high-salt wash buffer (50 mM HEPES-KOH, pH 7.5, 500 mM KCl, 0.05% (v/v) NP40, 0.5 mM DTT, complete EDTA-free protease inhibitor cocktail (Roche)) and resuspended in one volume of dephosphorylation buffer (50 mM Tris-HCl, pH 7.9, 100 mM NaCl, 10 mM MgCl2, 1 mM DTT). Calf intestinal alkaline phosphatase (NEB) was added to obtain a final concentration of 0.5 U/μl, and the suspension was incubated for 10 min at 37° C. Beads were washed twice with 1 ml of phosphatase wash buffer (50 mM Tris-HCl, pH 7.5, 20 mM EGTA, 0.5% (v/v) NP40) and twice with 1 ml of polynucleotide kinase (PNK) Buffer (50 mM Tris-HCl, pH 7.5, 50 mM NaCl, 10 mM MgCl2, 5 mM DTT). Beads were resuspended in one original bead volume of PNK Buffer.

Radiolabeling of RNA Segments Crosslinked to Immunoprecipitated Proteins

To the bead suspension described above, γ-32P-ATP was added to a final concentration of 0.5 μCi/μl and T4 PNK (NEB) to 1 U/μl in one original bead volume. The suspension was incubated for 30 min at 37° C. Thereafter, non-radioactive ATP (Fermentas) was added to obtain a final concentration of 100 μM and the incubation was continued for another 5 min at 37° C. The magnetic beads were then washed 5 times with 800 μl of PNK Buffer and resuspended in 70 μl of SDS-PAGE Loading Buffer (10% glycerol (v/v), 50 mM Tris-HCl, pH 6.8, 2 mM EDTA, 2% SDS (w/v), 100 mM DTT, 0.1% Bromophenol blue).

SDS-PAGE and Electroelution of Crosslinked RNA Protein Compounds from Gel Slices The radiolabeled bead suspension was incubated for 5 min at 95° C. and vortexed. The magnetic beads were separated on a magnetic separator and 40 μl of supernatant were loaded per well of an SDS-PAGE. The gel was analyzed by phosphorimaging. The radioactive band migrating at the expected molecular weight of the target protein was excised from the gel and electroeluted in a D-Tube Dialyzer Midi (Novagen) in 800 μl SDS running buffer according to the instructions of the manufacturer.

Proteinase K Digestion

An equal volume of 2× Proteinase K Buffer (100 mM Tris-HCl, pH 7.5, 150 mM NaCl, 12.5 mM EDTA, 2% (w/v) SDS) with respect to the electroeluate was added, followed by the addition of Proteinase K (Roche) to a final concentration of 1.2 mg/ml, and incubation for 30 min at 55° C. The RNA was recovered by acidic phenol/chloroform extraction followed by a chloroform extraction and an ethanol precipitation. The pellet was dissolved in 10.5 μl of water.

cDNA Library Preparation and Deep Sequencing

The recovered RNA was carried through a cDNA library preparation protocol originally described for cloning of small regulatory RNAs (Hafner et al., 2008). The first step, 3' adapter ligation, was carried out as described on a 20 μl scale using 10.5 μl of the recovered RNA. UV 254 nm crosslinked RNAs were processed using standard adapter sets, followed by PCR to introduce primers compatible with 454 sequencing; UV 365 nm crosslinked sample RNAs were processed using Solexa sequencing adapter sets. Depending on the amount of RNA recovered, 5'-adapter-3'-adapter products without inserts may be detected after amplification of the cDNA as additional PCR band. In such case, the longer PCR product of expected size was excised from a 3% NuSieve lowmelting point agarose, eluted from the gel pieces with the Illustra GFX-PCR purification kit (GE Healthcare) and Solexa sequenced.

Generation of Digital Gene Expression (DGEX) Libraries

1 μg each of total RNA from HEK293 cells inducibly expressing tagged IGF2BP1 before and after induction was converted into cDNA libraries for expression profiling by sequencing using the DpnII DGE kit (Illumina) according to instructions of the manufacturer. For details of the analysis, see Bioinformatics section.

Bioinformatics

Adapter Removal and Sequence Annotation

The basic method for removing adaptors and assigning a functional annotation to the tags was described in (Berninger et al., 2008). Briefly, we used an in-house free ends local alignment algorithm (score parameters: 2 for match, −3 for mismatch, −2 for gap opening, −3 for gap extension) to align the Solexa adapter to the 3' end of each tag, allowing for the possibility that the adapter was not completely sequenced. We then discarded sequences that were either too short (less than 20 nc) or too repetitive (using a cutoff of 0.7 and 1.5 in the entropy of the mono- and dinucleotide distributions, respectively, of individual tags (Berninger et al., 2008)) and would probably map to multiple genomic locations. We mapped the remaining sequences to the hg18 version of the human genome assembly that we downloaded from the University of California at Santa Cruz and to a database of sequences whose function (rRNA, tRNA, sn/snoRNA, miRNA, mRNA, etc.) is already known. These were obtained from the sources specified in (Berninger et al., 2008). We used the oligomap algorithm (Berninger et al., 2008) for this purpose, and we obtained all the perfect and 1-error (mismatch or indel) mappings. Based on the GMAP (Wu and Watanabe, 2005) genome mapping of human mRNA transcripts from NCBI downloaded on Nov. 4, 2008, we determined whether the tags mapped to intronic or exonic regions of genes. Based on the coding region annotation of transcripts in GenBank, we determined whether the exonic tags originated from the 5' UTR, CDS or 3' UTR.

Generation of Clusters of Mapped Sequence Reads

For subsequent analyses we only used sequence tags of at least 20 nt in length and mapping uniquely to the genome, with at most 1 error. We performed single-linkage clustering of the tags, with two tags being placed in the same cluster if they overlapped by at least one nucleotide in their genomic mappings. Each cluster was then annotated based on the functional annotation of tags that covered most of the cluster length. We then considered all the mRNA-annotated clusters containing at least 5 mRNA-annotated tags, and we defined a scoring scheme to identify the clusters that had the highest probability of being real crosslinking sites (see below: Identification of high confidence clusters).

Analysis of Mutational Spectra

From the clusters defined above, we used all tags that mapped uniquely and with one error (mismatch or indel) to the genome to infer the mutational bias of the method. For each library, we calculated the proportion of mutations involving each of the four nucleotides as well as the proportion of each of the four nucleotides in the CLIPed tags (see Supplementary FIG. 3).

Identification of High-Confidence Clusters

We used the CLIPed clusters of PUM2 and QKI, to define criteria for selecting high confidence binding sites. The criteria that we tested reflected the mechanistic aspects of generating the sequence reads. They were the absolute sequence read counts and the presence of a guanosine in the genomic sequence directly upstream of the sequence read cluster, because RNase T1 cleaves after G nucleotides, and criteria reflecting our preliminary analysis of mutation patterns in the tags. For each cut-off on a given property, we calculated an enrichment of binding sites, which is defined as the fraction of clusters with at least one binding site above the given cut-off divided by the fraction of clusters with no crosslinking sites (no T to C mutations) that have at least one binding site. For Pumilio, there are 1020 clusters with no T to C mutation and 27% of these clusters contain the binding motif. For QKI, there are 1482 clusters with no T to C mutation, 35% of which contain the consensus motif. Our preliminary analysis revealed that T to C mutations are by far the most frequently observed mutations in these data sets, and that they are most frequent inside or in the immediate vicinity of the binding motifs as opposed to the rest of the sequence (see FIGS. 2D, 3D, and 4D). This suggested that the observed mutational bias is directly linked to the crosslinking event and should thus be a good criterion for separating true crosslinked sites from background tags. The preliminary analysis also indicates a strong bias for G nucleotides at the last position of a tag and also at the genomic position immediately upstream of a tag. This bias reflects the sequence specificity of the RNase T1, and may again help in the identification of tags that map to multiple sites or for discriminating random RNA turnover products unrelated to RNase T1 treatment. Finally, we observed that many clusters with abundantly sequenced tags contained more than one position with a T to C mutation. The results of testing these criteria for their ability to select clusters that contained the known binding motif are shown in Supplementary FIG. 5. For QKI, binding motifs were defined as occurrences of ACUAA or AUUAA. For Pumilio, in order to account for additional motif variants besides the consensus UGUANAUA, binding motifs were identified as matches to the weight matrix (as inferred by MotEvo) that resulted from the motif search (see below). We found that ranking of the clusters by the number of T to C mutations in all tags in the clusters of sequence reads leads to the strongest enrichment in clusters with a binding site (Supplementary FIG. 5). The figures show the fraction of the CLIPed clusters that contain at least one occurrence of the known binding motif as a function of the number of clusters that passed a given cutoff in the selection criterion (e.g. total number of tags, total number of T to C mutations, total number of tags with a G at position −1 in relative to their genomic locus). It is clear, particularly for PUM2, that the number of T to C mutations strongly correlates with the presence/absence of the motif in the cluster. For comparison, we also show the same plots when using as the ranking criterion not the total number of T to C mutations in the cluster, but just the total number of tags per cluster. For QKI, this leads to a significantly lower enrichment of clusters with recognition elements. We also investigated how the fraction of clusters with the known binding motif depends on the number of distinct crosslinking positions (i.e. positions with at least one T to C mutation) inside the cluster (Supplementary FIG. 5). The fraction of clusters with a binding site increases steadily from 0 to 5 crosslinking positions for both proteins, with the strongest increase from 0 to 1 for PUM2 and between 0 and 2 crosslinking positions for QKI. When requiring that at least two positions with T to C mutations are present in the cluster, the fraction of clusters with a binding site increases roughly by 10% for PUM2, and by more than 40% for QKI, These considerations lead us to the following procedure for defining high confidence clusters for any given RBP. 16 We first selected all the clusters with at least two crosslinking positions and, secondly, within this subset, we ranked all clusters by the total number of T to C mutations in all tags in the cluster.

Extraction of Peaks and T to C-Anchored Regions from Sequence Read Clusters

From each ranked, mRNA-annotated cluster a peak region, defined as a 32-nt long region with the highest average tag density, was extracted. Because the T to C mutation was diagnostic for the site of crosslinking, we focused our motif analysis on regions anchored at the position in a cluster with the most T to C mutations. We then investigated the mutational profile around this position and we found that this profile approaches the background profile after about 20 nt to the left and right of the main site of T to C mutations. Thus, these 41-nt long regions centered on the main site of T to C mutations are most likely to contain the binding sites and we focused our motif search on these regions.

RNA Recognition Site and Motif Search

For the motif search defining the core of a RNA recognition site we selected, for each RBP, the top 100 high confidence clusters, defined as described above. We selected the 41-nt region centered on the main T to C mutation site and searched for over-represented sequence motifs using PhyloGibbs (Siddharthan et al., 2005). We used a first-order Markov model as the background model and searched each set of sequences for three motifs of lengths varying between 4 and 8 nt, demanding an expected total number of 50 motifs. We did not search for motifs shorter than 4 nucleotides as the algorithm is then very likely to get stuck in local maxima. Additionally, significantly overrepresented short motifs are reproducibly found when using longer weight matrices. For each parameter setting, we performed five replicate runs. This generally resulted for each RBP in various shifted versions of the same motif Therefore we hierarchically clustered all the weight matrices that we obtained from these runs, allowing for partial overlap of at least 4 nucleotides between pairs of weight matrices. In the clustering procedure, two weight matrices were fused if the posterior probability of their stemming from the same as opposed to two different probability distribution was larger than 0.2 (for a description of the Bayesian calculation, see (Berninger et al., 2008), section 4.1). For each protein, we selected the largest cluster of weight matrices, i.e. the cluster that contained most of the weight matrices that we obtained in replicate runs, and created the final weight matrix by summing up the counts for each nucleotide of the weight matrices belonging to this cluster. Since the clustering procedure also allows the fusion of only partially overlapping weight matrices, the resulting weight matrices are typically longer (roughly 10 nucleotides) than the motif length that we imposed in individual runs, and can contain stretches of low information content. We therefore selected for each RBP, the window with highest information content. For PUM and QKI, the length of this window was 8 and 6 nt, respectively, in accordance with the known or expected consensus motifs (Galarneau and Richard, 2005; Gerber et al., 2006). For the IGF2BPs, we chose a window length of 4 nt, which is believed to be the size of binding motifs of KHdomains (Valverde et al., 2008). To identify binding sites in Pumilio clusters of aligned sequence reads using the inferred weight matrix, we used the MotEvo algorithm (van Nimwegen, 2007), which is based on a hidden Markov model that models the input sequences as contiguous stretches of nucleotides drawn from a background or a weight matrix model. We chose for the background a first order Markov model (which makes every nucleotide dependent on the preceding nucleotide in the sequence). The background model parameters (di-nt frequencies) were estimated from the set of input sequences. MotEvo was run in the prior-update mode, meaning that we attempted to find the prior probabilities for sites and background that maximize the likelihood of the sequence data. MotEvo generates as an output a list of sites for the given input weight matrix as well as their corresponding posterior probabilities. Note that not all matches to the weight matrix are reported, but only the subset of matches whose corresponding sequence is more likely under the weight matrix model than the background model. We chose a cut-off of 0.4 on the posterior probability to define the set of binding sites.

Determination of the Location of Clusters of Mapped Sequence Reads within Functional mRNA Regions For each RBP, we investigated whether clusters of mapped sequence reads preferentially originated in 5'UTR, CDS or 3'UTR. As a result of our annotation pipeline, we can assign probabilities to each cluster to belong to each of the three regions based on the annotation of individual tags within the cluster (see above). Taking together these probabilities for all clusters, we get estimates of the numbers of clusters originating in each of these three regions. We compare these numbers to those that we would expect if clusters were sampled uniformly from anywhere along the transcripts. This would for instance result in many more clusters from 3' compared to 5' UTR regions simply because 3' UTRs tend to be longer than the 5' UTRs. We determined all the transcripts to which a cluster mapped, and based on the GenBank annotation of the CDS of these transcripts, we calculated the fraction of the cluster nucleotides that fell in the 5' UTR (f_5), CDS (f_CDS), and 3' UTR (f_3) cluster. In the cases in which the cluster mapped to several transcripts belonging to the same gene, these fractions were averaged over all transcripts. The expected proportion of nucleotides sequenced from each region can then be calculated by summing these fractions for all clusters. The variance can be determined by noting that the probability that a nucleotide was sampled from a particular region, e.g. 5' UTR, is Bernoulli distributed with parameter f_5, which has a variance of f_5(1−f_5). The total variance is then given as the sum of all the variances.

Distance Distribution Between Consecutive CAT-Motifs in the IGF2BP RNA Binding Sites Since each of the IGF2BPs has 4 KH domains and we found only one clear motif, we hypothesized that all KH domains have the same or a very similar binding specificity. In analogy to what has been observed for Nova (Ule et al., 2006), we propose that the binding specificity of the IGF2BPs arises from the concerted action of several KHdomains that each recognize the same 4 letter sequence (CAUH), which should be apparent by a preferred spacing between subsequent occurrences of the motif as determined by the distance of corresponding KH-domains in the structure of the IGF2BPs. We calculated, for each IGF2BP separately, the distribution of distances between subsequent occurrences of the CAT-motif in clusters unambiguously derived from the 3'UTR of protein coding genes. We restricted ourselves to these clusters since 3'UTR regions are overrepresented in clusters of the IGF2BPs and each region, 5'UTR, CDS and 3' UTR, has different sequence biases that need to be taken into account when modeling background distributions. In order to reduce boundary effects due to the finite length of the clusters, we extended each cluster region 32 nt to the right and left. We then compared this distance distribution to the distance distribution of consecutive occurrences of the CAT motif in randomly chosen 3' UTR regions of the same length distribution as the clusters of mapped sequence reads. To estimate the mean and standard deviation of the relative frequency of each inter-motif distance in the background dataset, we repeated the random selection of 3' UTR regions 1000 times. In Supplementary FIG. 8, we show that for each IGF2BP target set, there is a bias for CAT-motifs to occur at inter-motif distances of 3 to 6 nt.

Analysis of siRNA Knockdown Experiments for QKI and IGF2BPs:

The procedure for the knockdown experiments for QKI and IGF2BP1-3 were described above. We imported the CEL files into the R software using the BioConductor affy package (Gentleman et al., 2004). The transcript probe set intensities were background-corrected, adjusted for non-specific binding and quantile normalized with the GCRMA algorithm (Wu, 2006). Probe sets with more than 6 of the 11 probes mapping ambiguously to the genome were discarded, as were probe sets that mapped to multiple genes. We then collected all probe sets matching a given gene, and we selected for further analysis the RefSeq transcript with median 3' UTR length corresponding to that gene. In total 16,063 transcripts were identified. The log-intensity of probe sets mapping to the gene were then averaged to obtain the expression level per RefSeq transcript. The level of transcript degradation was computed as the logarithm of the ratio of transcript expression in the cocktails of siRNA treated samples and mocktransfected cells.

To study the effect of individual proteins on the mRNA stability of their targets, we performed the following analysis. We first made the links between clusters of mapped Solexa sequence reads and expression data based on the NCBI Gene ID. That is, both the transcripts that were CLIPed and those whose expression was measured on microarrays have associated Gene IDs in the Gene database of NCBI. We mapped both the mapped sequence read clusters as well as the transcripts on microarrays to their corresponding genes, and thus identified which genes that were represented on microarrays have been CLIPed. From this set of genes we removed those that are likely off-targets of the transfected siRNAs. As previous studies showed, complementarity to the first 8 nucleotides of the miRNA is a good indicator that the transcript will be downregulated by a miRNA or siRNA, so we defined as putative off-targets those genes whose representative RefSeq transcripts carried such complementary sites in their 3'UTR. We divided the list of genes sorted by the maximum score of any cluster associated with a given gene. In order to improve the target identification and the assessment of the target response, we used some specific information that was available for individual data sets. For instance, for the IGF2BPs we only considered clusters with at least 2 positions of T to C changes, because we previously observed that this criterion improves the accuracy of target identification for the positive controls (PUM2 and QKI). Thus, for the IGF2BPs we divided the bound transcripts into the following bins, top 100 genes, 101th-300$^{th}$ genes, 301th-500th genes and 501th-1000th genes, 1001th-2000th, 2001th-3497th, and calculated the log 2 fold change of transcript abundance. To determine whether the siRNA knockdown has an effect on mRNA stability, we compared these distributions with the distribution of log-fold changes of genes that did not have any associated clusters from CLIP analysis. For QKI, whose binding motif is known, we performed the same analysis starting from clusters with a single T to C site, but that additionally contained the known QKI motif.

Generation and Ranking of Clusters of Mapped Sequence Reads for AGO and TNRC6

For subsequent analyses we only used extracted sequence reads of at least 20 nt in length and with unique, perfect or 1-error mapping to the genome. We clustered the reads with single-linkage criterion, meaning that we placed two reads in the same cluster if they overlapped by at least one nucleotide in their genomic mappings. We then selected the clusters that contained at least 5 mRNA-annotated reads and at least 2 positions at which T-to-C mutations occurred in the tags relative to the genomic sequence, and we ranked them by the total number of T-to-C mutations. This is because in our previous analyses of PURE-CLIP data (Landthaler et al., co-submitted) we found that the position of the crosslink is indicated by a T-to-C mutation in the tag relative to the genome sequence, and that clusters with at least two crosslinking positions are enriched in protein-binding sites roughly in proportion to the number of T-to-C mutations in the cluster.

Extraction of T-to-C-Anchored Regions from Sequence Read Clusters for AGO and TNRC6

In each ranked, mRNA-annotated cluster we identified the position with the largest number of T-to-C mutations, and we constructed the mutation frequency profile around this position. We found that this profile approaches the background after about 20 nucleotides to the left and right of the position with the maximum number of T-to-C changes, and we therefore extracted a genomic region of 41 nucleotides centered on this position for further analyses.

Filtering Out “Background” Clusters for AGO and TNRC6

It is still possible that a fraction of the clusters that we obtained simply contain degradation products of abundantly expressed mRNAs. Moreover, because a number of proteins that associate with the RISC complex have a molecular weight that is similar to that of AGO proteins, some of the tags/clusters that we obtained in the experiment with FLAG-tagged AGO may actually have been bound by other proteins. We have collected PURE-CLIP data for a number of proteins and we used to identify the AGO-specific clusters as follows. We built similar clusters for all the proteins that we investigated previously (IGF2BP1-3) (Landthaler, co-submitted). Then we compared the clusters that we obtained for different proteins, and when two clusters bound by two different proteins overlapped by more than 75% of their total length we considered that the two proteins shared a cluster. Finally, we discarded the following AGO clusters: clusters in which no position had a T-to-C mutation rate greater than 0.2, the experimentally determined T-to-C mutation rate at non-crosslinked sites; clusters that were shared between AGO libraries and libraries of other RBPs, with the number of tags in the AGO libraries being less than 1/10 of the number of tags in the other library. After applying these filters we obtained 17,319 AGO1-4 binding regions. We applied the same procedure to the clusters that we obtained from miR-124 and miR-7 transfection experiments.

Location of Clusters of Mapped Sequence Reads within Functional mRNA Regions

To investigate whether the clusters of mapped sequence reads preferentially originated in the 5'UTR, CDS or 3'UTR of protein-coding transcripts, we identified all the transcripts to which a cluster mapped, and based on the GenBank annotation of the CDS of these transcripts, we calculated the fraction of the cluster nucleotides that fell in the 5' UTR, CDS, and 3' UTR. When a cluster mapped to several transcripts belonging to the same gene, these fractions were averaged over all transcripts. The expected proportion of nucleotides sequenced from each functional region can then be calculated by summing these fractions for all clusters. The variance can be similarly determined by summing the variance over all clusters. This can be determined by noting that if the probability to sample a nucleotide from a particular region is Bernoulli distributed with parameter f its variance is $f(1-f)$. We compared these numbers to those that we would expect if clusters were sampled uniformly from anywhere along the transcripts. This would for instance result in many more clusters from 3' compared to 5' UTR regions simply because 3' UTRs tend to be longer than the 5' UTRs.

Position of the Crosslink Relative to miRNA Seed-Complementary Sequence

We identified all the target regions (T-to-C anchored regions of 41 nucleotides) that have an 8-mer (A opposite miRNA position 1 and perfect match at miRNA positions 2-8) seed match and we extended symmetrically the seed-complementary region by 20 nts to the left and right. We then computed the positional T-to-C mutation frequency in these regions and normalized it over the length of the target region.

Regions of the miRNAs that Pair Contiguously with the Target Sites

To determine whether positions other than the seed region may be involved in base-pairing interaction with targets, we first took the T-to-C anchored target regions and identified those that had at least a 6mer (2-6 and A opposite miRNA position 1, 2-7 or 3-8) seed complementarity to at least one of the top 100 most expressed miRNAs in HEK293 cells. For each of these T-to-C anchored regions and each miRNA that matched to it, we identified all the occurrences of complementarities of at least 4 nucleotides between the miRNA and the putative target region. Each of these was counted with a weight 1/n towards the positional profile of miRNA-target site matches, with n being the number of miRNAs that matched the putative target region.

Analysis of miRNA Knockdown and Overexpression Experiments

CEL files of mRNA profiles from miRNA/2'O-methyl oligonucleotide and mocktransfected cell were loaded into the R software using the BioConductor affy package (Gentleman et al., 2004). The transcript probe set intensities were background-corrected, adjusted for non-specific binding and quantile normalized with the GCRMA algorithm (Wu, 2006). Probe sets with more than 6 of the 11 probes mapping ambiguously to the genome were discarded, as were probe sets that mapped to multiple genes. We then collected all probe sets matching a given gene, and we computed the logarithm of gene-level expression as the average of the log-intensity of probe sets mapping to that gene. For sequence analyses we also selected a representative transcript for each gene. This was the Genbank transcript with median 3' UTR length corresponding to that gene. In total this procedure gave us expression measurements for 16,063 genes (and representative transcripts). The difference between the log-expression levels of a gene in samples treated with a cocktail of 2'-O-methyl oligoribonucleotides and mock transfected cells was taken as a measure of transcript stabilization upon miRNA inhibition.

We made the link between microarray and PURE-CLIP data through the NCBI Gene ID. That is, both the transcripts that were CLIPed and those whose expression was measured on microarrays have associated Gene IDs in the Gene database of NCBI, and we used this to identify the genes that were represented on microarrays and also yielded PURE-CLIP clusters. Of the 16063 transcripts measured by the Affymetrix array, 6,166 did not have any associated PURE-CLIP clusters.

Analysis of Transcript Stabilization as a Function of the Type of miRNA Target Sites We constructed the distribution of log-fold-changes of transcripts with various types of PURE-CLIP clusters, and we compared them with the distribution of log-fold27 changes of transcripts that did not yield PURE-CLIP clusters, although they were expressed, as determined by the microarray measurements. The categories of transcripts were the following:

1. Transcripts with various types of miRNA seed matches

At most 6mer match: 1-6 (with A opposite miRNA position 1), 2-7, 3-8, 4-9 match to at least one of the antagonized miRNA sequences. At most 7mer match: 1-7 (with A opposite miRNA position 1), 2-8, 3-9 match to at least one of the antagonized miRNA sequences At most 8mer match: 1-8 (with A opposite miRNA position 1), 2-9 match to at least one of the antagonized miRNA sequences At most 9mer match: 1-9 (with A opposite miRNA position 1) match to at least one of the antagonized miRNA sequences.

2. Transcripts with PURE-CLIP clusters originating exclusively in a particular transcript region (5'UTR, CDS, 3'UTR).
3. Transcripts with 1, 2, 3, 4 or more non-overlapping PURE-CLIP clusters.

Digital Gene Expression

The sequence reads from the Digital Gene Expression experiment have been analyzed in a manner similar to that described above in the section “Adapter removal and sequence annotation”. We only considered genomic and transcript matches containing the GATC recognition sequence of the DpnII restriction enzyme directly upstream of the mapped sequence tag. For our analyses we further used sequence reads that had a perfect match in the genome. The probability that a tag originates in a given locus was then computed as 1/n of loci to which the tag can be mapped. The sequence reads were also mapped to the mRNA sequences and then we computed an expression level per gene. This was defined as the sum of the weighted copies of all tags that can be mapped to transcripts that originate in that gene. Finally, to assess the accuracy of the expression level measurements, we correlated the logarithm of the expression level measured on the lysate Affymetrix GeneChip® microarray with the logarithm expression level measured using the Digital Gene Expression technology. The Spearman correlation coefficient was higher than 0.68. We found a considerable number of transcripts that could be detected by sequencing (20,993) and that were undetectable on the microarrays (altogether 16,063 transcripts). Correlation between biological replicates of HEK293 cells was higher than 0.99. We correlated the logarithm of the expression level measured on the lysate Affymetrix GeneChip microarray with the logarithm expression level measured using the Digital Gene Expression technology. The Spearman correlation coefficient was 0.68. We could detect 22'466 genes by sequencing and 16'063 by microarray measurements. The correlation between biological replicates of the DGE experiment for HEK293 RNA was higher than 0.99.

Analysis of miRNA-Induced Destabilization of CLIPed and UNCLIPed miR-124 and miR-7 Targets We intersected the transcripts with the background-noise-filtered PURE-CLIP clusters obtained after miR-124 and miR-7 transfection (see "filtering the background" section above) with those for which we had destabilization and AGO-IP Affymetrix microarray measurements. We then constructed, for each miRNA, three non-overlapping sets of transcripts: those with PURE-CLIP clusters exclusively in the 3'UTR, with PURECLIP clusters exclusively in the CDS only, and transcripts that did not yield any PURECLIP clusters. For each set, we computed the average log 2 fold change upon miRNA transfection, and the average log 2 fold enrichment in the AGO-IP. We compared these values between transcripts with and transcripts without PURE-CLIP clusters (FIG. S9A). The error bars on the bar plot represent 95% confidence intervals on the mean log 2 fold changes. Finally, we performed Wilcoxon's rank sum test to assess the significance of the difference in the log 2 fold changes of pairs of transcript sets. We also looked at various combinations of CLIP cluster locations (Supplementary FIG. 9)) that occurred more than 25 times in a given data set. Finally, we also compared the destabilization and AGObinding of PURE-CLIPed and UNCLIPed single miR-124 and miR-7 seed matches (Supplementary FIG. 9*c*). A seed match was defined as a match to nucleotides 1-7, 2-8 or 1-8 of the miRNA (both miRNAs start with U, so a 1-7 or 1-8 seed match also means having an A opposite nucleotide 1 of the miRNA). A seed match was considered "CLIPed" if it overlapped with a CLIP cluster from the corresponding transfection library.

Estimation of miRNA Expression Based on Deep Sequencing

The miRNA profile was generated from a Solexa deep sequencing run containing small RNAs from the following libraries: AGO1-IP and lysates of AGO1-4 IP, which were combined and denoted lysate in FIG. 1*c*. The miRNA annotation was preformed as described in (Berninger et al., 2008; Landgraf et al., 2007).

Plots of Motif Frequency-Vs-Enrichment

We performed a 7mer word enrichment analysis based on the T-to-C anchored target regions from the miRNA transfection experiments. We enumerated all words of length 7 and we determined their frequency in the real set as well as in a background set of shuffled sequences with the same dinucleotide content. For each 7-mer, we then calculated its enrichment as the ratio of the two frequencies. Additionally, we calculated for each 7mer the posterior probability that the frequency of the 7-mer is different in foreground and background allowing for sampling noise (Berninger et al., 2008). To determine whether the enriched motifs may correspond to miRNAs, all significantly enriched motifs (with a posterior>=0.99) were aligned with Needleman-Wunsch algorithm (penalties: gapopening −4, gapextension −4) to the reverse complemented of the transfected and to the top 20 most expressed in HEK293 miRNAs. We only reported cases in which the enriched word mapped with 0 or 1 errors to the first 9 positions of one of these miRNAs.

Identification of Significantly Enriched miRNA Binding Site Types

In order to identify individual miRNA binding sites in the sequence data we first defined a set of putative "binding models". These were either contiguous matches to at least 6 nucleotides of a miRNA, or matches that had a single structural defect. This was defined as either an internal loop or a bulge either in the miRNA or in the mRNA. For each of the 553 miRNAs we enumerated all these binding models, and we determined the enrichment of the T-to-C anchored regions in each of these models, relative to 10 dinucleotide randomized sequence sets. Using a cutoff of 1.0e-20 in the probability that the real set had a lower frequency of occurrence compared to the randomized sets, which we used as a measure of the significance of the enrichment, we found all the T-to-C anchored regions that contained at least one significantly enriched binding model from one of the top 100 most expressed miRNAs within 10 nucleotides of the T-to-C mutation site. To obtain a comprehensive list of target sites we added to these the 7mer nucleotide matches (within the same 10 nucleotides of the T-to-C mutation) to positions 1-7 or 2-8 of one of the top 100 most expressed miRNAs, irrespective of whether the T-to-C anchored regions were enriched in these 7mers.

Correlation of miRNA Seed Expression with Seed-Complementary Motif

From all samples of smirnadb (Landgraf et al., 2007), all miRNAs that had at least 50 counts in total from all samples were used to build seed groups (defined by the motif found at positions 2-8). We added an additional sample which was generated by pooling together the miRNA reads from deep sequencing of HEK293 lysate as well as AGO1-4 IPs without crosslinking. For each sample, we computed the expression of a seed group as the sum of the tags of all miRNAs that were part of the seed group. We correlated the seed expression with the frequency of the seed-complementary motif in the T-to-C anchored regions.

Co-Occurrence of miRNA Seed Pairs

We set to determine if the CLIPed regions are enriched in pairs of binding sites for highly expressed miRNAs. Assuming that not all of these sites may have been captured in our experiment, we used for this purpose the 17,319 cluster regions which we extended by 32 nucleotides on either side. We scanned these regions for non-overlapping 7mers corresponding to the positions 2-8 of the top 20 most expressed miRNAs in HEK293 cells. We performed a similar procedure using 100 randomized variants of the extended clusters that preserved the di-nucleotide composition. The results are shown in Supplementary FIG. 6*a*. As additional controls we performed 1. The same procedure using 20 randomly selected miRNAs (Supplementary FIG. 6*b*): 2. Counting of the number of seed match pair occurrence in the extended clusters for 100 sets of 20 randomly selected miRNAs (Supplementary FIG. 6*c*). A visualization of seed match pair occurrence is shown in Supplementary FIG. 6*d.*

Properties of PURE-CLIPed and UNCLIPed miRNA Seed Matches

For the analyses whose results are presented in Supplementary FIG. 9 we needed to intersect the CLIP transcript sets with the transcript set measured by the Affymetrix microrray. In order to study the properties of CLIPed and UNCLIPe seed matches we do not need to make this intersection, and we therefore considered the entire set of miRNA seed matches that are present in the representative RefSeq transcripts. We chose as the representative RefSeq transcript for a given gene that transcript that had the median 3'UTR length from all RefSeq transcripts corresponding to a gene. RefSeq transcripts that could not be detected in the DGE transcriptome profile were discarded. For the analysis of the miR-124 and miR-7 transfection libraries, we scanned the 5'UTR, CDS and 3'UTRs of representative expressed RefSeq transcripts for 7mer or 8mer seed matches to miR-124 or miR-7, and intersected these with the background-noise-filtered miR-124 and miR-7 PURE-CLIP clusters to CLIPed and UNCLIPed seed matches. In parallel, we scanned the 5'UTR, CDS and 3'UTRs of representative expressed RefSeq transcripts for 7mer and 8mer seed matches to miR-15, miR-20, miR-103, miR-19, let-7 representing the top expressed miRNA families in HEK293 cells. These seed matches were then intersected with the background-noise-filtered AGO1-4, PURE-CLIP clusters.

Furthermore, because we wanted to analyze properties of the environment of the putative miRNA target sites, we only considered seed matches located at least 100 nucleotides away from either of the boundaries of the transcript. For each individual seed match, we computed the following quantities: Selection pressure: is the posterior probability that a seed complementary region is under evolutionary selection pressure, as computed by the ElMMo algorithm described in (Gaidatzis et al., 2007).

Predicted destabilization score: is a score that characterizes the extent to which the environment of a seed match is favorable for its functionality in mRNA destabilization, as computed by the TargetScanS algorithm (Grimson et al., 2007). For the analysis, we downloaded the TargetScan 4.2 from the TargetScan website. local AU content: was defined as the proportion of A+U nucleotides within 50 nucleotides upstream and 50 nucleotides downstream of the miRNA binding site, which was a 20 nt-long region, anchored at the 3'end by the seed-matching region.

Target site Eopen: was similarly defined in terms of the energy required to open the secondary structure of the target in a region of 20 nucleotides, anchored at the 3'end by the seed-complementary region (opposite positions 1-8 of the miRNA). This was computed using the program RNAup of the Vienna package (Hofacker, 2003) with the following parameters: u=20 (length of the window required to be single-stranded), w=50 (maximal distance between 2 nucleotides allowed to interact). The rest of the parameters were left with their default values. The negative value of this energy can be viewed as a measure of accessibility. We tested whether the four properties introduced above took significantly different values when comparing CLIPed to unCLIPed seed matches using Wilcoxon's rank sum test.

Codon Adaptation Index Around PURE-CLIPed and UNCLIPed Seed Matches

We compared the Codon Adaptation Index (CAI) (Sharp and Li, 1987) around CLIPed and unCLIP seed matches as follows. We obtained a reference codon usage by analyzing all the CDS from representative RefSeq transcripts from all expressed genes. We then anchored all sequences at the codon covering the 5' end of seed match (1-7, 2-8, or 1-8 of miR-15, miR-20, miR-103, miR-19, let-7 miRNAs) and computed the CAI for the 70 codons upstream and downstream of the anchor, i.e. a total of 141 codons. The 7mer or 8mer seed match is entirely covered by codons 0, 1 and 2, which highly constrains the codon usage at these positions, making it uninformative. The figure therefore does not show the CAI at these positions. For CLIPed seed matches, we smoothed the profile using a moving average of 5.

Analysis of Positional Bias of CLIPed and UNCLIPed Regions

We set to determine whether CLIPed seed matches (1-7, 2-8, or 1-8 of miR-15, miR-20, miR-103, miR-19, let-7 miRNAs) have a positional bias relative to the STOP codon. Noting that at least in the 4 Ago libraries, CLIPed seed matches tended to be located in CDS of shorter lengths than their unCLIPed counterparts, we performed local polynomial regression (loess, see W. S. Cleveland, E. Grosse and W. M. Shyu (1992) Local regression models. Chapter 8 of Statistical Models in S, eds J. M. Chambers and T. J. Hastie, Wadsworth & Brooks/Cole), fitting the distance between the seed matches and the STOP codon to the CDS length. The loess fit and standard errors on the distance to the STOP codon given the CDS length were obtained using R's loess and predict.loess functions with default parameters. The miRNA transfection (Supplementary FIG. 11*a*) and Ago (Supplementary FIG. 11*b*) CLIP libraries were analyzed separately, and loess fits were computed separately for crosslinked and uncrosslinked seed matches (shown in red and black, respectively). Finally, we represented the expected distance to the STOP codon as a function of the CDS length assuming that seed matches are distributed uniformly over the CDS (dashed blue curve). We used the same methodology to determine whether CLIPed sites are located preferentially towards a 3'UTR boundary (STOP codon or polyA tail) instead of the STOP codon.

REFERENCES

Berninger, P., Gaidatzis, D., van Nimwegen, E., and Zavolan, M. (2008). Computational analysis of small RNA cloning data. Methods 44, 13-21.

Gaidatzis, D., van Nimwegen, E., Hausser, J., and Zavolan, M. (2007). Inference of miRNA targets using evolutionary conservation and pathway analysis. BMC bioinformatics 8, 69.

Galarneau, A., and Richard, S. (2005). Target RNA motif and target mRNAs of the Quaking STAR protein. Nat Struct Mol Biol 12, 691-698.

Gentleman, R., et al. (2004). Bioconductor: open software development for computational biology and bioinformatics. Genome Biology 5, R80.

Gerber, A. P., et al. (2006). Genome-wide identification of mRNAs associated with the translational regulator PUMILIO in *Drosophila melanogaster*. PNAS 103, 4487-4492.

Grimson, A., et al. (2007). MicroRNA targeting specificity in mammals: determinants beyond seed pairing. Mol Cell 27, 91-105.

Hafner, M., et al. (2008). Identification of microRNAs and other small regulatory RNAs using cDNA library sequencing. Methods 44, 3-12.

Hofacker, I. L. (2003). Vienna RNA secondary structure server. Nucleic Acids Res 31, 3429-3431.

Landgraf, P., et al. (2007). A Mammalian microRNA Expression Atlas Based on Small RNA Library Sequencing. Cell 129, 1401-1414.

Landthaler, M., et al. (2008). Molecular characterization of human Argonaute-containing ribonucleoprotein complexes and their bound target mRNAs. RNA 14, 2580-2596.

Meister, G., et al. (2004). Human Argonaute2 mediates RNA cleavage targeted by miRNAs and siRNAs. Mol Cell 15, 185-197.

Sharp, P. M., and Li, W. H. (1987). The codon Adaptation Index—a measure of directional synonymous codon usage bias, and its potential applications. Nucleic Acids Res 15, 1281-1295.

Siddharthan, R., Siggia, E. D., and van Nimwegen, E. (2005). PhyloGibbs: A Gibbs Sampling Motif Finder That Incorporates Phylogeny. PLoS Computational Biology 1, e67.
Ule, J., et al. (2006). An RNA map predicting Nova-dependent splicing regulation. Nature 444, 580-586.
Valverde, R., Edwards, L., and Regan, L. (2008). Structure and function of KH domains. FEBS Journal 275, 2712-2726.
van Nimwegen, E. (2007). Finding regulatory elements and regulatory motifs: a general probabilistic framework. BMC bioinformatics 8, S4.
Wu (2006). A Model-Based Background Adjustment for Oligonucleotide Expression Arrays. Johns Hopkins University Biostat.
Wu, T. D., and Watanabe, C. K. (2005). GMAP: a genomic mapping and alignment program for mRNA and EST sequences. Bioinformatics 21, 1859-1875.
Baek, D., et al. (2008). The impact of microRNAs on protein output. Nature 455, 64-71.
Bartel, D. P. (2009). MicroRNAs: Target Recognition and Regulatory Functions. Cell 136, 215-233.
Bezerra, R., and Favre, A. (1990). In vivo incorporation of the intrinsic photolabel 4-thiouridine into *Escherichia coli* RNAs. Biochemical and Biophysical Research Communications 166, 29-37.
Bishop, J. O., Morton, J. G., Rosbash, M., and Richardson, M. (1974). Three abundance classes in HeLa cell messenger RNA. Nature 250, 199-204.
Boyerinas, B., et al. (2008). Identification of Let-7-Regulated Oncofetal Genes. Cancer Res 68, 2587-2591.
Brennecke, J., Stark, A., Russell, R. B., and Cohen, S. M. (2005). Principles of MicroRNA:Target Recognition. PLoS Biology 3, e85.
Burchard, J., et al. (2009). MicroRNA-like off-target transcript regulation by siRNAs is species specific. RNA 15, 308-315.
Chen, T., and Richard, S. (1998). Structure-Function Analysis of Qk1: a Lethal Point Mutation in Mouse quaking Prevents Homodimerization. Mol Cell Biol 18, 4863-4871.
Chenard, C. A., and Richard, S. (2008). New implications for the QUAKING RNA binding protein in human disease. Journal of Neuroscience Research 86, 233-242.
Chi, S. W., Zang, J. B., Mele, A., and Darnell, R. B. (2009). Argonaute HITS-CLIP decodes microRNA-mRNA interaction maps. Nature.
Clery, A., Blatter, M., and Allain, F. H. T. (2008). RNA recognition motifs: boring? Not quite. Current Opinion in Structural Biology 18, 290-298.
Diabetes Genetics Initiative of Broad Institute of Harvard and MIT, L.U.a.N.I.o.B.R., et al. (2007). Genome-Wide Association Analysis Identifies Loci for Type 2 Diabetes and Triglyceride Levels. Science 316, 1331-1336.
Dimitriadis, E., et al. (2007). Expression of oncofetal RNA-binding protein CRDBP/IMP1 predicts clinical outcome in colon cancer. International Journal of Cancer 121, 486-494.
Dreyfuss, G., Adam, S. A., and Choi, Y. D. (1984). Physical change in cytoplasmic messenger ribonucleoproteins in cells treated with inhibitors of mRNA transcription. Mol Cell Biol 4, 415-423.
Ebersole, T. A., Chen, Q., Justice, M. J., and Artzt, K. (1996). The quaking gene product necessary in embryogenesis and myelination combines features of RNA binding and signal transduction proteins. Nat Genet 12, 260-265.
Farh, K. K., et al. (2005). The widespread impact of mammalian MicroRNAs on mRNA repression and evolution. Science 310, 1817-1821.
Favre, A., et al. (1986). 4-thiouridine photosensitized RNA-protein crosslinking in mammalian cells. Biochemical and Biophysical Research Communications 141, 847-854.
Filipowicz, W., Bhattacharyya, S. N., and Sonenberg, N. (2008). Mechanisms of posttranscriptional regulation by microRNAs: are the answers in sight? Nat Rev Genet 2008, 102-114.
Forman, J. J., Legesse-Miller, A., and Coller, H. A. (2008). A search for conserved sequences in coding regions reveals that the let-7 microRNA targets Dicer within its coding sequence. PNAS 105, 14879-14884.
Gaidatzis, D., van Nimwegen, E., Hausser, J., and Zavolan, M. (2007). Inference of miRNA targets using evolutionary conservation and pathway analysis. BMC bioinformatics 8, 69.
Galarneau, A., and Richard, S. (2005). Target RNA motif and target mRNAs of the Quaking STAR protein. Nat Struct Mol Biol 12, 691-698.
Galgano, A., et al. (2008). Comparative Analysis of mRNA Targets for Human PUFFamily Proteins Suggests Extensive Interaction with the miRNA Regulatory System. PLoS ONE 3, e3164.
Gardner, P. P., et al. (2009). Rfam: updates to the RNA families database. Nucleic Acids Res 37, D136-140.
Gerber, A. P., et al. (2006). Genome-wide identification of mRNAs associated with the translational regulator PUMILIO in *Drosophila melanogaster*. PNAS 103, 4487-4492.
Granneman, S., Kudla, G., Petfalski, E., and Tollervey, D. (2009). Identification of protein binding sites on U3 snoRNA and pre-rRNA by UV cross-linking and highthroughput analysis of cDNAs. Proc Natl Acad Sci USA.
Grimson, A., et al. (2007). MicroRNA targeting specificity in mammals: determinants beyond seed pairing. Mol Cell 27, 91-105.
Grun, D., et al. (2005). microRNA target predictions across seven *Drosophila* species and comparison to mammalian targets. PLoS Comput Biol 1, e13.
Gu, S., et al. (2009). Biological basis for restriction of microRNA targets to the 3' untranslated region in mammalian mRNAs. Nat Struct Mol Biol 16, 144-150.
Guil, S., and Caceres, J. F. (2007). The multifunctional RNA-binding protein hnRNP A1 is required for processing of miR-18a. Nat Struct Mol Biol 14, 591.
Gupta, Y. K., Nair, D. T., Wharton, R. P., and Aggarwal, A. K. (2008). Structures of Human Pumilio with Noncognate RNAs Reveal Molecular Mechanisms for Binding Promiscuity. Structure 16, 549-557.
Hafner, M., et al. (2008). Identification of microRNAs and other small regulatory RNAs using cDNA library sequencing. Methods 44, 3-12.
Hieronymus, H., and Silver, P. A. (2004). A systems view of mRNP biology. Genes & Development 18, 2845-2860.
Hwang, H. W., Wentzel, E. A., and Mendell, J. T. (2007). A hexanucleotide element directs microRNA nuclear import. Science 315, 97-100.
John, B., et al. (2004). Human miRNA targets. PLoS Biol 2, e363.
Kapranov, P., et al. (2007). RNA maps reveal new RNA classes and a possible function for pervasive transcription. Science 316, 1484-1488.
Keene, J. D. (2007). RNA regulons: coordination of post-transcriptional events. Nat Rev Genet 8, 533-543.
Kirino, Y., and Mourelatos, Z. (2008). Site-specific crosslinking of human microRNPs to RNA targets. RNA 14, 2254-2259.

Kloosterman, W. P., Wienholds, E., Ketting, R. F., and Plasterk, R. H. A. (2004). Substrate requirements for let-7 function in the developing zebrafish embryo. Nucl Acids Res 32, 6284-6291.
Komili, S., and Silver, P. A. (2008). Coupling and coordination in gene expression processes: a systems biology view. Nat Rev Genet 9, 38-48.
Krek, A., et al. (2005). Combinatorial microRNA target predictions. Nat Genet 37, 495-500.
Lai, E. C. (2002). Micro RNAs are complementary to 3' UTR sequence motifs that mediate negative post-transcriptional regulation. Nat Genet 30, 363-364.
Landgraf, P., et al. (2007). A Mammalian microRNA Expression Atlas Based on Small RNA Library Sequencing. Cell 129, 1401-1414.
Landthaler, M., et al. (2008). Molecular characterization of human Argonaute-containing ribonucleoprotein complexes and their bound target mRNAs. RNA 14, 2580-2596.
Lewis, B. P., Burge, C. B., and Bartel, D. P. (2005). Conserved seed pairing, often flanked by adenosines, indicates that thousands of human genes are microRNA targets. Cell 120, 15-20.
Licatalosi, D. D., et al. (2008). HITS-CLIP yields genome-wide insights into brain alternative RNA processing. Nature 456, 464-469.
Lim, L. P., et al. (2005). Microarray analysis shows that some microRNAs downregulate large numbers of target mRNAs. Nature 433, 769-773.
Lopez de Silanes, I., et al. (2004). Identification of a target RNA motif for RNA-binding protein HuR. Proc Natl Acad Sci USA 101, 2987-2992.
Lunde, B. M., Moore, C., and Varani, G. (2007). RNA-binding proteins: modular design for efficient function. Nat Rev Mol Cell Biol 8, 479-490.
Lytle, J. R., Yario, T. A., and Steitz, J. A. (2007). Target mRNAs are repressed as efficiently by microRNA-binding sites in the 5' UTR as in the 3' UTR. Proc Natl Acad Sci USA 104, 9667-9672.
Martin, K. C., and Ephrussi, A. (2009). mRNA Localization: Gene Expression in the Spatial Dimension. Cell 136, 719-730.
McKee, A. E., et al. (2005). A genome-wide in situ hybridization map of RNA-binding proteins reveals anatomically restricted expression in the developing mouse brain. BMC Dev Biol 5, 14.
Meisenheimer, K. M., and Koch, T. H. (1997). Photocross-linking of nucleic acids to associated proteins. Crit Rev Biochem Mol Biol 32, 101-140.
Meister, G., et al. (2004). Human Argonaute2 mediates RNA cleavage targeted by miRNAs and siRNAs. Mol Cell 15, 185-197.
Melvin, W. T., et al. (1978). Incorporation of 6-Thioguanosine and 4-Thiouridine into RNA. European Journal of Biochemistry 92, 373-379.
Mili, S., Moissoglu, K., and Macara, I. G. (2008). Genome-wide screen reveals APCassociated RNAs enriched in cell protrusions. Nature 453, 115-119.
Moore, M. J., and Proudfoot, N. J. (2009). Pre-mRNA Processing Reaches Back to Transcription and Ahead to Translation. Cell 136, 688-700.
Moore, M. J., and Query, C. C. (1998). Use of site-specifically moified RNAs constructed by RNA ligation. In RNA-protein interactions: A practical approach, C. Smith, ed. (Oxford, UK, Oxford University Press), pp. 75-108.
Morris, A. R., Mukherjee, N., and Keene, J. D. (2008). Ribonomic analysis of human Pum1 reveals cis-trans conservation across species despite evolution of diverse mRNA target sets. Mol Cell Biol 28, 4093-4103.
Orom, U. A., Nielsen, F. C., and Lund, A. H. (2008). MicroRNA-10a Binds the 5'UTR of Ribosomal Protein mRNAs and Enhances Their Translation. Molecular Cell 30, 460-471.
Pena, J. T. G., et al. (2009). miRNA in situ hybridization in formaldehyde and EDC-fixed tissues. Nat Meth 6, 139-141.
Robb, G. B., Brown, K. M., Khurana, J., and Rana, T. M. (2005). Specific and potent RNAi in the nucleus of human cells. Nat Struct Mol Biol 12, 133-137.
Sanford, J. R., et al. (2009). Splicing factor SFRS1 recognizes a functionally diverse landscape of RNA transcripts. Genome Res 19, 381-394.
Scott, L. J., et al. (2007). A Genome-Wide Association Study of Type 2 Diabetes in Finns Detects Multiple Susceptibility Variants. Science 316, 1341-1345.
Selbach, M., et al. (2008). Widespread changes in protein synthesis induced by microRNAs. Nature 455, 58-63.
Sharp, P. M., and Li, W. H. (1987). The codon Adaptation Index—a measure of directional synonymous codon usage bias, and its potential applications. Nucleic Acids Res 15, 1281-1295.
Siddharthan, R., Siggia, E. D., and van Nimwegen, E. (2005). PhyloGibbs: A Gibbs Sampling Motif Finder That Incorporates Phylogeny. PLoS Computational Biology 1, e67.
Sonenberg, N., and Hinnebusch, A. G. (2009). Regulation of Translation Initiation in Eukaryotes: Mechanisms and Biological Targets. Cell 136, 731-745.
Sood, P., et al. (2006). Cell-type-specific signatures of microRNAs on target mRNA expression. PNAS 103, 2746-2751.
Stark, A., et al. (2005). Animal MicroRNAs Confer Robustness to Gene Expression and Have a Significant Impact on 3'UTR Evolution. Cell 123, 1133-1146.
Stark, A., Brennecke, J., Russell, R. B., and Cohen, S. M. (2003). Identification of *Drosophila* MicroRNA Targets. PLoS Biology 1, e60.
Tay, Y., et al. (2008). MicroRNAs to Nanog, Oct4 and Sox2 coding regions modulate embryonic stem cell differentiation. Nature 455, 1124-1128.
Tenenbaum, S. A., Carson, C. C., Lager, P. J., and Keene, J. D. (2000). Identifying mRNA subsets in messenger ribonucleoprotein complexes by using cDNA arrays. Proceedings of the National Academy of Sciences of the United States of America 97, 14085-14090.
Ule, J., et al. (2003). CLIP identifies Nova-regulated RNA networks in the brain. Science 302, 1212-1215.
Vella, M. C., et al. (2004). The *C. elegans* microRNA let-7 binds to imperfect let-7 complementary sites from the lin-41 3'UTR. Genes & Development 18, 132-137.
Wagenmakers, A. J., Reinders, R. J., and van Venrooij, W. J. (1980). Cross-linking of mRNA to proteins by irradiation of intact cells with ultraviolet light. Eur J Biochem 112, 323-330.
Wang, X., McLachlan, J., Zamore, P. D., and Hall, T. M. T. (2002). Modular Recognition of RNA by a Human Pumilio-Homology Domain. Cell 110, 501-512.
Wang, Y., et al. (2008a). Structure of an argonaute silencing complex with a seedcontaining guide DNA and target RNA duplex. Nature 456, 921-926.
Wang, Y., et al. (2008b). Structure of the guide-strand-containing argonaute silencing complex. Nature 456, 209-213.
Weinmann, L., et al. (2009). Importin 8 Is a Gene Silencing Factor that Targets Argonaute Proteins to Distinct mRNAs. Cell 136, 496-507.

Wickens, M., Bernstein, D. S., Kimble, J., and Parker, R. (2002). A PUF family portrait: 3'UTR regulation as a way of life. Trends Genet 18, 150-157.

Wightman, B., Ha, I., and Ruvkun, G. (1993). Posttranscriptional regulation of the heterochronic gene lin-14 by lin-4 mediates temporal pattern formation in *C. elegans*. Cell 75, 855-862.

Wu, J. I., Reed, R. B., Grabowski, P. J., and Artzt, K. (2002). Function of quaking in myelination: Regulation of alternative splicing. Proceedings of the National Academy of Sciences of the United States of America 99, 4233-4238.

Yeo, G. W., et al. (2009). An RNA code for the FOX2 splicing regulator revealed by mapping RNA-protein interactions in stem cells. Nat Struct Mol Biol advanced online publication.

Yisraeli, J. K. (2005). VICKZ proteins: a multi-talented family of regulatory RNAbinding proteins. Biology of the cell/under the auspices of the European Cell Biology Organization 97, 87-96.

Zamore, P. D., Williamson, J. R., and Lehmann, R. (1997). The Pumilio protein binds RNA through a conserved domain that defines a new class of RNA-binding proteins. RNA 3, 1421-1433.

INCORPORATION OF SEQUENCE LISTING

Incorporated herein by reference in its entirety is the Sequence Listing for the application. The Sequence Listing is disclosed on a computer-readable ASCII text file titled, "sequence_listing__1119-29PCTUS.txt", created on Jan. 26, 2011. The sequence_listing.txt file is 39.9 kb in size.

What is claimed:

1. A method for identifying a binding site on an RNA transcript, wherein the binding site binds to one or more binding moieties, the method comprising a) introducing a 4-thiouridine photoreactive nucleoside into living cells wherein the living cells incorporate the photoreactive nucleoside into RNA transcripts during transcription thereby producing modified RNA transcripts;

b) irradiating said cells at a wavelength significantly absorbed by the photoreactive nucleoside to covalently cross-link a binding site on the modified RNA transcripts to one or more binding moieties;

c) removing all or part of the modified RNA transcripts which is not covalently cross-linked to the one or more binding moieties to form cross-linked segments having the photoreactive nucleoside, wherein the cross-linked segments comprise at least a portion of the binding site;

d) isolating the cross-linked segments thereby generating isolated cross-linked segments;

e) reverse transcribing the RNA of isolated cross-linked segments thereby generating cDNA transcripts with a deoxyguanosine (G) to deoxyadenosine (A) mutation wherein the photoreactive nucleoside is transcribed to a mismatched deoxynucleoside;

f) amplifying the cDNA transcripts thereby generating amplicons with a deoxythymidine (T) to deoxycytidine (C) mutation;

g) determining the nucleotide sequences of the amplicons having at least 15 nucleotides;

h) aligning the sequences of the amplicons against a reference sequence; and i) analyzing the sequences of the amplicons aligned against the reference sequence so as to identify the binding site, wherein the sequences of each amplicon having the T to C mutation resulting from the introduction of the photoreactive nucleoside is considered to be a valid amplicon comprising at least a portion of a binding site on the RNA transcript.

2. The method according to claim 1 further comprising removing the binding moiety from the isolated cross-linked segments thereby generating isolated segments prior to step (e).

3. The method of claim 1 further comprising determining the sequence of a consensus motif, wherein the determination comprises using the mutation as an anchor and comparing the sequence surrounding the mutation to the reference sequence, wherein the mutation is within a sequence window that includes the mutation plus at least one nucleotide on either side of the mutation.

4. The method of claim 3 wherein the sequence window includes five to twenty nucleotides on either side of the mutation.

5. The method of claim 3 wherein the mutation is at the center of the sequence window.

6. The method according to claim 1 wherein the reference sequence is a genomic sequence.

7. The method according to claim 6 wherein the genomic sequence is a sequence that produced the RNA transcript.

8. The method according to claim 1 wherein the reference sequence is a synthetic RNA sequence.

9. The method according to claim 1 wherein the reference sequence is derived from an expressed sequence tag database.

10. The method according to claim 1 further comprising identifying a feature required for interaction of the binding site and the binding moiety.

11. The method of claim 1 wherein the binding moiety is a protein or a protein complex.

12. The method of claim 11 wherein the protein complex comprises miRNA, piRNA, siRNA, endo-siRNA, snoRNA, snRNA, tRNA, rRNA or a combination thereof.

13. The method of claim 11 wherein the protein is an RNA-binding protein, an RNA-associated protein or a combination thereof.

14. The method of claim 1 wherein the binding site is a coding transcript.

15. The method of claim 1 wherein the binding moiety is epitope-tagged.

16. The method of claim 1 wherein step (c) comprises (i) forming a soluble extract of the cells; and (ii) treating the extract with a nuclease thereby forming the cross-linked segments.

17. The method of claim 16 wherein the nuclease is ribonuclease-T1.

18. The method of claim 17 wherein aligning the sequences of the amplicons comprises determining which amplicons have the characteristic that, when aligned with the reference sequence, the reference sequence has a guanosine one nucleotide upstream from the 5' end of the amplicons.

19. The method of claim 17 wherein analyzing the sequences of the amplicons comprises determining which amplicons have the characteristic that, when aligned with the genomic sequence, the genomic sequence has a guanosine one nucleotide upstream from the 5' end of the amplicons, wherein such amplicons are valid amplicons.

20. The method of claim 1 wherein aligning the sequences of the amplicons comprises determining which amplicons have a mutation wherein a deoxythymidine of the reference sequence is replaced by a deoxycytidine in the amplicons.

21. The method of claim 1 wherein analyzing the sequences of the amplicons comprises determining which amplicons have only one mutation wherein a deoxythymidine of the reference sequence is replaced by a deoxycytidine in the amplicons, wherein such amplicons are valid amplicons.

22. The method of claim 15 wherein isolating the cross-linked segments comprises immunoprecipitation.

23. The method of claim 22 further comprising separating the cross-linked segments by length after immunoprecipitation.

24. The method of claim 22 further comprising treating the cross-linked segments with nuclease after immunoprecipitation.

25. The method of claim 1 wherein removing the binding moiety comprises digesting the binding moiety with a protease.

26. The method of claim 1 wherein the wavelength is greater than 300 nm.

27. The method of claim 1 wherein the living cell is part of a cell culture, a cell extract, whole tissue, or a whole organ.

* * * * *